US011725056B2

United States Patent
Noble et al.

(10) Patent No.: US 11,725,056 B2
(45) Date of Patent: Aug. 15, 2023

(54) METHODS FOR TARGETING THE IMMUNE CHECKPOINT PD1 PATHWAY FOR TREATING PULMONARY FIBROSIS

(71) Applicant: Cedars-Sinai Medical Center, Los Angeles, CA (US)

(72) Inventors: Paul W. Noble, Beverly Hills, CA (US); Dianhua Jiang, Encino, CA (US); Carol Jiurong Liang, Encino, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/652,966

(22) PCT Filed: Oct. 3, 2018

(86) PCT No.: PCT/US2018/054244
§ 371 (c)(1),
(2) Date: Apr. 1, 2020

(87) PCT Pub. No.: WO2019/070908
PCT Pub. Date: Apr. 11, 2019

(65) Prior Publication Data
US 2020/0262923 A1    Aug. 20, 2020

Related U.S. Application Data

(60) Provisional application No. 62/567,513, filed on Oct. 3, 2017.

(51) Int. Cl.
*A61K 39/395* (2006.01)
*A61K 39/00* (2006.01)
*C07K 16/28* (2006.01)
*A61P 35/00* (2006.01)

(52) U.S. Cl.
CPC .......... *C07K 16/2818* (2013.01); *A61P 35/00* (2018.01); *C07K 16/2827* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,010,175 A | 4/1991 | Rutter et al. |
| 5,288,514 A | 2/1994 | Ellman |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,582,981 A | 12/1996 | Toole et al. |
| 5,593,853 A | 1/1997 | Chen et al. |
| 5,595,877 A | 1/1997 | Gold et al. |
| 5,637,459 A | 6/1997 | Burke et al. |
| 6,133,031 A | 10/2000 | Monia et al. |
| 10,705,074 B2 | 7/2020 | Noble et al. |
| 10,973,842 B2 | 4/2021 | Noble et al. |
| 10,973,882 B2 | 4/2021 | Liang et al. |
| 2007/0238692 A1 | 10/2007 | Sylvia et al. |
| 2010/0047810 A1 | 2/2010 | Evans et al. |
| 2010/0184113 A1 | 7/2010 | Zhao et al. |
| 2012/0159661 A1 | 6/2012 | Gimcher |
| 2014/0050740 A1 | 2/2014 | Noble et al. |
| 2014/0093486 A1 | 4/2014 | Chiou et al. |
| 2014/0235844 A1 | 8/2014 | Elmen et al. |
| 2015/0210769 A1* | 7/2015 | Freeman ............... A61P 1/04 424/136.1 |
| 2015/0258192 A1 | 9/2015 | Brophy et al. |
| 2017/0247456 A1 | 8/2017 | Freeman et al. |
| 2017/0275705 A1* | 9/2017 | Topalian .............. A61P 35/00 |
| 2017/0340735 A1* | 11/2017 | Hicklin ............... A61P 43/00 |
| 2018/0264141 A1 | 9/2018 | Noble et al. |
| 2019/0099471 A1 | 4/2019 | Liang et al. |
| 2019/0170732 A1 | 6/2019 | Noble et al. |
| 2020/0206332 A1* | 7/2020 | Sutton ................ A61P 35/00 |

FOREIGN PATENT DOCUMENTS

| | | | |
|---|---|---|---|
| EP | 3352799 A1 | 1/2018 |
| EP | 3352792 A1 | 8/2018 |
| EP | 3352792 B1 | 8/2020 |
| EP | 3692073 A1 | 8/2020 |
| WO | 91/19735 A1 | 12/1991 |
| WO | 92/00091 A1 | 1/1992 |
| WO | 93/20242 A1 | 10/1993 |
| WO | 2005112936 A1 | 12/2005 |
| WO | WO 2015/013508 A2 | 1/2015 |
| WO | 2016081475 A1 | 5/2016 |

(Continued)

OTHER PUBLICATIONS

Khunger and Velcheti., A Case of a Patient with Idiopathic Pulmonary Fibrosis with Lung Squamous Cell Carcinoma Treated with Nivolumab. J Thorac Oncol Jul. 2017;12(7):e96-e97. (Year: 2017).*
Habiel et al. Role of Immune Checkpoint Proteins in Idiopathic Pulmonary Fibrosis. (bioRxiv, Aug. 8, 2017, p. 1-35). (Year: 2017).*
Ni et al. PD-1/PD-L1 Pathway Mediates the Alleviation of Pulmonary Fibrosis by Human Mesenchymal Stem Cells in Humanized Mice. American Journal of Respiratory Cell and Molecular Biology, 58 (6):684-695, Jun. 2018. (Year: 2018).*
Delaunay et al Immune-checkpoint inhibitors associated with interstitial lung disease in cancer patients. Eur Respir J Aug. 2017; 50:1-13. (Year: 2017).*
Khunger and Velcheti. A Case of a Patient with Idiopathic Pulmonary Fibrosis with Lung Squamous Cell Carcinoma Treated with Nivolumab. Journal of Thoracic Oncology. vol. 12, Issue 7, Jul. 2017, pp. e96-e97. (Year: 2017).*

(Continued)

*Primary Examiner* — Maher M Haddad
(74) *Attorney, Agent, or Firm* — Nixon Peabody LLP

(57) ABSTRACT

The invention relates to methods for treating or preventing progressive pulmonary fibrosis in a subject.

18 Claims, 44 Drawing Sheets
Specification includes a Sequence Listing.

(56) References Cited

FOREIGN PATENT DOCUMENTS

| WO | 2016092082 A1 | 6/2016 |
|---|---|---|
| WO | WO 2017/051402 A1 | 3/2017 |
| WO | WO 2017/053952 A1 | 3/2017 |
| WO | WO 2017/053963 A1 | 3/2017 |
| WO | WO 2019/070908 A1 | 4/2019 |

OTHER PUBLICATIONS

Ni et al. Human mesenchymal stem cells alleviate bleomycin-induced pulmonary fibrosis in humanized mice. Journal of Immunology, (May 2017) vol. 198, No. 1, Supp. Supplement 1. Abstract No. 82.21. (Year: 2017).*
Patsoukis et al., Revisiting the PD-1 pathway, Sci. Adv. 6:eabd2712 (2020).
Han et al., PD-1/PD-L1 pathway: current researches in cancer, Am. J. Cancer Res. 10:727-4 (2020).
U.S. Appl. No. 16/150,379, filed Oct. 3, 2018, US-2019-0099471-A1, Published.
Lee et al., Interleukin-13 induces tissue fibrosis by selectively stimulating and activating transforming growth factor beta(1), J Exp Med. Sep. 17, 2001; 194(6): 809-21.
Li and Jimenez, Protein kinase Cd and c-Abl kinase are required for transforming growth factor ß induction of endothelial-mesenchymal transition in vitro, Arthritis Rheum. Aug. 2011; 63(8): 2473-83.
Li Y et al., Severe lung fibrosis requires an invasive fibroblast phenotype regulated by hyaluronan and CD44, The Journal of experimental medicine. 2011 208(7):1459-71.
Liang et al., Parallel synthesis and screening of a solid phase carbohydrate library, Science, 274:1520-1522 (1996).
Liu et al., IL-13 induces connective tissue growth factor in rat hepatic stellate cells via TGF-ß-independent Smad signaling, J Immunol. Sep. 1, 2011 ; 187(5): 2814-23.
Liu et al., Inflammasome inhibitors: promising therapeutic approaches against cancer, J Exp Med. Aug. 2, 2010; 207(8) : 1 589-97.
Loewe & Muischnek, 1926, Arch. Exp. Pathol Pharmacol. 114: 313-326 (Abstract Only).
Lok, S.S. et al.Murine gammaherpes virus as a cofactor in the development of pulmonary fibrosis in bleomycin resistant mice. Eur Respir J. Nov. 2002; 20(5): 1228-32.
Lown, J.W., et al. The mechanism of the bleomycin-induced cleavage of DNA1. Biochem Biophys Res Commun. Aug. 22, 1977; 77(4): 1150-7.
Mailleuix A A et al., Fgf10 expression identifies parabronchial smooth muscle cell progenitors and is required for their entry into the smooth muscle cell lineage, Development. May 2005; 132(9): 2157-66.
Mason DP et al., Lung Transplantation for Idiopathic Pulmonary Fibrosis, Ann Thorac Surg 84:1121-8, 2007.
Mason, RJ, Biology of alveolar type II cells Respirology, Jan. 2006; 11 Suppl: S12-5.
McDonald, S. et al. Combined betaseron R (recombinant human interferon beta) and radiation for inoperable non-small cell lung cancer. Radiother Oncol. Mar. 1993; 26(3): 212-8.
McLean GW, et al., The role of focal-adhesion kinase in cancer—a new therapeutic opportunity, Nat Rev Cancer. 2005;5(7):505-15.
McQualter & Bertoncello, Consider Review: Deconstructing tje Lung to Reveal Its Regenerative Potential, Stem Cells. May 2012; 30(5): 811-6.
McQualter et al., Endogenous Fibroblastic Progenitor Cells in the Adult Mouse Lung Are Highly Enriched in the Sca-1 Positive Cell Fraction, Stem Cells. 2009; 27: 61 2-22.
McQualter, J.L., et al. Evidence of an epithelial stem/progenitor cell hierarchy in the adult mouse lung. Proc Natl Acad Sci USA 2010; 107: 1414-19.
Meltzer and Nobel, Idiopathetic pulmonary fibrosis, Orphanet J Rare Dis. Mar. 26, 2008; 3: 8. Doi: 10,1 186/1750-1172-3-8.
Mentink-Kane et al., Accelerated and progressive and lethal liver fibrosis in mice that lack interleukin (IL)-10, IL-12p40, and IL-13Ra2, Gastroenterology. Dec. 2011; 141 (6): 2200-9.
Mentink-Kane, M.M., et al. Opposing roles for IL-13 and IL-13 receptor a2 in health and disease. Immunol Rev. Dec. 2004; 202: 191-202.
Miyazaki, Y. et al. Expression of a Tumor Necrosis Factor-a Transgene in Murine Lung Causes Lymphocytic and Fibrosing Alveolitis A Mouse Model of Progressive Pulmonary Fibrosis. J Clin Invest. Jul. 1995; 96(1): 250-9.
Moore et al., Murine models of pulmonary fibrosis, Am J Physiol Lung Cell Mol Physiol. Feb. 2008; 294(2): L152-60.
Moore, B.B. et al. Animal Models of Fibrotic Lung Disease. Am J Respir Cell Mol Biol. Aug. 2013; 49(2): 167-79.
Moreno HB et al., Anti-programmed cell death protein-1/ligand-1 therapy in different cancers, Br J Cancer. 2015;112(9):1421-7.
Morrisey E E & Hogan, Preparing for the first breath: genetic and cellular mechanisms in lung development, Dev Cell. Jan. 19, 2010; 18(1 ): 8-23.
Muggia, F. et al., Pulmonary toxicity of antitumor agents, Cancer Treat Rev, 10: 221-243, 1983.
Murray, L.A., et al. Hyper-responsiveness of IPF/UIP fibroblasts: interplay between TGFbeta1, IL-13 and CCL2. Int J Biochem Cell Biol. 2008; 40(10): 2174-82.
Myers, J.L., et al. Epithelial Necrosis and Alveolar Collapse in the Pathogenesis of Usual Interstitial Pneumonia. Chest. Dec. 1988; 94(6): 1309-11.
Needleman et al., A general method applicable to the search for similarities in the amino acid sequence of two proteins. J Mol Biol. Mar. 1970;48(3):443-53.
Nguyen LT et al., and Clinical blockade of PD1 and LAG3-potential mechanisms of action. Nat Rev Immunol, 2015;15(1):45-56.
Noble et al, Hyaluronan as an immune regulator in human diseases, Physiol Rev. Jan. 2011; 91 (1 ): 221-64.
Noble P W et al., Idiopathic pulmonary fibrosis: new insights into pathogenesis, Clin Chest Med 25:749-758, 2004.
Noble PW et al., Pirfenidone in patients with idiopathic pulmonary fibrosis (CAPACITY): two randomised trials, Lancet. 2011;377(9779):1760-9.
Noble PW et al., Pulmonary fibrosis: patterns and perpetrators, The Journal of clinical investigation. 2012;122(8):2756-62.
Nuovo, G. J., The distribution of immunomodulatory cells in the lungs of patients with idiopathic pulmonary fibrosis, (Molec.Pathol (2012) 25(3): 416-33.
Osterreicher et al., Fibroblast-specific protein 1 identifies an inflammatory subpopulation of macrophages in the liver, Proc Natl Acad Sci USA. Nov. 23, 2010; 108(1 ): 308-13.
Ostrand-Rosenberg S et al., The programmed death-1 immune-suppressive pathway: barrier to antitumor immunity, J Immunol. 2014;193(8):3835-41.
Parry RV, et al., CTLA-4 and PD-1 receptors inhibit T-cell activation by distinct mechanisms, Mol. Cell. Biol. 2005;25:9543-9553.
Patsoukis N, et al., Selective effects of PD-1 on Akt and Ras pathways regulate molecular components of the cell cycle and inhibit T cell proliferation, Sci Signal. 2012.
Paulin, D., et al. Desmin: a major intermediate filament protein essential for the structural integrity and function of muscle.Exp Cell Res. Nov. 15, 2004; 301(1): 1-7.
PCT/US2018/54244; International Search Report and Written Opinion 5 pages, dated Feb. 22, 2019.
Pearson and Lipman, Improved tools for biological sequence comparison, Proc. Natl. Acad. Sci. 85:2444 (1988).
Pearson W.R. (1994) Using the FASTA Program to Search Protein and DNA Sequence Databases. In: Griffin A.M., Griffin H.G. (eds) Computer Analysis of Sequence Data. Methods in Molecular Biology 24:307-331 1994 Humana Press.
Phan, S. et al., Bleomycin-induced pulmonary fibrosis in rats: biochemical demonstration of increased rate of collagen synthesis, Am Rev Respir Dis 121: 501-506, 1980.
Phan, S. et al., Chest, A comparative study of pulmonary fibrosis induced by bleomycin and an O2 metabolite producing enzyme system, Chest., 83(5 Suppl): 44S-45S, 1983.

(56) References Cited

OTHER PUBLICATIONS

Phillips, R.J., et al. Circulating fibrocytes traffic to the lungs in response to CXCL12 and mediate fibrosis. J Clin Invest. Aug. 2004; 114(3): 438-46.
Piguet et al., Expression and localization of tumor necrosis factor-alpha and its mRNA in idiopathic pulmonary fibrosis, Am J Pahtol. Sep. 1993; 143(3): 651-5.
Piguet, Tumor Necrosis Factor/Cachectin Plays a Key Role in Bleomycin-Induced Pneumopathy and Fibrosis. J. Exp Med, Sep. 1, 1989, vol. 170, No. 3, p. 655-663; abstract; p. 661, para 2.
Prasse et al., Serum CC-chemokine ligand 18 concentration predicts outcome in idiopathic pulmonary fibrosis, Am J Respir Crit Care Med. Apr. 15, 2009; 179(8): 717-23.
Rafii et al., A review of current and novel therapies for idiopathic pulmonary fibrosis, J Thorac Dis. 2013; 5(1 ): 48-73.
Werner & Gross, Regulation of wound healing by growth factors and cytokines, Physiol Rev. Jul. 2003; 83(3): 835-70.
White ES et al., Pathogenetic mechanisms in usual interstitial pneumonia/idiopathic pulmonary fibrosis, J Pathol. 2003;201(3):343-54.
White, E.S., et al. Negative Regulation of Myofibroblast Differentiation by PTEN (Phosphatase and Tensin Homolog Deleted on Chromosome 10) Sem. Am J Respir Crit Care Med. Jan. 1, 2006; 173(1): 112-21.
Wilson et al. Bleomycin and IL-1 beta-mediated pulmonary fibrosis is IL-17A dependent, J Exp Med. Mar. 15, 2010; 207(3): 535-52.
Wilson et al., Colitis and intestinal inflammation in IL10-/- mice results from IL-13Ra2-mediated attenuation of IL-13 activity, Gastroenterology. Jan. 2011; 140(1 ): 254-64.
Wipff, P., et al. Myofibroblast contraction activates latent TGF-beta1 from the extracellular matrix. J Cell Biol. Dec. 17, 2007; 179(6): 1311-23.
Wu X, et al., FAK-mediated src phosphorylation of endophilin A2 inhibits endocytosis of MT1-MMP and promotes ECM degradation, Dev Cell. 2005;9(2):185-96.
Wynn, T.A., et al. Mechanisms of fibrosis: therapeutic translation for fibrotic disease. Nat Med. Jul. 6, 2012; 18(7): 1028-40.
Xiao Y et al., RGMb is a novel binding partner for PD-L2 and its engagement with PD-L2 promotes respiratory tolerance, The Journal of experimental medicine, 2014;211(5):943-59.
Yamamoto H et al., Epithelial-vascular cross talk mediated by BEGF-A and HGF signaling directs primary septae formation during distal lung morphogenesis, Dev Biol. Aug. 1, 2007 ; 308(1 ) 44-53.
Yoder, Progenitor Cells in the Pulmonary Circulation, Proc Am Thorac Soc. 2011; 8: 466-70.
Yokosuka T, et al., Programmed cell death 1 forms negative costimulatory microclusters that directly inhibit T cell receptor signaling by recruiting phosphatase SHP2, J. Exp. Med. 2012;209:1201-1217.
Zasloff, M. Antimicrobial peptides of multicellular organisms. Nature. Jan. 24, 2002; 415(6870): 389-95.
Zeisberg, M., et al. Cellular Mechanisms of Tissue Fibrosis. 1. Common and organ-specific mechanisms associated with tissue fibrosis. Am J Physiol Cell Physiol. Feb. 1, 2013; 304(3): C216-25.
Zhang & Kaminski, Biomarkers in idiopathic pulmonary fibrosis, Curr Opin Pulm Med. Sep. 2012; 18(5): 441-6.
Zhang et al., Enhanced IL-1 beta and tumor necrosis factor-alpha release and messenger RNA expression in macrophages from idiopathic pulmonary fibrosis or after asbestos exposure, J Immunol. May 1, 1993 ; 150(9): 4188-96.
Zhang, K., et al. Lung monocyte chemoattractant protein-1 gene expression in bleomycin-induced pulmonary fibrosis. J Immunol. Nov. 15, 1994; 153(10): 4733-41.
Zhang. K., et al. Myofibroblasts and Their Role in Lung Collagen Gene Expression during Pulmonary Fibrosis. Am J Pathol. Jul. 1994; 145(1): 114-25.
Zhao et al., Secretion of complement components of the alternative pathway (C3 and factor B) by the human alveolar type II epithelial cell line A549, Int J Mol Med. 2000; 5: 415-419.
Zhou et al., Inhibition of mechanosensitive signaling in myofibroblasts ameliorates experimental pulmonary fibrosis, J Clin Invest. Mar. 2013; 123(3): 1096-108.
Zhu, F., et al. IL-17 induces apoptosis of vascular endothelial cells—A potential mechanism for human acute coronary syndrome. Clin Immunol. Nov. 2011; 141(2): 152-60.
Zhu, S. et al., Urokinase receptor mediates lung fibroblast attachment and migration toward provisional matrix proteins through interaction with multiple integrins, Am J Physiol: Lung Cell Mol Physiol 297:L97-108, 2009.
Zhu, X., et al. Age-dependent fate and lineage restriction of single NG2 cells. Development. Feb. 2011; 138(4): 745-53.
Zuo et al., Gene expression analysis reveals matrilysin as a key regulator of pulmonary fibrosis in mice and humans, Proc Natl Acad Sci USA. Apr. 30, 2002; 99(9): 6292-7.
Agata et al., Expression of the PD-1 antigen on the surface of stimulated mouse T and B lymphocytes, (1996) Int Immunol. 8:765-72.
Alberts et al., Molecular Biology of the Cell. 4th Ed. New York: Garland Science; 2002. Fibroblasts and Their Transformations: The Connective-Tissue Cell Family, 1300-1301.
Altschul et al., Gapped BLAST and PSI-BLAST: a new generation of protein database search programs, Nucleic Acids Res. 25:3389-3402 (1997).
Alvarez et al., Lung microvascular endothelium is enriched with progenitor cells that exhibit vasculogenic capacity, Am J Physiol Lung Cell Mol Physiol. 2008; 294: L419-30.
American Thoracic Society, Idiopathic Pulmonary Fibrosis: Diagnosis and Treatment International Consensus Statement, Am J Respir Crit Care Med 161:646-664, 2000.
Andersson-Sjoland, A., et al. Fibrocytes are a potential source of lung fibroblasts in idiopathic pulmonary fibrosis. Int J Biochem Cell Biol. 2008; 40(10) 2129-40.
Arch, R., et al. Participation in normal immune responses of a metastasis-inducing splice variant of CD44. Science. Jul. 31, 1992; 257(5070): 682-5.
Balasubramian et al., Bone marrow-dervied angiogenic cells restore lung alveolar and vascular structure after neonatal hyperoxia in infant mice, Am J Physiol Lung Cell Mol Physiol. 2010; 298: L315-23.
Barkauskas, C. E. & Noble, Cellular Mechanisms of Tissue Fibrosis. 7. New insights into the cellular mechanisms of pulmonary fibrosis Am J Physiol Cell Physiol. Jun. 1, 2014 ; 306(1 1 ): C987-96.
Bell CH, et al., Structure of the repulsive guidance molecule (RGM)-neogenin signaling hub. Science. 2013;341(6141):77-80.
Bellusci S, et al., Fibroblast growth factor 10 (FGF10) and branching morphogenesis in the embryonic mouse lung, Development. Dec. 1997; 124(23): 4867-78.
Bird et al., Single-chain antigen-binding proteins, (1988) Science 242:423-426.
Bjermer, L., et al. Hyaluronan and type III procollagen peptide concentrations in bronchoalveolar lavage fluid in idiopathic pulmonary fibrosis. Thorax. Feb. 1989; 44(2): 126-31.
Blank C. et al., PD-L1/B7H-1 inhibits the effector phase of tumor rejection by T cell receptor (TCR) transgenic CD8+ T cells. Cancer Res. 2004;64(3):1140-5.
Blank et al., Interaction of PD-L1 on tumor cells with PD-1 on tumor-specific T cells as a mechanism of immune evasion: implications for tumor immunotherapy, (2005) Cancer Immunol. Immunother. 54:307-314.
Blank, C. et al., Contribution of the PD-L1/PD-1 pathway to T-cell exhaustion: an update on implications for chronic infections and tumor evasion, (Epub Dec. 29, 2006) Immunol. Immunother. 56(5):739-745).
Brown et al., Blockade of programmed death-1 ligands on dendritic cells enhances T cell activation and cytokine production, (2003) J. Immunol. 170:1257-66.
Brown JA et al., Blockade of programmed death-1 ligands on dendritic cells enhances T cell activation and cytokine production, J Immunol. 2003;170(3):1257-66.
Bujak et al., The role of IL-1 in the pathogenesis of heart disease, Arch Immulon Ther Exp (Warsz). May-Jun. 2009;57(3): 165-76.

(56) References Cited

OTHER PUBLICATIONS

Busse et al., Investigative bronchoprovocation and bronchoscopy in airway diseases, (2005) Am J Respir Crit Care Med 172:807-816.
Camenisch et al, Disruption of hyaluronan synthase-2 abrogates normal cardiac morphogenesis and hyaluronan-mediated transformation of epithelium to mesenchyme, J Clin Invest. Aug. 2000; 106(3): 349-60.
Campbell et al., Phosphonate Ester Synthesis Using a Modified Mitsunobu Condensation, J. Org. Chem. 59:658 (1994).
Carter et al., PD-1:PD-L inhibitory pathway affects both CD4(+) and CD8(+) T cells and is overcome by IL-2, (2002) Eur. J. Immunol. 32:634-43.
Chambers, R.C. Abnormal wound healing responses in pulmonary fibrosis: focus on coagulation signalling. Eur Respir Rev. 2008; 17(109): 130-137.
Chamoto K et al., CD+ Progenitor to Endothelial Cell Transition in Post-Pneumoectomy Angiogensis, Am J Respir Cell Mol Biol. Mar. 2012; 46(3): 283-9.
Chemnitz JM, et al., SHP-1 and SHP-2 associate with immunoreceptor tyrosine-based switch motif of programmed death 1 upon primary human T cell stimulation, but only receptor ligation prevents T cell activation, J. Immunol. 2004;173:945-954.
Chen et al., "Analogous" Organic Sythesis of Small-Compound Libraries: Validation of Combinatorial Chemistry in Small-Modecule Sythesis, J. Amer. Chem. Soc. 116:2661 (1994).
Chiaramonte et al., An IL-13 inhibitor blocks the development of hepatic fibrosis during a T-helper type 2-dominated inflammatory response, J Clin Invest. Sep. 1991; 104(6): 777-85.
Chiaramonte et al., Regulation and function of the interleukin 13 receptor alpha 2 during a T helper cell type 2-dominant immune response, J Exp Med. Mar. 17, 2003; 197(6): 687-701.
Chilosi, M., et al. Aberrant Wnt/beta-Catenin Pathway Activation in Idiopathic Pulmonary Fibrosis. Am J Pathol. May 2003; 162(5): 1495-502.
Cho et al., An unnatural biopolymer, Science 261:1303 (1993).
Cho, C. Y., et al., Dressing the Part. Dermatol Clin. Jan. 1998; 16(1): 25-47.
Chou & Talalay, Quantitative Analysis of Dose-Effect Relationships: The Combined Effectsof Multiple Drugs or Enzyme Inhibitors, 1984, Adv. Enzyme Regul. 22:27-55.
Chung, M.P. et al. Role of Repeated Lung Injury and Genetic Background in Bleomycin-Induced Fibrosis. Am J Respir Cell Mol Biol. Sep. 2003; 29(3 Pt 1): 375-80.
Chunn, J. L. et al. Partially adenosine deaminase-deficient mice develop pulmonary fibrosis in association with adenosine elevations. Am J Physiol Lung Cell Mol Physiol. Mar. 2006; 290(3): L579-87.
Collard et al., Acute exacerbatations of idiopathic pulmonary fibrosis, Am J Respir Crit Care Med. Oct. 1, 2007 ; 176(7): 636-43.
Collard et al., Changes in clinical and physiologic variables predict survival in idiopathic pulmonary fibrosis, Am J Respir Crit Care Med. Sep. 1, 2003; 168(5): 538-42.
Collard et al., Plasma biomarker profiles in acute exacerbation of idiopathic pulmonary fibrosis, Am J Physiol Lung Cell Mol Physiol. Jul. 2010; 299(1 ): L3-7.
Corpet et al., Multiple sequence alignment with hierarchical clustering, Nucleic Acids Research 16: 10881-90 (1988).
Cortez et al., IL-17 stimulates MMP-1 expression in primary human cardiac fibroblasts via p38 MAPK- and ERK1/2-dependent C/EBP-beta , NF-kappaB, and AP-1 activation, Am J Physiol Heart Circ Physiol. Dec. 2007; 293(6): H3356-65.
Crivellato E, The role of angiogenic growth factors in organogenesis, Int J Dev Biol. 2011 ; 55(4-5): 365-75.
Curiel TJ et al., Blockade of B7-H1 improves myeloid dendritic cell-mediated antitumor immunity. Nat Med. 2003;9(5):562-7.
Dang-Nguyen, et al., "Raise: A Raw Images Dataset for Digital Image Forensics," in Proceedings of the 6th ACM Multimedia Systems Conference, ACM, (2015) pp. 219-224 (6 pages).
Darby et al., Fibroblasts and myofibroblasts in wound healing, Clin Cosmet Investig Dermatol. 2014; 7: 301-11.
Davies, HR, et al., Immunomodulatory agents for idiopathic pulmonary fibrosis. The Cochrane database of systematic reviews. 20033):CD003134.
De Langhe SP et al., Levels of mesenchymal FGFR2 signaling modulate smooth muscle progenitor cell commitment in the lung, Dev Biol. Nov. 1, 2006; 299(1): 52-62.
De Wever & Mareel, Role of tissue stroma in cancer cell invasion, J Pathol. Jul. 2003; 200(4): 429-47.
Degryse, A.L., et al. Repetitive intratracheal bleomycin models several features of idiopathic pulmonary fibrosis. Am J Physiol Lung Cell Mol Physiol. Oct. 2010; 299(4): L442-52.
Demedts M et al., High-dose acetylcysteine in idiopathic pulmonary fibrosis. N Engl J Med. 2005;353(21):2229-42.
Ding et al., Enothelial-Dervied Andiocrine Signals Induce and Sustain Regenerative Lung Alveolarization, Cell. Oct. 28, 2011; 147(3): 539-53.
Bork, Powers and Pitfalls in Sequence Analysis: The 70% Hurdle, 2000, Genome Research 10:398-400.
Cantor, Potential therapeutic applications of hyaluronan in the lung, International Journal of COPD, 2007, vol. 3, No. 3, pp. 283-288.
Doerks et al., Protein annotation: detective work for function prediction, 1998, Trends in Genetics 14:248-250.
Kobayashi et al., Bidirectional role of IL-6 signal in pathogenesis of lung fibrosis, Respiratory Research;2015; vol. 16:99, pp. 1-14.
Lauer et al, The Rise and Fall of Hyaluronan in Respiratory Diseases, International Journal of Cell Biology, vol. 2015, Article ID 712507, 15 pages.
Lennon et al, Role of hyaluronan and hyaluronan-binding proteins in lung pathobiology, The American Journal of Physiology-Lung Cellular and Molecular Physiology, 201, vol. 301, No. 2, pp. L137-L147.
Moeller et al., The bleomycin animal model: a useful tool to investigate treatment options for idiopathic pulmonary fibrosis?, The International Journal of Biochemistry & Cell Biology, 2008; 40(3): 362-382.
Skolnick et al., From genes to protein structure and function: novel applications of computational approaches in the genomic era, 2000, Trends in Biotech. 18(1):34-39.
Tokuriki et al., Stability effects of mutations and protein evolvability, Current Opinion in Structural Biology 2009, 19:596-604.
Wells, Additivity of Mutational effects in Proteins, 1990, Biochemistry 29:8509-8517.
Raghu et al., Incidence and prevalence of idiopathic pulmonary fibrosis, Am J Respir Crit Care Med. Oct. 1, 2006 ; 174(7): 810-6.
Ramalingam et al., Unique functions of the type II intedeukin 4 receptor identified in mice lacking the interleukin 13 receptor alpha1 chain, Nat Immunol. Jan. 2008; 9(1 ): 25-33.
Ramasamy S K et al., Fgf10 dosage is critical for the amplification of epithelial cell progenitors and for the formation of multiple mesenchymal lineages during lung development, Dev Biol. Jul. 15, 2007; 307(2): 237-47.
Ramirez et al., Myofibroblast transdifferentiation in obliterative bronchiolitis: tgf-beta signaling through smad3-dependent and -independent pathways, Am J Transplant. Sep. 2006; 6(9): 2080-8.
Ramos et al., Fibroblasts from idiopathic pulmonary fibrosis and normal lungs differ in growth rate, apoptosis, and tissue inhibitor of metalloproteinases expression, Am J Respir Cell Mol Biol. May 2001; 24(5): 591-8.
Richeldi L et al., Coriicosteroids for idiopathic pulmonary fibrosis, The Cochrane database of systematic reviews. 20033):CD002880.
Riise et al., Bronchial brush biopsies for studies of epithelial inflammation in stable asthma and nonobstructive chronic bronchitis, (1992) Eur Resp J 5:382.
Riise et al., Bronchial brush biopsies for studies of epithelial inflammation in stable asthma and nonobstructive chronic bronchitis, (1996) Eur Resp J 9:1665.
Rock, J.R., et al. Multiple stromal populations contribute to pulmonary fibrosis without evidence for epithelial to mesenchymal transition. Proc Natl Acad Sci USA. Dec. 27, 2011; 108(52): E1475-83.
Romer LH, et al., Tyrosine kinase activity, cytoskeletal organization, and motility in human vascular endothelial cells, Mol Biol Cell. 1994;5(3):349-61.

(56) References Cited

OTHER PUBLICATIONS

Rothman, B. L. et al., Cytokine regulation of C3 and C5 production by the human type II pneumocyte cell line, A549, J Immunol. 1990; 145: 592-598.
Satelli & Li., Vimentin in cancer and its potential as a molecular target for cancer therapy, Cell Mol Life Sci. Sep. 2011; 68(18): 3033-46.
Satoh et al., Increased levels of KL-6 and subsequent mortality in patients with interstitial lung diseases, J Intern Med. Nov. 2006; 260(5): 429-34.
Sausville, E., et al. A role for ferrous ion and oxygen in the degradation of DNA by bleomycin. Biochem Biophys Res Commun. Dec. 6, 1976; 73(3): 814-22.
Schniedermann et al., Mouse lung contains endothelial progenitors with high capacity to form blood and lymphatic vessels. Cell Biol. 2010; 11 :50.
Schrier D. et al., The Role of Strain Variation in Murine Bleomycin-Induced Pulmonary Fibrosis. Am Rev Respir Dis., 127(1):63-6,1983.
Selman M et al., Emerging drugs for idiopathic pulmonary fibrosis, Expert Opin Emerg Drugs 16:341-62, 2011.
Selman M et al., Idiopathic Pulmonary Fibrosis: Prevailing and Evolving Hypotheses about Its Pathogenesis and Implications for Therapy, Ann Intern Med 134:136-151, 2001.
Shan L et al., Centrifugal migration of mesenchymal cells in embryonic lung, Dev Dyn. 2008; 237: 750-5.
Shannon & Deterding, Epithelial-mesenchymal interactions in lung development. In: McDonald JA, ed. Lung Biology in Health and Disease. vol. 100. New York: Marcel Dekker Inc., 1997, pp. 81-118.
Shannon, JM. and Deterding RR. Epithelial-mesenchymal interactions in lung development. In: Lung Growth and Development, (ed. JA McDonald) vol. 100, New York: Marcel Dekker Inc, 1997, pp. 81-118.
Sheppard KA, et al., PD-1 inhibits T-cell receptor induced phosphorylation of the ZAP70/CD3zeta signalosome and downstream signaling to PKCtheta, FEBS Lett. 2004;574:37-41.
Shetty S et al., Differential expression of the urokinase receptor in fibroblasts from normal and fibrotic human lungs, Am J Respir Cell Mol Biol 15:78-87, 1996.
Shibata K, et al., Both focal adhesion kinase and c-Ras are required for the enhanced matrix metalloproteinase 9 secretion by fibronectin in ovarian cancer cells, Cancer Res. 1998;58(5):900-3.
Smith et al., Hippocampal sclerosis of aging, a prevalent and high-morbidity brain disease, J Clin Pathol. Oct. 2013;66(1 ): 896-903.
Snider, G. et al, Chronic interstitial pulmonary fibrosis produced in hamsters by endotracheal bleomycin. Lung volumes, volume-pressure relations, carbon monoxide uptake, and arterial blood gas studied, Am Rev Respir Dis. 117: 289-297, 1978.
Song et al., Acute exacerbation of idiopathic pulmonary fibrosis: incidence, risk factors and outcome, Eur Respir J. Feb. 2011; 37(2): 356-63.
Starcher, B. et al., Increased elastin and collagen content in the lungs of hamsters receiving an intratracheal injection of bleomycin, Am Rev Respir Dis., 117(2): 299-305, 1978.
Staron MM, et al., The transcription factor FoxO1 sustains expression of the inhibitory receptor PD-1 and survival of antiviral CD8(+) T cells during chronic infection, Immunity. 2014;41:802-814.
Strieter RM et al., The role of CXC chemokines in pulmonary fibrosis, The Journal of clinical investigation. 2007;117(3):549-56.
Strunk, R. C. et al., Pulmonary alveolar type II epithelial cells synthesize and secrete proteins of the classical and alternative complement pathways, Clin Invest. 1988; 81 : 1419-1426.
Suganuma, H et al., Enhanced migration of fibroblasts derived from lungs with fibrotic lesions. Thorax 50:984-9, 1995.
Summer et al., Isolation of an Adult Mouse Lung Mesenchymal Progenitor Cell Population, Am J Respir Cell Mol Biol. 2007; 37: 152-9.
Tanjore et al, Contribution of epithelial-derived fibroblasts to bleomycin-induced lung fibrosis, Am J Respir Crit Care Med. Oct. 1, 2009 ; 180(7): 657-65.
Thannickal et al., J Biol Chem . Apr. 4, 2003;278(14):12384-9. doi: 10.1074/jbc.M208544200. Epub Jan. 16, 2003. Myofibroblast differentiation by transforming growth factor-beta 1 is dependent on cell adhesion and integrin signaling via focal adhesion kinase, J Biol Cehm. Apr. 4, 2003; 278(14): 12384-9.
Thebaud & Yoder. Pulmonary endothelial progenitor cells. In: Voelkel NF, Rounds S, eds. The Pulmonary Endothelium: Function in Health and Disease. Chichester, West Sussex: Wiley, 2009: 203-16.
Thrall, R. et al., Bleomycin-induced pulmonary fibrosis in the rat: inhibition by indomethacin. Am J Pathol, 95: 117-130, 1979.
Timmermans et al., Endothelial progentior cells: identity defined?, J Cell Mol Med. 2009; 13: 87-102.
Tomasek et al., Myofibroblasts and mechano-regulation of connective tissue remodelling, Nat Rev Mol Cell Biol. May 2002; 3(5): 349-63.
Toole, B. P. Hyaluronan: from extracellular glue to pericellular cue. Nat Rev Cancer. Jul. 2004; 4(7): 528-39.
Torry et al, Anchorage-independent colony growth of pulmonary fibroblasts derived from fibrotic human lung tissue, . J Clin Invest. Apr. 1994; 93(4): 1525-32.
Umezawa, H. et al., Studies on bleomycin, Cancer 20: 891-895, 1967.
Umezawa, H., Chemistry and mechanism of action of bleomycin, Fed Proc, 33: 2296-2302, 1974.
Vaughn et al., Human antibodies with sub-nanomolar affinities isolated from a large non-immunized phage display library, Nature Biotechnology, 14(3):309-314 (1996).
Vittal R. et al., Effects of the protein kinase inhibitor, imatinib mesylate, on epithelial/mesenchymal phenotypes: implications for treatment of fibrotic diseases, J Pharmacol Exp Ther., 321(1): 35-44, 2007.
Vittal, R. et al., Modulation of prosurvival signaling in fibroblasts by a protein kinase inhibitor protects against fibrotic tissue injury, Am J Pathol., 166(2): 367-75, 2005.
Voelkel NF, Rounds S, eds. The Pulmonary Endothelium: Function in Health and Disease. Chichester, West Suxssex: Wiley-Blackwell, 2009: 51-72.
Volckaert et al., Parabronchial smooth muscle constitutes an airway epithelial stem cell niche in the mouse lung after injury, J Clin Invest. 2011 ; 121 : 4409-19.
Waghray et al., Hydrogen peroxide is a diffusible paracrine signal for the induction of epithelial cell death by activated myofibroblasts, FASEB J. May 2005; 19(7): 854-6.
Wang et al., A pure population of lung alveolar epithelial type II cells derived from human embryonic stem cells, Proc Natl Acad Sci USA. Mar. 13, 2007; 104(11 ): 4449-54.
Dong et al., B7-H1 pathway and its role in the evasion of tumor immunity, (2003) J. Mol. Med. 81:281-7.
Dong H et al., Tumor-associated B7-H1 promotes T-cell apoptosis: a potential mechanism of immune evasion. Nat Med. 2002;8(8):793-800.
Dong Y et al., Blocking follistatin-like 1 attenuates bleomycin-induced pulmonary fibrosis in mice. The Journal of experimental medicine. 2015;212(2):235-52.
DR, Noble, Kumar et al., Let-7 micro RNA-mediation regulation of IL-13 and allergic airway inflammation, J. Allergy Clin. Immunol. 128:1077-85 (2011).
Du Bois, RM. Strategies for treating idiopathic pulmonary fibrosis. Nature reviews Drug discovery. 2010;9(2):129-40.
Dulauroy, S. et al. Lineage tracing and genetic ablation of ADAM12+ perivascular cells identify a major source of profibrotic cells during acute tissue injury. Nat Med. Aug. 2012; 18(8): 1262-70.
Duong, H., et al. Pro-angiogenic Hematopoietic Progenitor Cells and Endothelial Colony Forming Cells in Pathological Angiogenesis of Bronchial and Pulmonary Circulation. Angiogenesis. 2011; 14(4): 411-22.
Fala, L. et al, (2015), Ofev (Nintedanib): First Tyrosine Kinase Inhibitor Approved for the Treatment of Patients with Idiopathic Pulmonary Fibrosis, Am. Health Drug benefits 8 (Spec. Features): 101-104.

(56) References Cited

OTHER PUBLICATIONS

Fan, J et al. Interleukin-1 induces tubular epithelial-myofibroblast transdifferentiation through a transforming growth factor-beta1-dependent mechanism in vitro. Am J Kidney Dis. Apr. 2001; 37(4): 820-31.
Flaherty, K.R., et al. Prognostic Implications of Physiologic and Radiographic Changes in Idiopathic Interstitial PneumoniaAm J Respir Crit Care Med. Sep. 1, 2003; 168(5): 543-8.
Flies DB and Chen L, The new B7s: playing a pivotal role in tumor immunity, (2007) J Immunother. 30 (3): 251-60.
Francisco LM, et al., PD-L1 regulates the development, maintenance, and function of induced regulatory T cells, J. Exp. Med. 2009;206:3015-3029.
Frazdottir et al., Airway branching morphogenesis in three dimensional cutlture, Respir Res. 2010; 11 : 162.
Freeman et al., Protect the killer: CTLs need defenses against the tumor, (2002) Nat. Med. 8:787-9.
Freeman GJ, et al., Engagement of the PD-1 immunoinhibitory receptor by a novel B7 family member leads to negative regulation of lymphocyte activation, J. Exp. Med. 2000;192:1027-1034.
Friedman, Fibrogenic cell reversion underlies fibrosis regression in liver, Proc Natl Acad Sci USA. Jun. 12, 2012; 109(24): 9230-1.
Furka, General method for rapid synthesis of multicomponent peptide mixtures, Int. J. Pept. Prot. Res. 37:487-493 (1991).
Gangadharan, B. et al. Murine gammaherpesvirus-induced fibrosis is associated with the development of alternatively activated macrophages. J Leukoc Biol. Jul. 2008; 84(1): 50-8.
Gasse et al. IL-1R1/MyD88 signaling and the inflammasome are essential in pulmonary inflammation and fibrosis in mice, J Clin Invest. Dec. 2007; 1 17(12): 3786-99.
Gasse, P., et al. IL-1 and IL-23 Mediate Early IL-17A Production in Pulmonary Inflammation Leading to Late Fibrosis. PLoS One. 2011; 6(8): e23185.
Gates RE, et al., Potential role for focal adhesion kinase in migrating and proliferating keratinocytes near epidermal wounds and in culture, Cell Growth Differ. 1994;5(8):891-9.
Giangreco et al., Molecular phenotype ofairway side population cells, Am J Physiol Lung Cell Mol Physiol. 2004;286: L624-30.
Giannone, G., et al. Substrate rigidity and force define form through tyrosine phosphatase and kinase pathways. Trends Cell Biol. Apr. 2006; 16(4): 213-23.
Gilmore AP, Romer LH., Inhibition of focal adhesion kinase (FAK) signaling in focal adhesions decreases cell motility and proliferation, Mol Biol Cell. 1996;7(8):1209-24.
Goldstein R., et al., Failure of mechanical properties to parallel changes in lung connective tissue composition in bleomycin-induced pulmonary fibrosis in hamsters, Am Rev Respir Dis., 120(1 ):67-73, 1979.
Golubovskaya VM, at al., Focal adhesion kinase and p53 signaling in cancer cells, Int Rev Cytol. 2007;263:103-53.
Grinnell & Harrington. Pulmonary endothelial cell interactions with the extracellular matrix. In: Voelkel NF, Rounds S, eds. The Pulmonary Endothelium: Function in Health and Disease. Chichester, West Suxssex: Wiley-Blackwell, 2009: 51-72.
Habif, Dermatologic surgical procedures. Clinic Dermatology: A Color Guide to Diagnosis and Therapy. 3rd ed. 1996. 809-810.
Hagohara et al., Vinylogous Polypeptides: An Alternative Peptide Backbone, J. Amer. Chem. Soc. 114:6568 (1992).
Harari & Caminati, IPF: new insight on pathogenesis and treatment, Allergy. May 2010; 65(5):537-53.
Hashimoto et al, Endothelial-mesenchymal transition in bleomycin-induced pulmonary fibrosis, Am J Respir Cell Mol Biol. Aug. 2010; 43(2): 161-72.
Hashimoto, N., et al. Bone marrow-derived progenitor cells in pulmonary fibrosis. J Clin Invest. Jan. 2004; 113(2):243-52.
Haxhinasto S, et al., The AKT-mTOR axis regulates de novo differentiation of CD4+Foxp3+ cells, J. Exp. Med. 2008;205:565-574.

He et al., Matrix metalloproteinase-7 as a surrogate marker predicts renal Wnt/?-catenin activity in CKD, J Am Soc Nephrol. Feb. 2012; 23(2): 294-304.
Hecker L. et al., NADPH oxidase-4 mediates myofibroblast activation and fibrogenic responses to lung injury, Nat. Med., 15(9): 1077-81, 2009.
Hegab et al., Catalytic Combustion and NO Formation of Natural Gas, Stem Cells Dev. 2010; 19: 523-3.
Henikoff & Henikoff , Amino acid substitution matrices from protein blocks, Proc. Natl. Acad. Sci. USA, 1989, 89 :10915.
Higgins and Sharp, CLUSTAL: A package for performing multiple sequence alignment on a microcomputer, Gene 73:237-244 (1988).
Higgins and Sharp, Fast and sensitive multiple sequence alignments on a microcomputer, CABIOS 5: 151-153 (1989).
Hinz et al., The myofibroblast: one function, multiple origins, Am J Pathol. Jun. 2007; 170(6): 1807-16.
Hinz, B., Masters and servants of the force: The role of matrix adhesions in myofibroblast force perception and transmission. Eur J Cell Biol. Apr. 2006; 85(3-4): 175-181.
Hinz, Formation and Function of the Myofibroblast during Tissue Repair, J Invest Dermatol. Mar. 2007; 127(3): 526-37.
Hinz, Myofibroblast development is characterized by specific cell-cell adherens junctions, et al. Mol Biol Cell. Sep. 2004; 15(9): 4310-20.
Hinz, The myofibroblast: one function, multiple origins et al., Am J Pathol. Jun. 2007; 170(6): 1807-16.
Hirschmann et al., Nonpeptidal Peptidomimetics with a ß-D-Glucose Scaffolding. A Partial Somatostatin Agonist Bearing a Close Structural Relationship to a Potent, Selective Substane P Antagonist, J. Amer. Chem. Soc. 114:9217-9218 (1992).
Hobbs et al., "Diversomers": an approach to nonpeptide, nonoligomeric chemical diversity, Proc. Nat. Acad. Sci. USA 90:6909-6913 (1993).
Hoffman et al., Lung-Derived Mesenchymal Stromal Cell Post-Transplantation Survival, Persistence, Paracrine Expresion, and Repair of Elastase-Injured Lung, Stem Cells Dev. 2011 ; 20: 1779-92.
Holford & Scheiner, Understanding the dose-effect relationship: clinical application of pharmacokinetic-pharmacodynamic models 19981, Clin. Pharmacokinet. 6: 429-453.
Homet Moreno B, and Ribas A. Anti-programmed cell death protein-1/ligand-1 therapy in different cancers. Br J Cancer. 2015;112(9):1421-7.
Horowitz et al., Activation of the pro-survival phosphatidylinositol 3-kinase/AKT pathway by transforming growth factor-beta1 in mesenchymal cells is mediated by p38 MAPK-dependent induction of an autocrine growth factor, J Biol Chem. Jan. 9, 2004; 279(2): 1359-67.
Horowitz et al., Combinatorial activation of FAK and AKT by transforming growth factor-beta1 confers an anoikis-resistant phenotype to myofibroblasts, Cell Signal. Apr. 2007; 19(4): 761-71.
Houghton et al., Generation and Use of Synthetic Peptide Combinatorial Libraries for Basic Research and Drug Discovery, Nature 354:84-88 (1991).
Hsia DA, et al., Differential regulation of cell motility and invasion by FAK, J Cell Biol. 2003;160(5):753-67.
Hu et al., Gut-enriched Kruppel-like factor interaction with Smad3 inhibits myofibroblast differentiation, Am J Respir Cell Mol boil. Jan. 2007; 36(1 ): 78-84.
Huang et al., Matrix stiffness-induced myofibroblast differentiation is mediated by intrinsic mechanotransduction, Am J Respir Cell Mol Biol. Sep. 2012; 47(3): 340-8.
Huang et al., Parallelization of a local similarity algorithm, Computer Applications in the Biosciences 8: 155-65 (1992).
Hung et al. , Role of lung pericytes and resident fibroblasts in the pathogenesis of pulmonary fibrosis, Am J Respir Crit Care Med. Oct. 1, 2013 ; 188(7): 820-30.
Huston et al., Protein engineering of antibody binding sites: recovery of specific activity in an anti-digoxin single-chain Fv analogue produced in *Escherichia coli*, (1988) Proc. Natl. Acad. Sci. USA 85:5879-5883.
Ilic D, et al., Reduced cell motility and enhanced focal adhesion contact formation in cells from FAK-deficient mice, Nature. 1995;377(6549):539-44.

(56) References Cited

OTHER PUBLICATIONS

Ishida, Y. et al., Induced expression of PD-1, a novel member of the immunoglobulin gene superfamily, upon programmed cell death, (1992) EMBO J. 11:3887-3895.
Ishikawa et al., Utility of KL-6/MUC1 in the clinical management of interstitial lung diseases, Respir Investig. Mar. 2012; 50(1): 3-13.
Iwai Y et al., Involvement of PD-L1 on tumor cells in the escape from host immune system and tumor immunotherapy by PD-L1 blockade, Proc Natl Acad Sci U S A. 2002;99(19):12293-7.
Izbicki, G. et al., Time course of bleomycin-induced lung fibrosis, Int J Exp Pathol., 83(3): 111-9, 2002.
Jakubzick, C. et al Impact of Interleukin-13 Responsiveness on the Synthetic and Proliferative Properties of Th1- and Th2-Type Pulmonary Granuloma Fibroblasts. Am J Pathol. May 2003; 162(5): 1475-86.
Janick-Buckner, D. et al., Alteration of bronchoalveolar lavage cell populations following bleomycin treatment in mice. Toxicol Appl Pharmacol., 100(3):465-73, 1989.
Jiang, D., et al. Regulation of lung injury and repair by Toll-like receptors and hyaluronan. Nat Med. Nov. 2005; 11(11): 1173-9.
Jones, L. K., et al. IL-1RI deficiency ameliorates early experimental renal interstitial fibrosis. Nephrol Dail Transplant. 2009; 24: 3024-32.
Jordana, M., et al. Heterogeneous Proliferative Characteristics of Human Adult Lung Fibroblast Lines and Clonally Derived Fibroblasts from Control and Fibrotic Tissue. Am Rev Respir Dis. Mar. 1988; 137(3): 579-84.
Kalluri, R & Weinberg, R.A.. The basics of epithelial-mesenchymal transition. J Clin Invest. Jun. 1, 2009; 119(6): 1420-28.
Karlin & Altschul, Applications and statistics for multiple high-scoring segments in molecular sequences, Proc. Natl. Acad. Sci USA, 1993, 90: 5873-5787.
Katzenstein et al., Idiopathic pulmonary fibrosis: clinical relevance of pathologic classification, Am J Respir Crit Care Med. Apr. 2008; 157(4 Pt 1): 1301-15.
Katzenstein, A.-L., et al. Erratum to "Diagnosis of usual interstitial pneumonia and distinction from other fibrosing interstitial lung diseases". Hum Pathol. Sep. 2008; 39(9): 1275-94.
Kaviratne et al., IL-13 activates a mechanism of tissue fibrosis that is completely TGF-beta independent, J Immunol. Sep. 15, 2004; 173(6): 4020-9.
Keir ME et al., PD-1 and its ligands in tolerance and immunity, Annu Rev Immunol. 2008;26(677-704.
Kidiyoor, A, et al., Gene and Cell Therapy: Therapeutic Mechanisms and Strategies 761 (Nancy Smyth Templeton ed., 4th ed. 2015.
Kim et al, Alveolar epithelial cell mesenchymal transition develops in vivo during pulmonary fibrosis and is regulated by the extracellular matrix, Proc Natl Acad Sci USA. Aug. 29, 2006; 103(35): 13180-5.
Kinder, B.W., et al. Baseline BAL Neutrophilia Predicts Early Mortality in Idiopathic Pulmonary Fibrosis. Chest. Jan. 2008; 133(1): 226-32.
Kinder, B.W., et al. Serum Surfactant Protein-A Is a Strong Predictor of Early Mortality in Idiopathic Pulmonary Fibrosis. Chest. Jun. 2009; 135(6): 1557-63.
King et al., Structural and functional characteristics of lung macro- and microvascular endothelial cell phenotypes, Microvasc Res. 2004; 67: 139-51.
King TE, Jr. et al., A phase 3 trial of pirfenidone in patients with idiopathic pulmonary fibrosis, N Engl J Med. 2014;370(22):2083-92.
King TE, Jr. et al., BUILD-3: a randomized, controlled trial of bosentan in idiopathic pulmonary fibrosis, American journal of respiratory and critical care medicine. 2011;184(1):92-9.
King TE, Jr.et al., Effect of interferon gamma-1b on survival in patients with idiopathic pulmonary fibrosis (INSPIRE): a multicentre, randomised, placebo-controlled trial, Lancet. 2009;374(9685):222-8.
Kisseleva et al., Myofibroblasts revert to an inactive phenotype during regression of liver fibrosis, Proc Natl Acad Sci USA. Jun. 12, 2012; 109(24): 9448-53.
Kitani, A., et al. Transforming growth factor (TGF)-beta1-producing regulatory T cells induce Smad-mediated interleukin 10 secretion that facilitates coordinated immunoregulatory activity and amelioration of TGF-beta1-mediated fibrosis. J Exp Med. Oct. 20, 2003; 198(8): 1179-88.
Kolodsick, J.E. et al. Protection from Fluorescein Isothiocyanate-Induced Fibrosis in IL-13-Deficient, but Not IL-4-Deficient, Mice Results from Impaired Collagen Synthesis by Fibroblasts1. J Immunol. Apr. 1, 2004; 172(7): 4068-76.
Konigshoff et al., WNT1-inducible signaling protein-1 mediates pulmonary fibrosis in mice and is upregulated in humans with idiopathic pulmonary fibrosis, J Clin Invest. Apr. 2009; 1 19(4): 772-87.
Konishi et al., B7-H1 expression on non-small cell lung cancer cells and its relationship with tumor-infiltrating lymphocytes and their PD-1 expression, (2004) Clin. Cancer Res. 10:5094-100.
Konishi, K., et al. Gene Expression Profiles of Acute Exacerbations of Idiopathic Pulmonary Fibrosis. Am J Respir Crit Care med. Jul. 15, 2009; 180(2): 167-75.
Kramann et al, Perivascular Gli1+ progenitors are key contributors to injury-induced organ fibrosis, Cell Stem Cell. Jan. 8, 2015; 16(1 ): 51-66.
Krenning et al, The origin of fibroblasts and mechanism of cardiac fibrosis. J Cell Physiol. Nov. 2010; 225(3): 631-7.
Krizhanovsky et al., Senescence of activated stellate cells limits liver fibrosis, Cell. Aug. 22, 2008; 134(4): 657-67.
Kuperman, D.A., et al. Direct effects of interleukin-13 on epithelial cells cause airway hyperreactivity and mucus overproduction in asthma. Nat Med. Aug. 2002; 8(8): 885-9.
Largares et al., Inhibition of Focal Adhesion Kinase Prevents Experimental Lung Fibrosis and Myofibroblast Formation, Arthritis and Rheumatism. Arthritis Rheum, May 2012, vol. 64, No. 5; abstract; p. 1663, col. 1, para 2.
Latchman et al., PD-L2 is a second ligand for PD-1 and inhibits T cell activation, Nat Immunol. Mar. 2001;2(3):261-8).
Latsi, P.I., et al. Fibrotic Idiopathic Interstitial Pneumonia the Prognostic Value of Longitudinal Functional Trends. Am J Respir Crit Care Med. Sep. 1, 2003; 168(5): 531-537.
Latsi,. P., et al. Analysis of IL-12 p40 subunit gene and IFN-? G5644A polymorphisms in Idiopathic Pulmonary Fibrosis. Respir Res. 2003. 4:6.
Lawson, W. et al., Increased and prolonged pulmonary fibrosis in surfactant protein C-deficient mice following intratracheal bleomycin, Am J Pathol. 2005; 167(5): 1267-1277.
Leblue et al. Origin and function of myofibroblasts in kidney fibrosis, Nat Med. Aug. 2013; 19(8): 1047-53.
Leblue et al., Identification of human epididymis protein-4 as a fibroblast-derived mediator of fibrosis, Nat Med. Feb. 2013; 19(2): 227-31.
Lee et al., Interleukin-13 induces dramatically different transcriptional programs in three human airway cell types, Am J Respir Cell Mol Biol. Oct. 2001; 25(4): 474-85Lee e.
U.S. Appl. No. 15/761,404, filed Mar. 19, 2018, U.S. Pat. No. 10,705,074, Issued.
U.S. Appl. No. 15/761,403, filed Mar. 19, 2018, US-2018-0264141-A1, Published.
Brody, R. et al., "PD-L1 expression in advanced NSCLC: Insights into risk stratification and treatment selection from a systematic literature review", Lung Cancer., vol. 112, Aug. 10, 2017.
Habiel, D. et al., "Abstract", bioRxiv (Aug. 8, 2017), XP055775160, DOI: 10.1101/173237 Retrieved from the Internet: URL:<https://www.biorxiv.org/content/10.110>1/173237v1.full.pdf [retrieved on Feb. 11, 2021].
Shukuya, T. et al., "Predictive Markers for the Efficacy of Anti-PD-1/PD-L1 Antibodies in Lung Cancer", Journal of Thoracic Oncology, Elsevier Inc, US, vol. 11, No. 7, (Jul. 1, 2016), pp. 976-988, XP008181232, ISSN: 1556-0864, DOI: 10.1016/J.JTH0.2016.02.015 [retrieved on Mar. 2, 2016].

(56) References Cited

OTHER PUBLICATIONS

European Search Report for Application No. 18864905.7, dated Apr. 29, 2021, issued by the European Searching Authority on Apr. 9, 2021.
International Search Report and Written Opinion for PCT/US2016/053743 dated Jan. 26, 2017, 6 pages.
International Preliminary Report on Patentability for PCT/US2016/053743 dated Mar. 27, 2018, 5 pages.
EP 16849854.1 Extended Search Report dated Mar. 1, 2019, 8 pages.
International Search Report and Written Opinion for PCT/US2016/053771 dated Feb. 17, 2017, 16 pages.
International Preliminary Report on Patentability for PCT/US2016/053771 dated Mar. 27, 2018, 10 pages.
International Search Report and Written Opinion for PCT/IB2016/056575 dated Jun. 16, 2017, 12 pages.
International Preliminary Report on Patentability for PCT/IB2016/056575 dated Mar. 27, 2018, 8 pages.
EP 16848258.6 Extended Search Report dated Mar. 21, 2019, 8 pages.
EP 16848258.6 First Examination Report dated Nov. 19, 2020, 4 pages.
EP 16848258.6 Second Examination Report dated Jul. 1, 2021, 4 pages.
International Search Report and Written Opinion for PCT/US2018/054244 dated Feb. 22, 2019, 14 pages.
International Preliminary Report on Patentability for PCT/US2018/054244 dated Apr. 8, 2020, 10 pages.
Abe et al., Peripheral Blood Fibrocytes: Differentiation Pathway and Migration to Wound Sites. J Immunol. 2001, vol. 15; 166(12): 7556-7562.
Abrahams et al., The T-box Transcription Factor Tbx2: Its Role in Development and Possible Implication in Cancer, IUBMB Life, 2010, vol. 62(2), pp. 92-102.
Abreu et al., Decreased expression of Toll-like receptor 4 and MD-2 correlates with intestinal epithelial cell protection against dysregulated proinflammatory gene expression in response to bacterial lipopolysaccharide. J. Immunol. 167,1609-1616 (2001).
Acharya et al., Fibroblast migration is mediated by CD44-dependent TGF beta activation. J Cell Sci. May 1, 2008; 121(Pt 9): 1393-402.
Ahn et al., A promoter SNP rs4073T>A in the common allele of the interleukin 8 gene is associated with the Development of idiopathic pulmonary fibrosis via the IL-8 protein enhancing mode. Respir Res. Jun. 8, 2011; 12:73.
Alder et al., Telomere dysfunction causes alveolar stem cell failure. Proc. Nall. Acad. Sci. USA 112, 5099-5104 (2015).
Amin et al., Surfactant protein deficiency in familial interstitial lung disease. J. Pedialr. 139, 85-92 (2001).
Armanios et al., Telomerase Mutations in Families with Idiopathic Pulmonary Fibrosis. N Engl J Med. Mar. 29, 2007; 356(13): 1317-26.
Armstrong et al., Expression of functional toll-like receptor-2 and -4 on alveolar epithelial cells. Am. J. Respir. Cell Mol. Biol. 31, 241-245 (2004).
Arora et al., Multiple Roles and Interactions of Tbx4 and Tbx5 in Development of the Respiratory System. PLos Genet. 2012; 8(8): e1002866.
Astarita et al., Podoplanin: emerging functions in development, the immune system, and cancer. Front Immunol. Sep. 12, 2012; vol. 3: Article 283, 1-11.
Baarsma et al., Activation of WNT/b-Catenin Signaling in Pulmonary Fibroblasts by TGF-b1 Is Increased in Chronic Obstructive Pulmonary Disease. PLoS One. 2011; 6(9): e25450.
Balestrini et al., The mechanical memory of lung myofibroblastswz. Integr Biol (Camb ). Apr. 2012; 4(4): 410-21.
Barkauskas et al., Type 2 Alveolar Cells are Stem Cells in Adulting, 2013, J Clin Inves., vol. 12397), pp. 3025-3026.
Bartel, DP, MicroRNAs: genomics, biogenesis, mechanism, and function. Cell 116(2):281-297 (2004).

Berge et al., Pharmaceutical Salts, J Pharm Sci, 66: 1-19 (1977).
Bergers et al., The role of pericytes in blood-vessel formation and maintenance. Neuro Oneal. Oct. 2005; 7(4): 152-64.
Birck et al., Human TAFll28 and TAFll18 Interact through a Histone Fold Encoded by Atypical Evolutionary Conserved Motifs Also Found in the SPT3 Family Cell 94: 239-49 (1998).
Birmingham et al., A Protocol for Designing siRNAs with High Functionality and Specificity, Nat. Protec. 2007, vol. 2(9), pp. 2068-2078.
Bisserier et al., Lung-targeted SERCA2a Gene Therapy: From Discovery to Therapeutic Application in Bleomycin-Induced Pulmonary Fibrosis, J Cell lmmunoL 2:149-56 {2020).
Bolanos et al., Role of Sonic Hedgehog in idiopathic pulmonary fibrosis, Am J Physiol Lung Cell Mol Physiol, 2012, vol. 303, pp. 978-990.
Bolton et al., Changes in Clara Cell 10 kDa Protein (CC10)-positive Cell Distribution in Acute Lung Injury following Repeated Lipopolysaccharide Challenge in the Rat. Toxicol Pathol. Apr. 2008; 36(3): 440-8.
Bournazos et al., Fcy Receptor lllb (CD16b) Polymorphisms are Associated with Susceptibility to Idiopathic Pulmonary Fibrosis. Lung, Dec. 2010; 188(6): 475-81.
Brummelkamp et al., A system for stable expression of short interfering RNAs in mammalian cells. Science 2002, vol. 296:550-553.
Bucala et al., Circulating fibrocytes define a new leukocyte subpopulation that mediates tissue repair. Mol Med. m94;1c1):11-a1.
Campbell et al., Calculation of the internal surface of a lung. Nature 17:117 (1952).
Cao et al. Targeting of the pulmonary capillary vascular niche promotes lung alveolar repair and ameliorates lbrosis, Nat Med, 22, 154-162 (2016).
Cebra-Thomas et al., T-box gene products are required for mesenchymal induction of epithelial branching in the embryonic mouse lung, Dev Dyn, 2003;226(1):82-90.
Chan et al. Antisense oligonucleotides: from design to therapeutic application. Clin. Exp. Pharmacol. Physiol. 33(5-6): 533-40 (2006).
Chang et al. GATHER: a systems approach to interpreting genomic signatures. Bioinformatics. 2006; 22(23): 2926-33.
Chapman HA., Epithelial-mesenchymal interactions in pulmonary fibrosis. Annu Rev Physiol. 2011 ;73:413-435.
Chapman et al., Integrin Integrin α6β4 identifies an adult distal lung epithelial population with regenerative potential in mice, J. Clin. Invest 121, 2855-2862 (2011).
Checa et al., MMP-1 polymorphisms and the risk of idiopathic pulmonary fibrosis. Hum Genet. Dec. 2008; 124(5): 465-72.
Chen et al., Beta-Catenin Mediates Mechanically Regulated, Transforming GrowthFactor-beta1-lnduced Myofibroblast Differentiation of Aortic Valve Interstitial Cells. Arterioscler Thromb Vase Biol. Mar. 2011; 31(3): 590-7.
Chen et al., Airway epithelial progenitors are region specific and show differential responses to bleomycin-induced lung injury, Stem Cells 2012, 30, 1948-1960.
Cherng et al., Alpha-Smooth Muscle Actin (α-SMA), J Am Sci. 2008: 4(4): 7-9.
Chilosi et al., Migratory marker expression in fibroblast foci of idiopathic pulmonary fibrosis , Respiratory Research, Biomed Central Ltd., London, GB, 2006, vol. 7(1), p. 95.
Chung, KF, Cytokines as targets in chronic obstructive pulmonary disease, (2006) Curr. Drug Targets 7: 675-81.
Clark et al. The genetics of neonatal respiratory disease.Semin Fetal Neonatal Med. Jun. 2005; 10(3): 271-82.
Claverie et al., Information Enhancement Methods for Large Scale Sequence Analysis. Comput. Chem., H:191-201 (1993).
Cronkhite et al., Telomere Shortening in Familial and Sporadic Pulmonary Fibrosis. Am J Respir Grit Care Med. Oct. 1, 2008; 178(7): 729-37.
Darby et al., a-Smooth muscle actin is transiently expressed by myofibroblasts during experimental wound healing Lab Invest. Jul. 1990; 63(1): 21-29.
Degrendele et al., Requirement for CD44 in Activated T Cell Extravasation into an Inflammatory Site. Science. Oct. 24, 1997; 278(5338): 672-5.

(56) References Cited

OTHER PUBLICATIONS

Desai et al., Alveolar progenitor and stem cells in lung development, renewal and cancer. Nature, 2014, vol. 507, 190-194.

Desmouliere et al., Apoptosis Mediates the Decrease in Cellularity during the Transition between Granulation 11"issue and Scar. Am J Pathol. Jan. 1995; 146(1): 56-66.

Di Sabatino et al., Blockade of transforming growth factor beta upregulates T-box transcription factor T-bet, and increases T helper cell type 1 cytokine and matrix metalloproteinase-3 production in the human gut mucosa. Gut. 2008;57(5):605-612.

DNAzymes Scientific Background. Stema Biologicals, GmbH & Co. KG, www.stema-biologicals.com. printed from internet Sep. 24, 2018.

Duffield, J.S. Cellular and molecular mechanisms in kidney fibrosis. J Clin. Invest. Jun. 2014; 124(6): 2299-306.

Eblaghie et al., Evidence that autocrine signaling through Bmprla regulates the proliferation, survival and morphogenetic behavior of distal lung epithelial cells. Dev Biol. 291, 67-82 {2006).

Fandino et al., GLP-1 receptor agonist ameliorates experimental lung fibrosis, Sci. Rep. 10:18091 {2020).

Fernando et al., The T-box transcription factor Brachyury promotes epithelial mesenchymal transition in human Tumor cells. J Clin Invest. 2010;120(2):533-544.

Foronjy et al. Structural emphysema does not correlate with lung compliance: lessons from the mouse smoking model. Exp Lung Res. 2005;31(6):547-562.

Fox, C., Drug Delivery & Development. Reversing Idiopathic Pulmonary Fibrosis. http://www.dddmag.com/riews/2014/10/reversing-idiopathic-pulmonary-fibrosis, Oct. 15, 2014; downloaded from internet Aug. 15, 2018.

Franzdottir et al., Airway branching morphogenesis in three dimensional culture. Respir Res. 2010; 11: 162.

Friedler et al., Development of a Functional Backbone Cyclic Mimetic of the HIV-1 Tat Arginine-rich Motif. U. Biol. Chem., 2000, 275:23783-23789.

Fujita et al., RNAi Therapeutic Platforms for Lung Diseases, Pharmaceuticals, 2013, vol. 6, 223-250.

Fukata et al., Cox-2 is regulated by Toll-like receptor 4 (TLR4) signaling: role in proliferation and apoptosis in the ntestine, Gastroenterology 131, 862-877 {2006).

Fukuda et al., Patterns of Pulmonary Structural Remodeling After Experimental Paraquat Toxicity Am J Pathol. mas Mar; 118(3): 452-75.

Furuhashi et al., Increased expression of YKL-40, a chitinase-like protein, in serum and lung of patients with diopathic pulmonary fibrosis. Respir Med. Aug. 2010; 104(8): 1204-10.

Gangloff et al., The histone fold is a key structural motif of transcription factor TFIID. Trends Biochem. Sci. 26: 250-257 (2001).

Garbuzenko et al., lntratracheal versus intravenous liposomal delivery of siRNA, antisense oligonucleotides and anticancer drug, Pharm Res, 26:382-94 (2009).

Garcia, C.K. Idiopathic pulmonary fibrosis: update on genetic discoveries. Proc. Am. Thorac., 2011, Soc. 8, pp. 158-162.

Gilani et al., CD28 Down-Regulation on Circulating CD4 T-Cells Is Associated with Poor Prognoses of Patients with Idiopathic Pulmonary Fibrosis, PLoS One, Jan. 29, 2010; 5(1): e8959.

Gilbert, H.S. Myelofibrosis revisited: characterization and classification of myelofibrosis in the setting of myeloproliferative disease. Prog Clin Biol Res. 1984; 154: 3-17 (Abstract).

Glaser et al., Tbx4 Interacts with the Short Stature Homeobox Gene Shox2 in Limb Development. Dev Dyn. 2014, vol. 243(5), pp. 629-639.

Gomperts et al., Foxj1 regulates basal body anchoring to the cytoskeleton of ciliated pulmonary epithelial cells. U Cell Sci. Mar. 15, 2004; 117(Pt 8): 1329-37.

Gonzalez et al., HT11-280, a biomarker specific to the apical plasma membrane of human lung alveolar type II cells, J. Histochem. Cytochem. 2010, vol. 58, 891-901.

Goodman et al., The Pharmacological Basis of Therapeutics, Ed. Joel G. Hardman, Lee E. Limbird, Eds., 10th Ed., McGraw Hill, New York (2001), p. 25, 50.

Greene et al., Serum surfactant proteins-A and -D as biomarkers in idiopathic pulmonary fibrosis. Eur Respir J. Mar. 2002; 19(3): 439-46.

Grutz, G., New Insights into the molecular mechanism of interleukin-10 mediated immunosuppression. J. Leukocyte Biol. 2005, 77: 3-15.

Gutbeir et al., RNAi-mediated suppression of constitutive pulmonary gene expression by small interfering RNA in mice, Pulm. Pharmacol Ther. 2010, 23:334-44.

Guzy et al., Fibroblast growth factor 2 is required for epithelial recovery, but not for pulmonary fibrosis, in response to bleomycin. Am. J. Respir. Cell Mol. Biol. 52, 116-128 {2015).

Hegab et al., Isolation and Characterization of Murine Multipotent Lung Stem Cells. Stem Cells Dev. 2010; 19: 523-36.

Heise et al., Mechanical Stretch Induces Epithelial-Mesenchymal Transition in Alveolar Epithelia via Hyaluronan Activation of Innate Immunity, J Biol Chem. May 20, 2011; 286(20): 17435-44.

Hinz, B., Tissue stiffness, latent TGF-betal activation, and mechanical signal transduction: implications for the pathogenesis and treatment offibrosis, Curr Rheumatol Rep, Apr. 2009; 11(2): 120-6.

Hinz et al., Alpha-Smooth Muscle Actin Expression Upregulates Fibroblast Contractile Activity, Mal Biol Cell. Sep. 2001; 12(9): 2730-41.

Hirano, T. et al., Roles of STAT3 in mediating the cell growth, differentiation and survival signals relayed through the L-6 family of cytokine receptors, Oncogene, 2000, vol. 19: 2548-56.

Hodgson et al., ELMOD2 Is a Candidate Gene for Familial Idiopathic Pulmonary Fibrosis. Am J Hum Genet. 006 Jul. 79(1): 149-54.

Hofer et al., Infection of mice with influenza A/WSN/33 (H1 N1) virus alters alveolar type II cell phenotype. Am. U. Physiol. Lung Cell. Mol. Physiol. 308, L628-L638 (2015).

Hogan et al., Repair and regeneration of the respiratory system: complexity, plasticity and mechanisms of lung Mem cell function. Cell Stem Cell 15, 123-138 (2014).

Holgate, ST., Cytokine and anti-cytokine therapy for the treatment of asthma and allergic disease, Cytokine, 2004, vol. 28: 152-57.

Hoyles et al., An Essential Role for Resident Fibroblasts in Experimental Lung Fibrosis Is Defined by Lineage-Specific Deletion of High-Affinity Type II Transforming Growth Factor b Receptor. Am J Respir Grit Care Med. Jan. 15, 2011; 183(2): 249-6.

Humbles et al., A Critical Role for Eosinophils in Allergic Airways Remodeling. Science. Sep. 17, 2004; 305(5691): 1776-9.

Humphreys et al., Fate tracing reveals the pericyte and not epithelial origin of myofibroblasts in kidney fibrosis. Am J Pathol. 2010;176(1):85-97.

Hutyrova et al., lnterleukin-1 Gene Cluster Polymorphisms in Sarcoidosis and Idiopathic Pulmonary Fibrosis. Am J Respir Grit Care Med. Jan. 15, 2002; 165(2): 148-51.

Iwaisako et al., Origin of myofibroblasts in the fibrotic liver in mice. Proc Natl Acad Sci USA. Aug. 12, 2014; 111 32): E3297-305.

Iwano et al., Evidence that fibroblasts derive from epithelium during tissue fibrosis. J Clin Invest. 2002; 110 3):341-350.

Jakubzick et al. Impact of lnterleukin-13 Responsiveness on the Synthetic and Proliferative Properties of Th1-2nd Th2-Type Pulmonary Granuloma Fibroblasts. Am J Pathol., 2003, 162(5): 1475-86.

Jana et al., RNA Interference Potential Therapeutic Targets, Appl. Microbial. Biotechnol., 2004, vol. 65:649-657.

Jeannotte et al., Unsuspected effects of a lung-specific Cre deleter mouse line, Genesis 49, 152-159 (2011).

Jensen et al., Essentials of Recombinase-Based Genetic Fate Mapping in Mice, Methods Mol Biol. 2014; 1092: J37-54.

Jensen et al., Spray drying of siRNA-containing PLGA nanoparticles intended for inhalation, J. Control Release 142:138-45 (2010).

Jiang et al., Regulation of pulmonary fibrosis by chemokine receptor CXCR3. J. Clin. Invest 114, 291-299 (2004).

Jiang et al., The role of Toll-like receptors in noninfectious lung injury. Cell Res. 16, 693-701 (2006).

(56) References Cited

OTHER PUBLICATIONS

Jiang et al., Hyaluronan in tissue injury and repair. Annu. Rev. Cell Dev. Biol. 23, 435-461 (2007).
Jiang et al., Inhibition of pulmonary fibrosis in mice by CXCL 10 requires glycosaminoglycan binding and syndecan 4, J. Clin. Invest 120, 2049-2057 (2010).
Jiang et al., Hyaluronan as an Immune Regulator in Human Diseases. Physiol Rev. Jan. 2011; 91(1): 221-64.
Jiang et al., Gene expression profile of quiescent and activated rat hepatic stellate cells implicates Wnt signaling oathway inactivation. J Hepatol. Sep. 2006; 45(3): 401-9.
Jozefczuk et al., Preparation of mouse embryonic fibroblast cells suitable for culturing human embryonic and nduced pluripotent stem cells, J Vis Exp, 2012;(64):3854.
Kalai et al., Analysis of the Human Interleukin-6/Human Interleukin-6 Receptor Binding Interface at the Amino Acid Level: Proposed Mechanism of Interaction, Blood, 1997, 89:1319-33.
Kalluri et al., Epithelial-mesenchymal transition and its implications for fibrosis. J Clin Invest. Dec. 2003; 112(12): H76-84.
Kamari et al., Lack of lnterleukin-1alpha or lnterleukin-1beta Inhibits Transformation of Steatosis to Steatohepatitis and Liver Fibrosis in Hypercholesterolemic Mice. J Hepatol. Nov. 2011; 55(5): 1086-94.
Kanasty et al., Delivery materials for siRNA therapeutics, 2013, Nat. Mater. 12:967-77.
Kawai et al., Unresponsiveness of MyDBB-deficient mice to endotoxin. Immunity 11, 115-122 (1999).
Keane et al., The importance of balanced pro-inflammatory and antiinflammatory mechanisms in diffuse lung Disease. Am J Physiol Lung Cell Mol Physiol. Jul. 2001; 281(1): L92-7.
Kim, V.N. MicroRNA biogenesis: coordinated cropping and dicing. Nature Reviews, Molecular Cell Biology 6(5):376-385 (2005).
Kolb et al., Transient expression of IL-1? induces acute lung injury and chronic repair leading to pulmonary fibrosis. J Clin Invest. Jun. 2001; 107(12): 1529-36.
Komiya et al., Wnt signal transduction pathways. Organogenesis. Apr.-Jun. 2008; 4(2): 68-75.
Korthagen et al., Serum and BALF YKL-40 levels are predictors of survival in idiopathic pulmonary fibrosis. Respir Med.Jan. 2011; 105(1): 106-13.
Kotton et al., Lung regeneration: mechanisms, applications and emerging stem cell Dopulations. Nat. Med. 20, 822-832 (2014).
Kretzschmar et al., Lineage Tracing. Cell. Jan. 20, 2012; 148(1-2): 33-45.
Kuan et al., Glycoprotein Nonmetastatic Melanoma Protein B, a Potential Molecular Therapeutic Target in Patients with Glioblastoma Multiforme. Clin. Cancer Res 12:(7) 1970-82 (2006).
Kumar et al., Defining a mesenchymal progenitor niche at single cell resolution. Science. Nov. 14, 2014; 346(6211): 1258810.
Laan et al., Neutrophil Recruitment by Human IL-17 via C-X-C Chemokine Release in the Airways. J lmmunol. Feb. 15, 1999; 162(4): 2347-52.
Lagares et al., Inhibition of Focal Adhesion Kinase Prevents Experimental Lung Fibrosis and Myofibroblast Formation. Arthritis Rheum, May 2012, vol. 64, No. 5. 1653-1664.
Lagana et al., Synthetic RNAs for Gene Regulation: Design Principles and Computational Tools, 2014, Front. Bioeng. Biotechnol. 2:65.
Lai et al., Comparison between the Repression Potency of siRNA Targeting the Coding Region and the 3'-Untranslated Region of mRNA, Biomed Res Int. 2013, vol. 2013:637850, pp. 1-5.
Larrucea et al., Expression of podocalyxin enhances the adherence, migration, and intercellular communication Pf cells. Exptl Cell Res. 314: 2004-15 (2008).
Larsson et al., Fibrotic Myofibroblasts Manifest Genome-Wide Derangements of Translational Control. PLoSOne. Sep. 16, 2008; 3(9): e3220.
Lawrence, T., The Nuclear Factor NF-kB pathway in inflammation, Cold Spring Harbor Perspectives in Biol. (2009) 1 (6): a001651.

Lawson et al., Genetic mutations in surfactant protein C are a rare cause of sporadic cases of IPF. Thorax. Nov. 2004; 59(11): 977-80.
Le et al., Blockade of IL-6 Trans-Signaling Attenuates Pulmonary Fibrosis, J. Immunol., 2014, vol. 193, pp. 3755-3768.
Lee et al., Lung stem cell differentiation in mice directed by endothelial cells via a BMP4-NFATc1 hrombospondin-1 axis. Cell 156, 440-455 (2014).
Lesley et al., CD44 and Its Interaction with Extracellular Matrix. Adv lmmunol. 1993; 54: 271-335.
Levick, et al., Cardiac Mast Cells Mediate Left Ventricular Fibrosis in the Hypertensive Rat Heart. Hypertension. Jun. 2009; 53(6): 1041-1047.
Levy et al., What does Stat3 do?, J. Clin. Invest. 2002, vol. 109(9): 1143-48.
Lewis et al., Efficient delivery of siRNA for inhibition of gene expression in postnatal mice, Nature Genetics, 2002, vol. 32:107-108.
Li et al. Severe lung fibrosis requires an invasive fibroblast phenotype regulated by hyaluronan and CD44. J Exp Med. Jul. 4, 2011; 208(7): 1459-1471.
Li et al., Transforming growth factor-beta1 induces EMT by the transactivation of epidermal grow1h factor signaling through HA/CD44 in lung and breast cancer cells, Int J Mol Med, 2015, vol. 36(1), pp. 113-122.
Liang et al., NF-kappaB and its regulation on the immune system, Cell. Mol. lmmunol. 2004, vol. 1(5): 343-50.
Liang et al., Role of hyaluronan and hyaluronan-binding proteins in human asthma. J. Allergy Clin. lmmunol., 2011, vol. 128, J03-411. e3.
Liang et al., A macrophage subpopulation recruited by CC chemokine ligand 2 clears apoptotic cells in non-nfectious lung injury. Am. J. Physiol. Lung Cell. Mol. Physiol. 302, L933-L940 (2012).
Liang et al., MK2 Inhibition Attenuates Fibroblast Invasion and Severe Lung Fibrosis, Am J. Respir. Grit Care Med, 2015, vol. 191, A5333, Abstract only.
Liang et al., Hyaluronan and TLR4 promote surfactant-protein-C-positive alveolar progenitor cell renewal and prevent severe pulmonary fibrosis in mice. Nat Med. 22 (11) :1285. Nov. 2016.
Liang et al., Hyaluronan and TLR4 Regulate Alveolar Stem Cell Renewal and Prevent Severe Pulmonary Fibrosis Gene Accession No. GSE68704 retrieved from https://www.ncbi.nlm.nih.gov/geo/query/acc.cgi?acc=GSE68704 on Apr. 17, 2019.
Liu et al., miR-21 mediates fibrogenic activation of pulmonary fibroblasts and lung fibrosis. J Exp Med. Aug. 2, 2010 207(8): 1589-97.
Liu et al., Sonic hedgehog signaling directly targets Hyaluronic Acid Synthase 2, an essential regulator of ohalangeal joint patterning, Dev Biol. Mar. 15, 2013; 375(2): 160-71.
Liu et al., Association of ENA-78, IP-10 and VEGF gene polymorphism with idiopathic pulmonary fibrosis. Zhonghuc vi xue za zhi. Oct. 20, 2009; 89(38): 2690-4 (Abstract).
Liu et al., Activation of type II cells into regenerative stem-cell-antigen-1+ cells during alveolar repair. Am. J. Respir. Cell Mol. Biol. 53, 113-124 (2015).
Livet et al., Transgenic strategies for combinatorial expression of fluorescent proteins in the nervous system. Nature, Nov. 1, 2007; 450: 56-62.
Loberg et al., Enhanced Glycogen Synthase Kinase-3beta Activity Mediates Hypoxia-induced Apoptosis of Vascular Smooth Muscle Cells and Is Prevented by Glucose Transport and Metabolism. J. Biol. Chem. 277 (44): 41667-673 (2002).
Lovgren et al., Beta-arrestin deficiency protects against pulmonary fibrosis in mice and prevents fibroblast invasion of extracellular matrix, Sci Transl Med, 2011, vol. 3. pp. 1-22.
Lown et al., The mechanism of the bleomycin-induced cleavage of DNA1. Biochem Biophys Res Commun. 2977 Aug. 22; 77(4): 1150-7.
Ma et al., Indian hedgehog mutations causing brachydactyly type A1 impair Hedgehog signal transduction at multiple levels, Cell Res. 21: 1343-57 (2011).
Madisen et al., A robust and high-throughput Cre reporting and characterization system for the whole mouse brain Nat Neurosci. Jan. 2010; 13(1): 133-40.

(56) References Cited

OTHER PUBLICATIONS

Mailleux et al., Fgf10 expression identifies parabronchial smooth muscle cell progenitors and is required for heir entry into the smooth muscle cell lineage, Development. May 2005; 132(9): 2157-66.
Martinelli et al., A role for epidermal growth factor receptor in idiopathic pulmonary fibrosis onset. Mol Biol Rep. Oct. 2011; 38(7): 4613-7.
Martinez, E. Multi-protein complexes in eukaryotic gene transcription. Plant Mol. Biol. 50: 925-47 (2002).
Martinez et al., The M1 and M2 paradigm of macrophage activation: time for reassessment. F1000Prime Rep 2014; 6:13.
Matsumoto et al., Conditional inactivation of Has2 reveals a crucial role for hyaluronan in skeletal growth, patterning, chondrocyte maturation and joint formation in the developing limb. Development 136, 2825-2835 (2009).
McGowan et al., Fibroblast growth factor signaling in myofibroblasts differs from lipofibroblasts during alveolar septation in mice, Am J Physiol Lung Cell Mol Physiol, 2015, vol. 309(5), pp. L463-L474.
Meltzer et al., Bayesian probit regression model for the diagnosis of pulmonary fibrosis: proof-of-principle. BMC Med Genomics. Oct. 5, 2011; 4:70.
Merkel et al., Nonviral siRNA Delivery to the Lung: Investigation of PEG-PEI Polyplexes and Their In Vivo Performance, Mol. Pharm, 6:1246-60 (2009).
Mikecz et al., Anti-CD44 treatment abrogates tissue oedema and leukocyte infiltration in murine arthritis, Nat Med. Jun. 1995; 1(6): 558-63.
Minshall et al., Eosinophil-associated TGF-beta1 mRNA expression and airways fibrosis in bronchial asthma, Am J Respir Cell Mal boil. Sep. 1997; 17(3): 326-33.
Moeller et al., Circulating Fibrocytes Are an Indicator of Poor Prognosis in Idiopathic Pulmonary Fibrosis. Am J R.espir Crit Care Med. Apr. 1, 2009; 179(7): 588-94.
Monroe et al., Platelets and Thrombin Generation. Arterioscler Thromb Vase Biol. 2002; 22:1381-1389.
Moore et al., CCR2-mediated recruitment of fibrocytes to the alveolar space after fibrotic injury. Am J Pathol. 2005; 166(3):675-684.
Mummert et al., Development of a peptide inhibitor of hyaluronan-mediated leukocyte trafficking. J. Exp. Med., 2000, 192, pp. 769-779.
Murphy et al., Janeway's Immunology, 9th Ed. 2017, Garland Science, New York, Chapter 3, pp. 109-110.
Mushiroda et al., A genome-wide association study identifies an association of a common variant in TERT with susceptibility to idiopathic pulmonary fibrosis. J Med Genet. Oct. 2008; 45(10): 654-6.
Myers et al., Optimal alignments in linear space. Computer Applic. Biol. Sci., 4:11-17 (1988).
Naiche et al., Identity and Fate of Tbx4-Expressing Cells Reveal Developmental Cell Fate Decisions in the Allantois, Limb, and External Genitalia. Dev Dyn, Oct. 2011; 240(10): 2290-300.
Naito et al., siRNA Design Software for a Target Gene-Specific RNA Interference, 2012, Front. Genet. 3:102.
Neal et al., Toll-like receptor 4 is expressed on intestinal stem cells and regulates their proliferation and apoptosis via the p53-upregulated modulator of apoptosis. J. Biol. Chem. 2012. 287, pp. 37296-37308.
Nelson, AL, Antibody fragments, Mabs 2010, 2(1): 77-83.
Ni et al., PD-1/PD-L 1 Pathway Mediates the Alleviation of Pulmonary Fibrosis by Human Mesenchymal Stem Cells in 3 Humanized Mice. American Journal of Respiratory Cell and Molecular Biology, 2018, vol. 58 (6):684-695.
Noble et al., Hyaluronate Activation of CD44 Induces Insulin-like Growth Factor-1 Expression by a Tumor Necrosis Factor-alpha-dependent Mechanism in Murine Macrophages, J Clin Invest. Jun. 1993; 91 (6): 2368-77.
Noble et al., Matrix regulation of lung injury, inflammation and repair: the role of innate immunity. Proc. Am. Thorac. 2006, Soc. 3, pp. 401-404.

O'Donoghue et al., Genetic partitioning of interleukin-6 signaling in mice dissociates Stat3 from Smad3-mediated lung fibrosis. EMBO Mol. Med., 2012, vol. 4, pp. 939-951.
Ogawa et al., Suppression of type I collagen production by microRNA-29b in cultured human stellate cells. Biochem Biophys Res Commun. Jan. 1, 2010; 391(1): 316-21.
Oh et al., Epithelial transglutaminase 2 is needed for T cell interleukin-17 production and subsequent pulmonary nflammation and fibrosis in bleomycin-treated mice. J. Exp. Med., 2011, vol. 208, pp. 1707-1719.
Ozerdem et al., NG2 Proteoglycan is Expressed Exclusively by Mural Cells During Vascular Morphogenesis. Dev Dyn, Oct. 2001; 222(2): 218-27.
Paddison et al., Stable suppression of gene expression by RNAi in mammalian cells. PNAS 2002, vol. 99(3):1443-1448.
Pandit et al., Inhibition and role of let-7d in idiopathic pulmonary fibrosis, 2010, Am. J. Respir. Crit. Care Med. 182:220-29.
Papaioannou, The T-box gene family: emerging roles in development, stem cells and cancer, Development, 2014, vol. 141, 3819-3833.
Pardo et al., Up-Regulation and Profibrotic Role of Osteopontin in Human Idiopathic Pulmonary Fibrosis. PLoS Med. Sep. 2005; 2(9): e251.
Paul et al., Effective expression of small interfering RNA in human cells. Nature Biotechnology 2002. vol. 20(5):505-508.
Perl et al., Silencing of Fas, but not caspase-8, in lung epithelial cells ameliorates pulmonary apoptosis, inflammation, and neutrophil influx after hemorrhagic shock and sepsis, Am. J. Pathol. 167:1545-59 (2005).
Peterson et al., Prognostic Role of Eosinophils in Pulmonary Fibrosis. Chest. Jul. 1987; 92(1): 51-6.
Piguet et al., Requirement of tumour necrosis factor for development of silica induced pulmonary fibrosis. Nature, Mar. 15, 1990; 344(6263): 245-7.
Pivarcsi et al., Expression and function of Toll-like receptors 2 and 4 in human keratinocytes. Int. lmmunol. 2003, vol. 15, pp. 1721-1730.
Pontoglio et al., Hepatocyte Nuclear Factor 1 Inactivation Results in Hepatic Dysfunction, Phenylketonuria, and Renal Fanconi Syndrome. Cell 84: 575-85 (1996).
Rafii et al., Platelet-derived SDF-1 primes the pulmonary capillary vascular niche to drive lung alveolar regeneration Nat. Cell Biol. 2015, vol. 17, pp. 123-136.
Rakoff-Nahoum et al., Recognition of commensal microflora by toll-like receptors is required for intestinal homeostasis, Cell, 2004, vol. 118, 229-241.
Rakoff-Nahoum et al., Role of toll-like receptors in spontaneous commensal-dependent colitis. Immunity, 2006, vol. 25, pp. 319-329.
Rehan et al., PPAR? Signaling Mediates the Evolution, Development, Homeostasis, and Repair of the Lung. DPAR Res. vol. 2012; Article ID 289867, 8 pages 2012.
Reiman et al., lnterleukin-5 (IL-5) Augments the Progression of Liver Fibrosis by Regulating IL-13 Activity. nfect lmmun. Mar. 2006; 74(3): 1471-9.
Richards et al., Peripheral Blood Proteins Predict Mortality in Idiopathic Pulmonary Fibrosis. Am J Respir Grit Care Med.Jan. 1, 2012; 185(1): 67-76.
Rinkevich et al., Identification and isolation of a dermal lineage with intrinsic fibrogenic potential. Science, 2016, vol. 348(6232): aaa2151.
Roberts et al., A novel model for human interstitial lung disease: Hapten-driven lung fibrosis in rodents, J Pathol. Jul. 1995; 176(3): 309-18.
Rodriguez-Esteban et al., The T-box genes Tbx4 and Tbx5 regulate limb outgrowth and identity, Nature. 1999; vol. 398(6730):814-818.
Rosas et al., MMP1 and MMP7 as Potential Peripheral Blood Biomarkers in Idiopathic Pulmonary Fibrosis. PLoS Med. Apr. 29, 2008; 5(4): e93.
Rosas-Taraco et al., Intrapulmonary Delivery of XCL 1-Targeting Small Interfering RNA in Mice Chronically Infected with *Mycobacterium tuberculosis*, Am. J. Respir. Cell Mal. Biol., 41:136-45 (2009).

(56) References Cited

OTHER PUBLICATIONS

Ross et al., miRNA the New Gene Silencer, Am J Clin Pathol. 2007; 128(5): 830-36.
Sakiyama et al., Tbx4-Fgfl0 system controls lung bud formation during chicken embryonic development. Development. 2003; 130(7): 1225-1234.
Sanders et al., Molecular Characterization of *Saccharomyces cerevisiae* TFIID. Mol Cell Biol. 22: 6000-6013 (2002).
Sanders et al., Identification of Two Novel TAF Subunits of the Yeast *Saccharomyces cerevisiae* TFIID Complex, J. Biol. Chem. 275: 13895-900 (2000).
Sauer et al., Site-specific DNA recombination in mammalian cells by the Cre recombinase of pacteriophage P1, PNAS 1988; 85: 5166-70.
Scholzen et al., The Ki-67 protein: From the known and the unknown, J. Cell Physiol (2000) 182(3): B11-22.
Seibold et al., A Common MUC5B Promoter Polymorphism and Pulmonary Fibrosis. N Engl J Med. 2011; 364(16): 1503-12.
Selman et al., Idiopathic pulmonary fibrosis: an epithelial/fibroblastic cross-talk disorder. Respir Res. 2002; 3: 3.
Selman et al., Idiopathic pulmonary fibrosis: pathogenesis and therapeutic approaches. Drugs 64, 405-430 (2004).
Selman et al., Idiopathic pulmonary fibrosis: aberrant recapitulation of developmental programs?. PLoS Med. 2008;5(3):e62.
Senftleben et al., Activation by IKKalpha of a second, evolutionary conserved, NF?B signaling oathway, (2001) Science 293: 1495-99.
Shao et al., Pivotal Advance: Th-1 cytokines inhibit, and Th-2 cytokines promote fibrocyte differentiation. J reukoc Biol. Jun. 2008; 83(6): 1323-33.
Siegelman et al., Activation and interaction of CD44 and hyaluronan in immunological systems. J Leukoc Biol. rn99 Aug. 66(2): 315-21.
Silva et al., Second-generation shRNA libraries covering the mouse and human genomes. Nature Genetics, 2005, 37(11):1281-1288.
Simpson et al., Interleukin-6: structure-function relationships, Protein Sci. 1997, vol. 6:929-55.
Sizemore et al., Podocalyxin Increases the Aggressive Phenotype of Breast and Prostate Cancer Cells In vitro hrough Its Interaction with Ezrin Cancer Res. 67: 6183-91 (2007).
Smith et al., Comparison of Biosequences. Adv. Appl. Math. 2:482-489(1981).
Smith et al., Usual interstitial pneumonia-pattern fibrosis in surgical lung biopsies. Clinical, radiological and riistopathological clues to aetiology, J Clin Pathol. Oct. 2013; 66(1): 896-903.
Sternberg et al., Bacteriophage P1 site-specific recombination: I. Recombination between loxP sites J Mal Biol. 1981; 150: 467-86.
Sun et al., The T-box transcription factor Brachyury promotes renal interstitial fibrosis by repressing E-cadherin expression, Cell Communication and Signaling, 2014, vol. 12(1).
Sun et al., Oligonucleotide Aptamers: New Tools for Targeted Cancer Therapy. Malec. Therapy—Nucleic Acids eo14, 3: e182; doi: 10.1O38/mbna.2O14.32.
Suzuki et al., CD24 Induces Apoptosis in Human B Cells via the Glycolipid-Enriched Membrane Domains/Rafts—Mediated Signaling System, J. Immunol. (2001) 166: 5567-77.
Tadokoro et al., IL-6-STAT3 promotes regeneration of airway ciliated cells from basal stem cells. Proc. Nall. Aad. Sci. USA 111, E3641-E3649 (2014).
Tager et al., Inhibition of Pulmonary Fibrosis by the Chemokine IP-10/CXCL 10. Am J Respir Cell Mol Biol. Oct. 2004; 31(4): 395-404.
Takeda et al., Targeted disruption of the mouse Stat3 gene3 leads to early embryonic lethality, (1997) Proc. Nall Acad. Sci. USA 94: 3801-3804.
Takeuchi et al., Differential roles of TLR2 and TLR4 in recognition of Gram-negative and Gram-positive bacterial cell wall components. Immunity 11, 443-451 (1999).
Takeuchi et al., Tbx5 and Tbx4 genes determine the wing/leg identity of limb buds. Nature. Apr. 29, 1999; 398(6730): 810-4.
Takeuchi et al. Tbx5 and Tbx4 trigger limb initiation through activation of the Wnt/Fgf signaling cascade. Development. 2003;130(12):2729-2739.
Tebbutt et al., Reciprocal regulation of gastrointestinal homeostasis by SHP2 and STAT-mediated trefoil gene Activation in gp130-mutant mice. Nat. Med. 8, 1089-1097 (2002).
Teder et al., Resolution of Lung Inflammation by CD44, Science, Apr. 5, 2002; 296: 155-8.
Tesari et al., Transcriptional Activation of the Cyclin A Gene by the Architectural Transcription Factor HMGA2. Mal. Cell Biol. 23:(24) 9104-9116 (2003).
Thannickal et al., Myofibroblast Differentiation by Transforming Growth Factor-beta 1 Is Dependent on Cell Mhesion and lntegrin Signaling via Focal Adhesion Kinase, J Biol Gehm Apr. 4, 2003; 278(14): 12384-12389.
Thomas, et al., Heterozygosity for a Surfactant Protein C Gene Mutation Associated with Usual Interstitial Aneumonitis and Cellular Nonspecific Interstitial Pneumonitis in One Kindred, Am J. Respir Grit Care Med. May 1, 2002; 165(9): 1322-8.
Treutlein et al., Reconstructing lineage hierarchies of the distal lung epithelium using single-cell RNA-seq. Nature 509, 371-375 (2014).
Tsakiri et al., Adult-onset pulmonary fibrosis caused by mutations in telomerase. Proc Natl Acad Sci USA. 200/ May 1; 104(18): 7552-7.
Ulloa et al., Inhibition of transforming growth factor-b/SMAD signaling by the interferon-g/STA T pathway. Nature rn99 Feb. 25; 397(6721): 710-3.
Vaccaro et al., Alveolar Wall Basement Membranes in Bleomycin-induced Pulmonary Fibrosis. Am Rev Respir bis. Oct. 1985; 132(4): 905-12.
Valenta et al., The many faces and functions of b-catenin. EMBO J. Jun. 13, 2012; 31(12): 2714-36.
Van Deventer et al., Circulating fibrocytes prepare the lung for cancer metastasis by recruiting Ly-6C+ monocytes via CCL2. J lmmunol. 2013;190(9):4861-4867.
Vaughan et al., Lineage-negative progenitors mobilize to regenerate lung epithelium after major injury. Nature 517, 621-625 (2015).
Voehringer et al., Homeostasis and Effector Function of Lymphopenia-lnduced "Memory-Like" T Cells in Constitutively T Cell-Depleted Mice, J lmmunol. Apr. 1, 2008; 180(7): 47 42-53.
Wang et al., Genetic Defects in Surfactant Protein A2 Are Associated with Pulmonary Fibrosis and Lung Cancer. Am J Hum Genet. Jan. 2009; 84{ 1 ): 52-9.
Wang et al., Attenuation offibrosis in vitro and in vivo with SPARC siRNA, Arthritis Res. Ther. 12:R60 (2010).
Wendling et al., Efficient temporally-controlled targeted mutagenesis in smooth muscle cells of the adult mouse. Genesis, Jan. 2009; 47(1): 14-8.
Weterman et al., nmb, a novel gene, is expressed in low-metastatic human melanoma cell lines and Kenografts, Intl. J. Cancer 60: 73-81 (1995).
Wiegand et al., Global Quantitative Phosphoproteome Analysis of Human Tumor Xenografts Treated with a CD44 Antagonist. Cancer Res. Sep. 2012; 72(17): 4329-39.
Williams et al., Cytokine inhibitors in rheumatoid arthritis and other autoimmune diseases, Curr. Opin. Dharmacol., 2017, vol. 7: 412-17.
Willis et al., Induction of epithelial-mesenchymal transition in alveolar epithelial cells by transforming growth actor-p1: potential role in idiopathic pulmonary fibrosis. Am J Pathol. 2005;166(5):1321-1332.
Wooten et al., Statistics of Local Complexity in Amino Acid Sequences and Sequence Databases. Comput. Chem., 17:149-163 {1993).
Wynn et al., An IL-12-based vaccination method for preventing fibrosis induced by schistosome infection. Nature, Aug. 17, 1995; 376(6541 ): 594-6.
Wynn et al., Macrophages: Master Regulators of Inflammation and Fibrosis. Semin Liver Dis. Aug. 2010; 30(3): N5-57.
Xie et al., Mesenchymal Transcription Factor Tbx4 Regulates Pulmonary Fibrosis, American Thoracic Society International Conference, Meeting Absuact, 2015, [http://www.atsjournals.org/doi/abs/10.1164/ajrccm-conference.2015.191.1.MeetingAbstracts.A2343] Entire Abstract.

(56) References Cited

OTHER PUBLICATIONS

Xie et al., Transcription Factor TBX4 Regulates Myofibroblast Accumulation and Lung Fibrosis, The Journal of Clinical Investigation, 2016; vol. 126(8), pp. 3063-3079.

Xie et al., MicroRNA-29c Prevents Pulmonary Fibrosis by Regulating Epithelial Cell Renewal and Apoptosis, Am. J. Respir. Cell. Mol. Biol., 2017, 57:721-732.

Yokoyama et al., Prognostic value of circulating KL-6 in idiopathic pulmonary fibrosis. Respirology. Mar. 2006; 11 2): 164-8.

Zeisberg et al., BMP-7 counteracts TGF-beta1-induced epithelial-to-mesenchymal transition and reverses chronic Renal injury Nat Med. 2003;9(7):964-968.

Zhang et al., A Variant in the Promoter of MUC5B and Idiopathic Pulmonary Fibrosis. N Engl J Med. Apr. 21, 2011; 364(16): 1576-7.

Zhang et al., Spatial-Temporal Targeting of Lung-Specific Mesenchyme by A Tbx4enhancer, BMC Biology, 2013, vol. 11(1), pp. 1-13.

Zhang et al., Interleukin 6 mediates the therapeutic effects of adipose-derived stromal-stem cells in ipopolysaccharide-induced acute lung injury, Stem Cells 32, 1616-1628 (2014).

Zheng et al., Ligand-Dependent Genetic Recombination in Fibroblasts a Potentially Powerful Technique for nvestigating Gene Function in Fibrosis Am J Pathol., May 2002; 160(5): 1609-17.

Zorzetto et al., Complement Receptor 1 Gene Polymorphisms Are Associated with Idiopathic Pulmonary Fibrosis. Am J Respir Crit Care Med. Aug. 1, 2003; 168(3): 330-4.

Zorzetto et al., Nod2/CARD15 gene polymorphisms in idiopathic pulmonary fibrosis. Sarcoidosis Vase Diffuse rung Dis. Oct. 2005; 22(3): 180-5.

Gen Bank AK147984, Mus musculus melanocyte cDNA, RIKEN full-length enriched library, clone: G270128B06 product: T-box 4, full insert sequence. GenBank Accession No. AK147984, 2010, Retrieved from the Internet: [URL: https://www.ncbi.nlm.nih.gov/nuccore/AK147984], pp. 1-4.

Gen Bank NM172798, Mus Musculus T-Box 4 (Tbx4), Transcript Variant 2, mRNA; Accession No. NM172798' Publication [online], 2015, Retrieved from the Internet: [https://www.ncbi.nlm.nih.gov/nucleotide/156938284?report=genbank&log$-nucltop&blast_rank-12&RID-G6KXU3TV01R]; pp. 1-3.

CD44 Molecule (Indian Blood Group) retrieved from www.genecards.org/cgi-bin/carddisp.pl?gene=CD44 on Sep. 7, 2018.

CTNNB1 Gene—Catenin Beta 1 retrieved from www.genecards.org/cgi-bin/carddisp.pl?gene=CTNNB1 on Aug. 20, 2018.

TBX4 Gene—T-Box Transcription Factor 4 retrieved from www.genecards.org/cgi-bin/carddisp.pl?gene=TBX4 on Apr. 18, 2019.

WNT1 Gene—Wnt Family Member 1 retrieved from www.genecards.org/cgi-bin/carddisp.pl?gene=WNT1 on Aug. 20, 2018.

\* cited by examiner

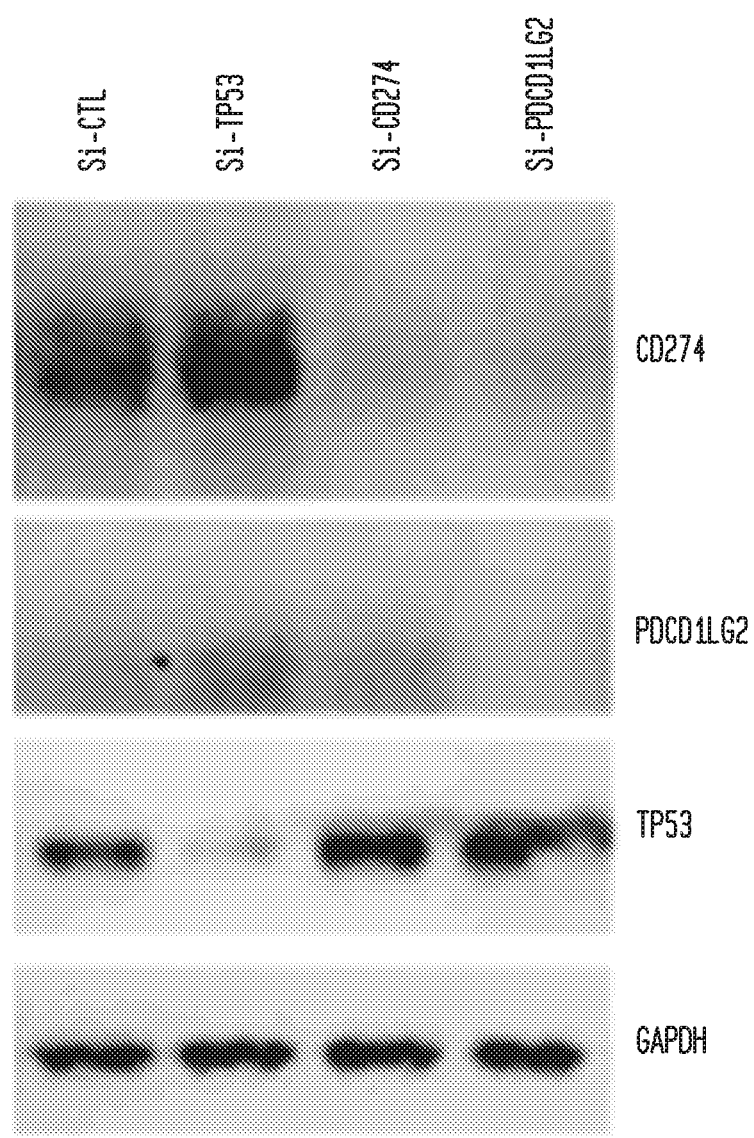

METHODS FOR TARGETING THE IMMUNE CHECKPOINT PD1 PATHWAY FOR TREATING PULMONARY FIBROSIS

CROSS REFERENCE TO RELATED APPLICATIONS

This application is a 35 U.S.C. § 371 national stage filing of International Application No. PCT/US2018/054244, filed on Oct. 3, 2018, which claims priority to U.S. Provisional Patent Application No. 62/567,513, filed on Oct. 3, 2017. The contents of each of the aforementioned applications are incorporated herein by reference in their entireties.

STATEMENT REGARDING FEDERALLY SPONSORED RESEARCH OR DEVELOPMENT

This invention was made with government support under Grant Nos. HL108793, HL060539, AI052201 and HL122068 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 19, 2018, is named 128549-00520_SeqID_ST25.txt and is 32,768 bytes in size.

BACKGROUND OF THE INVENTION

Summary

Fibrosis is the common scarring reaction associated with chronic injury that results from prolonged parenchymal cell injury and/or inflammation that may be induced by a wide variety of agents, e.g., drugs, toxins, radiation, any process disturbing tissue or cellular homeostasis, toxic injury, altered blood flow, infections (viral, bacterial, spirochetal, and parasitic), storage disorders, and disorders resulting in the accumulation of toxic metabolites. Fibrosis is most common in the heart, lung, peritoneum, and kidney.

Idiopathic pulmonary fibrosis (IPF) is a poorly understood progressive and fatal lung disease for which no treatment exists other than lung transplantation (Mason D P et al., Ann Thorac Surg 84:1121-8, 2007). Median survival of five years after diagnosis is less than 20%. Most forms of interstitial lung diseases and other forms of pulmonary fibrosis are characterized by fibrotic lesions, progressive distortion of alveolar architecture occurs and replacement with fibrotic or scar tissues with excess extracellular matrix (ECM) deposition (American Thoracic Society, Am J Respir Crit Care Med 161:646-664, 2000; Noble P W et al., Clin Chest Med 25:749-758, 2004; Selman M et al., Ann Intern Med 134:136-151, 2001). This results in progressive dyspnea and loss of lung function. A hallmark morphological lesion is spatial and temporal heterogeneity incorporating areas of normal lung being directly adjacent to areas of fully established fibrosis, microscopic honeycombing, and areas of evolving fibrosis containing actively proliferating and collagen-producing fibroblasts/myofibroblasts, the so called "fibrotic foci".

IPF is the most common chronic, progressive and fatal interstitial lung disease of unknown etiology with an estimated incidence of 40-50 cases per 100,000 individuals in the United States, and about 40,000 deaths each year in the U.S. Increased fibrotic lung fibroblasts (or myofibroblast) viability, activation, production and deposition of ECM are typical of IPF lungs (Selman M et al., Expert Opin Emerg Drugs 16:341-62, 2011; Shetty, S et al. Am J Respir Cell Mol Biol 15:78-87, 1996; Zhu S et al., Am J Physiol: Lung Cell Mol Physiol 297:L97-108, 2009; Suganuma H et al., Thorax 50:984-9, 1995; American Thoracic Society, supra; Noble P W et al., supra)

The FDA-approved therapies for IPF slow disease progression and are important first steps in treating patients suffering from IPF. Clinical trials with several approaches and targeting various pathways have been employed. Unfortunately most of these clinical trials end unsuccessfully (15). For example, neither corticosteroid (16) nor immunosuppressant treatment (17) has any beneficial effect in patients with IPF. Since there is Th1/Th2 imbalance in lung fibrosis (18), replenishment of interferon-gamma has been tested in several trials. Interferon gamma-1b did not improve survival for patients with IPF (19). Endothelin receptor antagonist Bosentan was not better than placebo for patients with IPF (20). To date, there are two drugs showing some effect. High dose acetylcysteine has shown some benefits (21). Pirfenidone has a favorable benefit risk profile, reduces disease progression, and represents an appropriate treatment option for patients with IPF (22, 23). While these FDA-approved therapies for IPF slow disease progression and are important first steps in treating patients suffering from IPF, neither pirfenidone (an orally administered drug with antifibrotic, anti-inflammatory and antioxidant effects, including abrogating TGFβ1 stimulated collagen synthesis (see Margaritopoulos, G A et al, 2016, Core Evid. 11:11-22) nor nintedanib (a tyrosine kinase inhibitor FDA-approved for the treatment of patients with IPF (see Fala, L. et al, (2015) Am. Health Drug benefits 8 (Spec. Features): 101-104) improve lung function or reduce fibrosis. Lung transplant is the only therapy to prolong life.

The described invention addresses the need for the development of effective targeted therapeutics for lung fibrosis, and in particular IPF.

Anatomy and Physiology of the Lungs

The lungs comprise a pair of organs occupying the pulmonary cavities of the thorax, and are the organs of respiration in which aeration of the blood takes place.

Normal human lungs weigh about 1 kg, of which 40% to 50% is blood. The lungs contain about 2.5 L of air at end expiration and 6 L of air at full inflation. In human lungs, the right lung is slightly larger than the left, because ⅔ of the heart is located on the left side of the body. The right lung is divided into three lobes (superior lobe, middle lobe, and inferior, or basal lobe), while the left lung is divided into two lobes (superior lobe and inferior, or basal lobe), and contains the cardiac notch, an indentation in the lung that surrounds the apex of the heart.

Each lung is surrounded by the pleura, which are double-layered serous membranes. The parietal pleura forms the outer layer of the membrane and is attached to the wall of the thoracic cavity; the visceral pleura forms the inner layer of the membrane covering the outer surface of the lungs. Between the parietal and visceral pleura is the pleural cavity, which creates a hollow space into which the lungs expand during inhalation. Serous fluid secreted by the pleural membranes lubricates the inside of the pleural cavity to prevent irritation of the lungs during breathing.

The lungs occupy the majority of the space within the thoracic cavity; they extend laterally from the heart to the ribs on both sides of the chest and continue posteriorly toward the spine. Each lung is roughly cone-shaped with the superior end of the lung forming the point of the cone and the inferior end forming the base. The superior end of the lungs narrows to a rounded tip known as the apex. The inferior end of the lungs, known as the base, rests on the dome-shaped diaphragm. The base of the lungs is concave, following the contours of the diaphragm.

Air enters the body through the nose or mouth and passes through the pharynx, larynx, and trachea. Prior to reaching the lungs, the trachea splits into the left and right bronchi, which are large, hollow tubes made of hyaline cartilage and lined with ciliated pseudostratified epithelium. The hyaline cartilage of the bronchi adds rigidity and prevents the bronchi from collapsing and blocking airflow to the lungs. The pseudostratified epithelium lines the inside of the hyaline cartilage. Each lung receives air from a single, large primary bronchus.

As the primary bronchi enter the lungs, they branch off into smaller secondary bronchi that carry air to each lobe of the lung. The secondary bronchi further branch into many smaller tertiary bronchi within each lobe. The secondary and tertiary bronchi improve the efficiency of the lungs by distributing air evenly within each lobe.

The pseudo stratified epithelium that lines the bronchi contains many cilia and goblet cells. The goblet cells secrete mucus. The cilia move together to push mucus secreted by the goblet cells away from the lungs.

Particles of dust and even pathogens like viruses, bacteria, and fungi in the air entering the lungs stick to the mucus and are carried out of the respiratory tract, helping to keep the lungs clean and free of disease.

Many small bronchioles branch off from the tertiary bronchi. Bronchioles differ from bronchi both in size and in the composition of their walls. While bronchi have hyaline cartilage rings in their walls, bronchioles are comprised of elastin fibers and smooth muscle tissue. The tissue of the bronchiole walls allows the diameter of bronchioles to change to a significant degree. When the body requires greater volumes of air entering the lungs, such as during periods of physical activity, the bronchioles dilate to permit increased airflow.

In response to dust or other environmental pollutants, the bronchioles can constrict to prevent pollution of the lungs.

The bronchioles further branch off into many tiny terminal bronchioles. Terminal bronchioles are the smallest air tubes in the lungs and terminate at the alveoli of the lungs. Like bronchioles, the terminal bronchioles are elastic, capable of dilating or contracting to control airflow into the alveoli.

The alveoli, the functional units of the lungs, permit gas exchange between the air in the lungs and the blood in the capillaries of the lungs. Alveoli are found in small clusters called alveolar sacs at the end of the terminal bronchiole. Each alveolus is a hollow, cup-shaped cavity surrounded by many fine capillaries. The alveolar epithelium covers >99% of the internal surface area of the lungs (Wang et al. Proc Natl Acad Sci USA. 2007 Mar. 13; 104(1 1): 4449-54).

Adult lungs are very complicated organs containing at least 40-60 different cell types including fibroblasts (McQualter & Bertoncello. Stem Cells. 2012 May; 30(5): 81 1-6).

The walls of each alveolus are lined with simple squamous epithelial cells known as alveolar cells, ciliated cells, secretory cells, mainly nonciliated bronchiolar secretory cells which express Secretoglobin 1 A member 1 (Scgb1 a1+club cells) (Kidiyoor et al., Gene and Cell Therapy: Therapeutic Mechanisms and Strategies 761 (Nancy Smyth Templeton ed., 4th ed. 2015)), and mesenchymal cell types including resident fibroblasts, myofibroblasts, and perivascular cells that wrap around capillaries (pericytes) (Barkauskas & Noble. Am J Physiol Cell Physiol. 2014 Jun. 1; 306(1 1): C987-96). The term "club cells" as used herein refers to dome-shaped cells with short microvilli, found in the bronchioles of the lungs that are the epithelial progenitor cells of the small airways. Club cells were formerly known as "Clara cells." A thin layer of connective tissue underlies and supports the alveolar cells. Present within this connective tissue are fibroblasts, the least specialized cells in the connective tissue family, which are found dispersed in connective tissue throughout the body, and play a key role in the wound healing process (Alberts et al. Molecular Biology of the Cell. 4th Ed. New York: Garland Science; 2002. Fibroblasts and Their Transformations: The Connective-Tissue Cell Family, 1300-1301). Surrounding the connective tissue on the outer border of the alveolus are capillaries. A respiratory membrane is formed where the walls of a capillary touch the walls of an alveolus. At the respiratory membrane, gas exchange occurs freely between the air and blood through the extremely thin walls of the alveolus and capillary.

There are two major types of alveolar cells, type 1 alveolar epithelial cells (AEC1s), and type 2 alveolar epithelial cells (AEC2s). AEC1s are large flat cells through which the exchange of $CO_2/O_2$ takes place; they cover approximately 95% of the alveolar surface, comprise approximately 40% of the alveolar epithelium, and 8% of the peripheral lung cells; in contrast, AEC2s are small, cuboidal cells that cover approximately 5% of the alveolar surface, comprise 60% of the alveolar epithelium, and 15% of the peripheral lung cells, and are characterized by their ability to synthesize and secrete surfactant protein C (SPC) and by the distinct morphological appearance of inclusion bodies known as lamellar bodies (Wang et al. Proc Natl Acad Sci USA. 2007 Mar. 13; 104(11): 4449-54; Barkauskas & Noble. Am J Physiol Cell Physiol. 2014 Jun. 1; 306(11): C987-96): AEC2s function: 1) to synthesize, store, and secrete surfactant, which reduces surface tension, preventing collapse of the alveolus; 2) to transport ions from the alveolar fluid into the interstitium, thereby minimizing alveolar fluid and maximizing gas exchange; 3) to serve as progenitor cells for AEC 1s, particularly during reepithelialization of the alveolus after lung injury; and 4) to provide pulmonary host defense by synthesizing and secreting several complement proteins including C3 and C5 (Strunk et al. J Clin Invest. 1988; 81: 1419-1426; Rothman et al. J Immunol. 1990; 145: 592-598; Zhao et al. Int J Mol Med. 2000; 5: 415-419) as well as numerous cytokines and interleukins that modulate lymphocyte, macrophage, and neutrophil functions (Mason. Respirology. 2006 January; 1 1 Suppl: S12-5; Wang et al. Proc Natl Acad Sci USA. 2007 Mar. 13; 104(1 1): 4449-54).

Septal cells and macrophages are also found inside the alveoli. Septal cells produce alveolar fluid that coats the inner surface of the alveoli. Alveolar fluid is a surfactant that moistens the alveoli, helps maintain the elasticity of the lungs, and prevents the thin alveolar walls from collapsing. Macrophages in the alveoli keep the lungs clean and free of infection by capturing and phagocytizing pathogens and other foreign matter that enter the alveoli along with inhaled air.

The lungs receive air from the external environment through the process of negative pressure breathing, which requires a pressure differential between the air inside the alveoli and atmospheric air. Muscles surrounding the lungs, such as the diaphragm, intercostal muscles, and abdominal muscles, expand and contract to change the volume of the thoracic cavity. Muscles expand the thoracic cavity and decrease the pressure inside the alveoli to draw atmospheric air into the lungs, in a process known as inhalation or inspiration. Muscles contract the size of the thoracic cavity to increase the pressure inside of the alveoli and force air out of the lungs, in a process known as exhalation or expiration.

External respiration is the process of exchanging oxygen and carbon dioxide between the air inside the alveoli and the blood in the capillaries of the lungs. Air inside the alveoli contains a higher partial pressure of oxygen compared to that in the blood in the capillaries. Conversely, blood in the lungs' capillaries contains a higher partial pressure of carbon dioxide compared to that in the air in the alveoli. These partial pressures cause oxygen to diffuse out of the air and into the blood through the respiratory membrane. At the same time, carbon dioxide diffuses out of the blood and into the air through the respiratory membrane. The exchange of oxygen into the blood and carbon dioxide into the air allows the blood leaving the lungs to provide oxygen to the body's cells, while depositing carbon dioxide waste into the air.

The lungs are a frequent target of infection, including those caused by viruses, bacteria, or fungal organisms, and are subject to myriad diseases and conditions. Lung diseases affecting the airways include, without limitation, asthma (an inflammatory disease of the lungs characterized by reversible (in most cases) airway obstruction), bronchitis (inflammation of the mucous membrane of the bronchial tubes), chronic obstructive pulmonary disease (general term used for those diseases with permanent or temporary narrowing of small bronchi, in which forced expiratory flow is slowed, especially when no etiologic or other more specific term can be applied), cystic fibrosis (a congenital metabolic disorder in which secretions of exocrine glands are abnormal, excessively viscid mucus causes obstruction of passageways, and the sodium and chloride content of sweat are increased throughout the patient's life), and emphysema (a lung condition characterized by increase beyond the normal in the size of air spaces distal to the terminal bronchiole (those parts containing alveoli), with destructive changes in their walls and reduction in their number).

Lung diseases affecting the alveoli include, without limitation, acute respiratory distress syndrome (acute lung injury from a variety of causes, characterized by interstitial and/or alveolar edema and hemorrhage as well as perivascular pulmonary edema associated with hyaline membrane formation, proliferation of collagen fibers, and swollen epithelium with increased pinocytosis), emphysema, lung cancer (any of various types of malignant neoplasms affecting the lungs), pneumonia (inflammation of the lung parenchyma characterized by consolidation of the affected part, the alveolar air spaces being filled with exudate, inflammatory cells, and fibrin), pulmonary edema (an accumulation of an excessive amount of watery fluid in cells or intercellular tissues affecting the lungs, usually resulting from mitral stenosis or left ventricular failure), pneumoconiosis (inflammation commonly leading to fibrosis of the lungs caused by the inhalation of dust incident to various occupations), and tuberculosis (a specific disease caused by infection by *Mycobacterium tuberculosis*, the tubercle *bacillus*, which can affect almost any tissue or organ of the body, the most common seat of the disease being the lungs).

Lung diseases affecting the interstitium, the thin lining between the alveoli, include, without limitation, pneumonia, pulmonary edema, and interstitial lung disease, a broad collection of lung conditions including, without limitation, autoimmune diseases (disorders in which the loss of function or destruction of normal tissue arises from humoral or cellular immune responses to the body's own tissue constituents), idiopathic pulmonary fibrosis (an acute to chronic inflammatory process or interstitial fibrosis of the lung of unknown etiology), and sarcoidosis (a systemic granulomatous disease of unknown cause, especially involving the lungs with resulting interstitial fibrosis, but also involving lymph nodes, skin, liver, spleen, eyes, phalangeal bones, and parotid glands).

Lung diseases affecting blood vessels of the lung include, without limitation, pulmonary embolism (obstruction or occlusion of pulmonary arteries by an embolus, most frequently by detached fragments of thrombus from a leg or pelvic vein) and pulmonary hypertension (high blood pressure in the pulmonary circuit).

Lung diseases affecting the pleura include, without limitation, pleural effusion (increased fluid within the pericardial sac), pneumothorax (the presence of free air or gas in the pleural cavity), and mesothelioma (a rare neoplasm derived from the lining of the cells of the pleura and peritoneum which grows as a thick sheet covering the viscera, and is composed of spindle cells or fibrous tissue which may enclose glandlike spaces lined by cuboidal cells).

Lung diseases affecting the chest wall include, without limitation, obesity hypoventilation syndrome (a combination of severe, grotesque obesity, somnolence, and general debility, theoretically resulting from hypoventilation induced by the obesity) and neuromuscular disorders, including, without limitation, amyotrophic lateral sclerosis (a fatal degenerative disease involving the corticobulbar, corticospinal, and spinal motor neurons, manifested by progressive weakness and wasting of muscles innervated by the affected neurons) and myasthenia gravis (a disorder of neuromuscular transmission marked by fluctuating weakness and fatigue of certain voluntary muscles, including those innervated by brainstem motor nuclei).

Regenerative Cells of the Lungs

The adult lung comprises at least 40-60 different cell types of endodermal, mesodermal, and ectodermal origin, which are precisely organized in an elaborate 3D structure with regional diversity along the proximal-distal axis. In addition to the variety of epithelial cells, these include cartilaginous cells of the upper airways, airway smooth muscle cells, interstitial fibroblasts, myofibroblasts, lipofibroblasts, and pericytes as well as vascular, microvascular, and lymphatic endothelial cells, and innervating neural cells. The regenerative ability of lung epithelial stem/progenitor cells in the different regions of the lung are thought to be determined not only by their intrinsic developmental potential but also by the complex interplay of permissive or restrictive cues provided by these intimately associated cell lineages as well as the circulating cells, soluble and insoluble factors and cytokines within their niche microenvironment (McQualter & Bertoncello. Stem Cells. 2012 May; 30(5); 81 1-16).

The crosstalk between the different cell lineages is reciprocal, multidirectional, and interdependent. Autocrine and paracrine factors elaborated by mesenchymal and endothelial cells are required for lung epithelial cell proliferation and differentiation (Yamamoto et al. Dev Biol. 2007 Aug. 1; 308(1) 44-53; Ding et al. Cell. 2011 Oct. 28; 147(3): 539-53), while endothelial and epithelial cell-derived factors also regulate mesenchymal cell proliferation and differentiation, extracellular matrix deposition and remodeling, and adhesion-mediated signaling (Crivellato. Int J Dev Biol. 201 1; 55(4-5): 365-75); Grinnell & Harrington. Pulmonary endothelial cell interactions with the extracellular matrix. In: Voelkel N F, Rounds S, eds. The Pulmonary Endothelium:

Function in Health and Disease. Chichester, West Suxssex: Wiley-Blackwell, 2009: 51-72). Chemotactic factors elaborated by these cell lineages also orchestrate the recruitment of inflammatory cells, which participate in the remodeling of the niche and the regulation of the proliferation and differentiation of its cellular constituents (McQualter & Bertoncello. Stem Cells. 2012 May; 30(5); 81 1-16).

Lung Mesenchymal Stem/Progenitor Cells

Tracheal and distal embryonic lung mesenchyme have been demonstrated to have inductive properties for the regional specification of the embryonic epithelium (Shannon & Deterding. Epithelial-mesenchymal interactions in lung development. In: McDonald J A, ed. Lung Biology in Health and Disease. Vol. 100. New York: Marcel Dekker Inc, 1997, pp. 81-1 18.). During lung development, mesenchymal stromal cells at the distal tip of the branching epithelium are known to secrete fibroblast growth factor (FGF)-10, which influences the fate and specificity of early lung epithelial progenitor cells (Bellusci et al. Development. 1997 December; 124(23): 4867-78; Ramasamy et al. Dev Biol. 2007 Jul. 15; 307(2): 237-47). FGF-10 is a component of a multifaceted epithelial-mesenchymal cell signaling network involving BMP, Wnt, and Shh pathways which coordinate the proliferation and differentiation of progenitor cells in the developing lung (reviewed in Morrisey & Hogan. Dev Cell. 2010 Jan. 19; 18(1): 8-23). Lineage tracing studies have also revealed that FGF-10+ mesenchymal cells residing at the branching tip of the epithelium function as stem/progenitor cells for smooth muscle cells, which become distributed along the elongating airways (De Langhe et al. Dev Biol. 2006 Nov. 1; 299(1): 52-62; Mailleuix et al. Development. 2005 May; 132(9): 2157-66). In other studies, mesenchymal stromal cells adjacent to the trachea and extrapulmonary bronchi have also been shown to give rise to bronchiolar smooth muscle cells (Shan et al. Dev Dyn. 2008; 237: 750-5). Collectively, these studies suggest that at least two distinct populations of mesenchymal stromal cells endowed with epithelial modulating properties emerge during development.

Several studies have identified resident mesenchymal stromal cells in adult lungs with the capacity for adipogenic, chondrogenic, osteogenic, and myogenic differentiation. These cells have been clonally expanded from heterogeneous populations of mixed lineage cells defined by their ability to efflux Hoechst 33342 (Giangreco et al. Am J Physiol Lung Cell Mol Physiol. 2004; 286: L624-30; Summer et al. Am J Respir Cell Mol Biol. 2007; 37: 152-9), by their capacity for outgrowth from lung explant cultures (Hoffman et al. Stem Cells Dev. 201 1; 20: 1779-92) or by their characteristic expression of Sca-1 (McQualter et al. Stem Cells. 2009; 27: 61 2-22; Hegab et al. Stem Cells Dev. 2010; 19: 523-36). In addition, further enrichment of CD45neg CD31 neg Sca-1 pos mesenchymal stromal cells has been achieved based on their lack of EpCAM expression, which selectively labels epithelial lineage cells (McQualter et al. Proc Natl Acad Sci USA 2010; 107: 1414-19). Resolution of the mesenchymal and epithelial lineages has revealed that the endogenous lung mesenchymal stromal cell population is necessary and sufficient to support the proliferation and differentiation of bronchiolar epithelial stem/progenitor cells in coculture (Id.). This suggests that adult mesenchymal stromal cells share similar epithelial inductive properties to their embryonic counterparts and are an important element of the epithelial stem/progenitor cell niche in the adult lung. This concept is also supported by recent in vivo studies showing that following naphthalene injury of club cells, parabronchial mesenchymal cells secrete FGF-10 to support epithelial regeneration from surviving epithelial stem/progenitor cells (Volckaert et al. J Clin Invest. 201 1; 121: 4409-19).

Lung Endothelial Progenitor Cells

Endothelial-epithelial cell interactions and angiogenic and angiocrine factors elaborated in the lung epithelial stem/progenitor cell microenvironment also play a role in the regulation of endogenous lung epithelial stem/progenitor cell regeneration and repair (Yamamoto et al. Dev Biol. 2007 Aug. 1; 308(1) 44-53; Ding et al. Cell. 2011 Oct. 28; 147(3): 539-53; Crivellato. Int J Dev Biol. 201 1; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). For example, it has been reported that the coculture of human vascular endothelial cells with a human bronchial epithelial cell line promotes the generation of branching bronchioalveolar epithelial structures in a 3D culture system (Frazdottir et al. Respir Res. 2010; 1 1: 162). While considerable progress has been made in understanding the heterogeneity, functional diversity, and pathophysiological behavior of lung vascular and microvascular endothelial cells, the immunophenotypic profiling, quantitation, and functional analysis of lung endothelial progenitor cells (EPC) lags far behind. As for EPC derived from human umbilical cord blood, bone marrow, and mobilized peripheral blood (Timmermans et al. J Cell Mol Med. 2009; 13: 87-102), the rarity of EPC in the lung, their lack of distinguishing markers, and the inability to discriminate circulating EPC and tissue resident EPC have been major impediments in assessing the contribution of endogenous lung EPC in lung vascular repair, and lung regeneration and remodeling (Thebaud & Yoder. Pulmonary endothelial progenitor cells. In: Voelkel N F, Rounds S, eds. The Pulmonary Endothelium: Function in Health and Disease. Chichester, West Sussex: Wiley, 2009: 203-16; Yoder. Proc Am Thorac Soc. 201 1; 8: 466-70).

Lung macrovascular and microvascular endothelial cells can be resolved on the basis of their preferential binding to the lectins *Helix pomatia* and Griffonia simplicifolica, respectively (King et al. Microvasc Res. 2004; 67: 139-51), but there are no other cell surface markers that can discriminate mature lung endothelial cells and EPC (Yoder. Proc Am Thorac Soc. 201 1; 8: 466-70). In addition, the rarity of EPC has necessitated the ex vivo expansion and passaging of adherent heterogeneous rat (Alvarez et al. Am J Physiol Lung Cell Mol Physiol. 2008; 294: L419-30) or mouse (Schniedermann et al. BMC Cell Biol. 2010; 11: 50) lung endothelial cells in liquid culture prior to quantitation and flow cytometric and functional analysis of lung-derived EPC in in vitro assays. These assays suggest that the lung microvasculature is a rich source of EPC. However, the incidence, immunophenotypic and functional properties of EPC in the primary explanted endothelial cells compared with their ex vivo manipulated, selected, and expanded counterparts remains indeterminate. The ability of these endogenous lung EPCs to contribute to vascular repair and remodeling in vivo is also unproven (Yoder. Proc Am Thorac Soc. 201 1; 8: 466-70). Recent studies suggest it likely that both circulating EPC and resident lung EPC contribute to endothelial cell regeneration and repair (Balasubramian et al. Am J Physiol Lung Cell Mol Physiol. 2010; 298: L315-23; Duong et al. Angiogenesis. 201 1: 41 1-22; Chamoto et al. Am J Respir Cell Mol Biol. 2012 March; 46(3): 283-9).

General Principles of Wound Healing

The term "wound healing" refers to the processes by which the body repairs trauma to any of its tissues, especially those caused by physical means and with interruption of continuity.

A wound-healing response can be viewed as comprising four separate phases, comprising: 1) an initial phase post injury involving hemostasis; 2) a second phase involving inflammation; 3) a third phase involving granulation and proliferation; and 4) a fourth phase involving remodeling and maturation. The culmination of the wound-healing response results in the replacement of normal tissue structures with fibroblastic mediated scar tissue. Processes involved in the wound healing response, however, can go awry and produce an exuberance of fibroblastic proliferation, which can result in tissue damage, including hypertrophic scarring (a widened or unsightly scar that does not extend the original boundaries of the wound).

Initial Phase—Hemostatsis

An initial injury results in an outflow of blood and lymphatic fluid. This is also the process during which the initial reparative blood clot is created. Both the intrinsic coagulation pathways, so called because all of the components are intrinsic to plasma, and the extrinsic coagulation pathways are activated. The intrinsic and extrinsic systems converge to activate the final common pathways causing fibrin formation. FIG. 1 shows an illustrative representation of the classical coagulation cascades. It is generally recognized that these systems function together and interact in vivo.

The intrinsic coagulation pathway is initiated when blood contacts any surface except normal endothelial and blood cells. This pathway, also known as the contact activation pathway, begins with formation of the primary complex on collagen by high-molecular weight kininogen (HMWK), prekallikrein, and coagulation factor (Factor) XII (Hageman factor). Prekallikrein is converted to kallikrein and Factor XII becomes Factor XI la. Factor XIIa converts Factor XI into Factor XIa. Factor XIa activates Factor IX, which, with its co-factor FVIIIa form the tenase complex, which activates Factor X to Factor Xa.

The extrinsic coagulation pathway, also known as the tissue factor pathway, generates a thrombin burst and is initiated when tissue thromboplastin activates Factor VII. Upon vessel injury, tissue factor (TF), a nonenzymatic lipoprotein cofactor that greatly increases the proteolytic efficiency of Factor VIIa, is exposed to the blood and enzyme coagulation factor VII (proconvertin) circulating in the blood. Once bound to TF, Factor VII is activated to Factor VIIa by different proteases, including thrombin (Factor IIa), Factors Xa, IXa, XIIa and the Factor VIIa-TF complex itself. The Factor VIIa-TF complex activates Factors IX and X. The activation of Factor Xa by the Factor VIIa-TF complex almost immediately is inhibited by tissue factor pathway inhibitor (TFPI). Factor Xa and its cofactor Va form the prothrombinase complex which activates the conversion of prothrombin to thrombin.

Thrombin then activates other components of the coagulation cascade, including Factors V and VIII (which activates Factor XI, which, in turn, activates Factor IX), and activates and releases Factor VIII from being bound to von Willebrand Factor (vWF). Factors VIIa and IXa together form the "tenase" complex, which activates Factor X, and so the cycle continues.

As currently understood, coagulation in vivo is a 3-step process centered on cell surfaces. In the first step, coagulation begins primarily by initiation with tissue factor, which is present on the subendothelium, tissues not normally exposed to blood, activated monocytes and endothelium when activated by inflammation. Factors VII and VIIa bind to tissue factor and adjacent collagen. The factor VIIa-tissue factor complex activates factor X and IX. Factor Xa activates factor V, forming a prothrombinase complex (factor Xa, Va and calcium) on the tissue factor expressing cell. In the second step, coagulation is amplified as platelets adhere to the site of injury in the blood vessel. Thrombin is activated by platelet adherence and then acts to fully activate platelets, to enhance their adhesion and to release factor V from the platelet a granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin. Propagation, the third step, is a combination of activation of the prothrombinase complexes that allow large amounts of thrombin to be generated from prothrombin. More platelets can be recruited, as well as activation of fibrin polymers and factor XIII.

The inflammatory phase (see below) begins during the hemostasis phase. Thrombocytes, as well as recruited white blood cells, release numerous factors to ramp up the healing process. Alpha-granules liberate platelet-derived growth factor (PDGF), platelet factor IV, and transforming growth factor beta (TGF-β). The processes of inflammation, collagen degradation and collagenogenesis, myoblastic creation from transformed fibroblasts, growth of new blood vessels, and reepithelialization are mediated by a host of cytokines and growth factors. The interleukins strongly influence the inflammatory process. Vascular endothelial growth factor (VEGF) and other factors enhance blood vessel formation, and some have multiple roles, such as fibroblast growth factor (FGF)-2, which affects not only the process of angiogenesis but also that of reepithelialization. Vasoactive amines, such as histamine and serotonin, are released from dense bodies found in thrombocytes. PDGF is chemotactic for fibroblasts and, along with TGF-β, is a potent modulator of fibroblastic mitosis, leading to prolific collagen fibril construction in later phases. Fibrinogen is cleaved into fibrin, and the framework for completion of the coagulation process is formed. Fibrin provides the structural support for cellular constituents of inflammation. This process starts immediately after the insult and may continue for a few days.

Second Phase: Inflammation

The early component of the inflammatory phase is predominated by the influx of the polymorphonuclear leukocytes (PMNs) and the later component of the inflammatory phase is predominated by monocytes/macrophages.

Within the first 6-8 hours, PMNs engorge the wound. TGF-β facilitates PMN migration from surrounding blood vessels, from which they extrude themselves from these vessels. These cells cleanse the wound, clearing it of debris. The PMNs attain their maximal numbers in 24-48 hours and commence their departure by hour 72. Other chemotactic agents are released, including FGF, TGF-β and TGF-alpha (TGF-α), PDGF, and plasma-activated complements C3a and C5a (anaphylactic toxins). They are sequestered by macrophages or interred within the scab or eschar (Id.; Habif. Dermatologic surgical procedures. Clinic Dermatology: A Color Guide to Diagnosis and Therapy. 3rd ed. 1996. 809-81 0).

As the process continues, monocytes also exude from surrounding blood vessels. Once they leave the vessel, these are termed macrophages. The macrophages continue the cleansing process, manufacture various growth factors during days 3-4, and orchestrate the multiplication of endothelial cells with the sprouting of new blood vessels, the duplication of smooth muscle cells, and the creation of the milieu created by the fibroblast. Many factors influencing the wound healing process are secreted by macrophages, including TGFs, cytokines and interleukins, tumor necrosis factor (TNF), and PDGF.

Third Phase: Granulation and Proliferation

ASXZal cells. Basic FGF and vascular endothelial growth factor are believed to modulate angiogenesis.

Re-epithelization occurs with the migration of cells from the periphery of the wound and accessory or adjoining tissues. This process commences with the spreading of cells within 24 hours. Division of peripheral cells occurs in hours 48-72, resulting in a thin epithelial cell layer, which bridges the wound. Epidermal growth factors are believed to play a key role in this aspect of wound healing.

This succession of subphases can last up to 4 weeks in the clean and uncontaminated wound.

Fourth Phase: Remodeling and Maturation

After the third week, the wound undergoes constant alterations, known as remodeling, which can last for years after the initial injury occurred. Collagen is degraded and deposited in an equilibrium-producing fashion, resulting in no change in the amount of collagen present in the wound. The collagen deposition in normal wound healing reaches a peak by the third week after the wound is created. Contraction of the wound is an ongoing process resulting in part from the proliferation of specialized fibroblasts termed myofibroblasts, which provide mechanical support and integrity to the tissue after initial injury. Wound contraction occurs to a greater extent with secondary healing (i.e., healing by second intention, which describes a wound left open and allowed to close by reepithelialization and contraction by myofibroblasts) than with primary healing (i.e., healing by first intention, which describes a wound closed by approximation of wound margins or by placement of a graft or flap, or wounds created and closed in the operating room, unlike via reepithelialization and contraction by myofibroblasts). Maximal tensile strength (the greatest longitudinal stress a substance can bear without tearing apart) of the wound is achieved by the 12th week, and the ultimate resultant scar has only 80% of the tensile strength of the original skin that it has replaced. At the end of tissue repair, the reconstructed ECM takes over the mechanical load and myofibroblasts disappear by massive apoptosis (Tomasek et al. Nat Rev Mol Cell Biol. 2002 May; 3(5): 349-63).

Fibroblastic Cells and Myofibroblast Differentiation in Normal Conditions

Under normal conditions, fibroblastic cells exhibit few or no actin-associated cell-cell and cell-matrix contacts and little ECM production (Tomasek et al. Nat Rev Mol Cell Biol. 2002 May; 3(5): 349-63), but after tissue injury, they become activated to migrate into the damaged tissue and to synthesize ECM components (Hinz. J Invest Dermatol. 2007 March; 127(3): 526-37) by cytokines locally released from inflammatory and resident cells (Werner & Grose. Physiol Rev. 2003 July; 83(3): 835-70) or from malignant epithelial cells (De Wever & Mareel. J Pathol. 2003 July; 200(4): 429-47).

Another important stimulus for this phenotypic transition is the change of the mechanical microenvironment; whereas fibroblasts in intact tissue are generally stress-shielded by the crosslinked ECM, this protective structure is lost in the continuously remodeled ECM of injured tissue (Tomasek et al. Nat Rev Mol Cell Biol. 2002 May; 3(5): 349-63). In response to mechanical challenge, fibroblasts acquire contractile stress fibers that are first composed of cytoplasmic actins (Tomasek et al. Nat Rev Mol Cell Biol. 2002 May; 3(5): 349-63), hallmarking the "protomyofibroblast." Stress fibers are connected to fibrous ECM proteins at sites of integrin-containing cell-matrix junctions (Hinz. Eur J Cell Biol. 2006 April; 85(3-4): 175-81) and between cells via de novo established N-cadherin-type adherens junctions (Hinz et al. Mol Biol Cell. 2004 September; 15(9): 4310-20).

In culture, protomyofibroblasts are a stable phenotype, representing an intermediate step in most in vivo conditions where they proceed toward the "differentiated myofibroblast" that is characterized by de novo expression of α-smooth muscle actin (a-SMA), its most commonly used molecular marker, and by increased production of ECM proteins. Expression of a-SMA in stress fibers confers to the differentiated myofibroblast at least a twofold stronger contractile activity compared with a-SMA-negative fibroblasts in culture (Hinz et al. Am J Pathol. 2007 June; 170(6): 1807-16).

At least three local events are needed to generate a-SMA-positive differentiated myofibroblasts: 1) accumulation of biologically active transforming growth factor (TGF) (31; 2) the presence of specialized ECM proteins like the ED-A splice variant of fibronectin; and 3) high extracellular stress, arising from the mechanical properties of the ECM and cell remodeling activity (Tomasek et al. Nat Rev Mol Cell Biol. 2002 May; 3(5): 349-63). Mechanoperception is mediated by specialized cell-matrix junctions, called "fibronexus" in vivo and "supermature focal adhesions" (FAs) in vitro (Hinz. Eur J Cell Biol. 2006 April; 85(3-4): 175-81). Analogously, small N-cadherin-type cell-cell adhesions develop into larger OB-cadherin (cadherin-11)-type junctions during generation of the differentiated myofibroblast in vitro and in vivo (Hinz et al. Mol Biol Cell. 2004 September; 15(9): 4310-20; Hinz et al. Am J Pathol. 2007 June; 170(6): 1807-16).

The main myofibroblast inducer TOPPI up-regulates expression of fibronectin and its integrin receptors in lung fibroblasts; this is closely linked to the activation/phosphorylation of focal adhesion kinase essential for the induction of myofibroblast differentiation (Thannickal et al. J Biol Cehm. 2003 Apr. 4; 278(14): 12384-9). At the end of tissue repair, the reconstructed ECM again takes over the mechanical load and myofibroblasts disappear by massive apoptosis (Tomasek et al. Nat Rev Mol Cell Biol. 2002 May; 3(5): 349-63); stress release is a powerful promoter of myofibroblast apoptosis in vivo (Hinz et al. Am J Pathol. 2007 June; 170(6): 1807-16).

After injury, the main myofibroblast progenitor appears to be the locally residing fibroblast, which transiently differentiates into a protomyofibroblast, characterized by a-SMA-negative stress fibers. In the lung, the endothelial-to-mesenchymal transition (the biologic process that allows an epithelial cell to undergo multiple biochemical changes that enable it to assume a mesenchymal cell phenotype (Kalluri & Weinberg. J Clin Invest. 2009 Jun. 1; 1 19(6): 1420-28)) may provide an additional mechanism to generate fibroblasts (Hinz et al. Am J Pathol. 2007 June; 170(6): 1807-16).

Pulmonary Fibrosis

Pulmonary fibrosis, an interstitial lung disease, is a general term used to describe an increased accumulation of extracellular matrix ("ECM") in the distal lung, rendering the lung stiff and compromising its ability to facilitate normal gas exchange. Patients typically present with the insidious onset of shortness of breath with exertion as the disease often goes unnoticed in its early stages. Pulmonary fibrosis can be associated with a number of underlying diseases (such as connective tissue/rheumatologic disease) or environmental exposures (asbestosis), or it can be idiopathic, i.e., of unknown cause, in nature (Barkauskas & Nobel. Am J Physiol Cell Physiol. 2014 Jun. 1; 306(1 1): C987-96).

Progressive tissue fibrosis is a major cause of morbidity, and idiopathic pulmonary fibrosis (IPF) is a terminal illness characterized by unremitting ECM deposition in the lung with very limited choice of therapies (Noble et al. J Clin Invest. 2012 August; 122(8): 2756-62). Although certain mediators have been identified as initiating progressive fibrosis, the mechanisms that contribute to the disease are unknown.

IPF, a chronic, terminal disease that manifests over several years, is the most common form of fibrotic lung disease with a prevalence of 14.0-42.7 cases per 100,000 individuals in the United States (depending on the case definition used) and a median survival of 2.5-3.5 yr (Raghu et al. Am J Respir Crit Care Med. 2006 Oct. 1; 174(7): 810-6). It is characterized by excess ECM components and scar tissue within the lungs, and exercise-induced breathlessness and chronic dry cough are the prominent symptoms. IPF is viewed as a disease of aging, with the median age at diagnosis being in the mid-60s. There are few effective therapies for IPF short of lung transplant (Meltzer and Nobel. Orphanet J Rare Dis. 2008 Mar. 26; 3: 8. Doi: 10, 1 186/1750-1 172-3-8). Because a pharmacologic therapy capable of halting or at least slowing the progression of the disease has been elusive, there are intense efforts to better understand the factors that trigger and perpetuate this disease.

IPF belongs to a family of lung disorders known as interstitial lung diseases ("ILD"), or more accurately, the diffuse parenchymal lung diseases ("DPLD"). Within this broad category of diffuse lung diseases, IPF belongs to the subgroup known as idiopathic interstitial pneumonia ("IIP"). By definition, the etiology of IIP is unknown. There are seven distinct IIPs, differentiated by specific clinical features and pathological patterns (Katzenstein et al. Am J Respir Crit Care Med. 2008 April; 157(4 Pt 1): 1301-15). IPF is the most common form of IIP, and is associated with the pathologic pattern known as usual interstitial pneumonia (UIP). The UIP pattern of fibrosis is characterized by two features: 1) Spatial or geographic heterogeneity, which refers to a patchy distribution of dense lung scarring with areas of less affected or normal lung tissue; and 2) Temporal heterogeneity, which refers to areas of densely collagenized fibrosis with variable smooth muscle proliferation alternating with active fibroblast foci (Smith et al. J Clin Pathol. 2013 October; 66(1): 896-903). Therefore, IPF is often referred to as IPF/UIP. IPF is usually fatal, with an average survival of approximately three years from the time of diagnosis (Collard et al. Am J Respir Crit Care Med. 2003 Sep. 1; 168(5): 538-42; Flaherty, et al. Am J Respir Crit Care Med. 2003 Sep. 1; 1 68(5): 543-8; Latsi et al. Am J Respir Crit Care Med. 2003 Sep. 1; 1 68(5): 531-7).

IPF arises in the alveolar regions of the lung, a region that consists of AEC2s, and AEC1s, as well as a number of mesenchymal cell types. It is hypothesized that cross talk between the alveolar epithelium and its associated mesenchyme is dysregulated in IPF pathogenesis, and this leads to the unchecked proliferation of extracellular matrix-producing cells. Evidence from genetic analysis of rare familial cases of IPF suggests that defects that incite the development of the disease can originate in the alveolar epithelium (Barkauskas & Noble. Am J Physiol Cell Physiol. 2014 Jun. 1; 306(1 1): C987-96).

Examples of non-medication based interventions for IPF include pulmonary rehabilitation, long-term oxygen therapy, mechanical ventilation, and lung transplantation. Of these treatments, the only intervention that improves survival in select patients with IPF is lung transplantation (Rafii et al. J Thorac Dis. 2013; 5(1): 48-73). However, lung transplantation is not without significant risks, including infection, given the need for immunosuppression, acute and chronic graft rejection, and airway stenosis (Id.).

Many proposed medication based treatments have failed to date (Id.). These include anti-inflammatory or immunomodulatory therapies, such as corticosteroid monotherapy, azathioprine, cyclophosphamide, everolimus; anticoagulants and therapies targeting the coagulation cascade, such as warfarin, heparin, and prednisolone; endothelin receptor antagonists and vasodilators, such as bosentan, ambrisentan, macitentan, and sildenafil; and antifibrotics and cytokine/kinase inhibitors, such as interferon-gamma, etanercept, imatinib, and CC-930 (Id.). Many of these failures have been associated with a high degree of side effects, which would be expected for medications of these classes, and limited therapeutic effects.

To date, two therapeutic medications have been FDA approved for the treatment of IPF. ESBRIET (pirfenidone), a small molecule antifibrotic that acts on multiple pathways, including the transforming growth factor beta (TGF-$\beta$) pathway, and OFEV (nintedanib), a small molecule inhibitor of the receptors for tyrosine kinases, fibroblast growth factor (FGF), platelet-derived growth factor (PDGF), and vascular endothelial growth factor (VEGF). Although these medications have side effects and do not appear to be able to reverse IPF, they have been shown to significantly slow the progression of the disease.

Recently, microRNAs have shown promise as a therapeutic tool in the treatment of IPF. MicroRNAs (miRNAs) include a broad class of small evolutionarily conserved noncoding RNAs that have important roles in a variety of patho-physiological processes by blocking translation or promoting degradation of complementary target mRNAs (Wynn & Ramalingam. Nat Med. 2012 Jul. 6; 18(7): 1 028-40). Although unique subsets of miRNAs have been identified in various fibrotic diseases, a much smaller subset of miRNAs have emerged as regulators of the fibrotic process. For example, miR-21 is expressed in the lungs of individuals with IPF, and mice treated with miR-21 antisense probes were protected from bleomycin-induced pulmonary fibrosis (Liu et al. J Exp Med. 2010 Aug. 2; 207(8): 1 589-97). Mechanistically, miR-21 is thought to promote fibrosis by regulating TGF-$\beta$I and MAP kinase signaling in activated myofibroblasts (Id.), and miR-29 also seems to promote fibrosis in human cells by directly regulating type I collagen expression (Ogawa et al. Biochem Biophys Res Commun. 2010 Jan. 1; 391 (1): 31 6-21). In addition, miR-29 has been found to be down regulated in various forms of fibrosis, including IPF. Animal studies injecting a miR-29 mimic into mice has demonstrated promising results even in cases of "established fibrosis." (Fox. Drug Discovery & Development—http://www.dddmag.com/news/2014/10/reversing-idiopathic-pulmonary-fibrosis).

Wound Healing in Pulmonary Fibrosis

Pulmonary fibrosis is hypothesized to develop because epithelial injuries and/or cellular stress is met by a dysregulated mesenchymal response, leading to a deposition of excess collagen and other ECM components into the fibrotic lung (Barkauskas & Noble. Am J Physiol Cell Physiol. 2014 Apr. 16; 306L C987-96).

The wound healing response is dysregulated in pulmonary fibrosis, and disruptions to the highly coordinated wound-repair processes result in pathological scar formation and excessive deposition of ECM components, such as collagen (Chambers. Eur Respir Rev. 2008; 1 7(109): 130-7). It is thought that in pulmonary fibrosis, aberrant activation of alveolar epithelial cells provokes the migration, proliferation, and activation of mesenchymal cells with the formation of fibroblastic/myofibroblastic foci, leading to the exaggerated accumulation of extracellular matrix with the irreversible destruction of lung tissue (Harari & Caminati. Allergy. 2010 May; 65(5):537-53).

Following injury or "wear and tear" to the alveolar epothelium in otherwise normal lungs, dead or damaged alveolar epithelial cells are replaced by descendants of AEC2s that self-renew and differentiate to AEC1s. It is hypothesized that Scgb1 a1+club secretory cells and/or basal cells serve as a source of AEC2s following injury. These repair processes effectively cover denuded basal lamina, and in the normal healing process, fibrosis does not occur (Barkauskas & Noble. Am J Physiol Cell Physiol. 2014 Jun. 1; 306(1 1): C987-96). However, in pulmonary fibrosis, abnormal AEC2s are observed, usually overlying fibroblast foci (Rock et al. Proc Natl Acad Sci USA. 2011 Dec. 27; 108(52): E1475-83). The abnormal, hyperplastic morphology of the AEC2s in IPF is thought to relate to cellular stress and the failure to regenerate AEC1s lost by injury or wear and tear. The inability of defective AEC2s to cover the basement membrane denuded by the loss of AEC1s results in the release of profibrotic signals and may perpetuate the development of fibroblast foci (Id.).

In addition to activating the coagulation cascade, platelets and damaged epithelial and endothelial cells release a variety of chemotactic factors that recruit inflammatory monocytes and neutrophils to the site of tissue damage (Wynn & Ramalingam. Nat Med. 2012 Jul. 6; 18(7): 1028-40).

Various growth factors and cytokines secreted by innate inflammatory cells (including macrophages, neutrophils, mast cells and eosinophils) have emerged as potential targets for antifibrotic therapy (Id.). Tumor necrosis factor-alpha (TNF-α) and interleukin-1 (3 (IL-1 β), in particular, have been identified as important targets in a variety of fibrotic diseases (Zhang et al. J Immunol. 1993 May 1; 150(9): 4188-96). Mice that overexpress TNF-α or IL-1 β in the lung develop highly progressive pulmonary fibrosis (Miyazaki et al. J Clin Invest. 1995 July; 96(1): 250-9; Kolb et al. J Clin Invest. 2001 June; 107(12): 1529-36). Studies have also shown an essential role for TNF-α in the development of silica- and bleomycin-induced pulmonary fibrosis in mice (Piguet et al. Nature. 1990 Mar. 15; 344(6263): 245-7; Piguet et al. J Exp Med. 1989 Sep. 1; 170(3): 655-63). In support of these experimental findings, patients with idiopathic or systemic sclerosis-associated pulmonary fibrosis have high levels of TNF-α (Piguet et al. Am J Pahtol. 1993 September; 143(3): 651-5). Other studies have documented profibrotic activity for IL-1 β and NALP3/ASC inflammasome signaling in macrophages (Gasse et al. J Clin Invest. 2007 December; 1 17(12): 3786-99). Pulmonary fibrosis induced by bleomycin and silica is reduced in IL-1 β-deficient mice (Bujak et al. Arch Immulon Ther Exp (Warsz). 2009 May-June; 57(3): 165-76; Jones et al. Nephrol Dail Transplant. 2009; 24: 3024-32; Kamari et al. J Hepatol. 201 1 November; 55(5): 1 086-94). Like TNF-α, IL-1 β is a potent proinflammatory mediator that exacerbates parenchymal-cell injury. It also induces epithelial-mesenchymal transition (EMT) and myofibroblast activation through a TGFβ1-mediated mechanism (Fan et al. Am J Kidney Dis. 2001 April; 37(4): 820-31), confirming that it functions as a potent upstream driver of fibrosis. IL-1 β and TNF-α also increase expression of IL-6, which shows autocrine growth-factor activity in fibroblasts. Studies suggest that the cellular source of TGF-β1 dictates its activity, with TGF-βI derived from macrophages generally showing wound-healing and profibrotic activity and TGF-βI secreted from CD4+ T regulatory cells (Treg cells) functioning as an anti-inflammatory and antifibrotic mediator (Kitani et al. J Exp Med. 2003 Oct. 20; 1 98(8): 1 179-88). Mice deficient in TGF-βI develop numerous autoimmune disorders and are more susceptible to cancer (Id.).

The CD4+ TH17 cell subset that expresses the proinflammatory cytokine IL-17A is emerging as a driver of fibrosis. IL-17A expression has been implicated in the pathogenesis of pulmonary fibrosis (Wilson et al. J Exp Med. 2010 Mar. 15; 207(3): 535-52). In many cases, IL-17A expression is associated with persistent neutrophilia (Laan et al. J Immunol. 1999 Feb. 1 5; 162(4): 2347-52), and it has been suggested that exaggerated neutrophil recruitment contributes to the development of tissue damage and fibrosis by inducing apoptosis in vascular endothelial cells (Zhu et al. Clin Immunol. 201 1 November; 141 (2): 152-60). Neutrophil recruitment is also an important predictor of early mortality in IPF patients (Kinder et al. Chest. 2008 January; 133(1): 226-32). Mechanistic studies investigating the IL-17 pathway of fibrosis in mice have identified the proinflammatory cytokines IL-1 β and IL-23 as important upstream initiators of profibrotic TH17 responses (Wilson et al. J Exp Med. 2010 Mar. 15; 207(3): 535-52; Gasse et al. PLoS One. 201 1; 6(8): e231 85). A link between IL-17A and TGF-βI has also been identified (Wilson et al. J Exp Med. 2010 Mar. 15; 207(3): 535-52). In addition to its role in promoting neutrophilic inflammation, IL-17A has been shown to directly induce expression of matrix metalloproteinase-1 in primary human cardiac fibroblasts (Cortez et al. Am J Physiol Heart Circ Physiol. 2007 December; 293(6): H3356-65), suggesting that IL-17A promotes fibrosis by both exacerbating the upstream inflammatory response and regulating the downstream activation of fibroblasts (Wynn & Ramalingam. Nat Med. 2012 Jul. 6; 18(7): 1 028-40).

IL-13 has emerged as a dominant mediator of fibrotic tissue remodeling in several experimental and natural models of fibrosis (Chiaramonte et al. J Clin Invest. 1 999 September; 104(6): 777-85). IL-13 production has been implicated in the development of IPF (Murray et al. Int J Biochem Cell Biol. 2008; 40(10): 2174-82). Mechanistically, IL-13 has been hypothesized to induce fibrosis by stimulating the production and activation of TGF-β (Lee et al. J Exp Med. 2001 Sep. 17; 194(6): 809-21). Other studies have suggested that IL-13 can promote fibrosis independently of TGF-β (Liu et al. J Immunol. 2011 Sep. 1; 187(5): 2814-23; Kaviratne et al. J Immunol. 2004 Sep. 15; 173(6): 4020-9) by directly activating the synthetic and proliferative properties of fibroblasts, epithelial cells and smooth-muscle cells (Kuperman et al. Nat Med. 2002 August; 8(8): 885-9; Lee et al. Am J Respir Cell Mol Biol. 2001 October; 25(4): 474-85). Unlike IL-17A—which seems to promote fibrosis indirectly by inducing tissue damage and inflammation—IL-13 and TGF-β show direct fibrotic activity. TH2 cells that produce IL-13 and Treg cells that express TGF-β are also known to inhibit TH17 responses (Wilson et al. Gastroenterology. 201 1 January; 140(1): 254-64), suggesting dual roles for IL-13 and TGF-β in the wound-healing response, as both cytokines suppress inflammation while promoting fibrosis. The profibrotic activity of IL-13 is controlled by the abundance of the IL-13Ra1 signaling receptor and IL-13Ra2 decoy receptor expressed on target cells such as myofibroblasts (Ramalingam et al. Nat Immunol. 2008 January; 9(1): 25-33; Chiaramonte et al. J Exp Med. 2003 Mar. 17; 197(6): 687-701). When decoy receptor expression is low or absent, IL-13-dependent fibrosis is exacerbated (Mentink-Kane et al. Gastroenterology. 201 1 December; 141 (6): 2200-9). However, mice deficient in IL-13Ra2 are more resistant to IL-13- and IL-17-driven inflammation, probably because of the enhanced IL-13 activity (Wilson et al. Gastroenterology. 201 1 January; 140(1): 254-64), suggesting that IL-13Ra2 functions as a key regulator of both TH17-mediated inflammation and TH2-driven fibrosis (Mentink-Kane & Wynn. Immunol Rev. 2004 December; 202: 191-202).

Mechanistically, IFN-γ is believed to inhibit fibrosis, at least in part, by antagonizing the profibrotic activity of TGF-βI. IFN-γ inhibits the TGF-β-induced phosphorylation of the signal transducer Smad3 and subsequent activation of TGF-β-responsive genes (Ulloa et al. Nature 1999 Feb. 25; 397(6721): 710-3). IFN-γ also acts through a pathway dependent on Janus-associated kinase (Jak1) and the transcription factor Stat1 and induces expression of Smad7, which can prevent the interaction of Smad3 with the TGF-β receptor, thus further attenuating TGFB-induced signaling. IFN-γ also directly inhibits fibroblast proliferation, TGF-βI-induced expression of the genes encoding procollagen I and procollagen III, and collagen synthesis in activated myofibroblasts. IFN-γ also prevents the TH2 cytokine-induced differentiation of CD14+ peripheral blood monocytes into fibroblast-like cells called fibrocytes, which are believed to participate in the development of fibrosis in many organ systems Shao et al. J Leukoc Biol. 2008 June; 83(6): 1323-33). By virtue of its ability to stimulate IFN-γ production in TH1 and natural killer cells, IL-12 has shown similar antifibrotic activity in vivo in mice (Wynn et al. Nature. 1995 Aug. 17; 376(6541): 594-6; Keane et al. Am J Physiol Lung Cell Mol Physiol. 2001 July; 281 (1): L92-7). But despite an abundance of in vitro and in vivo evidence supporting an antifibrotic role for TH1-type immunity, clinical studies investigating the therapeutic potential of IFN-γ in the treatment of IPF, systemic sclerosis and other fibrotic disorders have so far been mostly unsuccessful (King et al. Lancet. 2009 Jul. 18; 374(9685): 222-8).

The circulating myeloid cells respond to a gradient of CCL2 and are recruited to damaged tissues, where they differentiate into macrophages that phagocytose the fibrin clot and cellular debris.

Macrophages that appear early in the wound-healing response are also major producers of TGF-β, which is one of the drivers of fibrosis (Wynn & Ramalingam. Nat Med. 2012 Jul. 6; 18(7): 1028-40). Macrophages have also been implicated in the pathogenesis of fibrosis (Wynn & Ramalingam. Nat Med. 2012 Jul. 6; 18(7): 1028-40). Recent literature indicates that various factors should be taken in account in evaluating macrophage activity (Martinez & Gordon. FlOOOPrime Rep. 2014; 6: 13). Martinez & Gordon have hypothesized that macrophages do not form stable subsets but respond to a combination of factors present in tissues, and that various pathways interact to form complex, even mixed, macrophage phenotypes (Id.).

Although it is widely recognized that monocytes, macrophages and neutrophils have important roles in the progression and resolution of fibrosis (Wynn & Barron. Semin Liver Dis. 2010 August; 30(3): 245-57), other myeloid-lineage cells (such as mast cells, eosinophils and basophils) have also been implicated in the pathogenesis of fibrosis in multiple organ systems (Wynn & Ramalingam. Nat Med. 2012 Jul. 6; 18(7): 1028-40). Mechanistic studies in rats have suggested that mast cells promote fibrosis by recruiting inflammatory leukocytes and by producing profibrotic mediators (Levick et al. Hypertension. 2009 June; 53(6): 1041-7). Eosinophils seem to function in a similar fashion and are considered to be important sources of TGF-βI and IL-13 (Reiman et al. Infect Immun. 2006 March; 74(3): 1471-9; Minshall et al. Am J Respir Cell Mol boil. 1997 September; 17(3): 326-33).

Eosinophils have been most commonly associated with the development of pulmonary fibrosis (Humbles et al. Science. 2004 Sep. 17; 305(5691): 1776-9. Bronchoalveolar-lavage eosinophilia has also been identified as a predictive biomarker of progressive lung disease in IPF and pulmonary fibrosis associated with collagen vascular disorder (Peterson et al. Chest. 1987 July; 92(1): 51-6). Although basophils have a less clear role in the development of fibrosis than the other myeloid-cell populations, they have been implicated in the pathogenesis of myelofibrosis and are frequently found in greater numbers in patients with interstitial lung disease (Gilbert. Prog Clin Biol Res. 1984; 154: 3-17).

ECM fragments, including hyaluronan, have also been shown to be important drivers of fibrosis by stimulating chemokine and proinflammatory cytokine production by inflammatory monocytes and macrophages (Li et al. J Exp Med. 2011 Jul. 4; 208(7): 1459-71).

While in normal wound healing, myofibroblasts are lost via apoptosis when the tissue integrity has been sufficiently restored to be mechanically coherent (Darby et al. Lab Invest. 1990 July; 63(1): 21-9); Desmouliere et al. Am J Pathol. 1995 January; 146(1): 56-66), in the wound healing response in pulmonary fibrosis, myofibroblasts remain, failing to undergo apoptosis, and in turn lead to ongoing pathology of accumulation of collagen and other ECM components, and scarring (Darby et al. Clin Cosmet Investig Dermatol. 2014; 7: 301-1 1). In other words, in pulmonary fibrosis, there is a defect in the granulation and proliferation and remodeling phases; if the remodeling phase of the granulation tissue fails to happen (neither apoptosis of the cells present in the granulation tissue, myofibroblasts, and vascular cells, nor the reorganization of the ECM), myofibroblasts may persist, leading to pathological situations characterized by pulmonary fibrosis (Id.).

Fibroblastic Cells and Myofibroblast Differentiation in Fibrotic Conditions

Fibroblasts and myofibroblasts from IPF patients have been shown to have distinct properties, including the ability to invade the ECM. A hallmark and defining pathological feature of IPF is the formation of fibroblastic foci, which are the accumulation of myofibroblasts in the interstitium of the lung juxtaposed to the alveolar epithelium with destruction of the adjoining alveolar basement membrane (Selman & Pardo. Respir Res. 2002; 3: 3). The destruction of alveolar basement membrane was also observed in experimental lung fibrosis (Fukuda et al. Am J Pathol. 1985 March; 1 18(3): 452-75; Vaccaro et al. Am Rev Respir Dis. 1985 October; 132(4): 905-12). In view of the many characteristics that encompass features of fibrosis, such as the elaboration of ECM and expression/activation of TOPPI (Zhang et al. Am J Pathol. 1994 July; 145(1): 1 14-25); Zhang et al. J Immunol. 1994 Nov. 15; 153(10): 4733-41), the persistence of the myofibroblast is thought to be of significance in the propagation of fibrosis in pulmonary fibrosis. Early studies of the origin of the myofibroblast in lung injury and fibrosis suggest several possibilities based on observations of its cytoskeletal phenotype, tissue localization, and in vitro studies. Based on evidence that myofibroblasts arise de novo and on the kinetics of the induction of a-SMA expression, the perivascular and peribronchiolar adventitial fibroblasts, i.e., the local fibroblasts, are suggested as precursors (Zhang et al. Am J Pathol. 1994 July; 145(1): 1 14-25), but it has also been reported that circulating fibrocytes (expressing CD45, CD34, collagen I, and CXCR4) can migrate to sites of tissue injury and differentiate into myofibroblasts (Abe et al. J Immunol. 2001 Jun. 15; 166(12): 7556-62; Phillips et al. J Clin Invest. 2004 August; 1 14(3): 438-46).

The mechanism underlying the source of myofibroblasts in pulmonary fibrosis is complex; it has been determined that the presence of Smad3, an intracellular signal transducer for TGF-βI, may have an essential role in myofibroblast differentiation (Ramirez et al. Am J Transplant. 2006 September; 6(9): 2080-8; Hu et al. Am J Respir Cell Mol boil. 2007 January; 36(1): 78-84). However, regulation of the a-SMA gene is quite complex (Giannone & Sheetz. Trends Cell Biol. 2006 April; 16(4): 213-23; Ramirez et al. Am J Transplant. 2006 September; 6(9): 2080-8; Hu et al. Am J Respir Cell Mol boil. 2007 January; 36(1): 78-84). Additional transcription factors, including C/EBPβ (CCAAT/enhancer-binding protein β), GKLF (gut-enriched Kruppel-like factor), Sp1/Sp3, c-myb, and the downstream effector component of Notch signaling, have been implicated to regulate this gene in a complex and interactive manner, and in addition to inducers, suppressors such as the liver-enriched inhibitory protein isoform of C/EBPβ may serve to keep the precursor fibroblast in an undifferentiated state under normal homeostasis (Hinz et al. Am J Pathol. 2007 June; 170(6): 1807-16). Epigenetic modifications in fibroblasts also contribute to the pathogenesis of fibrosis by stably altering the activation status of myofibroblasts (Wynn & Ramalingam. Nat Med. 2012 Jul. 6; 18(7): 1028-40).

In pulmonary fibrosis, myofibroblasts are found in abundance in areas of high ECM expression and represent the predominant source of heightened ECM and cytokine gene expression (Zhang et al. Am J Pathol. 1994 July; 145(1): 1 14-25). The myofibroblast is a factor in alveolar epithelial apoptosis, denudation, and retardation of epithelial regeneration (Waghray et al. FASEB J. 2005 May; 19(7): 854-6). Thus, in addition to its potential contribution to reduction in lung tissue compliance, the myofibroblast is likely to play significant roles in promoting ECM deposition, release of inflammatory mediators, and epithelial injury, all of which are considered to be key factors in perpetuating the cycle of injury and fibrosis. As noted above, in pulmonary fibrosis, myofibroblasts fail to undergo apoptosis, as in the normal wound healing response, which leads to ongoing pathology of accumulation of collagen and other ECM components, and scarring (Darby et al. Clin Cosmet Investig Dermatol. 2014; 7: 301-11).

TOPPI can induce p38 mitogen-activated protein kinase pathway activation with subsequent activation of the pro-survival phosphatidylinositol 3-kinase-AKT pathway (Horowitz et al. J Biol Chem. 2004 Jan. 9; 279(2): 1359-67). Deficiency in PTEN, a phosphatidylinositol 3-kinase-AKT pathway inhibitor, is associated with increased myofibroblast differentiation (White et al. Am J Respir Crit Care Med. 2006 Jan. 1; 173(1): 1 12-21). Thus, in addition to promoting myofibroblast differentiation, combinatorial activation of the adhesion-dependent focal adhesion kinase pathway and the soluble growth factor-mediated AKT pathway confers apoptosis/anoikis (programmed cell death induced by anchorage-dependent cells detaching from surrounding ECM) resistance to TOPPI-differentiated myofibroblasts (Horowitz et al. Cell Signal. 2007 April; 19(4): 761-71).

IPF Fibroblasts Possess a Malignant Phenotype with an Increased Capacity for Invasion It has been proposed that fibroblasts in the IPF lung acquire a phenotype that is reminiscent of malignant cells (Barkauskas & Noble. Am J Physiol Cell Physiol. 2014 Jun. 1; 306(1 1): C987-96). Fibroblasts from the IPF lung display enhanced migratory capacity when assessed in a chemotaxis chamber with platelet-derived growth factor (PDGF) as the chemoattractant. Fibroblasts from tissues with more dense fibrosis displayed capacity for migration compared with fibroblasts isolated from earlier stage disease (Suganuma et al. Thorax. 1995 September; 50(9): 984-9). IPF fibroblasts, compared with fibroblasts from normal human lung, display slower growth rates, higher rates of apoptosis, and a profibrotic secretory phenotype (Ramos et al. Am J Respir Cell Mol Biol. 2001 May; 24(5): 591-8). In addition, fibrotic lung fibroblasts, unlike normal fibroblasts and more consistent with cancer-derived cells, are able to survive in the absence of attachment and interaction with extracellular matrix and neighboring cells, displaying anchorage-independent growth in soft agar (Torry et al. J Clin Invest. 1994 April; 93(4): 1525-32).

IPF Fibroblasts Demonstrate Impaired Mechanosensitive Signaling

It has long been viewed that myofibroblasts, with their contractile properties, are key effector cells in wound healing (Barkauskas & Noble. Am J Physiol Cell Physiol. 2014 Jun. 1; 306(11): C987-96). After facilitating wound closure, these cells typically disappear from granulation tissue, presumably via a de-differentiation mechanism (Kisseleva et al. Proc Natl Acad Sci USA. 2012 Jun. 12; 109(24): 9448-53), a clearance mechanism (Friedman. Proc Natl Acad Sci USA. 2012 Jun. 12; 109(24): 9230-1; Krizhanovsky et al. Cell. 2008 Aug. 22; 134(4): 657-67), or a combination of both. In IPF, myofibroblasts are believed to persist inappropriately, leading to progressive fibrosis. It has been shown that mechanical stimuli (e.g., stiff extracellular matrix with myofibroblasts generating high contractile forces) can be converted to fibrogenic signals (e.g., liberation of TGF-βI), which, in turn, maintains the myofibroblastic phenotype (Wipff et al. J Cell Biol. 2007 Dec. 17; 179(6): 131 1-23). An intrinsic mechanotransduction mechanism that promotes myofibroblast differentiation regulated by nuclear translocation of MKL1 (myocardin-related transcription factor-A, a mechanosensitive transcription factor that is involved in activating the fibrotic gene program) that results in stiff matrix-promoting aSMA gene expression by normal lung fibroblasts (Huang et al. Am J Respir Cell Mol Biol. 2012 September; 47(3): 340-8) has been described. These experiments were done by comparing (myo)fibroblast behavior on polyarylamide hydrogels of differing stiffness. This intrinsic mechanotransduction is mediated by the Rho kinase (ROCK) pathway, which regulates myofibroblast contractility, differentiation, and survival experiments (Zhou et al. J Clin Invest. 2013 March; 123(3): 1096-108). These experiments also demonstrated that preexisting myofibroblasts can be shuttled to an apoptotic fate if their contractile properties are disrupted (Barkauskas & Noble. Am J Physiol Cell Physiol. 2014 Jun. 1; 306(1 1): C987-96).

Mechanisms and Pathways of Fibrosis

Because ECM-secreting myofibroblasts are central to the pathogenesis of fibrotic diseases, fibrosis research has focused on elucidating the molecular and immunological mechanisms that initiate, maintain and terminate the differentiation of quiescent fibroblasts into actively proliferating, ECM-producing myofibroblasts (Wynn & Ramalingam. Nat Med. 2012 Jul. 6; 18(7): 1028-40). The mechanisms that control progressive fibrosis, however, are largely unknown (Li et al. J Exp Med. 2011 Jul. 4; 208(7): 1459-71).

Origin of Profibrotic Fibroblasts

The origin of fibrotic fibroblasts has been of great interest in understanding the pathogenesis of tissue fibrosis (Dulauroy et al. Nat Med. 2012 August; 18(8): 1262-70; Hung et al. Am J Respir Crit Care Med. 2013 Oct. 1; 188(7): 820-30; LeBleu et al. Nat Med. 2013 February; 19(2): 227-31; Rock et al. Proc Natl Acad Sci USA. 2011 Dec. 27; 108(52): E1475-83). Fibrotic fibroblasts in IPF are extremely heterogeneous (Jordana et al. Am Rev Respir Dis. 1988 March; 137(3): 579-84.), suggesting they may be raised from different cell types, or represent different stages of activation, or are influenced by their milieu (Zeisberg and Kalluri. Am J Physiol Cell Physiol. 2013 Feb. 1; 304(3): C216-25.). The heterogeneous nature of fibroblasts is also demonstrated in mouse models (Rock et al. Proc Natl Acad Sci USA. 2011 Dec. 27; 108(52): E1475-83). A common, long-sought-after, marker for fibroblasts has not been identified, because fibroblasts seem to be a heterogeneous cell population (Zeisberg and Kalluri. Am J Physiol Cell Physiol. 2013 Feb. 1; 304(3): C216-25), and the major source of profibrotic fibroblasts has not yet been discovered.

Markers such as a smooth muscle actin (a SMA, encoded by ACTA2 gene, the actin isoform that predominates within smooth-muscle cells and plays an important role in fibrogenesis (Cherng et al. J Am Sci. 2008: 4(4): 7-9)), FSP1/S100A4 (fibroblast-specific protein 1/S100A4-positive protein, a marker of fibroblasts in different organs undergoing tissue remodeling (Osterreicher et al. Proc Natl Acad Sci USA. 2010 Nov. 23; 108(1): 308-13)), Vimentin (a major constituent of the intermediate filament (IF) family of proteins, known to maintain cellular integrity and provide resistant against stress (Satelli & Li. Cell Mol Life Sci. 201 1 September; 68(18): 3033-46)), Desmin (a major muscle-specific IF protein essential for structural integrity and muscle function (Paulin & Li. Exp Cell Res. 2004 Nov. 15; 301 (1): 1-7)), and PDGFRB (platelet-derived growth factor receptor, beta polypeptide, a tyrosine kinase receptor for members of the PDGF family) are either not exclusively expressed by fibroblasts or specific to all fibroblasts (Krenning et al. J Cell Physiol. 2010 November; 225(3): 631-7; Rock et al., Proc Natl Acad Sci USA. 2011 Dec. 27; 108(52): E1475-83).

It has been suggested that several cellular sources contribute to fibrotic fibroblasts. For example, it has been suggested that circulating fibrocytes or other bone marrow-derived progenitor cells of extrapulmonary origin might be able to migrate to active fibrotic lesions and become fibrotic cells (Andersson-Sjoland et al. Int J Biochem Cell Biol. 2008; 40(10) 2129-40; Hashimoto et al. J Clin Invest. 2004 January; 1 13(2): 243-52; Phillips et al. J Clin Invest. 2004 August; 1 14(3): 438-46). Experimental fibrosis models have led to the proposal that epithelial cells (Degryse et al. Am J Physiol Lung Cell Mol Physiol. 2010 October; 299(4): L442-52; Kim et al. Proc Natl Acad Sci USA. 2006 Aug. 29; 103(35): 13180-5; Tanjore et al. Am J Respir Crit Care Med. 2009 Oct. 1; 180(7): 657-65) or endothelial cells (Hashimoto et al. Am J Respir Cell Mol Biol. 2010 August; 43(2): 161-72; LeBleu et al. Nat Med. 2013 August; 19(8): 1047-53; Li and Jimenez. Arthritis Rheum. 201 1 August; 63(8): 2473-83) may be able to transform to stromal cells in experimental fibrosis models. However, a genetic tracing approach showed that lung epithelial cells such as Sftpc-lineage AEC2s, as well as Scgb1 a1-lineage club cells, do not give rise to fibroblasts (Rock et al. Proc Natl Acad Sci USA. 2011 Dec. 27; 108(52): E1475-83). Genetic fate-mapping methods have confirmed that pericytes proliferate during fibrogenesis, where the pericytes were trace-labeled with either NG2, FoxJ1 or Foxdl (Hung et al. Am J Respir Crit Care Med. 2013 Oct. 1; 188(7): 820-30 Rock et al. Proc Natl Acad Sci USA. 2011 Dec. 27; 108(52): E1475-83). However, neither these cells nor their progeny express high levels of the myofibroblast marker aSMA; expression of aSMA marks myofibroblasts and smooth muscle cells. Some perivascular GN1+ cells with distinct characteristics of mesenchymal stem cells (MSCs) can differentiate into myofibroblasts in tissue fibrosis (Kramann et al. Cell Stem Cell. 2015 Jan. 8; 16(1): 51-66).

Intrinsic, Autocrine and Epigenetic Mechanisms Regulate Fibrosis

Hyaluronan (HA) is a nonsulfated glycosaminoglycan produced by mesenchymal cells and a variety of tumor cells and has been suggested to contribute to tumor metastasis through interactions with its cognate cell surface receptor CD44 (Arch et al. Science. 1992 Jul. 31; 257(5070): 682-5; Toole, Nat Rev Cancer. 2004 July; 4(7): 528-39). HA is nearly ubiquitous in its distribution, being present in the interstitial spaces of most animal tissues. Accumulation of HA has been shown to be a characteristic of disorders that are associated with progressive tissue fibrosis (Bjermer et al. Thorax. 1989 February; 44(2): 126-31). HA has also been shown to accumulate in the lungs of rats after bleomycin-induced injury, and has a role in regulating the inflammatory response (Jiang et al. Nat Med. 2005 November; 11 (11: 1173-9; Noble et al. Physiol Rev. 2011 January; 91 (1): 221-64). Three HA synthase genes (HAS1-3) have been identified. Targeted deletion of HAS2 generates an embryonic lethal phenotype caused by impaired cardiac development (Camenisch et al. J Clin Invest. 2000 August; 106(3): 349-60).

CD44 is a ubiquitous cell-surface glycoprotein involved in myriad processes, comprising over 25 signaling super pathways (www.genecards.org/cgi-bin/carddisp.pl?gene-CD44). CD44 is a major cell surface receptor for HA and plays an important role in inflammatory cell recruitment (Mikecz et al. Nat Med. 1995 June; 1 (6): 558-63; Siegelman et al. J Leukoc Biol. 1999 August; 66(2): 315-21) and activation (Nobel et al. J Clin Invest. 1993 June; 91 (6): 2368-77; DeGrendele et al. Science. 1997 Oct. 24; 278 (5338): 672-5), as well as tumor growth and metastasis (Lesley et al. Adv Immunol. 1993; 54: 271-335). CD44 is necessary for hematopoietic cells to clear HA from sites of inflammation (Teder et al. Science. 2002 Apr. 5; 296(5565: 155-8), and is critical for the recruitment of fibroblasts to the injury sites (Acharya et al., J Cell Sci. 2008 May 1; 121 (Pt 9): 1393-402.).

The inexorable course of progressive fibrosis in IPF has led to the theory that fibroblasts may take on properties similar to metastatic cancer cells that overexpress HA. Consistent with this concept is a recent study showing that IPF fibroblasts have abnormalities in translational control (Larsson et al. PLoS One. 2008 Sep. 16; 3(9): e3220) that can be found in cancer cells. One of the seminal properties of metastatic cancer cells is the ability to invade basement membrane. It has been suggested that fibrotic fibroblasts and myofibroblasts drive fibrogenesis by invasion and destruction of basement membrane and that HA-CD44 interactions may regulate this process.

Mechanical modifications to the ECM and cell-intrinsic changes in fibroblasts and epithelial cells have been shown to contribute to the progression of fibrosis by maintaining the activation of the following fibrogenic pathways (Wynn & Ramalingam. Nat Med. 2012 Jul. 6; 18(7): 1028-40).

Biomarkers in IPF

Researchers have made efforts to identify diagnostic and predictive biomarkers to improve the drug development in IPF, especially in view of the devastating effects and lethality of IPF and its unknown origin (Zhang & Kaminski. Curr Opin Pulm Med. 2012 September; 18(5): 441-6).

Diagnostic Biomarkers

In the context of peripheral blood markers, multiple molecules have been shown to distinguish patients with IPF from controls. These include KL-6 (a high molecular weight glycoprotein used as a serum marker for interstitial lung diseases (Yokoyama et al. Respirology. 2006 March; 1 1 (2): 164-8), surfactant proteins SP-A and SP-D (collagenous glycoproteins investigated at biomarkerse for IPF (Greene et al. ur Respir J. 2002 March; 19(3): 439-46)), matrix metalloproteases MMP-1 and MMP-7 (interstitial collagenases investigated as biomarkers for IPF (Rosas et al. PLoS Med. 2008 Apr. 29; 5(4): e93)), SPP1 (glycoprotein observed to be upregulated in human IPF (Pardo et al. PLoS Med. 2005 September; 2(9): e251)) and YKL-40 (a mammalian chitinase-like protein observed to be upregulated in IPF (Furuhashi et al. Respir Med. 2010 August; 104(8): 1204-10). However, the diagnostic utility of any of these molecules is in doubt as the majority of the studies usually only compared IPF to control individuals, and when smoking controls or other interstitial lung diseases ("ILDs") were analyzed, they often had increased levels of the markers (Zhang & Kaminski. Curr Opin Pulm Med. 2012 September; 18(5): 441-6).

Disease Susceptibility Biomarkers

Multiple mutations associated with familial and sporadic forms of IPF have been reported including mutations in surfactant (Thomas et al. Am J. Respir Crit Care Med. 2002 May 1; 165(9): 1322-8; Lawson et al. Thorax. 2004 November; 59(1 1): 977-80; Wang et al. Am J Hum Genet. 2009 January; 84(1): 52-9) and telomerase proteins (Armanios et al. N Engl J Med. 2007 Mar. 29; 356(1 3): 1317-26; Tsakiri et al. Proc Natl Acad Sci USA. 2007 May 1; 1 04(18): 7552-7). Polymorphisms within TERT (telomerase reverse transcriptase) have also been identified [single nucleotide polymorphism (SNP) in intron 2 of the TERT gene-rs2736100] in a genome-wide association (GWA) study including a derivation cohort of 159 sporadic IPF patients and 934 controls as well as a replication cohort of 83 sporadic IPF cases and 535 controls (Mushiroda et al. J Med Genet. 2008 October; 45(10): 654-6). Leukocyte telomere shortening was found in 24% of familial pulmonary fibrosis and 23% of sporadic IPF cases when compared to control individuals ($P=2.6\chi 10-8$) (Cronkhite et al. Am J Respir Crit Care med. 2008 Oct. 1; 1 78(7): 729-37) in a study that contained 201 control individuals, 59 probands with familial pulmonary fibrosis and 73 sporadic pulmonary fibrosis cases without TERT or TERC (telomerase RNA component) mutations. Other genetic variants have been described in IPF, including genes encoding ELMOD2 (a GPTase-activating protein (Hodgson et al. Am J Hun Genet. 2006 July; 79(1): 149-54)), IL-1 (cytokine involved in immune and inflammatory responses (Hutyrova et al. Am j Respir Crit Care Med. 2002 Jan. 15; 165(2): 148-51)), CR-1 (complement receptor 1, a transmembrane glycoprotein, (Zorzetto et al. Am J Respir Crit Care Med. 2003 Aug. 1; 168(3): 330-4)), IL1 2p40 and IFN-γ (IL-12 p40 subunit and IFN-Y (Latsi et al. Respir Res. 2003. 4:6)), NOD2/CARD15 (an intracellular innate immune sensor (Zorzetto et al. Sarcoidosis Vase Diffuse Lung Dis. 2005 October; 22(3): 180-5)), MMP-1 (matrix metalloproteinase-1 (ENA-78, epithelial neutrophil activating peptide 78; VEGF, vascular endothelial growth factor; IP-10, interferon-inducible protein 10 (Checa et al. Hum Genet. 2008 December; 124(5): 465-72)), ENA-78, IP-10 and VEGF (Liu et al. Zhonghua Yi Xue Za Zhi. 2009 Oct. 20; 89(38): 2690-4)), CD16b (Fey receptor 1 Mb (Bournazos et al. Lung. 2010 December; 188(6): 475-81)), IL-8 (interleukin 8 (Ahn et al. Respir Res. 2011 Jun. 8; 1 2:73)) and HER2 (human epidermal growth factor receptor 2 (Martinelli et al. Mol Biol Rep. 201 1 October; 38(7): 461 3-7)), but the majority have not been replicated. Recently, a SNP in the putative promoter of MUCSB (rs35705950) that was associated with familial interstitial pneumonia (minor allele frequency of 34%, $P=1\ 0.2\chi\ 1\ 0"15$) and IPF (minor allele frequency of 38%, $P=2.5\times 10"37$) has been identified; in controls, the minor allele frequency was 9% (Seibold et al. N Engl J Med. 2011 Apr. 21; 364(1 6): 1 503-1 2). The odds ratio was 6.2 [95% confidence interval (CI) 3.7-10.4] for familial interstitial pneumonia and 8.3 (95% CI 5.8-1 1 0.9) for IPF (Id.). These findings were simultaneously confirmed by other researchers in an independent case-control study that included 341 IPF and 801 control individuals (Zhang et al. N Engl J Med. 2011 Apr. 21; 364(16): 1 576-7). The minor-allele frequency was 34.3% in patients with IPF and 11.1% in controls (allelic association, $P=7.6\chi 10$-40). (Id.).

Prognostic Biomarkers

High blood concentrations of KL-6, also known as MUC-1, repeatedly have been shown to be predictive of decreased survival in IPF (Zhang & Kaminski. Curr Opin Pulm Med. 2012 September; 18(5): 441-6). Most studies have been limited by cohort size and lack replication, but are still highly consistent and support the use of KL-6 in disease stratification (Ishikawa et al. Respir Investig. 201 2 March; 50(1): 3-13. Other studies have shown that serum CCL18 (chemokine (C-C motif) ligand 18) levels were able to predict the outcomes in IPF (higher serum CCL18 concentrations were predictive of decreased total lung capacity, decreased forced vital capacity and increased mortality (Prasse et al. Am J Respir Crit Care Med. 2009 Apr. 1 5; 179(8): 717-23)), that high serum SP-A concentrations was a predictor of early mortality in IPF (Kinder et al. Chest. 2009 June; 1 35(6): 1 557-63), and that high serum concentrations of YKL-40 distinguished two groups with distinct survival patterns with the hazard ratio for serum YKL-40 (cut-off 79 ng/ml) as 1 0.9 (95% CI 1 0.9-63.8, P<0.01) (Korthagen et al. Respir Med. 201 1 Janruary; 1 05(1): 106-13). Researchers using a targeted proteomic approach screened 95 proteins in the plasma of 140 IPF patients (derivation cohort) and validated the results in a replication cohort (101 patients) (Richards et al. Am J Respir Crit Care Med. 2012 Jan. 1; 185(1): 67-76). High plasma concentrations of MMP-7, ICAM-1 and IL-8 were predictive of poor overall survival in both cohorts (Id.). The derivation cohort was used to derive a personal clinical and molecular mortality prediction index (PCMI) using the step AIC approach (Venables & Ripley. Modern applied statistics with S. New York: Springer; 2002). This index [PCMI=1 14 χl (Male)+ 2χ (100%–FVC % predicted)+3χ (1 00%–Dlco % predicted)+1 1 1 χl (MMP-7≥4.3 ng/ml)] was highly predictive of mortality in the replication cohort with a C-index for early mortality of 84 (Richards et al. Am J Respir Crit Care Med. 2012 Jan. 1; 1 85(1): 67-76).

Similarly, changes in circulating blood cell populations have been associated with outcome. Recent studies have demonstrated in a cohort of 51 patients that increases in circulating fibrocytes predicted poor prognosis (Moeller et al. Am J Respir Crit Care Med. 2009 Apr. 1; 179(7): 588-94)

and other researchers have observed that downregulation of CD28 in circulating CD4 T cells was a marker of poor prognoses in a cohort of 89 IPF patients (Gilani et al. PLoS One. 2010 Jan. 29; 5(1): e8959.

Disease Activity Markers

There is no real definition of the disease activity of IPF. It is conceivable that KL-6, SP-A and MMP-7 are markers of alveolar epithelial cell injury and CCL-18 a marker of alveolar macrophage activation; however, at present, markers for some of the processes that happen in IPF such as deposition of excess collagen have not yet been discovered. Mechanistically, the biomarker that may be tied most closely to disease pathogenesis is MMP-7, a pluripotent matrix metalloprotease expressed in alveolar type II cells. MMP-7 is a WNT/β-catenin pathway target molecule (He et al. J Am Soc Nephrol. 2012 February; 23(2): 294-304), suggesting that increases of MMP-7 are reflective of aberrant WNT/β catenin that has been described in IPF (Chilosi et al. Am J Pathol. 2003 May; 1 62(5): 1495-502; Konigshoff et al. J Clin Invest. 2009 April; 1 19(4): 772-87). MMP-7 knockout mice are relatively protected from bleomycin-induced fibrosis, suggesting that it is mechanistically involved in the fibrosis pathways (Zuo et al. Proc Natl Acad Sci USA. 2002 Apr. 30; 99(9): 6292-7). However, at present, there is no data to support MMP-7 as a marker of disease activity (Id.).

Acute exacerbations of IPF (AE-IPF) are episodes of decline in respiratory status without an identifiable cause (Collard et al. Am J Respir Crit Care Med. 2007 Oct. 1; 176(7): 636-43), that lead to significant mortality (Song et al. Eur Respir J. February; 37(2): 356-63) Of the previous markers mentioned, KL-6 has been mostly widely studied in this context (Ishikawa et al. Respir Investig. 2012 March; 50(1): 3-1 3; Collard et al. Am J Physiol Lung Cell Mol Physiol. 201 0 July; 299(1): L3-7; Satoh et al. J Intern Med. 2006 November; 260(5): 429-34). It appears that AE-IPF is associated with increases in blood KL-6, although the mechanisms have not yet been elucidated. Comparisons of gene expression in the lungs of patients with AE-IPF lungs to stable IPF (Konishi et al. Am J Respir Crit Care med. 2009 Jul. 1 5; 180(2): 167-75) has identified 579 differentially expressed genes, and did not find any indication of infectious or inflammatory cause. Researchers have found increases in a-defensins, a group of innate antimicrobial peptides, in the mRNA levels as well as in the plasma protein level of AE-IPF patients, suggesting that they should be evaluated as biomarkers for acute exacerbations (Zasloff. Nature. 2002 Jan. 24; 41 5(6870): 389-95).

Drug Efficacy Biomarkers

There are no drug efficacy biomarkers in IPF (Zhang & Kaminski. Curr Opin Pulm Med. 2012 September; 1 8(5): 441-6).

Utility and Limitations of Animal Models in the Study of IPF

Bleomycin, a chemotherapeutic agent used in the treatment of certain human cancers, has been the most commonly used agent to induce pulmonary fibrosis in animal models of the disease. Bleomycin can be administered through a variety of routes including intratracheal (most common), intraperitoneal, oropharyngeal aspiration, and via osmotic pump. It induces DNA strand breaks (Lown & Sim. Biochem Biophys Res Commun. 1977 Aug. 22; 77(4): 1 150-7) and oxidative injury (Sausville et al. Biochem Biophys Res Commun. 1976 Dec. 6; 73(3): 814-22), thus leading to epithelial injury, inflammation, and ultimately fibrosis (Barkauskas & Noble. Am J Physiol Cell Physiol. 2014 Jun. 1; 306(1 1): C987-96).

The bleomycin model is well-documented and the best characterized murine model in use today to demonstrate efficacy of a particular drug or protein kinase inhibitor in the post-inflammatory/pre-fibrotic/fibro-preventive stages (Vittal, R. et al., J Pharmacol Exp Ther., 321 (1):35-44, 2007; Vittal, R. et al., Am J Pathol., 166(2):367-75, 2005; Hecker L. et al., Nat Med., 15(9):1077-81, 2009).

The antibiotic bleomycin was originally isolated from *Streptomyces verticillatus* (Umezawa, H. et al., Cancer 20: 891-895, 1967). This antibiotic was subsequently found to be effective against squamous cell carcinomas and skin tumors (Umezawa, H., Fed Proc, 33: 2296-2302, 1974); however, its usefulness as an anti-neoplastic agent was limited by dose-dependent pulmonary toxicity resulting in fibrosis (Muggia, F. et al., Cancer Treat Rev, 10: 221-243, 1983). The delivery of bleomycin via the intratracheal route (generally 1 0.25-4 U/kg, depending on the source) has the advantage that a single injection of the drug produces lung injury and resultant fibrosis in rodents (Phan, S. et al., Am Rev Respir Dis 121: 501-506, 1980; Snider, G. et al., Am Rev Respir Dis. 1 17: 289-297, 1978; Thrall, R. et al., Am J Pathol, 95: 1 17-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., Toxicol Appl Pharmacol., 100(3):465-73, 1989). Subsequently, alveolar inflammatory cells are cleared, fibroblast proliferation is noted, and extracellular matrix is synthesized (Schrier D. et al., Am Rev Respir Dis., 127(1):63-6, 1983). The development of fibrosis in this model can be seen biochemically and histologically by day 14 with maximal responses generally noted around days 21-28 (Izbicki G. et al., Ant J Exp Pathol., 83(3): 1 1 1-9, 2002; Phan, S. et al., Chest, 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., Am J Pathol., 95(1):1 17-30, 1979; Goldstein R., et al., Am Rev Respir Dis., 120(1):67-73, 1979; Starcher B. et al., Am Rev Respir Dis., 1 17(2):299-305, 1978; however, other reports demonstrate a self-limiting response that begins to resolve after this period (Thrall R. et al., Am J Pathol., 95(1):1 17-30, 1979; Phan, S. et al., Chest, 83(5 Suppl): 44S-45S, 1983; Lawson W. et al., Am J Pathol. 2005; 167(5):1267-1277). While the resolving nature of this model does not mimic human disease, this aspect of the model offers an opportunity for studying fibrotic resolution at these later time points.

The pathology generated by intratracheal bleomycin is not fully representative of IPF histology. The diagnostic criteria for IPF (usual interstitial pneumonia) are threefold: 1) nonuniform pattern of disease involvement with normal lung interspersed with diseased lung, 2) architectural distortion (honeycomb change and/or scar), and 3) presence of fibroblast foci, presumed to be indicative of current ongoing disease. These structures are covered by hyperplastic AEC2s (Katzenstein et al. Hum Pathol. 2008 September; 39(9): 1275-94). While not a diagnostic criterion, human IPF specimens also typically include areas of alveolar collapse with incorporation of basal lamina (Myers & Katzenstein. Chest. 1988 December; 94(6): 1309-11). While experimental bleomycin fibrosis can recapitulate alveolar collapse and cystic air spaces 14 days after intratracheal instillation (Moore et al. Am J Respir Cell Mol Biol), it is also typically characterized by significant neutrophilic inflammation and there rarely exist examples of the hyperplastic AEC2s that are pathognomonic for the human disease (Degryse et al.

Am J Physiol Lung Cell Mol Physiol. 2010 October; 299(4): L442-52; Moore et al. Am J Respir Cell Mol Biol. 2013 August; 49(2): 167-79; Barkauskas & Noble. Am J Physiol Cell Physiol. 2014 Jun. 1; 306(11): C987-96).

Unlike IPF, however, the fibrosis generated after intratracheal bleomycin is not progressive. Following intratracheal bleomycin, collagen content (as assessed by hydroxyproline assay) peaks around 21-28 days postinjury (Izbicki et al. Int J Exp Pathol. 2002 June; 83(3): 111-9). Recent reports suggest that the fibrosis induced by a single exposure to bleomycin is self-limited and can display some resolution/regression during the weeks following the injury (Chung et al. Am J Respir Cell Mol Biol. 2003 September; 29(3 Pt 1): 375-80; Lawson et al. Am J Pathol. 2005 November; 167(5): 1267-77; Rock et al. Proc Natl Acad Sci USA. 2011 Dec. 27; 108(52): E1475-83; Barkauskas & Noble. Am J Physiol Cell Physiol. 2014 Jun. 1; 306(1 1): C987-96).

Investigators have tried to optimize the bleomycin fibrosis model to better replicate the histology associated with human IPF. In one such study, a repetitive bleomycin model was developed in an attempt to recapitulate the recurrent alveolar injury that is hypothesized to drive IPF pathogenesis. Degryse et al. (Am J Physiol Lung Cell Mol Physiol. 2010 October; 299(4): L442-52) describe a model in which they administered intratracheal bleomycin biweekly up to eight times. The histology from this repetitive injury model revealed prominent hyperplastic AEC2s in areas of fibrosis as well as more of a temporally heterogeneous pattern of lung injury (i.e., fibrotic scar next to hyperplastic AEC2s next to normal tissue). Further, the fibrosis that developed seemed to persist until at least 10 weeks after the last bleomycin dose. While the histological results of this model do seem more consistent with human IPF, the time-intensive nature of this model may limit its applicability in the laboratory (Barkauskas & Noble. Am J Physiol Cell Physiol. 2014 Jun. 1; 306(1 1): C987-96).

Despite its imperfections, the bleomycin model of pulmonary fibrosis remains the most common in the study of fibrotic lung disease. Other fibrosis generating models include the following (reviewed in Moore et al. Am J Physiol Lung Cell Mol Physiol. 2008 February; 294(2): L152-60): granulomatous inflammation (Jakubzick et al Am J Pathol. 2003 May; 162(5): 1475-86), fluorescein isocyanate (Kolodsick et al. J Immunol. 2004 Apr. 1; 172(7): 4068-76; Roberts et al. J Pathol. 1995 July; 176(3): 309-18), irradiation-induced (McDonald et al. Radiother Oncol. 1993 March; 26(3): 212-8), adenosine deaminase deficiency (Chunn et al. Am J Physiol Lung Cell Mol Physiol. 2006 March; 290(3): L579-87), and murine gamma-herpesvirus (which is typically used to augment a fibrotic response to another stimulus) (Gangadharan et al. J Leukoc Biol. 2008 July; 84(1): 50-8; Lok et al. Eur Respir J. 2002 November; 20(5): 1228-32). While many investigators are now designing experiments with human IPF tissue/cells, the field at large still relies heavily on murine models of the disease. A murine model of IPF that recapitulates the disease more faithfully than bleomycin would be most welcome (Barkauskas & Noble. Am J Physiol Cell Physiol. 2014 Jun. 1; 306(11): C987-96).

The Programmed Cell Death Pathway

Programmed death (PD-1)/PD-1 ligands are members of the B7/CD28 family that consists of PD-1 receptor (CD279) and its ligands, PD-L1 (CD274) and PD-L2 (CD273). RGMb has been identified as another binding partner for PD-L2. The PD-1/PD-1 ligands pathway plays a role in immune suppression. PD-1 was generally thought to be expressed on activated T cells, natural killer (NK) cells, B cells and some myeloid cells. PD-L1 is expressed on immune cells such as T cells, B cells, and DCs, while PD-L2 is expressed on DCs and macrophages (8). Recent studies have shown that PD-L1 and PD-L2 are widely expressed on various cancer cells (8-12). Expression of PD-ligands prevents cancer cells from being killed by T cells and promotes cancer progression (5). Targeting the PD-1 pathway has been recognized as an effective immunotherapy for different cancers (5).

PD-1 is known as an immunoinhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

PD1 Signalling

Signaling through PD-1 is triggered by engagement with its known ligands, PD-L1 and PD-L2. Despite the name of the receptor, cell death is not the primary result of engagement. Instead, the primary effect of this signaling is to inhibit TCR and essential costimulatory signals (FIG. 9). Upon engagement, PD-1 clusters and localizes to the TCR complex (Yokosuka T, et al. J. Exp. Med. 2012; 209:1201-1217). PD-1 can inhibit the phosphorylation of the TCR CD3ζ chains and Zap-70, which are early steps following TCR engagement (Parry R V, et al. Mol. Cell. Biol. 2005; 25:9543-9553; Sheppard K A, et al. FEBS Lett. 2004; 574:37-41). Downstream activation of Ras, an enhancer of survival and proliferation, is also inhibited by PD-1 (Patsoukis N, et al. Sci Signal. 2012). Along with the direct TCR signals, CD28 delivers costimulatory signals by activation of the phosphatidylinositol 3-kinase (PI3K)/Akt pathway. PD-1 signaling represses this pathway by blocking PI3K activation (Yokosuka et al. 2012). This action begins with the phosphorylation of the intracellular immunoreceptor tyrosine-based switch motif (ITSM) and immunoreceptor tyrosine-based inhibitory motif (ITIM). The ITSM appears to be the more important of these two motifs (Sheppard et al., 2004; Chemnitz J M, et al. J. Immunol. 2004; 173:945-954). The phosphorylated ITSM recruits the tyrosine phosphatase, SHP-2. This phosphatase leads to the inactivation of PI3K and downstream inhibition of the Akt pathway. Of note, although both PD-1 and CTLA-4 inhibit T cells, the mechanisms of these two receptors are distinct.

The downstream signaling effects through PD-1 are numerous (FIG. 9). As with other coinhibitory receptors, a decrease in T cell proliferation is seen along with a decrease in several inflammatory cytokines including tumor necrosis factor α (TNF-α), interferon γ (IFN-γ), and interleukin 2 (IL-2) (Freeman G J, et al. J. Exp. Med. 2000; 192:1027-1034). PD-1 signaling also appears to be self-reinforcing. Activation of this receptor protects the transcription factor, FoxO1, from degradation which leads to expression of more PD-1 (Staron M M, et al. Immunity. 2014; 41:802-814).

More global effects are also seen on T cells. It has been shown that PD-L1 plays an important role in the differentiation of inducible regulatory T cells (iTregs) both in vitro and in vivo (Francisco L M, et al. J. Exp. Med. 2009; 206:3015-3029). PD-L1 expression on not only APCs but also other non-hematopoietic tissues may be capable of this induction. PD-1 signaling is accompanied by a down-regulation of phospho-Akt, mechanistic target of rapamycin (mTOR), S6, and Erk2 and an upregulation of phosphatase and tensin homolog (PTEN) (Francisco et al. 2009). Work has also demonstrated that the Akt signaling pathway is a strong inhibitor of iTreg development which supports the proposed mechanism of the generation of PD-L1-induced Tregs (Haxhinasto S, et al. J. Exp. Med. 2008; 205: 565-574).

PD-1 Inhibitors

"Programmed cell death 1 ligand 1", "PD-L1", or "CD274," also known as B7-H; B7H1; PDL1; PD-L1; PDCD1L1; PDCD1LG1, B7 homolog 1, PDCD1 ligand 1, and programmed cell death ligand 1, has been shown to be constitutively expressed on mouse T and B cells, DCs, macrophages, mesenchymal stem cells, and bone marrow-derived mast cells. PD-L1 expression is also found on a wide range of nonhematopoietic cells and is upregulated on a number of cell types after activation. Upon IFN-γ stimulation, PD-L1 is expressed on T cells, NK cells, macrophages, myeloid DCs, B cells, epithelial cells, and vascular endothelial cells (Flies D B and Chen L (2007) *J Immunother.* 30 (3): 251-60). PD-L1 is notably expressed on macrophages. Further information on PD-L1 is provided, for example in the NCBI Gene database at www.ncbi.nlm.nih.gov/gene/29126 (which is incorporated herein by reference as of the date of filing this application).

PD-L1/CD274

As used herein, "programmed cell death 1 ligand 1" is used interchangeably with the term "PD-L1" (and optionally any of the other recognized names listed above) refers to the naturally occurring gene that encodes a programmed cell death 1 ligand 1 protein. The amino acid and complete coding sequences of the reference sequence of the human PDL-1 gene may be found in, for example, GenBank Accession No. GI: 390979638 (RefSeq Accession No. NM_001267706.1; SEQ ID NO:1) and GenBank Accession No. GI: 292658763 (RefSeq Accession No. NM_014143.3; SEQ ID NO: 5). Further splice variants are provided, for example, in Grzywnowicz et al., PLoS One. 2012; 7:e35178 which is incorporated herein by reference. Mammalian orthologs of the human PD-L1 gene may be found in, for example, GI: 755563510 (RefSeq Accession No. XM_006527249.2, mouse; SEQ ID NO: 2); GI: 672040129 (RefSeq Accession No. XM_006231248.2, rat; SEQ ID NO: 3); GenBank Accession Nos. GI: 544494555 (RefSeq Accession No. XM_005581779.1, cynomolgus monkey; SEQ ID NO: 4).

CD274/PD-L1 comprises seven exons, the first of which is noncoding and contains the 5' untranslated region (UTR). The next three exons contain the signal sequence, IgV-like domain, and IgC-like domains, respectively. The transmembrane domain and the intracellular domains are contained in the next two exons (exons 5 and 6). The last exon contains intracellular domain residues plus the 3' UTR. The intracellular domain of CD274/PD-L1 is short, only about 30 amino acids (aa), and highly conserved in all reported species. There is no known function for the intracellular tail of CD274/PD-L1. There is one reported splice variant of CD274/PD-L1 in humans consisting of a sequence lacking the immunoglobulin variable (IgV)-like domain encoded in exon 2. This mutant should not be able to bind PD-1, although the function of this splice variant has not yet been reported. No splice variants have been identified for mouse CD274/PD-L1. The binding interface of CD274/PD-L1 to one of its known ligands, PD-1, is via its IgV-like domain (Keir M E et al., 2008. Annu Rev Immunol. 26:677-704).

CD274/PD-L1 has been shown to be constitutively expressed on mouse T and B cells, DCs, macrophages, mesenchymal stem cells, and bone marrow-derived mast cells. CD274/PD-L1 expression is also found on a wide range of nonhematopoietic cells and is upregulated on a number of cell types after activation. Upon IFN-γ stimulation, PD-L1 is expressed on T cells, NK cells, macrophages, myeloid DCs, B cells, epithelial cells, and vascular endothelial cells (Flies D B and Chen L 2007: J Immunother. 30 (3): 251-60). PD-L1 is notably expressed on macrophages. In the mouse, it has been shown that classically activated macrophages (induced by type I helper T cells or a combination of LPS and interferon-gamma) greatly upregulate PD-L1 (Loke P and Allison JP, 2003: Proc. Natl. Acad. Sci. U.S.A. 100 (9): 5336-41). Alternatively, macrophages activated by IL-4 (alternative macrophages), slightly upregulate PD-L1, while greatly upregulating PD-L2. It has been shown by STAT1-deficient knock-out mice that STAT1 is mostly responsible for upregulation of PD-L1 on macrophages by LPS or interferon-gamma, but is not at all responsible for its constitutive expression before activation in these mice. Both type I and type II interferons (IFNs) upregulate PD-L1. Analyses of the human CD274/PD-L1 promoter demonstrate that both constitutive and inducible CD274/PD-L1 expression are dependent on two IFN regulatory factor-1 (IRF-1) binding sites that are between 200 and 320 by upstream of the transcriptional start site (Lee et al., 2006. FEBS Letters 580: 755-762), and these IRF-1 binding sites are also found in mouse. Several studies have examined which signaling pathways are required for PD-L1 expression by using pharmacological inhibitors. PD-L1 expression in cell lines is decreased when MyD88, TRAF6, and MEK are inhibited. JAK2 has also been implicated in PD-L1 induction. Loss or inhibition of phosphatase and tensin homolog (PTEN), a cellular phosphatase that modifies phosphatidylinositol 3-kinase (PI3K) and Akt signaling, increases post-transcriptional PD-L1 expression in cancers (Keir M E et al., 2008. Annu Rev Immunol. 26:677-704).

PD-L1 expression is involved in evasion of immune responses involved in chronic infection, e.g., chronic viral infection (including, for example, HIV, HBV, HCV and HTLV, among others), chronic bacterial infection (including, for example, *Helicobacter pylori*, among others), and chronic parasitic infection (including, for example, *Schistosoma mansoni*). PD-L1 expression has been detected in a number of tissues and cell types including T-cells, B-cells, macrophages, dendritic cells, and nonhematopoietic cells including endothelial cells, hepatocytes, muscle cells, and placenta.

PD-L1 can influence immune responses by engaging PD-1 or B7-1 (CD80) and modifying TCR or BCR signaling, but can also deliver signals into PD-L1 expressing cells, i.e., reverse signaling through PD-L1. Surface plasmon resonance studies demonstrate specific and unique interaction between both PD-L1 and B7-1, with an affinity of 1.7 µM, and an affinity of 0.5 µM for the interaction between PD-L1 and PD-1. Chemical cross-linking studies indicate that PD-L1 and B7-1, like PD-L1 and PD-1, can also interact through their IgV-like domains. The PD-L1:B7-1 interface overlaps at least partially with the putative PD-L1:PD-1 interface. B7-1:PD-L1 interactions can induce an inhibitory signal into T cells. Ligation of PD-L1 on CD4 T cells by B7-1, or ligation of B7-1 on CD4 T cells by PD-L1, delivers a functionally significant, inhibitory signal. Because both PD-L1 and B7-1 are expressed on T cells, B cells, DCs, and macrophages, there is the potential for bidirectional interactions between B7-1 and PD-L1 on these cell types. In addition, PD-L1 on nonhematopoietic cells may interact with B7-1 as well as with PD-1 on T cells to regulate cells (Keir M E et al., 2008. Annu Rev Immunol. 26:677-704).

PD-1 and its ligands have important roles in regulating immune defenses against microbes that cause acute and chronic infections. The PD-1:PD-L pathway appears to be a key determinant of the outcome of infection, regulating the delicate balance between effective antimicrobial immune defenses and immune-mediated tissue damage.

PD-L2/CD273

"Programmed cell death 1 ligand 2", "PD-L2", or "CD273," also known as PDCD1LG2, B7 dendritic cell molecule, B7-DC, PD-1-ligand 2, PDCD1 ligand 2, butyrophilin B7-DC and programmed death ligand 2, has been identified as a second ligand for PD1 (Latchman et al., Nat Immunol. 2001 March; 2(3):261-8). Further information on PD-L2 is provided, for example in the NCBI Gene database at www.ncbi.nlm.nih.gov/gene/80380 (which is incorporated herein by reference as of the date of filing this application).

PD-1

The term "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773. The PD-1 gene encodes a 55 kDa type I transmembrane protein (Agata et al. (1996) Int Immunol. 8:765-72). Although structurally similar to CTLA-4, PD-1 lacks the MYPPY motif that is important for B7-1 and B7-2 binding. Two ligands for PD-1 have been identified, PD-L1 (B7-H1) and PD-L2 (B7-DC) that have been shown to downregulate T cell activation upon binding to PD-1 (Freeman et al. (2000) J. Exp. Med. 192:1027-34; Carter et al. (2002) Eur. J. Immunol. 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9).

To date, only limited treatments or therapies exist for the treatment of IPF, and there is a substantial unmet need for effective treatments that can alter the course of IPF by slowing or reversing disease progression. Many clinical trials have ended unsuccessfully after showing negligible patient benefit or high incidence of side effects.

The described invention provides, in part, methods for treating progressive pulmonary fibrosis, such as idiopathic pulmonary fibrosis (IPF), and methods of improving lung function, by targeting the programmed death pathway including the PD-1 receptor (PDCD1, or CD279), PD-1 ligands PD-L1 (CD274) and PD-L2 (CD273), and PD-L2 binding partner repulsive guidance molecule b (RGMb, aka Dragon). The invention is based on the discovery from studies of invasive IPF fibroblasts that the immune checkpoint PD-1 system plays a role in tissue fibrosis. Thus, blocking the programmed death pathway signaling may represents an approach for treating subject with pulmonary fibrosis.

SUMMARY OF THE INVENTION

According to one aspect, the described invention provides a method for reducing progression of progressive pulmonary fibrosis in a subject, comprising administering to the subject a pharmaceutical composition comprising a therapeutic amount of a therapeutic agent, wherein the therapeutic amount is effective to modulate s the programmed cell death pathway, and to treat the progressive pulmonary fibrosis.

According to another aspect, the present invention provides a method for improving lung function in a subject, comprising administering to the subject a pharmaceutical composition comprising a therapeutic amount of a therapeutic agent, wherein the composition is effective to modulate the programmed cell death pathway, and to improve lung function. According to one embodiment, the subject is suffering from pulmonary fibrosis. According to another embodiment, the pulmonary fibrosis is idiopathic pulmonary fibrosis (IPF). According to one embodiment, the therapeutic agent is selected from the group consisting of: an inhibitor of programmed death-1 (PD-1) receptor, an inhibitor of programmed death receptor-ligand 1 (PD-L1), an inhibitor of programmed death receptor-ligand 1 (PD-L2), an inhibitor of repulsive guidance molecule B (RGMb), and a combination thereof. According to a related embodiment, the therapeutic agent is an antibody, or an antigen binding fragment thereof, a small molecule inhibitor or a nucleic acid inhibitor. According to a further related embodiment, the therapeutic agent is selected from the group consisting of MDX-1106 (nivolumab, OPDIVO), Merck 3475 (MK-3475, pembrolizumab, KEYTRUDA), CT-011 (pidilizumab), MEDI-0680 (AMP-514), PDR001, REGN2810, BGB-108, and BGB-A317, AMP-224, ONO-4538, BMS-936558, MK-3475, pembrolizumab, lambrolizumab, YW243.55.S70, MPDL3280A (atezolizumab), MEDI4736 (durvalumab), MDX-1105, MSB0010718C (avelumab), MDX-1105, MEDI4736, AMP-224 (B7-DCIg), and CA-170. According to another embodiment, the inhibitor of programmed death receptor-ligand 1 (PD-L1) is selected from the group consisting ofnivolumab (OPDIVO), pembrolizumab (KEYTRUDA), atezolizumab (TECENTRIQ), avelumab (BAVENCIO), durvalumab (IMFINZI) and ipilmumab (YERVOY). According to one embodiment, the inhibitor of programmed death receptor-ligand 2 (PD-L2) is selected from AMP-224 (B7-DCIg), and CA-170. According to another further embodiment, the therapeutic amount of the therapeutic agent may be effective to decrease the expression or biological activity of one or more of PD1, PD-L1, PD-L2, or RGMb compared to an untreated control. According to another embodiment, the therapeutic agent is effective (a) to decrease the invasiveness of pulmonary fibroblasts in the subject; (b) to decrease the migration of pulmonary fibroblasts in the subject; (c) to decrease cell adhesion of pulmonary fibroblasts in the subject; (d) to decrease pulmonary fibroblast proliferation and differentiation; (e) to decrease extracellular matrix production; (f) to decrease myofibroblast activation; or (g) a combination thereof. According to some embodiments, the composition comprises a first therapeutic agent effective to modulate the programmed cell death pathway in combination with a second therapeutic agent effective to modulate the programmed cell death pathway. According to another embodiment, the composition comprises a therapeutic agent effective to modulate s the programmed cell death pathway and a focal adhesion kinase (FAK) inhibitor. According to embodiment, the composition is effective to reduce a symptom of pulmonary fibrosis compared to an untreated control. According to some embodiments, the composition is effective to reduce lung hydroxyproline levels compared to an untreated control. According to one embodiment, the composition is effective to reduce lung density of the subject compared to an untreated control. According to one embodiment, the composition is effective to reduce total cell count (TCC) in bronchoalveolar lavage fluid (BALF) from the subject compared to an untreated control.

According to another aspect, the invention features a method of identifying a subject eligible for treatment for pulmonary fibrosis, with a composition comprising a therapeutic amount of a therapeutic agent effective to modulate the programmed cell death pathway, the method comprising assaying lung tissue of the subject for PD1, PD-L1, PD-L2, or RGMb expression levels, wherein, if PD1, PD-L1, PD-L2, or RGMb expression levels in the lung tissue of the subject are upregulated with respect to a control subject not suffering from pulmonary fibrosis, treating the subject by administering to the subject a composition containing a therapeutic amount of one or more of an inhibitor of PD-1 receptor, an inhibitor of PD-L1, an inhibitor of PD-L2 or an inhibitor of RGMb. According to some embodiments, the pulmonary fibrosis is idiopathic pulmonary fibrosis (IPF). According to one embodiment, the inhibitor of the PD-1 receptor, the inhibitor of PD-L1, the inhibitor of PD-L2 and the inhibitor of RGMb is an antibody, or an antigen binding fragment thereof, a small molecule inhibitor or a nucleic acid inhibitor. In a further embodiment, the therapeutic agent decreases the expression or biological activity of one or more of PD1, PD-L1, PD-L2, or RGMb. According to one embodiment, the subject is administered a first therapeutic agent in combination with at least a second therapeutic agent. In another embodiment, the therapeutic agent is administered in combination with a focal adhesion kinase (FAK) inhibitor. According to one embodiment, the composition is effective to decrease the expression or biological activity of one or more of PD1, PD-L1, PD-L2, or RGMb compared to an untreated control. In a further embodiment, the composition is effective to decrease lung hydroxyproline levels in the subject compared to an untreated control. According to one embodiment, the composition is effective to reduce lung density of the subject compared to an untreated control. According to one embodiment, the composition is effective to decrease total cell count (TCC) in bronchoalveolar lavage fluid (BALF) from the subject compared to an untreated control, According to one aspect, the described invention provides a method of identifying a subject eligible for treatment for lung cancer with a composition comprising a therapeutic amount of a therapeutic agent effective to modulate the programmed cell death pathway, the method comprising assaying lung tissue of the subject for PD1, PD-L1, PD-L2, or RGMb expression levels, wherein, if PD1, PD-L1, PD-L2, or RGMb expression levels in the lung tissue of the subject are upregulated with respect to a control subject not suffering from lung cancer, and treating the subject by administering to the subject a composition containing a therapeutic amount of one or more of an inhibitor of PD-1 receptor, an inhibitor of PD-L1, an inhibitor of PD-L2 or an inhibitor of RGMb. According to one embodiment, the inhibitor of the PD-1 receptor, the inhibitor of PD-L1, the inhibitor of PD-L2 and the inhibitor of RGMb is an antibody, or an antigen binding fragment thereof, a small molecule inhibitor or a nucleic acid inhibitor. According to one embodiment, a therapeutic amount of the therapeutic agent is effective to decrease the expression or biological activity of one or more of PD1, PD-L1, PD-L2, or RGMb. According to one embodiment, the subject is administered a first therapeutic agent in combination with at least a second therapeutic agent. According to one embodiment, the therapeutic agent is administered in combination with a focal adhesion kinase (FAK) inhibitor. According to one embodiment, the composition is effective to decrease the expression or biological activity of one or more of PD1, PD-L1, PD-L2, or RGMb compared to an untreated control.

BRIEF DESCRIPTION OF THE DRAWINGS

FIG. 10A is a schematic representation of an in vitro invasion assay: Lung fibroblasts were seeded in the upper part of transwells. Cells attached to the bottom of Matrigel-coated membrane after 24h were considered invasive fibroblasts. Cells that remained on top of Matrigel-coated membrane were considered non-invasive fibroblasts. Invasive and non-invasive IPF lung fibroblasts (n=9 per group) were isolated using the Matrigel invasion assay. RNA-seq was used to compare their gene expression. A total of 1,405 differentially expressed (DE) genes were identified with FDR<0.01 and |log 2FC|>0.5; among them, 719 DE genes were up-regulated, and 686 DE genes were down-regulated. FIG. 10B shows Principal Component Analysis (PCA) for the RNASeq Data. FIG. 10C shows a heatmap of all DE genes in RNA-seq data. FIG. 10D shows RNA-seq (n=9 per group) analysis of RGMB expression in invasive and noninvasive IPF lung fibroblasts. Data are mean±sem. **P<0.01 by student's t test.

FIG. 11A and FIG. 11B show invasive lung fibroblasts promoted interstitial lung fibrosis in a humanized SCID IPF model. Masson trichrome staining of collagen on lung sections is shown in the images in FIG. 11A. FIG. 11B is a graph showing hydroxyproline content in lung tissues from NSG mice injected with invasive and non-invasive IPF lung fibroblasts (n=6 per group). Scale bars: 1 mm (top panel), 100 µm (middle and lower panels). FIG. 11C-FIG. 11H show up-regulation of immune checkpoint CD274 and PDCD1LG2 in invasive lung fibroblasts. RNA-seq (n=9 per group) (FIG. 11C and FIG. 11D) and qRT-PCR analysis (n=6 per group) (FIG. 11E and FIG. 11F) of CD274 and PDCD1LG2 expression in invasive and non-invasive IPF lung fibroblasts. FIG. 11G and FIG. 11H show cell surface expression of CD274 and PDCD1LG2 expression in invasive and non-invasive IPF lung fibroblasts. FIG. 11I shows violin plots of CD274 expressing cells within total mesenchymal cells of lung single cell homogenate from IPF (n=3) or healthy subjects (n=4). Throughout, data are mean±sem. *P<0.05; **P<0.01 by student's t test (b-f).

As shown in FIG. 13D, CD274 expression (indicated by arrows) was co-localized with a small portion of PDGFRβ+ (lung fibroblast marker) and Endomucin+ (endothelial cell marker) cells, but not with □-SMA+ cells (myofibroblast marker). CD274 expression was also found adjacent to CD8 T cells FIG. 14B shows Western blot analysis of CD274, PDCD1LG2, TP53 and GAPDH in IPF lung fibroblasts treated Si-CTL, Si-CD274, Si-PDCD1LG2 or Si-TP53. GAPDH served as equal loading control in western blot. FIG. 14F shows representative images of migrated and invasive Si-CTL or Si-TP53 lung fibroblasts. Darker staining indicates more migration and invasion. Scale bar: 1 mm. FIG. 14G is a graph showing the cell migration or invasion index that was calculated as the number of cells attached to the bottom of control or Matrigel-coated membrane after 24h, normalized to respective Si-CTL lung fibroblasts (n=3 per group). Throughout, data are mean±sem *P<0.05, P<0.01, *P<0.01 by student's t test.

FIG. 19A shows representative images of migrating and invasive CD274$^{low}$ and CD274$^{high}$ IPF fibroblasts treated with VS4718 or vehicle DMSO. Scale bar: 1 mm. FIG. 19B and FIG. 19C are graphs that show cell migration index or invasion index, which was calculated as the number of cells attached to the bottom of control or Matrigel-coated membrane after 24h, normalized to respective CD274$^{low}$ lung fibroblasts. FIG. 19D shows Western blot analyses of CD274, PDCD1LG2, P-FAK1, and FAK1. GAPDH served as equal loading control. FIG. 19E, FIG. 19G, and FIG. 19I show hydroxyproline contents in lung tissues. FIG. 19F, FIG. 19H and FIG. 19J show Masson trichrome staining of collagen on lung sections from NSG mice injected with CD274$^{low}$ and CD274$^{high}$ IPF fibroblasts treated with VS4718, vehicle control CMC-Na, or from NSG mice receiving gRNA-CTL or CD274 KO lung fibroblasts (n=6 per group), or from NSG mice injected with CD274$^{high}$ IPF fibroblasts treated with □-CD274 (n=12 per group) or isotype control IgG (n=12 for DO-35 IgG, n=11 for D35-63 IgG). Scale bars (FIG. 19F, FIG. 19H): 1 mm (top panel), 100 μm (middle and lower panels). Throughout, data are mean±sem. *P<0.05; **P<0.01 by student's t test (FIG. 19B, FIG. 19C, FIG. 19E, FIG. 19G).

DETAILED DESCRIPTION OF THE INVENTION

Figure 1:
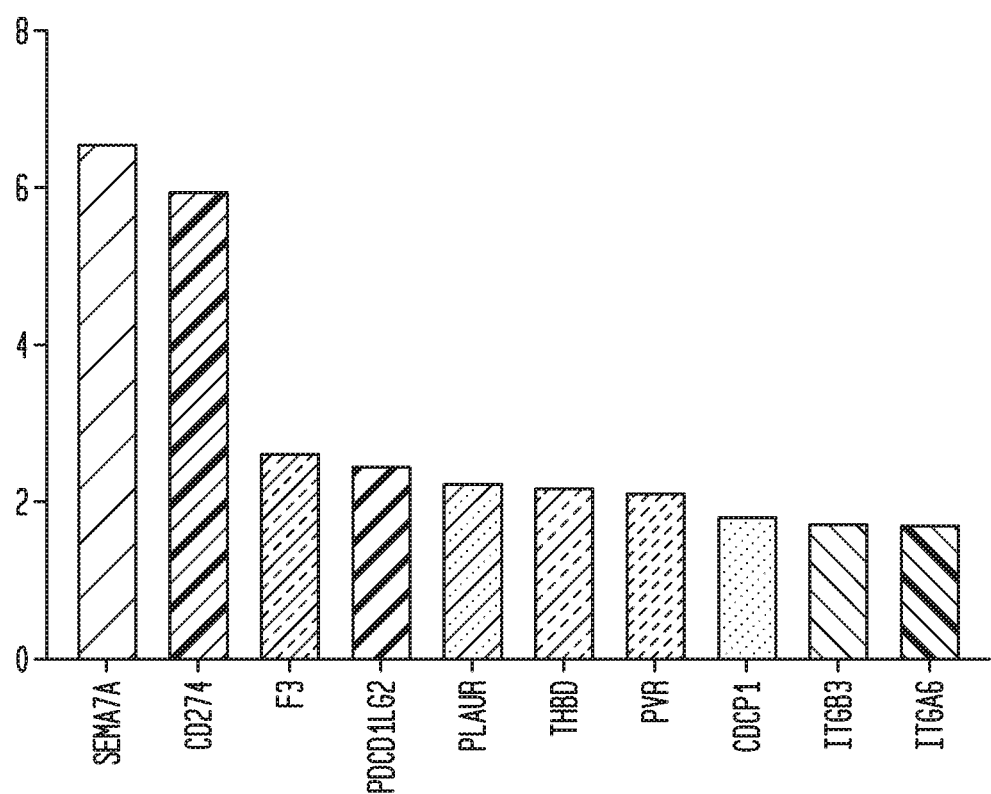
FIG. 1 is a graph that shows up-regulation of cell surface markers between invasive and non-invasive fibroblasts isolated from IPF patient lung determined by RNA-Seq analysis. Fold-change of cell surface markers SEMA7A, CD274, F3, PDCD1LG2, PLAUR, THBD, PVR, CDCP1, ITGB3, ITGA6 is shown on the y-axis. Cells that passed through matrigel were invasive fibroblasts, while the cells that remained on the top were noninvasive fibroblasts.

The described invention provides, in part, methods for treating progressive pulmonary fibrosis, such as idiopathic pulmonary fibrosis (IPF), and methods of improving lung function, by targeting the programmed death pathway including the PD-1 receptor (PDCD1, or CD279), PD-1 ligands PD-L1 (CD274) and PD-L2 (CD273), and PD-L2 binding partner repulsive guidance molecule b (RGMb, aka Dragon).

The following detailed description discloses methods for treating diseases and disorders that would benefit from inhibition or targeting the programmed death pathway.

I. Definitions

In order that the described invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to" or "including, without limitation."

The term "or" is used herein to mean, and is used interchangeably with, the term "and/or," unless context clearly indicates otherwise. For example, a nucleoside with a modified base or a modified sugar is understood to include the options of a nucleoside with a modified base, a nucleoside with a modified sugar, and a nucleoside with a modified base and a modified sugar.

The term "about" is used herein to mean within the typical ranges of tolerances in the art. For example, "about" can be understood as about 2 standard deviations from the mean. According to certain embodiments, about means+10%. According to certain embodiments, about means+5%. When about is present before a series of numbers or a range, it is understood that "about" can modify each of the numbers in the series or range.

The term "at least" prior to a number or series of numbers (e.g. "at least two") is understood to include the number adjacent to the term "at least", and all subsequent numbers or integers that could logically be included, as clear from context. When at least is present before a series of numbers or a range, it is understood that "at least" can modify each of the numbers in the series or range.

As used herein, "up to" as in "up to 10" is understood as up to and including 10, i.e., 0, 1, 2, 3, 4, 5, 6, 7, 8, 9, or 10.

Ranges provided herein are understood to include all individual integer values and all subranges within the ranges.

As used herein, the term "in combination with," is not intended to imply that the therapy or the therapeutic agents must be administered at the same time and/or formulated for delivery together, although these methods of delivery are within the scope described herein. The therapeutic agents can be administered concurrently with, prior to, or subsequent to, one or more other additional therapies or therapeutic agents.

The term "activate" is used to refer to stimulating a cell in a resting state to become active. This causes biochemical and functional changes in the activated cell.

The term "active agent" refers to the ingredient, component or constituent of the compositions of the described invention responsible for the intended therapeutic effect.

The term "additive" is used herein to refer to the combined effect of two drugs predicted from the sum of the quantitative effects of the individual components.

The term "administer" as used herein means to give or to apply. The term "administering" as used herein includes in vivo administration, as well as administration directly to tissue ex vivo.

The term "antibody" is used herein to refer to a protein, e.g., an immunoglobulin chain or fragment thereof, comprising at least one immunoglobulin variable domain sequence. The term "antibody" includes, for example, a monoclonal antibody (including a full length antibody which has an immunoglobulin Fc region). In an embodiment, an antibody comprises a full length antibody, or a full length immunoglobulin chain. In an embodiment, an antibody comprises an antigen binding or functional fragment of a full length antibody, or a full length immunoglobulin chain. Examples of antigen-binding fragments of an antibody molecule include: (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); (viii) a single domain antibody. These antibody fragments are obtained using conventional techniques known to those with skill in the art, and the fragments are screened for utility in the same manner as are intact antibodies.

The term "attenuate" and its various grammatical forms is used herein to refer to weakened or thinned.

The term "binding" and its other grammatical forms is used to mean a lasting attraction between chemical substances.

The term "binding specificity" as used herein is meant to reer to both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "biocompatible" as used herein refers to causing no clinically relevant tissue irritation, injury, toxic reaction, or immunological reaction to living tissue.

The term "biodegradable" as used herein refers to material that will break down actively or passively over time by simple chemical processes, by action of body enzymes or by other similar biological activity mechanisms.

The term "bronchoalveolar lavage" (BAL) is used herein to refer to a medical procedure in which a bronchoscope is passed through the mouth or nose into the lungs and fluid is squirted into a small part of the lung and then collected for examination. "Bronchoalveolar lavage fluid" (BALF) is used herein to refer to the fluid collected from a BAL procedure.

The term "carrier" as used herein describes a material that does not cause significant irritation to an organism and does not abrogate the biological activity and properties of the compound of the composition of the described invention. Carriers must be of sufficiently high purity and of sufficiently low toxicity to render them suitable for administration to the mammal being treated. The carrier can be inert, or it can possess pharmaceutical benefits. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "cell adhesion" is used herein to refer to the process by which cells interact and attach to a surface, substrate or another cell.

The term "clinical outcome" or "outcome" is used to refer to a specific result or effect that can be measured. Examples of outcomes include progression-free survival and overall survival.

The term "compatible" as used herein refers to the components of a composition are capable of being combined with each other in a manner such that there is no interaction that would substantially reduce the efficacy of the composition under ordinary use conditions.

The term "component" as used herein refers to a constituent part, element or ingredient.

The terms "composition" and "formulation" are used interchangeably herein to refer to a product of the described invention that comprises all active and inert ingredients.

The term "decrease" and its various grammatical forms is used herein to refer to a diminution, a reduction, an attenuation or abatement of the degree, intensity, extent, size, amount, density or number of occurrences, events or characteristics.

The term "differentiation" is used herein to refer to the process by which an immature cell becomes specialized in order to perform a specific function. According to certain embodiments, "differentiation" refers to fibroblast differentiation in fibrosis.

The term "drug" as used herein refers to any substance which is intended for use in the diagnosis, cure, mitigation, treatment or prevention of disease or disorder, or to affect the structure or function of the body The term "effective amount," is used herein to include the amount of an agent (e.g. a PD1 inhibitor, a PD-L1 inhibitor, a PD-L2 inhibitor or a focal adhesion kinase (FAK) inhibitor) that, when administered to a patient for treating a subject having pulmonary fibrosis, especially IPF, is sufficient to effect treatment of the disease (e.g., by diminishing, ameliorating or maintaining the existing disease or one or more symptoms of disease or its related comorbidities). The "effective amount" may vary depending on the agent, how it is administered, the disease and its severity and the history, age, weight, family history, genetic makeup, stage of pathological processes, the types of preceding or concomitant treatments, if any, and other individual characteristics of the patient to be treated. An effective amount includes an amount that results in a clinically relevant change or stabilization, as appropriate, of an indicator of a disease or condition.

The term "expression" as used herein refers to the action of a gene in the production of a protein or phenotype.

The term "extracellular matrix" (ECM) is used herein to refer to a network of material such as proteins and polysaccharides that are secreted locally by cells and remain closely associated with them to provide structural, adhesive and biochemical signalling support.

The term "inhibit" and its various grammatical forms is used to refer to a restraining, blocking, or limiting of the range or extent.

The term "immune checkpoint inhibitor" is used herein to refer to a type of drug that blocks certain proteins made by some tapes of immune system cells, such as T cells, which help keep immune responses in check, and can keep T cells from killing abnormal cells. When these proteins are blocked, the immune system can then respond to the abnormal cells. Examples of checkpoint proteins found on T cells include PD-1/PD-L1.

The term "immunomodulatory agent" is used herein to refer to an agent capable of augmenting or diminishing immune responses.

The term "invasion" or "invasiveness" is used herein to refer to a process that includes penetration of and movement of cells through surrounding tissues.

The term "lung function" is used herein to refer to a measure of how well the lung is working. Several types of lung function tests may be conducted, including spirometry, pulse oximetry, exercise stress test or arterial blood gas test.

Additionally, hydroxyproline levels, lung density and total cell count in bronchoalveolar lavage fluid may be used to assess lung function.

Hydroxyproline is a major component of collagen, where it serves to stabilize the helical structure. Because hydroxyproline is largely restricted to collagen, the measurement of hydroxylproline levels can be used as an indicator of collagen content. A decrease in hydroxyproline levels relative to an untreated control subject with pulmonary fibrosis, or relative to a subject with pulmonary fibrosis at a time point prior to treatment, are indicative of an increase in lung function.

Pulmonary fibrosis involves gradual exchange of normal lung parenchyma with fibrotic tissue, which corresponds with an increase in lung density. Increase in lung density can be measured by computed tomography (CT). A decrease in lung density relative to an untreated control, or relative to a patient at a time point prior to treatment, are indicative of an increase in lung function.

Bronchoalveolar lavage (BAL), performed during fiberoptic bronchoscopy, is a useful adjunct to lung biopsy in the diagnosis of nonneoplastic lung diseases. BAL is able to provide cells and solutes from the lower respiratory tract and may provide important information about diagnosis and yield insights into immunologic, inflammatory, and infectious processes taking place at the alveolar level. BAL has been helpful in elucidating the key immune effector cells driving the inflammatory response in IPF (Costabel and Guzman Curr Opin Pulm Med, 7 (2001), pp. 255-261). Increase in polymorphonuclear leukocytes, neutrophil products, eosinophils, eosinophil products, activated alveolar macrophages, alveolar macrophage products, cytokines, chemokines, growth factors for fibroblasts, and immune complexes have been noted in BAL of patients with IPF. [Id.]. Accordingly, lung function may be assessed by determining the amounts of polymorphonuclear leukocytes, neutrophil products, eosinophils, eosinophil products, activated alveolar macrophages, alveolar macrophage products, cytokines, chemokines, growth factors for fibroblasts, and immune complexes in BAL fluid in an untreated control, or relative to a patient at a time point prior to treatment, where a decrease in the amounts of polymorphonuclear leukocytes, neutrophil products, eosinophils, eosinophil products, activated alveolar macrophages, alveolar macrophage products, cytokines, chemokines, growth factors for fibroblasts, and/or immune complexes is indicative of an increase in lung function.

It is to be understood that any one or these tests may be used in combination with another, an combined with lung function tests, for example, but not limited to, spirometry, pulse oximetry, exercise stress test or arterial blood gas test.

The term "maximum tolerated dose" as used herein refers to the highest dose of a drug that does not produce unacceptable toxicity.

The term "migration" is used herein to refer to movement of a cell from one place or location to another.

The term "modulate" and its various grammatical forms is used to refer to adjusting, or changing.

The term "nucleic acid inhibitor" is used herein to refer to single-stranded nucleic acid molecules, double stranded nucleic acid molecules or expression constructs that causes a decrease in the expression of PD-1, PD-L1, PD-L2 or RGMb. Nucleic acid inhibitors include, for example, single stranded nucleic acid molecules, e.g., antisense nucleic acids, and double stranded nucleic acids such as siRNA, shRNA, dsiRNA (see, e.g., US Patent publication 20070104688, incorporated by reference herein). As used herein, double stranded nucleic acid molecules are designed to be double stranded over at least 12, preferably at least 15 nucleotides. Double stranded nucleic acid molecules can be a single nucleic acid strand designed to hybridize to itself, e.g., an shRNA. It is understood that a nucleic acid inhibitor can be administered as an isolated nucleic acid. Alternatively, the nucleic acid inhibitor can be administered as an expression construct to produce the inhibitor in the cell. According to certain embodiments, the nucleic acid inhibitor can include one or more chemical modifications to improve the activity and/or stability of the nucleic acid inhibitor. Such modifications are well known in the art. The specific modifications to be used will depend, for example, on the type of nucleic acid inhibitor.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" is used to refer to a sequence used as a basis for sequence comparison. A reference sequence may be a subset or the entirety of a specified sequence; for example, as a segment of a full-length cDNA or gene sequence, or the complete cDNA or gene sequence.

The term "comparison window" is used to refer to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. (see Henikoff & Henikoff, Proc. Natl. Acad. Sci. USA, 1989, 89: 10915).

In addition to calculating percent sequence identity, the BLAST algorithm also performs a statistical analysis of the similarity between two sequences (see, e.g., Karlin & Altschul, Proc. Natl. Acad. Sci. USA, 1993, 90: 5873-5787). One measure of similarity provided by the BLAST algorithm is the smallest sum probability (P(N)), which provides an indication of the probability by which a match between two nucleotide sequences would occur by chance. A number of low-complexity filter programs may be employed to reduce such low-complexity alignments. For example, the SEG (Wooten and Federhen, Comput. Chem., 1993, 17:149-163) and XNU (Claverie and States, Comput. Chem., 1993, 17: 191-201) low-complexity filters may be employed alone or in combination.

The term "overall survival" (or "OS") as used herein refers to the length of time from either the date of diagnosis or the start of treatment for a disease that patients diagnosed with the disease are still alive. "Overall survival rate" refers to the percentage of people in a study or treatment group who are still alive for a certain period of time after they were diagnosed with or started treatment for a disease.

The term "percentage of sequence identity" is used to refer to the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "pharmaceutical composition" is used herein to refer to a composition that is employed to prevent, reduce in intensity, cure or otherwise treat a target condition or disease.

The term "pharmaceutically acceptable carrier" as used herein refers to any substantially non-toxic carrier useable for formulation and administration of the composition of the described invention in which the product of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "pharmacologic effect", as used herein, refers to a result or consequence of exposure to an active agent.

The term "proliferation" and its other grammatical forms as used herein means multiplying or increasing in number.

The term "Programmed Death Ligand-1" ("PD-L1") or "cluster of differentiation 274" ("CD274") as used herein refers to a particular polypeptide expressed in a cell. PD-L1 is also known as CD274, B7-H1, PDCD1L1, PDCD1LG1, and PDL1.

The term "progression" is used herein to refer to the course of a disease, such as pulmonary fibrosis, as it becomes worse.

The term "progression-free survival" (or PFS) is used herein to refer to the length of time during and after the treatment of a disease that a patient lives with the disease but it does not get worse.

The term "reduce" and its various grammatical forms is used herein to refer to a diminution, a decrease, an attenuation or abatement of the degree, intensity, extent, size, amount, density or number of occurrences, events or characteristics.

The term "reduce" or "decrease" and the like in the context of the expression or biological activity of one or more of PD1, PD-L1, PD-L2, or RGMb refers to a statistically significant decrease in such level. The decrease can be, for example, at least 20%, 25%, 30%, 35%, 40%, 45%, 50%, 55%, 60%, 65%, 70%, 75%, 80%, 85%, 90%, or 95%. According to certain embodiments, the decrease is down to a level accepted as within the range of normal for an individual without such disorder which can also be referred to as a normalization of a level. For example, According to certain embodiments, the methods include a clinically relevant inhibition of expression of PD1, PD-L1, PD-L2, or RGMb, e.g. as demonstrated by a clinically relevant outcome after treatment of a subject with a therapeutic agent to decrease the expression or biological activity of one or more of PD1, PD-L1, PD-L2, or RGMb, compared to an untreated control.

According to certain embodiments, the reduction or decrease is the normalization of the level of a sign or symptom of a disease, a reduction in the difference between the subject level of a sign of the disease and the normal level of the sign for the disease (e.g., upper level of normal, lower level of normal, average of upper and lower level of normal). For example, reduction can be understood as normalization of lung hydroxyproline levels compared to a control level, or decreasing lung hydroxyproline levels compared to a level prior to treatment with a therapeutic agent. According to certain embodiments, the methods include a clinically relevant decrease in lung hydroxyproline levels, lung density or total cell count, e.g. as demonstrated by a clinically relevant outcome after treatment of a subject with a therapeutic agent to decrease the expression or biological activity of one or more of PD1, PD-L1, PD-L2, or RGMb. According to certain embodiments, the reduction or decrease is the normalization of the level of a disease marker, a reduction in the difference between the subject level of a disease marker and the normal level of a disease marker (e.g., upper level of normal, lower level of normal, average of upper and lower level of normal). Disease markers are described infra.

The term "RNA molecule" or "ribonucleic acid molecule," as used herein, refers to a linear, single-stranded polymer composed of ribose nucleotides, that is synthesized by transcription of DNA or by copying of RNA. It encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein.

The term, "sequence identity" or "identity" in the context of two nucleic acid sequences refers to the residues in the two sequences which are the same when aligned for maximum correspondence over a specified comparison window.

The term "small interfering RNAs," which comprises both microRNA (miRNA) and small interfering RNA (siRNA), are small noncoding RNA molecules that play a role in RNA interference. siRNAs are synthesized from double-stranded segments of matched mRNA via RNA-dependent RNA polymerase, and siRNAs regulate the degradation of mRNA molecules identical in sequence to that of the corresponding siRNA, resulting in the silencing of the corresponding gene and the shutting down of protein synthesis. The main mechanism of action of siRNA is the mRNA cleavage function. There are no genes that encode for siRNAs. siRNAs can also silence gene expression by triggering promoter gene methylation and chromatin condensation. miRNAs are synthesized from an unmatched segment of RNA precursor featuring a hairpin turn, and miRNAs are encoded by specific miRNA genes as short hairpin pri-miRNAs in the nucleus. miRNAs are also small noncoding RNAs, but they seem to require only a 7- to 8-base-pair "seed" match between the 5' region of the miRNA and the 3'UTR of the target. While the majority of miRNA targets are translationally repressed, degradation of the target mRNA can also occur. The main mechanism of action of miRNA may be the inhibition of mRNA translation, although the cleavage of mRNA is also an important role (Ross et al. Am J Clin Pathol. 2007; 128(5): 830-36).

The term "small molecule inhibitor" is used herein to refer to a low molecular weight (<900 daltons) organic compound that is used to inhibit a disease or process in a subject, e.g., inhibit progressive pulmonary fibrosis.

The term "subject" is used herein to refer to an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder, or condition that would benefit from a therapeutic agent that inhibits the programmed cell death pathway; a human at risk for a disease, disorder, or condition that would benefit from a therapeutic agent that inhibits the programmed cell death pathway; or a human having a disease, disorder or condition that would benefit from a therapeutic agent that inhibits the programmed cell death pathway.

The term "substantial identity" of polynucleotide sequences is used to refer to a polynucleotide comprising a sequence that has at least 70% sequence identity, at least 80% sequence identity, at least 90% sequence identity and at least 95% sequence identity, compared to a reference sequence using one of the alignment programs described using standard parameters.

The term "synergistic" is used herein to refer to an interaction of two or more drugs when their combined effect is greater than the sum of the effects seen when each drug is given alone.

The term "therapeutic agent" as used herein refers to a drug, molecule, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably.

The terms "therapeutic amount", "therapeutically effective amount" or an "amount effective" of one or more of the therapeutic agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. It is preferred generally that a maximum dose be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

Therapeutic window, potency and efficacy. The term "potency" as used herein refers to efficacy, effectiveness, or strength of a drug. The potency of a drug is the reciprocal of dose, and has the units of persons/unit weight of drug or body weight/unit weight of drug. Relative potency compares the relative activity of drugs in a series relative to some prototypic member of the series. "Efficacy" connotes the property of a drug to achieve the desired response, and maximum efficacy denotes the maximum achievable effect.

The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., 10th Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the drug is to be administered by transdermal absorption, a highly potent drug is required, since the capacity of the skin to absorb drugs is limited.

The slope of the dose-effect curve reflects the mechanism of action of a drug. The steepness of the curve dictates the range of doses useful for achieving a clinical effect.

Maximal or clinical efficacy refers to the maximal effect that can be produced by a drug. Maximal efficacy is determined principally by the properties of the drug and its receptor-effector system and is reflected in the plateau of the curve. In clinical use, a drug's dosage may be limited by undesired effects.

Biological variability. An effect of varying intensity may occur in different individuals at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the MEC. Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the minimum effective concentration (MEC) for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

II. Therapeutic Agents

Provided herein are methods of treating or preventing progressive pulmonary fibrosis and methods of improving lung function in a subject, comprising administering to a subject an amount of a therapeutic agent that is effective to inhibit the programmed cell death pathway. For example, the therapeutic agent is an inhibitor of programmed death-1 (PD-1) receptor, an inhibitor of programmed death receptor-ligand 1 (PD-L1), an inhibitor of programmed death receptor-ligand 1 (PD-L2) or an inhibitor of repulsive guidance molecule B (RGMb).

According to some embodiments, the PD-1 inhibitor is a molecule that is effective to inhibit the binding of PD-1 to its ligand binding partners. According to some embodiments, the PD-1 ligand binding partners include PD-L1, PD-L2, or both PD-L1 and PD-L2. According to another embodiment, a PD-L1 inhibitor is a molecule that is effective to inhibit the binding of PD-L1 to one or more of its binding partners. According to some embodiments, PD-L1 binding partners include PD-1, B7-1 or both PD-1 and B7-1. According to another embodiment, the PD-L2 inhibitor is a molecule that is effective to inhibit the binding of PD-L2 to its binding partners. According to some embodiments, a PD-L2 binding partner is PD-1. According to some embodiments, the inhibitor may be, e.g., an antibody, or an antigen binding fragment thereof, a small molecule inhibitor, a nucleic acid inhibitor or an oligopeptide.

PD1 Inhibitors

The described invention includes antibodies, or antigen binding fragments thereof, small molecules, oligopeptides, and/or nucleic acid inhibitors of PD1. According to some embodiments, any PD1 inhibitor described in the art or commercially available can be used in the presently described methods.

According to one embodiment, the PD-1 binding antagonist is an anti-PD-1 antibody (e.g., a human antibody, a humanized antibody, or a chimeric antibody). According to some embodiments, the anti-PD-1 antibody is selected from the group consisting of MDX-1106 (nivolumab, OPDIVO), Merck 3475 (MK-3475, pembrolizumab, KEYTRUDA), CT-011 (pidilizumab), MEDI-0680 (AMP-514), PDR001, REGN2810, BGB-108, and BGB-A317. According to some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). According to some embodiments, the PD-1 inhibitor is AMP-224. According to some embodiments, the PD-1 inhibitor is MDX-1106-04, ONO-4538, BMS-936558, or OPDIVO. Merck 3475, also known as MK-3475, pembrolizumab, lambrolizumab, KEYTRUDA, or SCH-900475, is an anti-PD-1 antibody.

PD-L1 Inhibitors

The described invention includes antibodies, or antigen binding fragments thereof, small molecules, oligopeptides, and/or nucleic acid inhibitors of PD-L1. According to some embodiments, any PD-L1 inhibitor described in the art or commercially available can be used in the presently described methods.

According to some embodiments, the inhibitor is an anti-PD-L1 antibody. According to some embodiments, the anti-PD-L1 antibody may be effective in inhibiting binding between PD-L1 and PD-1 and/or between PD-L1 and B7-1. According to some embodiments, the anti-PD-L1 antibody is a monoclonal antibody. According to some embodiments, the anti-PD-L1 antibody is an antibody fragment selected from the group consisting of Fab, Fab'-SH, Fv, scFv, and (Fab')$_2$ fragments. According to some embodiments, the anti-PD-L1 antibody is a humanized antibody. According to some embodiments, the anti-PD-L1 antibody is a human antibody.

According to some embodiments, the anti-PD-L1 inhibitor is selected from the group consisting of YW243.55.S70, MPDL3280A (atezolizumab), MEDI4736 (durvalumab), MDX-1105, and MSB0010718C (avelumab). MDX-1105, also known as BMS-936559, is an anti-PD-L1 antibody described in WO2007/005874. Antibody YW243.55.S70 is an anti-PD-L1 described in WO 2010/077634 A1. MEDI4736 is an anti-PD-L1 antibody described in WO2011/066389 and US2013/034559, incorporated by reference in their entireties herein. MDX-1106, also known as nivolumab.

According to some embodiments, the PD-L1 inhibitor is nivolumab (OPDIVO; Bristol-Myers Squibb).

According to some embodiments, the PD-L1 inhibitor is pembrolizumab (KEYTRUDA; Merck & Co Inc).

According to some embodiments, the PD-L1 inhibitor is atezolizumab (TECENTRIQ; Genentech Inc, Hoffmann-La Roche Ltd, Chugai Pharmaceutical Co Ltd).

According to some embodiments, the PD-L1 inhibitor is avelumab (BAVENCIO; EMD Serono Inc, Merck KGaA).

According to some embodiments, the PD-L1 inhibitor is durvalumab (IMFINZI; AstraZeneca Pharmaceuticals LP, Medimmune LLC).

According to some embodiments, the PD-L1 inhibitors are ipilimumab+nivolumab (YERVOY+OPDIVO; Bristol-Myers Squibb).

According to some embodiments, the PD-L1 inhibitor is an inhibitory RNA (iRNA) agent that is effective to inhibit expression of the CD274/PD-L1 gene. An iRNA refers to an agent that contains RNA as that term is defined herein, and which mediates the targeted cleavage of an RNA transcript via an RNA-induced silencing complex (RISC) pathway. iRNA agents that inhibit the expression of the CD274/PD-L1 gene are described in, for example, International Publication No. WO2011127180A1 and Iwamura et al. (Gene Ther. 2012 October; 19(10):959-6), both of which are incorporated by reference in their entireties herein. PD-L1 inhibitory RNAs are also commercially available from, e.g., Dharmacon (Accell CD274 siRNA; Lincode CD274 siRNA; ON-TARGETplus CD274 siRNA; siGENOME CD274 siRNA).

PD-L2 Inhibitors

The described invention includes antibodies, or antigen binding fragments thereof, small molecules, oligopeptides and/or nucleic acid inhibitors of PD-L2.

According to some embodiments, the inhibitor is an anti-PD-L2 antibody. According to some embodiments, the anti-PD-L1 antibody may be effective in inhibiting binding between PD-L2 and PD-1. According to some embodiments, the anti-PD-L2 antibody is a monoclonal antibody. According to some embodiments, the anti-PD-L2 antibody is an antibody fragment selected from the group consisting of Fab, Fab'-SH, Fv, scFv, and (Fab')$_2$ fragments. According to some embodiments, the anti-PD-L2 antibody is a humanized antibody. According to some embodiments, the anti-PD-L2 antibody is a human antibody.

AMP-224, also known as B7-DCIg, is a PD-L2-Fc fusion soluble receptor described in WO2010/027827 and WO2011/066342.

According to some embodiments, the PD-L2 inhibitor is CA-170 (Curis, Inc), a small molecule antagonist.

PD-L2 also binds to repulsive guidance molecule b (RGMb; DRAGON), which was originally identified in the nervous system as a co-receptor for bone morphogenetic proteins (BMPs). PD-L2 and BMP-2/4 bind to distinct sites on RGMb. Normal resting lung interstitial macrophages and alveolar epithelial cells express high levels of RGMb mRNA, whereas lung dendritic cells express PD-L2. Blockade of the RGMb-PD-L2 interaction has been reported to markedly impair the development of respiratory tolerance by interfering with the initial T cell expansion required for respiratory tolerance. Experiments with PD-L2-deficient mice showed that PD-L2 expression on non-T cells was critical for respiratory tolerance, but expression on T cells was not required.

RGMb, also known as DRAGON, is a member of the RGM family which consists of RGMa, RGMb, and RGMc/hemojuvelin (Severyn et al., 2009). RGMs are glycosylphosphatidylinositol-anchored membrane proteins that bind bone morphogenetic proteins (BMPs) and neogenin (Conrad et al., 2010). RGMs do not directly signal but can act as co-receptors that modulate BMP signaling (Samad et al., 2005). RGMb is expressed and functions in the nervous system (Severyn et al., 2009). In addition, RGMb expression is observed in macrophages and other cells of the immune system (Xia et al., 2011). However, the function of RGMb in the immune system is only beginning to emerge (Galligan et al., 2007; Xia et al., 2011). RGMb-deficient mice have an early lethal phenotype (Xia et al., 2011).

The described invention also includes antibodies, or antigen binding fragments thereof, small molecules, oligopeotides and/or nucleic acid inhibitors of RGMb. According to some embodiments, any RGMb inhibitor described in the art or commercially available can be used in the presently described methods.

Focal Adhesion Kinase (FAK) Inhibitors

PTK2 protein tyrosine kinase 2 (PTK2), also known as focal adhesion kinase (FAK), is a protein that, in humans, is encoded by the PTK2 gene. The FAK gene is highly conserved with over 90% sequence identity across different species including human, mouse, chicken and *Xenopus*. FAK is composed of a central kinase domain flanked by an N-terminal FERM (Band 4.1, ezrin-radixin-moesin) domain and a C-terminal domain that includes the focal adhesion targeting (FAT) sequence.

Numerous studies have established FAK as a central mediator of integrin signaling as well as an important component of signaling by other cell surface receptors. For example, regulation of cell migration by integrin signaling through FAK is well established in many cell types, which contribute to pathogenesis of cancer and other diseases (Golubovskaya V M, at al. Int Rev Cytol. 2007; 263:103-53; McLean G W, Nat Rev Cancer. 2005; 5(7):505-15).

Integrin signaling through FAK has been shown to promote cell migration in numerous studies. Initial suggestion for a role for FAK in cell migration was based on correlative observations of increased expression or activation of FAK in the migrating keratinocytes in epidermal wound healing or ECs migrating into the wounded monolayer in vitro, respectively (Romer L H, et al. Mol Biol Cell. 1994; 5(3):349-61; Gates R E, et al. Cell Growth Differ. 1994; 5(8):891-9). Increased levels of FAK expression have also been correlated with the invasive and metastatic potential of several human tumors. FAK knockout studies showed an early embryonic lethal phenotype with extensive mesodermal deficiency, and FAK−/− embryonic fibroblasts from these mice exhibited a profound defect in migration, providing more direct evidence for a role of FAK in promoting migration (Ilic D, et al. Nature. 1995; 377(6549):539-44). Consistent with these observations in vivo, microinjection of the FAK C-terminal recombinant protein (i.e. FRNK) inhibited FAK activation and reduced migration of both fibroblasts and ECs (Gilmore A P, Romer L H. Mol Biol Cell. 1996; 7(8):1209-24).

FAK signaling has been shown to promote invasion of both normal and transformed cells in addition to cell migration. In v-Src transformed cells, FAK was found to mediate Src phosphorylation of endophilin A2 to decrease its interaction with dynamin, which is important in the regulation of cell surface matrix metalloprotease MT1-MMP via endocytosis. The reduced internalization of MT1-MMP leads to its accumulation on the cell surface to stimulate the invasive activity of v-Src transformed cells (Wu X, et al. Dev Cell. 2005; 9(2):185-96). In addition, FAK also promotes both the expression of MMP2 and MMP9 through the v-Src-Cas-Crk-Dock180 signaling cascade and activation of Rac1 and JNK as well as their secretion into the matrix in cancer cells (Hsia D A, et al. J Cell Biol. 2003; 160(5):753-67; Shibata K, et al. Cancer Res. 1998; 58(5):900-3).

The described invention includes the finding that focal adhesion kinase (FAK) signaling can be a key downstream signaling pathway of PD-1 ligand interactions. Thus, targeting FAK can be important in inhibiting PD1-ligand-mediated fibrosis.

The described invention includes antibodies, or antigen binding fragments thereof, small molecules and/or nucleic acid inhibitors of FAK. According to some embodiments, any FAK inhibitor described in the art or commercially available can be used in the presently described methods.

Antisense compounds targeted to nucleic acids encoding FAK are described, for example, in U.S. Pat. No. 6,133,031, incorporated by reference in its entirety herein. Small molecule inhibitors of FAK are described, for example, in WO2008115369, incorporated by reference in its entireity herein.

According to some embodiments, the FAK inhibitor is defactinib hydrochloride (Verastem Inc.).

According to some embodiments, the FAK inhibitor is GSK-2256098 (GlaxoSmithKline Plc).

According to some embodiments, the FAK inhibitor is TPX-0005 (TP Therapeutics Inc.)

According to some embodiments, the FAK inhibitor is BI-853520 (Boehringer Ingelheim GmbH).

According to some embodiments, the FAK inhibitor is CEP-37440 (Teva Pharmaceutical Industries Ltd.).

According to some embodiments, the FAK inhibitor is CT-707 (Centaurus Biopharma Co Ltd.).

According to some embodiments, the FAK inhibitor is ASN-006 (Asana BioSciences LLC).

According to some embodiments, the FAK inhibitor is cilengitide (Iceni Pharmaceuticals Ltd.).

According to some embodiments, the FAK inhibitor is VS-6062 (Verastem Inc.).

According to some embodiments, the FAK inhibitor is C-10 (CureFAKtor Pharmaceuticals LLC).

According to some embodiments, the FAK inhibitor is C-9 (CureFAKtor Pharmaceuticals LLC).

According to some embodiments, the FAK inhibitor is C9A (CureFAKtor Pharmaceuticals LLC).

According to some embodiments, the FAK inhibitor is CFAKC-4 (CureFAKtor Pharmaceuticals LLC).

According to some embodiments, the FAK inhibitor is CFAKY-15 (CureFAKtor Pharmaceuticals LLC).

According to some embodiments, the FAK inhibitor is a drug to Inhibit PYK2 for Osteoporosis (Oscotec Inc.).

According to some embodiments, the FAK inhibitor is MG-1102 (Green Cross Corp).

According to some embodiments, the FAK inhibitor is VS-4718 (Verastem Inc).

According to some embodiments, the FAK inhibitor is VS-5095 (Verastem Inc).

According to some embodiments, the FAK inhibitor is CTX-0294886 (Cancer Research UK).

According to some embodiments, the FAK inhibitor is CTX-0294945 (Cancer Research UK).

According to some embodiments, the FAK inhibitors are benzisoselenazolone (BSZ) sugar derivatives; BSZ Molecules; Compound 2d; Triple targeted kinase inhibitors (McGill University).

According to some embodiments, the FAK inhibitors are 1; 3; 4-oxadiazole-2(3H)-thione derivatives; compound 5m; inhibitors (Nanjing University).

III. Methods of Treatment

The results disclosed herein indicate that elevated expression and/or activity of PD1, PD-L1, PD-L2, or RGMb may be associated with pulmonary fibrosis, including IPF.

The described invention thus provides methods for treating progressive pulmonary fibrosis in a subject, comprising administering to a subject a therapeutic amount of a therapeutic agent that is effective to modulate the programmed cell death pathway, thereby improving clinical outcome. The described invention also provides methods for improving lung function in a subject, comprising administering to a subject a therapeutic amount of a therapeutic agent that is effective to modulate the programmed cell death pathway, thereby improving lung function. The term "inhibiting," as used herein, includes any level of inhibition. Levels of inhibition can be a percent inhibition, for example 5%, 10%, 15%, 20%, 25%, 30%, 35%, 40%, 45%, 50%, 55%, 60%, 65%, 70%, 75%, 80%, 85%, 90%, 95% or more. Levels of inhibition can also be a fold inhibition, for example 1-fold, 2-fold, 3-fold, 4-fold, 5-fold, 6-fold, 7-fold, 8-fold, 9-fold, 10-fold or more. Ranges provided herein are understood to include all individual integer values and all subranges within the ranges.

According to one aspect, the invention provides a method of identifying a subject eligible for treatment for pulmonary fibrosis or lung cancer, the method comprising use of a composition comprising a therapeutic amount of a therapeutic agent effective to modulate the programmed cell death pathway, the method comprising assaying lung tissue of the subject for PD1, PD-L1 (CD274), PD-L2, or RGMb expression levels, and, if PD1, PD-L1, PD-L2, or RGMb expression levels in the lung tissue of the subject are upregulated with respect to a control subject (meaning a subject having no symptoms or other clinical evidence of pulmonary fibrosis), treating the subject by administering to the subject a composition containing a therapeutic amount of one or more of an inhibitor of PD-1 receptor, an inhibitor of PD-L1 (CD274), an inhibitor of PD-L2 or an inhibitor of RGMb.

According to some embodiments, the level of cell surface expression and/or total protein expression of PD1 is higher in the lung tissue obtained from a subject eligible for treatment for pulmonary fibrosis or lung cancer (e.g. higher in IPF lung fibroblasts) than in healthy controls. According to some embodiments, the level of cell surface expression and/or total protein expression of PD-L1/CD274 is higher in the lung tissue obtained from a subject eligible for treatment for pulmonary fibrosis (e.g. higher in IPF lung fibroblasts) than in lung tissue obtained from a control subject. According to some embodiments, the cell surface expression and/or total protein expression of PD-L2 is higher in the lung tissue obtained from a subject eligible for treatment for pulmonary fibrosis or lung cancer (e.g. higher in IPF lung fibroblasts) than in lung tissue obtained from a control subject. According to some embodiments, the level of cell surface expression and/or total protein expression of RGMb is higher in the lung tissue from a subject eligible for treatment for pulmonary fibrosis or lung cancer (e.g. higher in IPF lung fibroblasts) than in a control subject.

According to one aspect, the invention features a method of identifying a subject eligible for treatment for pulmonary fibrosis or lung cancer, the method comprising use of a composition comprising a therapeutic amount of a therapeutic agent that is effective to modulate the programmed cell death pathway, the method comprising assaying lung tissue of the subject for PD-L1 (CD274) expression levels, and if PD-L1 (CD274) expression levels in the lung tissue of the subject are upregulated with respect to a control subject, treating the subject by administering to the subject a composition containing a therapeutic amount of an inhibitor of PD-L1 (CD274).

The level or amount of a marker, such as PD1, PD-L1 (CD274), PD-L2, or RGMb, refers to the measurable quantity of a marker, e.g., level of RNA expression, level of protein expression. According to some embodiments, the amount may be either (a) an absolute amount as measured in molecules, moles or weight per unit volume or cells or (b) a relative amount, e.g., measured by densitometric analysis.

According to some embodiments, the lung tissue from a subject eligible for treatment for pulmonary fibrosis or lung cancer is determined to be PD-L1/CD274$^{high}$ if the level of cell surface expression and/or level of total protein expression of PD-L1/CD274 is higher in the lung tissue from a subject eligible for treatment for pulmonary fibrosis (e.g. higher in IPF lung fibroblasts) than in healthy controls. According to one embodiment, the lung tissue from a subject eligible for treatment for pulmonary fibrosis or lung cancer is determined to be PD-L1/CD274$^{high}$ by Fluorescence-activated cell sorting of CD274$^{high}$ and CD274$^{low}$ expression cells, where the cells in the top 10-15 percentile (e.g. top 10, 11, 12, 13, 14, 15 percentile) are categorized as CD274$^{high}$. According to one embodiment, the lung tissue from a subject eligible for treatment for pulmonary fibrosis or lung cancer is determined to be PD-L1/CD274$^{high}$ if the cell surface expression and/or total protein expression of PD-L1/CD274$^{high}$.

According to one embodiment, the lung tissue from a subject eligible for treatment for pulmonary fibrosis or lung cancer is determined to be PD-L1/CD274$^{high}$ if the level of expression of PD-L1/CD274 RNA or protein is statistically significantly higher than the level of PD-L1/CD274 RNA or protein obtained from a healthy control subject.

According to some embodiments, a level of expression obtained from a healthy control refers to an accepted or pre-determined level of expression of a marker, such as PD1, PD-L1 (CD274), PD-L2, or RGMb, which is used to compare the level of expression of the same marker derived from the sample of a patient. According to one embodiment, when compared to the known level of expression of a certain marker obtained from a healthy control, deviation from the level of expression obtained from a healthy control may indicate a diagnosis of a disease state (e.g. pulmonary fibrosis or lung cancer), or improvement or deterioration in the disease state, or, if the level of expression of a marker of the patient is obtained following therapeutic treatment for the disease, success or failure of a therapy to improve a patient's disease state.

Generally, a suitable control may also be a reference standard. A reference standard serves as a reference level for comparison, such that test samples can be compared to the reference standard in order to infer the level of expression of PD1, PD-L1 (CD274), PD-L2, or RGMb in a subject. A reference standard may be representative of the level of expression of one or more markers, such as PD1, PD-L1 (CD274), PD-L2, or RGMb in a known subject, e.g., a subject known to be a normal subject (healthy without pulmonary fibrosis or lung cancer), or a subject known to have pulmonary fibrosis or lung cancer. Alternatively, a reference standard may be representative of the level of expression of one or more markers, such as PD1, PD-L1 (CD274), PD-L2, or RGMb in a known subject, e.g., a population of subjects known to be a normal subject (healthy without pulmonary fibrosis or lung cancer), or a population of subjects known to have pulmonary fibrosis or lung cancer. The reference standard may be obtained, for example, by pooling samples from a plurality of individuals and determining the level of expression of a marker in the pooled samples, to thereby produce a standard over an averaged population. Such a reference standard represents an average level of expression of a marker among a population of individuals. A reference standard may also be obtained, for example, by averaging the level of expression of a marker determined to be present in individual samples obtained from a plurality of individuals. Such a standard is also representative of an average level of expression of a marker among a population of individuals. According to one embodiment, a comparison between the level of expression of one or more markers in a sample relative to a suitable control is made by executing a software classification algorithm. The skilled person can readily envision additional suitable controls that may be appropriate depending on the assay in question.

According to some embodiments, the therapeutic agent is selected from the group consisting of an inhibitor of programmed death-1 (PD-1) receptor, an inhibitor of programmed death receptor-ligand 1 (PD-L1), an inhibitor of programmed death receptor-ligand 1 (PD-L2) and an inhibitor of repulsive guidance molecule B (RGMb). The terms "inhibitor" and "antagonist" and like terms are used synonymously herein.

Exemplary inhibitors include antibodies, or antigen binding fragments thereof, small molecule inhibitors, nucleic acid inhibitors or oligopeptides.

According to some embodiments of the invention, a therapeutic amount of the therapeutic agent is effective (a) to decrease the invasiveness of pulmonary fibroblasts in the subject; (b) to decrease migration of pulmonary fibroblasts in the subject; (c) to decrease cell adhesion of pulmonary fibroblasts in the subject; (d) to decrease pulmonary fibroblast proliferation and differentiation; (e) to decrease extracellular matrix production; or (f) to decrease myofibroblast activation, or a combination thereof, compared to an untreated control.

Combination Treatment

Included in the described methods of the described invention is combination treatment. Combination treatment includes administering to a subject a therapeutic amount of two or more therapeutic agents that is effective to modulate the programmed cell death pathway. For example, combination treatment may include administering to a subject a therapeutic amount of two or more inhibitors of PD-1 receptor, PD-L1, PD-L2 and/or RGMb, in any combination. Combination treatment may also include administering to the subject a therapeutic amount of two or more different inhibitors of the same target (e.g. two or more inhibitors of PD1, two or more inhibitors of PD-L1, two or more inhibitors of PD-L2, or two or more inhibitors of RGMb).

According to certain embodiments, combination treatment includes administration of the therapeutic agent effective to modulate the programmed cell death pathway with a focal adhesion kinase (FAK) inhibitor.

According to certain embodiments, the compounds of the invention are useful in the methods of the invention in combination with at least one additional compound useful for treating or preventing pulmonary fibrosis. This additional compound may comprise compounds identified herein or compounds, e.g., commercially available compounds, known to treat, prevent or reduce the symptoms of fibrotic lung disease. Combinations of compounds according to the invention, or for use according to the invention, and other agents useful for the treatment of pulmonary fibrosis may be administered separately or in conjunction. The administration of one agent may be prior to, concurrent to, or subsequent to the administration of other agent(s).

According to some embodiments, the administration of one or more therapeutic agents provides a synergistic therapeutic effect. A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The therapeutic agents utilized herein can be administered orally, or parenterally, e.g., by intravenous, intramuscular, and subcutaneous injection, insufflation, inhalation, or locally by transdermal methods. The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the described invention to a patient, such as a mammal, such as a human, may be carried out using known procedures, at dosages and for periods of time effective to treat a disease or disorder contemplated in the invention, e.g. pulmonary fibrosis. The therapeutic amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the described invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of the described invention may be varied so as to obtain an amount of the active ingredient that is effective to achieve the desired therapeutic response for a particular patient, composition, and mode of administration, while limiting toxicity to the patient.

The therapeutically effective amount or dose of a compound of the described invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

IV. Diagnostic and Monitoring Criteria

Methods for detecting and identifying nucleic acids and proteins and interactions between such molecules involve conventional molecular biology, microbiology, and recombinant DNA techniques within the skill of the art. Such techniques are explained fully in the literature (see, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

For detection of gene or protein expression or activity, a biological sample can be obtained from nearly any tissue. One of skill in the art will understand that a blood sample or a cheek swab is expected to carry the same genetic sequence information as a lung cell. For detection of a given expression level, pulmonary tissue samples and other biological fluids are typically used.

Biological samples can include a pulmonary mucosal sample or biological fluid such as blood or blood components (plasma, serum), sputum, mucus, urine, saliva, etc.

A pulmonary mucosal sample can be obtained using methods known in the art, e.g., a bronchial epithelial brush or exhaled breath condensate. Additional methods include bronchial biopsy, bronchial wash, bronchoalveolar lavage, whole lung lavage, transendoscopic biopsy, translaryngoscopic catheter, and transtracheal wash. A review of commonly used techniques, including comparisons and safety issues, is provided in Busse et al. (2005) Am J Respir Crit Care Med 172:807-816.

For lavage techniques, a bronchoscope can be inserted to the desired level of the airway. A small volume of sterile, physiologically acceptable fluid (e.g., buffered saline) is released, and immediately aspirated. The wash material contains cells from the mucosa and upper epithelia (Riise et al. (1996) Eur Resp J 9:1665).

For use of a bronchial epithelial brush, a sterile, non-irritating (e.g., nylon) cytology brush can be used. Multiple brushings can be taken to ensure representative sampling. The brush is then agitated in physiologically acceptable fluid, and the cells and debris separated using routine methods (Riise et al. (1992) Eur Resp J 5:382).

Cellular components can be isolated using methods known in the art, e.g., centrifugation. Similarly, subcellular components (e.g., exosomes or vesicles) can be isolated using known methods or commercial separation products (available from BioCat, System Bio, Bioscientific, etc.). An exemplary method is described e.g., by Thery et al. (2006) Current Prot. Cell Biol. Chapter 3: Unit 3.22, doi: 10.1002/0471143030.cb0322s30.

Expression of a given gene, e.g., PD1, PD-L1, PD-L2, or RGMb, a pulmonary disease (e.g. pulmonary fibrosis) marker, or a standard (control), is typically detected by detecting the amount of RNA (e.g., mRNA) or protein. Sample levels can be compared to a control level.

Methods for detecting RNA are largely cumulative with the nucleic acid detection assays described above. RNA to be detected can include mRNA. According to some embodiments, a reverse transcriptase reaction is carried out and the targeted sequence is then amplified using standard PCR. Quantitative PCR (qPCR) or real time PCR (RT-PCR) is useful for determining relative expression levels, when compared to a control. Quantitative PCR techniques and platforms are known in the art, and commercially available (see, e.g., the qPCR Symposium website, available at qpersymposium.com). Nucleic acid arrays are also useful for detecting nucleic acid expression. Customizable arrays are available from, e.g., Affimatrix.

Protein levels can be detected using antibodies or antibody fragments specific for that protein, natural ligands, small molecules, aptamers, etc. Antibody based techniques are known in the art, and described, e.g., in Harlow & Lane (1988) Antibodies: A Laboratory Manual and Harlow (1998) Using Antibodies: A Laboratory Manual; Wild, The Immunoassay Handbook, 3d edition (2005) and Law, Immunoassay: A Practical Guide (1996). The assay can be directed to detection of a molecular target (e.g., protein or antigen), or a cell, tissue, biological sample, liquid sample or surface suspected of carrying an antibody or antibody target.

A non-exhaustive list of immunoassays includes: competitive and non-competitive formats, enzyme linked immunosorption assays (ELISA), microspot assays, Western blots, gel filtration and chromatography, immunochromatography, immunohistochemistry, flow cytometry or fluorescence activated cell sorting (FACS), microarrays, and more. Such techniques can also be used in situ, ex vivo, or in vivo, e.g., for diagnostic imaging.

Aptamers are nucleic acids that are designed to bind to a wide variety of targets in a non-Watson Crick manner. An aptamer can thus be used to detect or otherwise target nearly any molecule of interest, including a pulmonary fibrosis associated protein, e.g. PD1, PD-L1, PD-L2, or RGMb. Methods of constructing and determining the binding characteristics of aptamers are well known in the art. For example, such techniques are described in U.S. Pat. Nos. 5,582,981, 5,595,877 and 5,637,459 (incorporated by reference herein). Aptamers are typically at least 5 nucleotides, 10, 20, 30 or 40 nucleotides in length, and can be composed of modified nucleic acids to improve stability. Flanking sequences can be added for structural stability, e.g., to form 3-dimensional structures in the aptamer.

Protein detection agents described herein can also be used as a treatment and/or for diagnosis of pulmonary fibrosis or as a predictor of disease progression, e.g., propensity for survival, in a subject having or suspected of developing pulmonary fibrosis. According to certain embodiments, anti-PD1, PD-L1, PD-L2, or RGMb antibodies can be used to assess PD1, PD-L1, PD-L2, or RGMb protein levels in a subject having or suspected of developing pulmonary fibrosis. It is contemplated herein that antibodies or antibody fragments may be used to modulate PD1, PD-L1, PD-L2, or RGMb activity in a subject having or suspected of developing pulmonary fibrosis. According to certain embodiments, one or more agents effective for modulating PD1, PD-L1, PD-L2, or RGMb may be used to treat a subject having or suspected of developing pulmonary fibrosis.

According to some embodiments, the described invention includes a method of identifying a subject for treatment for pulmonary fibrosis, the method comprising assaying lung tissue of the subject for PD1, PD-L1, PD-L2, or RGMb expression levels, wherein, if PD1, PD-L1, PD-L2, or RGMb expression levels in the lung tissue of the subject are upregulated with respect to a control subject not suffering from pulmonary fibrosis, the subject is administered a therapeutic amount of one or more of an inhibitor of PD-1 receptor, an inhibitor of PD-L1, an inhibitor of PD-L2 or an inhibitor of RGMb. According to one embodiment, the pulmonary fibrosis is idiopathic pulmonary fibrosis (IPF).

According to some embodiments, identifying a subject for treatment of pulmonary fibrosis comprises assaying lung tissue of the subject for expression of PD-L1 (CD274), where the lung tissue of the subject is determined to be PD-L1/CD274$^{high}$ if the cell surface expression and/or total protein expression of PD-L1/CD274 is higher in the lung tissue from the subject with respect to a control subject not suffering from pulmonary fibrosis. According to one embodiment, the lung tissue from a subject eligible for treatment for pulmonary fibrosis or lung cancer is determined to be PD-L1/CD274$^{high}$ by Fluorescence-activated cell sorting of CD274$^{high}$ and CD274$^{low}$ expression cells, where the cells in the top 10-15 percentile (e.g. top 10, 11, 12, 13, 14, 15 percentile) are categorized as CD274$^{high}$. According to one embodiment, the lung tissue from a subject is determined to be PD-L1/CD274$^{high}$ by Fluorescence-activated cell sorting of CD274$^{high}$ and CD274$^{low}$ expression cells, where the cells in the top 10 percentile are categorized as CD274$^{high}$.

The detection methods described herein can be used for diagnosis, prognosis, risk prediction, determining a course of treatment, monitoring therapeutic efficacy, and monitoring disease progression. One of skill will appreciate that each of the detection methods can be used alone or in combination.

V. Methods for Identifying an Agent

The described invention further provides methods for identifying additional inhibitors of PD1, PD-L1, PD-L2, or RGMb expression and/or activity. Methods for screening for antagonists can involve measuring the ability of the potential antagonists to reduce an identifiable PD1, PD-L1, PD-L2, or RGMb activity or to compete for binding with a known binding agent (e.g., a known PD1, PD-L1, PD-L2, or RGMb-specific antibody).

According to one embodiment, the invention features a method of identifying an agent (a test inhibitor) for use in the treatment of pulmonary fibrosis, the method comprising administering a test inhibitor of PD1, PD-L1, PD-L2, or RGMb to a subject; and measuring a symptom of pulmonary fibrosis in the subject, wherein a reduction or inhibition of a symptom of pulmonary fibrosis compared to an untreated control patient identifies the test inhibitor as an agent for treating pulmonary fibrosis, including the progression of pulmonary fibrosis. According to one embodiment, the pulmonary fibrosis is idiopathic pulmonary fibrosis (IPF).

According to one embodiment, the test agent decreases the expression or biological activity of one or more of PD1, PD-L1, PD-L2, or RGMb.

According to one embodiment, identification of the agent for the treatment of pulmonary fibrosis comprises determining lung hydroxyproline levels, wherein lung hydroxyproline levels in the subject are reduced following administration of the test inhibitor compared to an untreated control subject.

According to one embodiment, identification of the agent for the treatment of pulmonary fibrosis comprises determining lung density, wherein the lung density of the subject is reduced following administration of the test inhibitor.

According to one embodiment, identification of the agent for the treatment of pulmonary fibrosis comprises determining total cell count in bronchoalveolar lavage fluid, herein total cell count in bronchoalveolar lavage fluid (from the subject is reduced following administration of the test inhibitor.

The screening methods of the described invention can be performed as in vitro or cell-based assays. Cell based assays can be performed in any cells in which PD1, PD-L1, PD-L2, or RGMb is expressed, either endogenously or through recombinant methods. Cell-based assays may involve whole cells or cell fractions containing PD1, PD-L1, PD-L2, or RGMb to screen for agent binding or modulation of PD1, PD-L1, PD-L2, or RGMb activity by the agent. Suitable cell-based assays are described in, e.g., DePaola et al., Annals of Biomedical Engineering 29: 1-9 (2001).

Agents that are initially identified as inhibiting PD1, PD-L1, PD-L2, or RGMb can be further tested to validate the apparent activity. For example, such studies are conducted with suitable cell-based or animal models of pulmonary disease, such as IPF. The basic format of such methods involves administering a lead compound identified during an initial screen to an animal that serves as a model and then determining if in fact the pulmonary disease is ameliorated. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential antagonists of PD1, PD-L1, PD-L2, or RGMb can be any small chemical compound, or a biological entity, such as a polypeptide, sugar, nucleic acid or lipid. The assays are designed to screen large chemical libraries by automating the assay steps and providing compounds from any convenient source to assays, which are typically run in parallel (e.g., in microtiter formats on microtiter plates in robotic assays).

According to one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, and U.S. Pat. No. 5,288,514).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless otherwise defined, all technical and scientific terms used herein have the same meaning as commonly understood by one of ordinary skill in the art to which this invention belongs. Although methods and materials similar or equivalent to any of those described herein can be used in the practice of the invention, suitable methods and materials are described below. In addition, the materials, methods, and examples are illustrative only and not intended to be limiting.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The Examples described herein illustrate several advantages of the described invention and are not intended to limit the scope of what the inventors regard as the mention, nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

In summary, first, the results described herein show that PD-1 ligands are differentially expressed on invasive fibroblasts, which are a small group of cells that have been proved to be important in fibrogenesis in vitro and in mouse models in vivo. Because targeting the PD1/PD-L1 pathway may have a minimal impact on the majority of fibroblasts, this strategy would lead to drugs that would not impair normal wound repair. Second, human antibodies and humanized antibodies targeting the PD1/PD-L1 pathway that have been developed for cancer treatment (e.g., two anti-PD1 antibodies n approved by US Food and Drug Administration for treatment of patients with metastatic melanoma (24)). can quickly be developed as therapeutic drugs for pulmonary fibrosis if their anti-fibrotic effects are verified by experiments. Third, combination therapies of anti-PD1 signaling with FAK signaling can be effective in the described invention in blocking fibroblast invasion Example 1. Gene Expression of Invasive and Noninvasive Fibroblasts from Lung Tissues of IPF Patients It has been shown that an invasive phenotype of fibroblasts contributes to severe lung fibrosis. The described invention is based, in part, on the results of RNA sequencing (RNA-Seq) of human lung fibroblasts. Gene expression of invasive and noninvasive fibroblasts from lung tissues of nine IPF patients and nine healthy donors was compared using RNA-Seq analysis. Among the top 10 up-regulated cell surface markers, programmed death ligand 1 (PD-L1 or CD274) and programmed death ligand 2 (PD-L2, also called PDCD1LG2, or CD273) were found to be highly expressed in invasive fibroblasts compared to noninvasive fibroblasts from IPF patient lungs and healthy donor lungs (FIG. 1).

Figure 2:
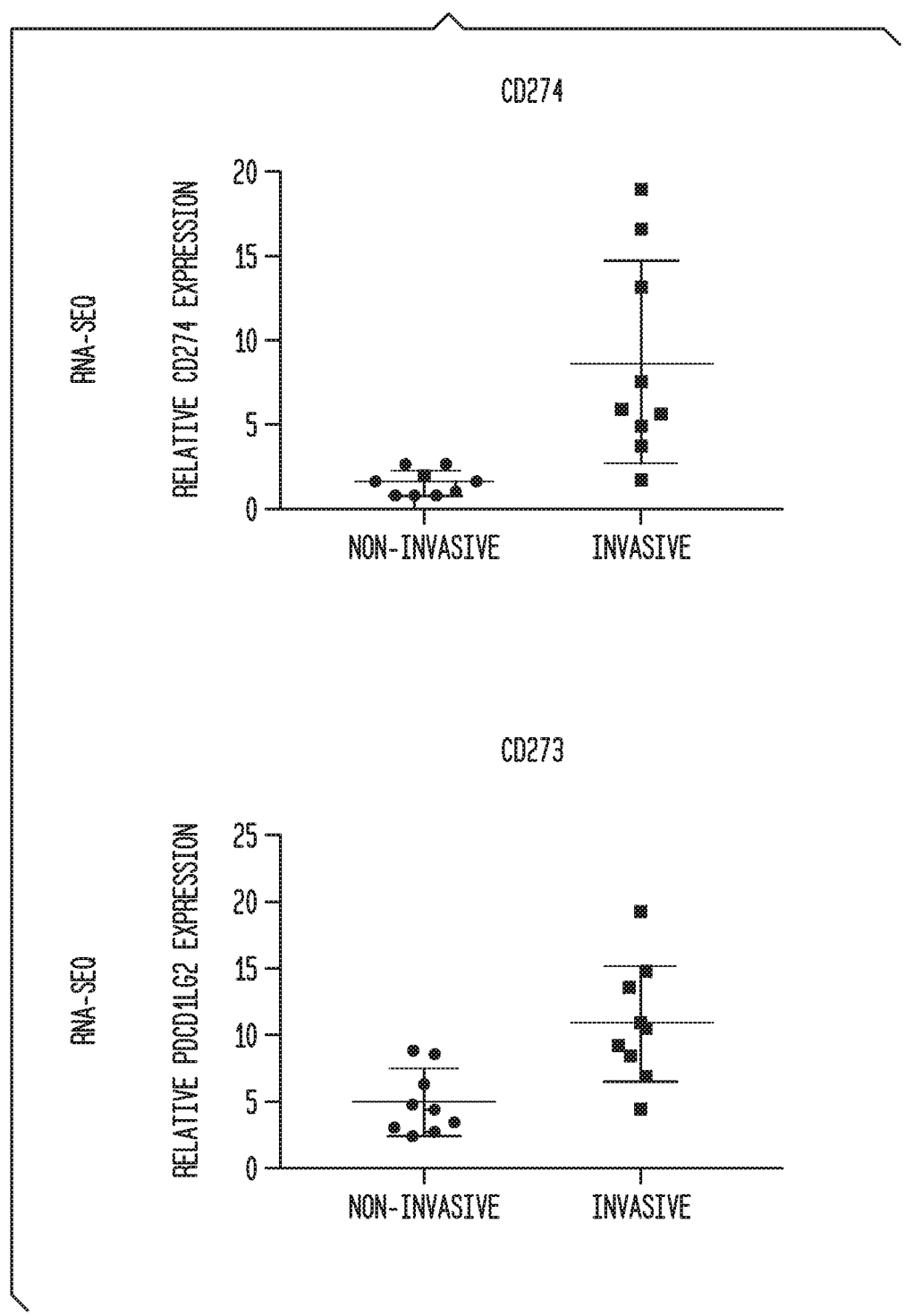
FIG. 2 is panel of graphs that shows upregulation of CD274 and CD273 in invasive fibroblasts from IPF lung by RNA-seq (n=9, P<0.01), RT-PCR (n=3, P<0.01), and flow cytometry (n=3).
Figures 1, 2:
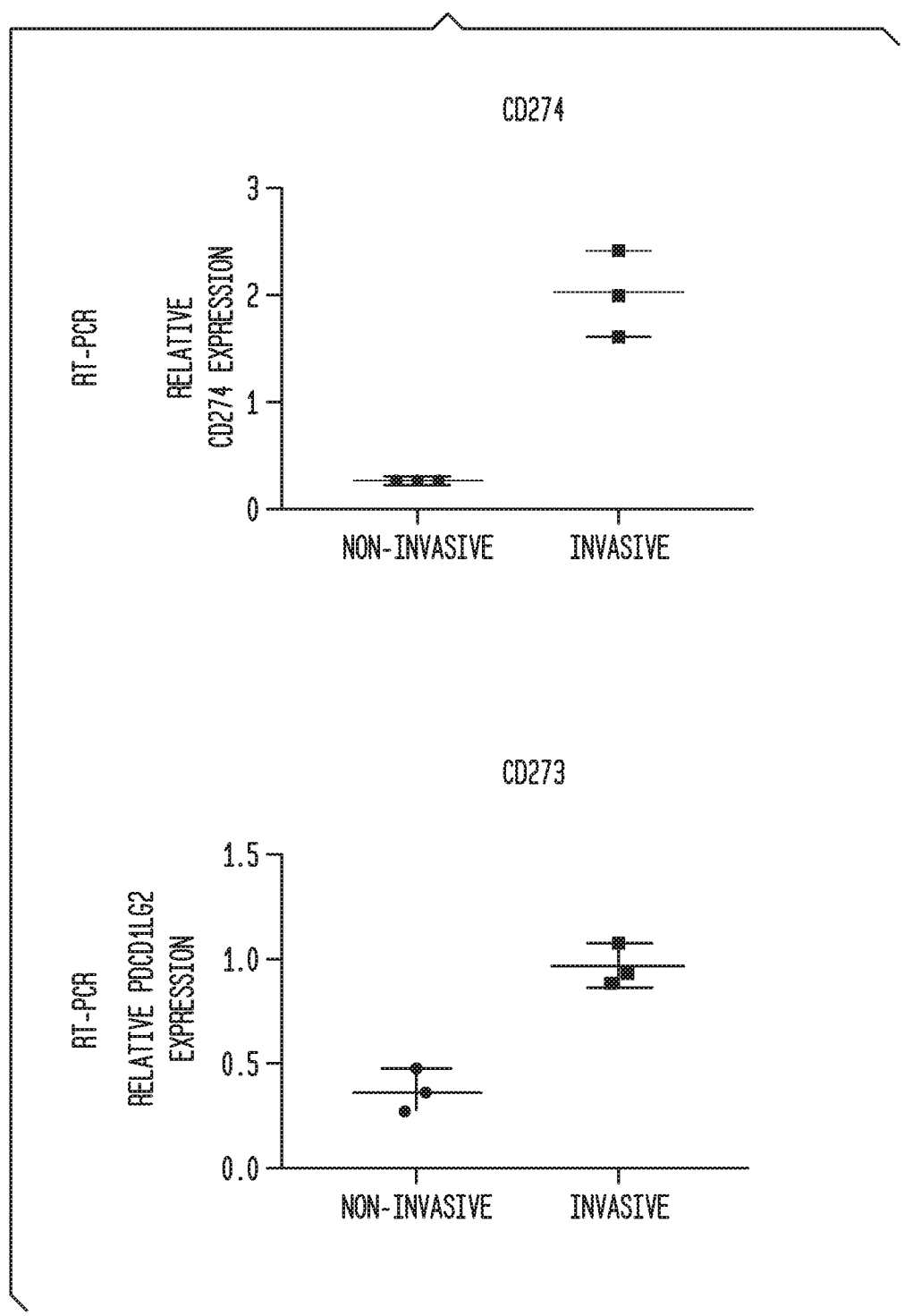
Figure 2:
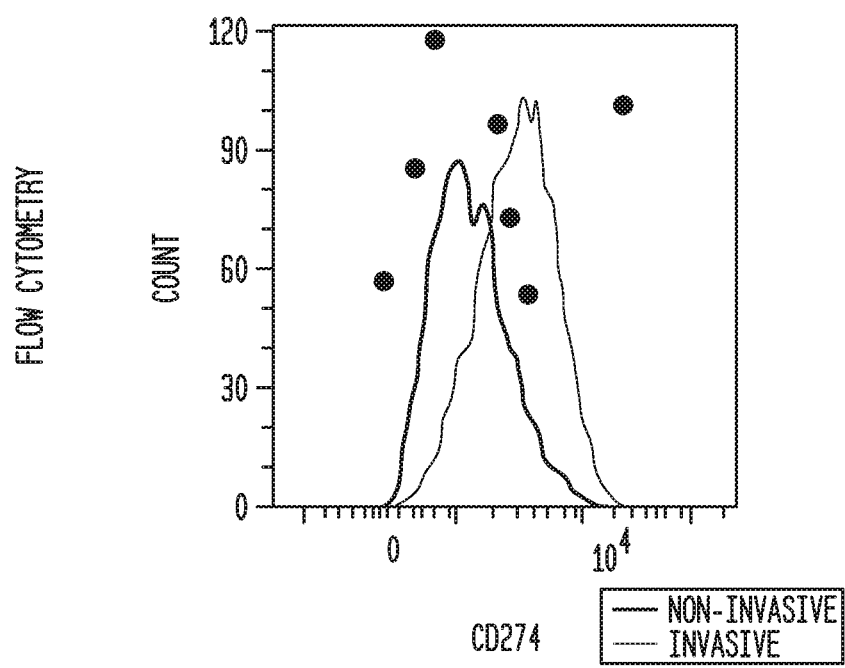

This up-regulation has been confirmed with RT-PCR, flow cytometry (FIG. 2), and Western analysis (data not shown).

Figure 3A:
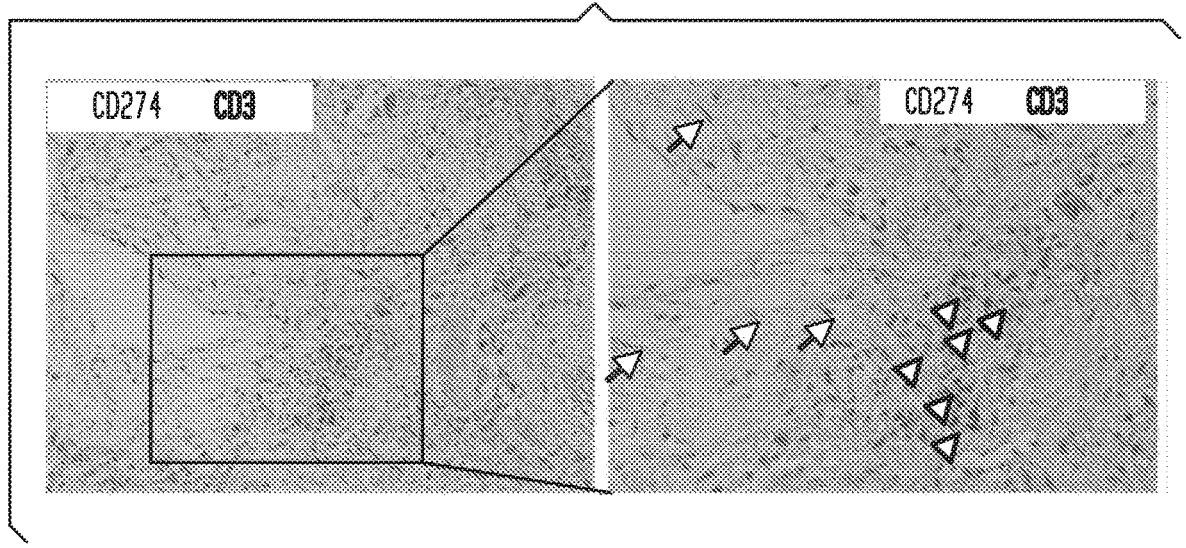
FIG. 3A is a graph that shows PD-L1 (CD274) expression in IPF lung. IPF lung slides were stained with Abs against CD274 (arrows) and CD3 (arrowheads). CD3 is used as a T-Cell marker.
Figure 3B:
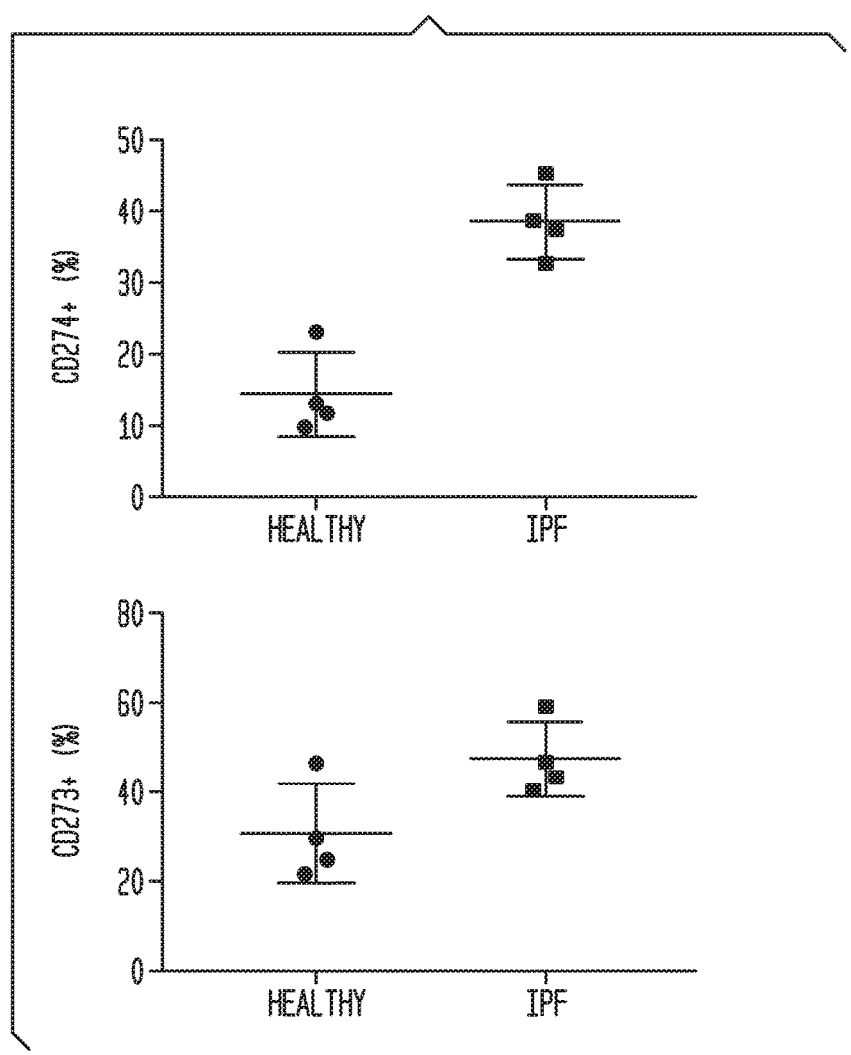
FIG. 3B is a graph that shows PD-L1 (CD274) expression in IPF lungs compared to healthy lungs. Fibroblasts isolated from healthy and IPF lungs were stained with anti-CD274 and anti-CD273 antibodies to show cell surface expression of CD274 (PD-L1) and CD273 (PD-L2). Percent of positive stained cells were graphed.

To examine the role of PD-L1 in IPF, sections of lung tissue mounted on glass slides were stained with mAbs against PD-L1, and PD-L1 was found to be expressed in fibroblasts (FIG. 3A). In FIG. 3A, CD3 is used as a T-Cell marker. Both CD3 immunomodulatory cells and macrophages express IL-17. Immunomodulatory cells participate in active-disease regions of IPF lung. See G. J. Nuovo (Molec. Pathol (2012) 25(3): 416-33). To test the biological function of the Immune Checkpoint PD1 pathway in pulmonary fibrosis, the expression levels of PD-L1 and PD-L2 in fibroblasts isolated from lungs of patients with IPF and healthy donors was analyzed. Both PD-L1 (CD274) and PD-L2 (CD273) expression were up regulated in IPF fibroblasts relative to the fibroblasts from healthy lungs (FIG. 3B).

Figure 4A:
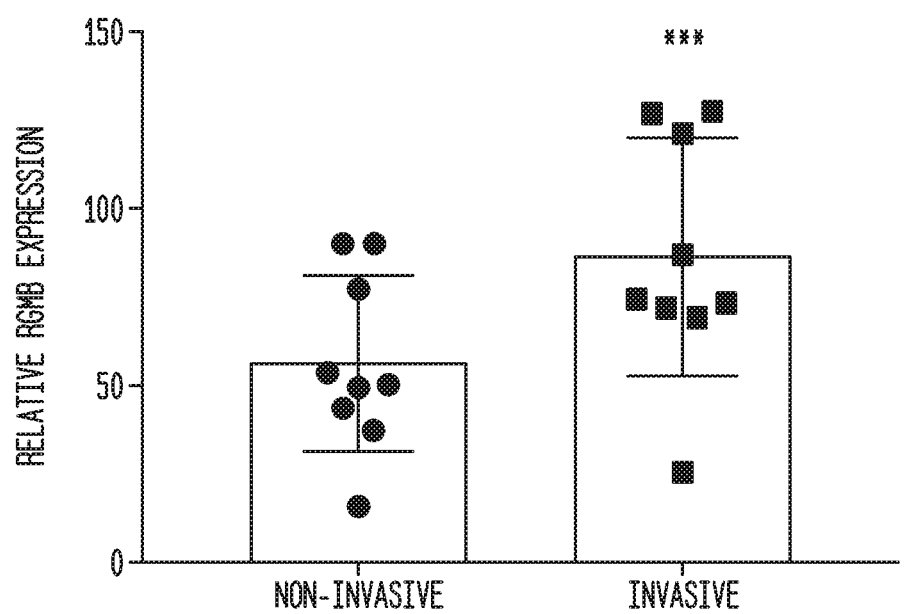
FIG. 4A is a graph that shows repulsive guidance molecule b (RGMb) expression compared between invasive and non-invasive IPF fibroblasts as determined by RNA-seq (n=9, P<0.001).
Figure 4B:
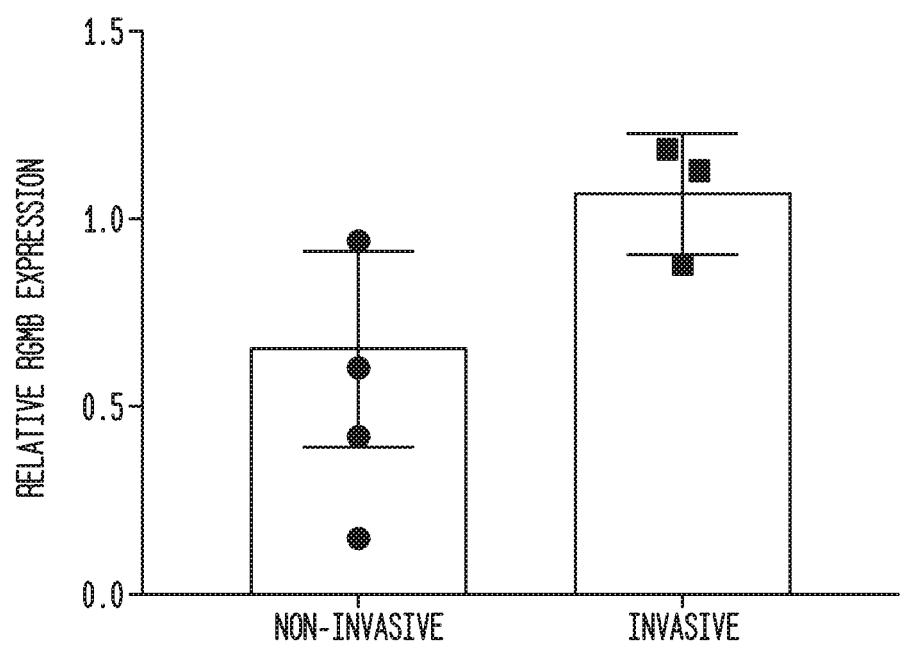
FIG. 4B is a graph that shows RGMb expression compared between invasive and non-invasive IPF fibroblasts as determined by RT-PCR (n=3).

Repulsive guidance molecule B (RGMb; also known as DRAGON), a PD-L2 binding partner, has been found in alveolar epithelial cells and interstitial macrophages. PD-L2 binds to RGMb Significant upregulation of RGMb expression was found in invasive fibroblasts (FIG. 4). Furthermore, RGMb can be detected on fibroblast surface by flow cytometry (data not shown).

CD274 and CD273 in addition to the cell surface markers previously identified will be used to further enrich invasive fibroblasts from fibrotic lungs.

The hypothesis that targeting programmed death-1 pathway attenuates pulmonary fibrosis is tested through in vitro and in vivo experiments in the Examples described below.

Example 2. Targeting PD1 Pathway on Invasive Phenotype of Fibroblasts

Figure 5A:
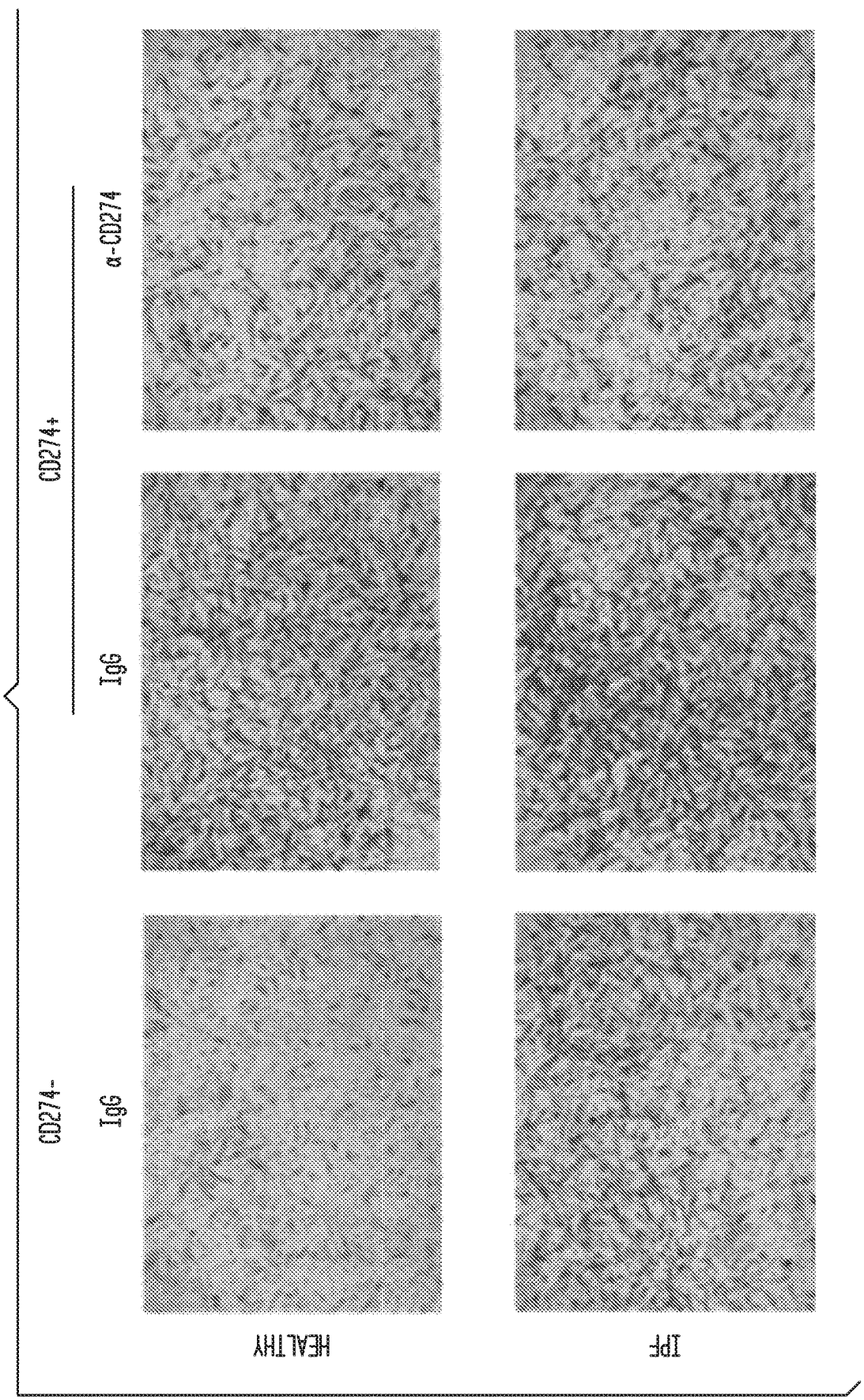
FIG. 5A shows increased migration of CD274+ fibroblasts. CD274+ and CD274− fibroblast were flow sorted from fibroblasts of healthy and IPF lungs. The cells were plated onto transwells for migration assay, with and without anti-CD274 antibody (α-CD274) and control IgG. Migratory fibroblasts were fixed, stained, and photographed.
Figure 5B:
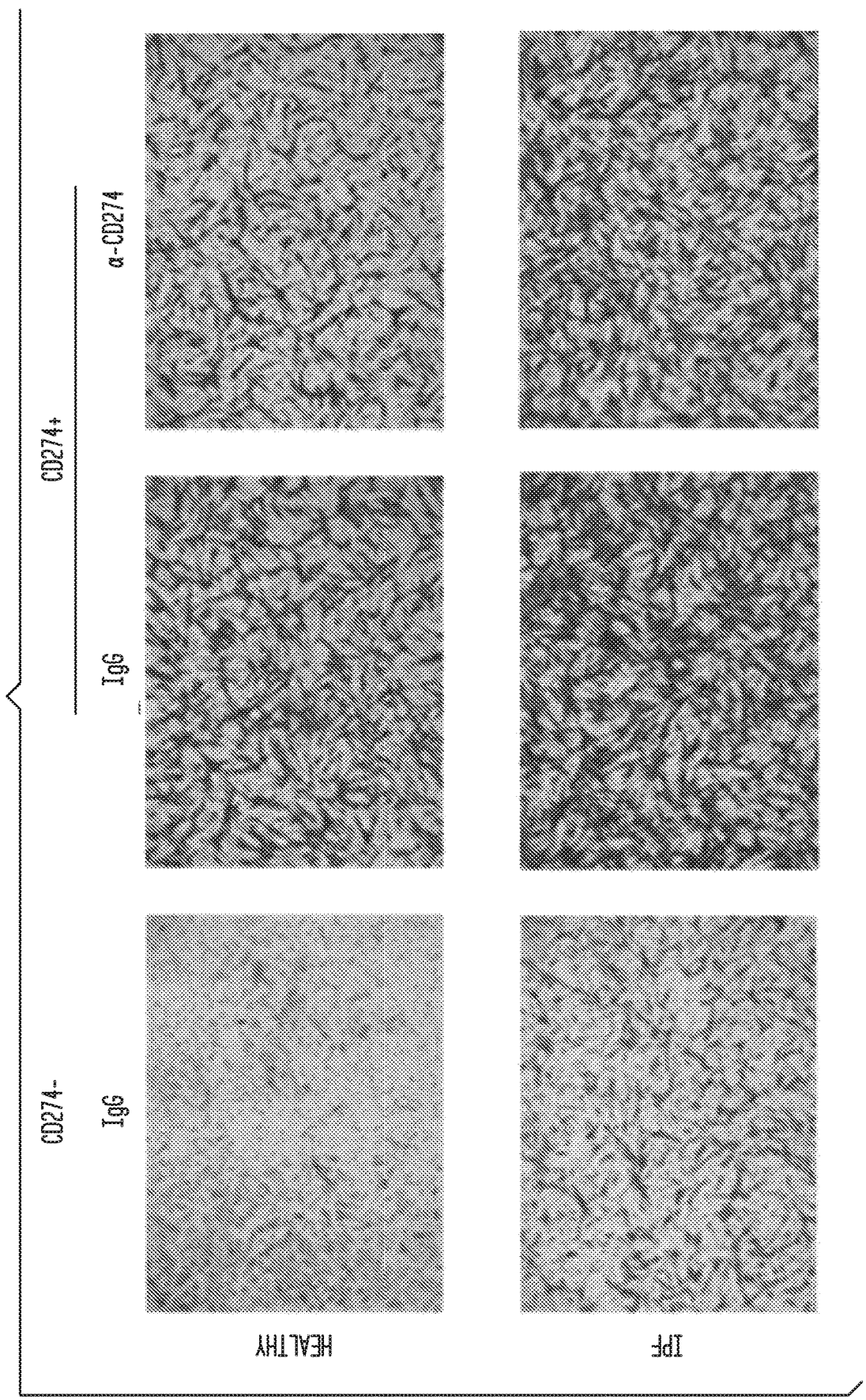
FIG. 5B shows increased invasion of CD274+ fibroblasts. CD274+ and CD274-fibroblast were flow sorted from fibroblasts of healthy and IPF lungs. The cells were plated onto matrigel chamber for invasion assay, with and without anti-CD274 antibody (α-CD274) and control IgG. Invasive fibroblasts were fixed, stained, and photographed.

Whether up-regulated PD1 signaling contributes to the invasive phenotype of IPF fibroblasts was tested next. CD274+ and CD274− fibroblasts from IPF and healthy lungs were flow sorted and analyzed with an invasion assay. The results demonstrated that CD274+ fibroblasts have increased invasive capacity compared to CD274− cells from the same lung. Application of a CD274 antibody (InVivoMab anti-human PD-L1, clone: 29E.2A3) was able to (partially) attenuate the invasive phenotype of CD274+IPF fibroblasts (FIG. 5A). CD274+ fibroblasts also showed increased migration capacity compared to that of the CD274− cells, and this phenotype was reversed by CD274 antibody (FIG. 5B).

Figure 6:
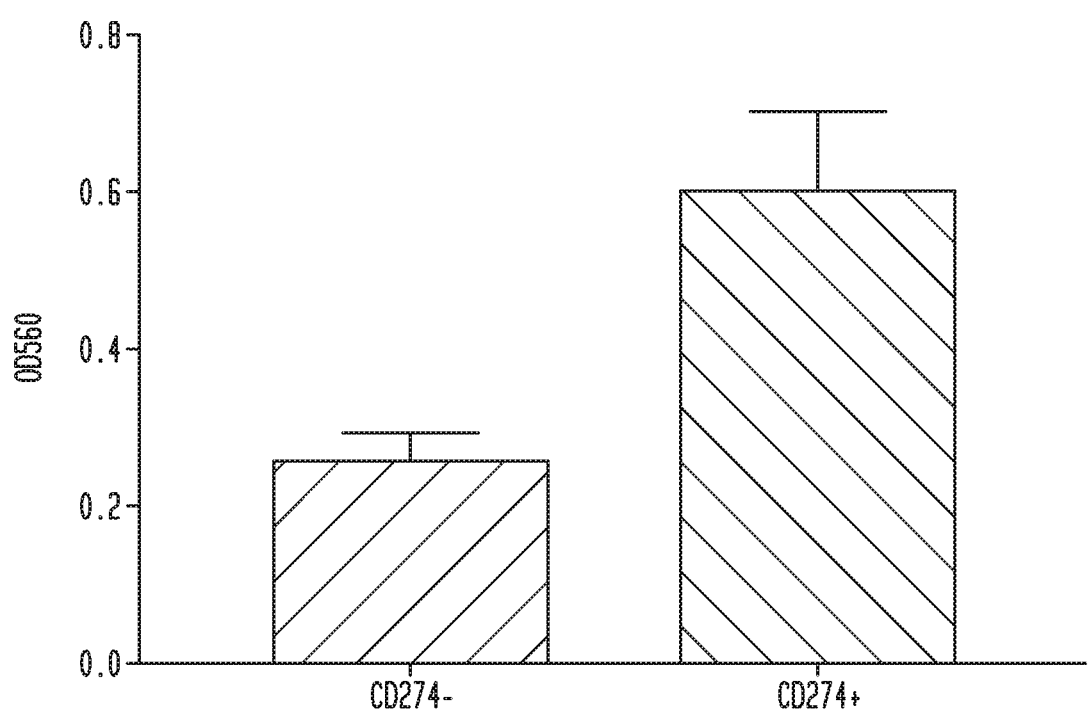
FIG. 6 is a graph that shows the results of a fibroblast adhesion assay. CD274+ and CD274− cells were flow sorted from IPF fibroblasts. Cells were then plated on collagen IV coated plate in serum free medium for an hour. Absorbance of cell lysis of adhesive cells was read with a microplate reader.

Cell adhesion assays showed that CD274+ fibroblasts from IPF lung demonstrated enhanced adhesion relative to CD274− cells from the same patient lung (FIG. 6). These data indicated that the up-regulated PD1 pathway altered fibroblast behavior toward a pro-fibrogenic phenotype in IPF lung, suggesting that targeting this pathway may attenuate lung fibrosis.

Example 3. Targeting PD1/PD-1 Ligand Pathway for Pulmonary Fibrosis In Vivo

Figure 7:
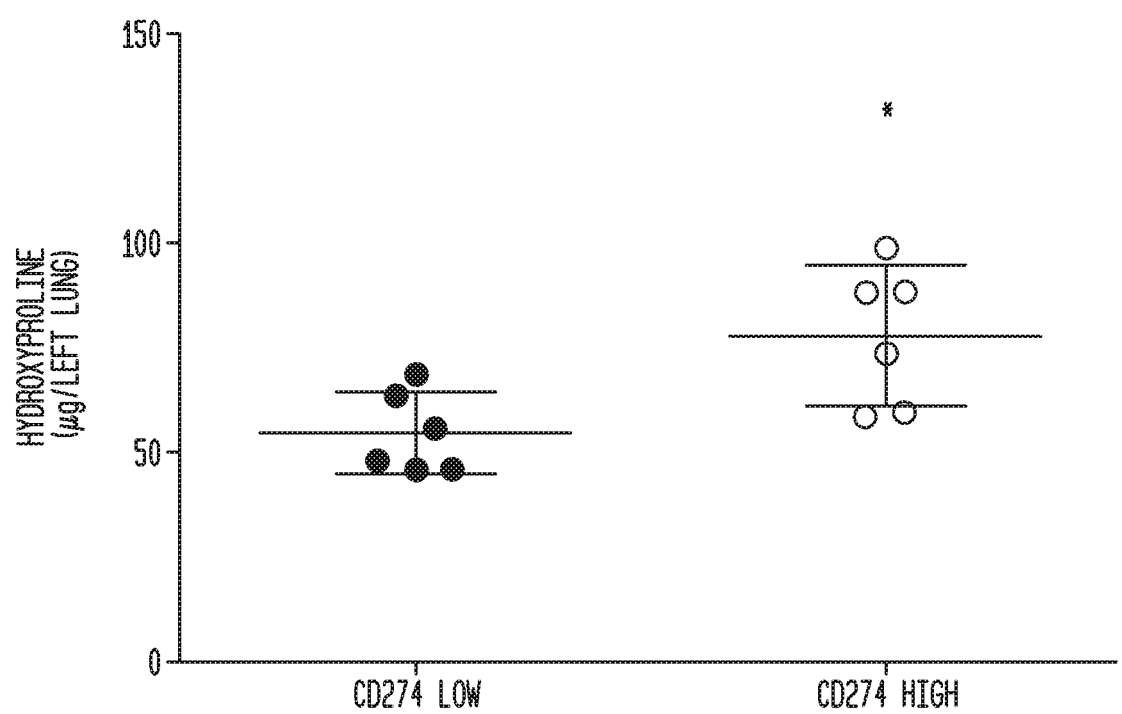
FIG. 7 is a graph that shows lung fibrosis outcomes in CD274+ fibroblast-injected mice compared to controls (CD274−). CD274+ and CD274− cells were flow sorted from IPF fibroblasts and injected into NSG mice via tail vein. Lung fibrosis was assessed 60 days after injection by measurement of hydroxyproline (□g/left lung).

CD274+ and CD274− fibroblasts from lungs of patients with IPF were sorted by flow cytometry and injected into immunocompromised mice (NOD-scid-IL2Rγc(−/−) (NSG) mice) subcutaneously. Lung fibrosis outcomes including trichrome staining and hydroxyproline contents were measured and compared between the mice injected with CD274+ and with CD274− fibroblasts 60 days after injection. Initial assessment showed an increase in collagen content in CD274+ fibroblast-injected mice (FIG. 7). This data suggests that the CD274+ invasive fibroblasts form more fibrotic foci in this in vivo model.

The effect of antibodies including anti-PD-L1 (InVivoMab anti-human PD-L1, clone: 29E.2A3) and anti-PD-L2 (InVivoMAb anti-mouse PD-L2 (B7-DC)) antibodies on pulmonary fibrosis will be tested using this mouse model. The antibodies and isotype controls will be administered to mice via intraperitoneal injection daily after injection of flow sorted CD274+ and CD274− cells subcutaneously. Different starting points of antibody treatment will be tested at day 0, day 10, day 20, and day 30 after injection of fibroblasts. Two doses of antibodies, 250 □g and 500 □g per mouse will be tested. The antibody treated and control IgG treated mice will be sacrificed at day 60 after CD274+ and CD274− IPF lung fibroblast injection and lung fibrosis will be compared between groups.

Example 4. Role of PD1/PD-1 Ligand Signaling in Fibroblasts on Alveolar Stem Cell Renewal in Fibrotic Lungs Epithelial injury is an essential contributing event to lung fibrosis in IPF. Injured epithelial cells release mediators that promote fibroblast proliferation and differentiation (13). The following experiments will be performed to investigate the role of CD274+ fibroblasts on alveolar type II stem cell renewal.

1. Compare CD274+ and CD274− fibroblasts from both healthy and IPF lungs on supporting alveolar type II stem cell renewal using 3D matrigel culture.

2. Compare epithelial cell apoptosis in the mouse lungs injected with CD274+ and CD274− fibroblasts.

3. Compare proliferation of epithelial cells in the lungs of mice injected with CD274+ and CD274− fibroblasts using BrdU labeling and Ki67 staining.

Briefly, BrdU: 5-bromo-2'-deoxyuridine (BrdU, 50 mg/kg, from Sigma) is intraperitoneally injected to mice daily for 5 days before harvesting. Cryosections are used for BrdU, Ki67, and SFTPC co-staining. BrdU antibody is from Accurate Chemical. SFTPC antibody is from Millipore. Antibody against Ki67 wis from eBioscience.

Example 5. FAK Activation in the PD1/PD-1 Ligand Pathway

Figure 8A:
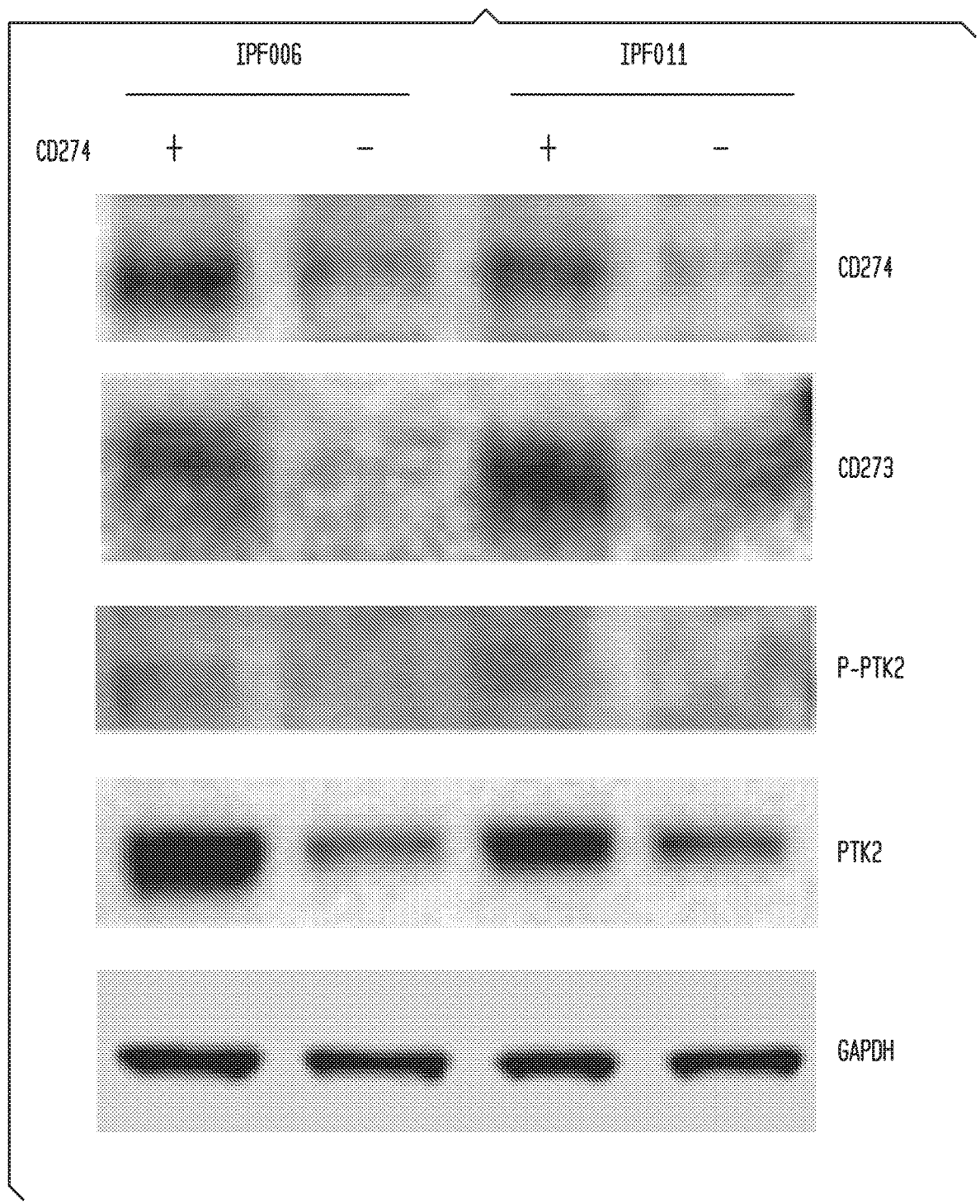
FIG. 8A shows the results of Western blot analysis to assess expression of total and phosphorylated PTK2 (focal adhesion kinase (FAK)). CD274+ and CD274− cells were flow sorted from IPF fibroblasts. Expression of CD274, CD273, phosphorylated and total PTK2 (FAK) is shown. Glyceraldehyde 2-phosphate dehydrogenase (GAPDH) is used as a loading control.

In experiments comparing gene expression of invasive and non-invasive fibroblasts, focal adhesion kinase (FAK) expression was markedly increased. Western blot analysis confirmed expression of total and phosphorylated PTK2 (FAK) (FIG. 8A). Significantly higher expression of total and phosphorylated PTK2 (FAK) was seen in CD274+ fibroblasts.

Figure 8B:
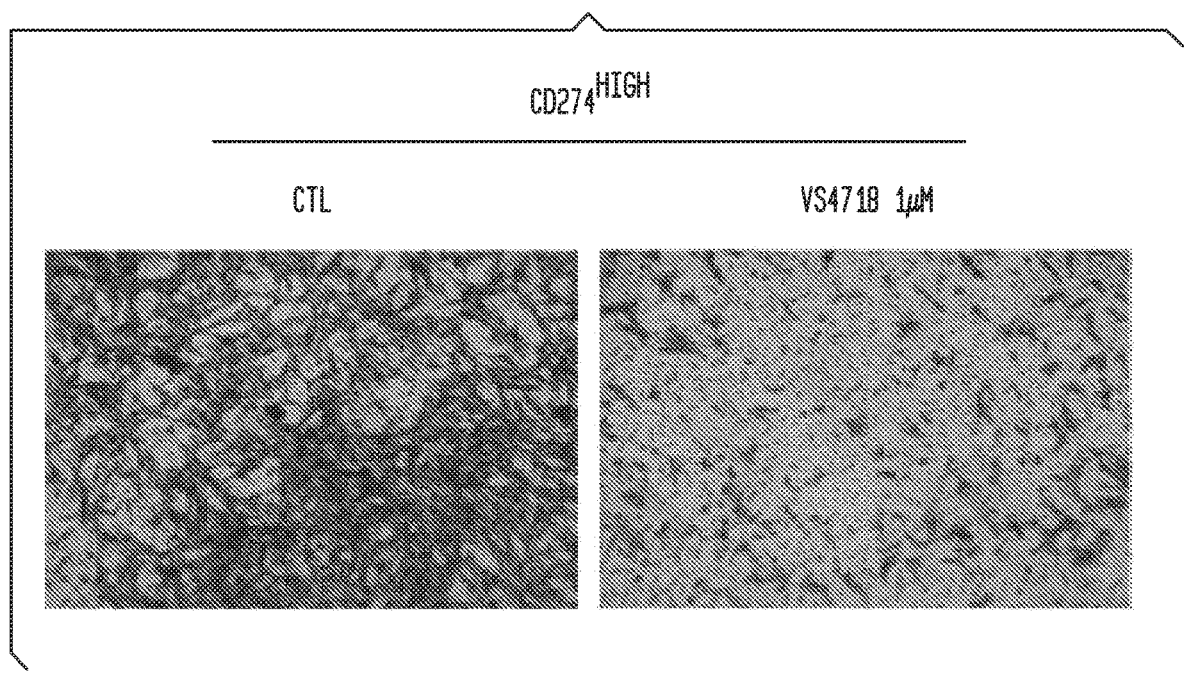
FIG. 8B shows that inhibition of FAK with a FAK inhibitor (VS4718, Veristem, Inc.) reduced invasiveness of CD274+ fibroblasts. The panel on the left shows control, untreated CD274+ fibroblasts ("CTL"). The panel on the right shows CD274+ fibroblasts treated with VS4718.
Figure 9:
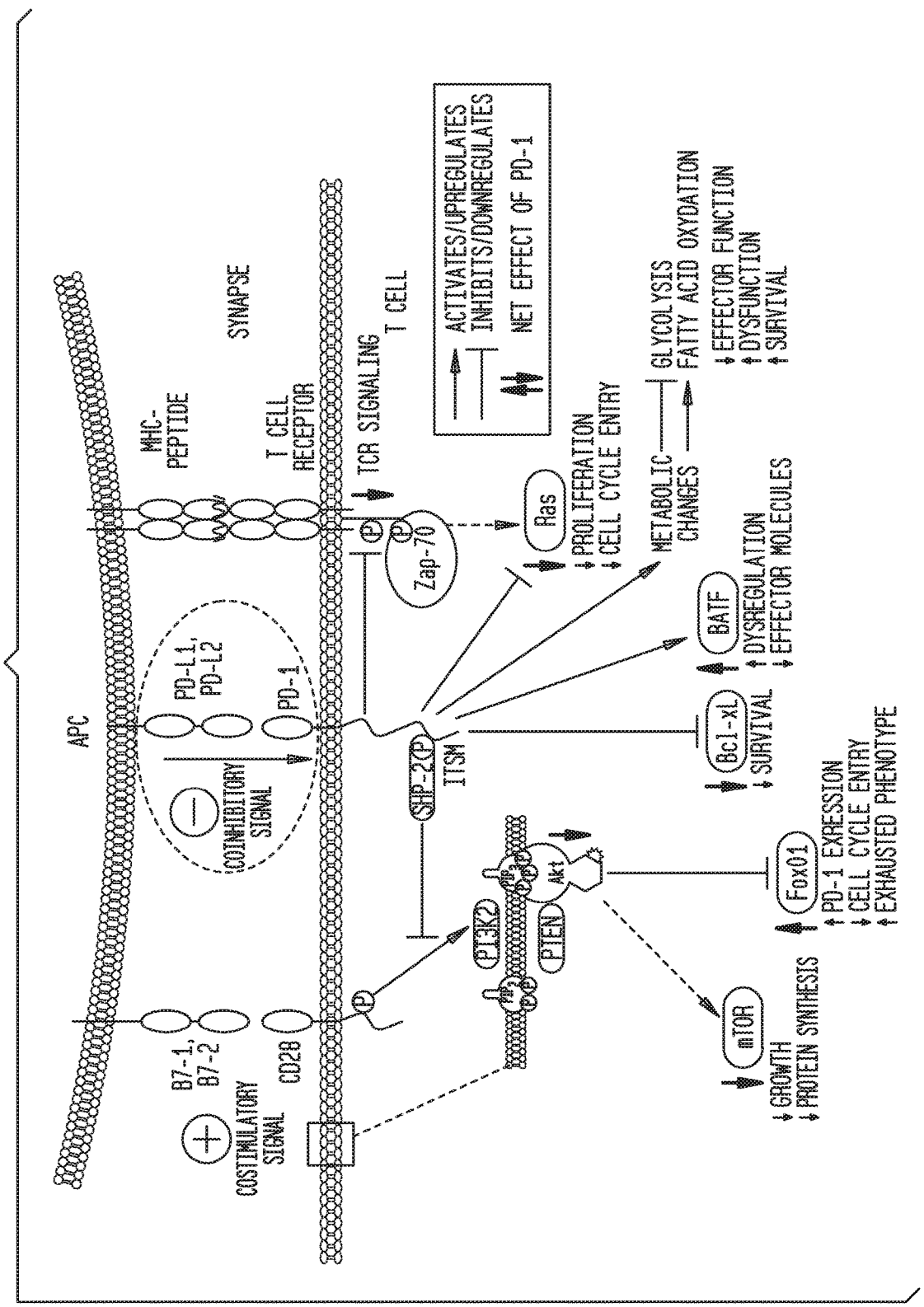
FIG. 9 is a schematic of PD1 signalling.

Furthermore, inhibition of FAK with a FAK inhibitor (VS4718, Chemietek, Indianapolis, Ind.) reduced invasiveness of CD274+ fibroblasts (FIG. 8B).

These results suggest that inhibition of FAK may be a key downstream signaling pathway of PD-1 ligand interactions, and that targeting FAK may be critical in inhibiting PD1-ligand-mediated fibrosis.

Example 6. Combination Treatment for Attenuating Pulmonary Fibrosis

Commercially available antibodies, small molecule agents, and other reagents targeting the PD-1 pathway, in combination with FAK inhibitors, will be tested for their effect on attenuating pulmonary fibrosis in in vitro and in vivo experiments.

For in vitro invasion assay, both FAK inhibition with VS4718 (Chemietek, Indianapolis, Ind.) and α-CD274 (In-VivoMab anti-human PD-L1, clone: 29E.2A3) are used to treat CD274+ fibroblasts, and their effect on invasiveness is assessed.

For in vivo experiments, both FAK inhibition with VS4718 (Chemietek, Indianapolis, Ind.) and α-CD274 (In-VivoMab anti-human PD-L1, clone: 29E.2A3) is used to treat the mice injected with CD274+ fibroblasts, either early stage (day 0-35) or late stage (day 35-day 63). The effect of the inhibition is assessed with hyroxyproline assay.

Example 7. Fibrogenic Potential of Invasive Fibroblasts

Figure 10A:
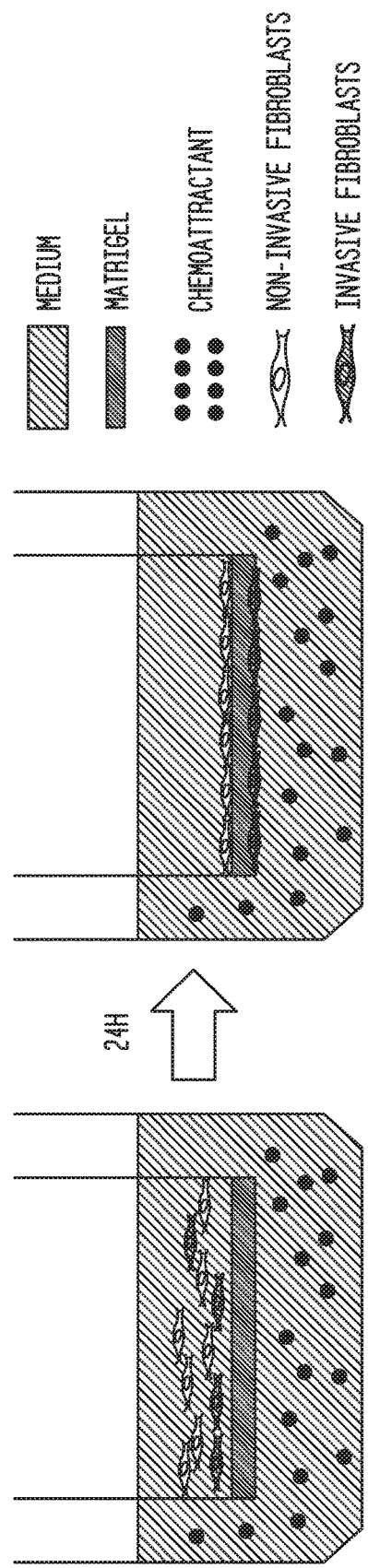
FIG. 10A-FIG. 10D shows RNA-seq analysis of invasive and non-invasive IPF lung fibroblasts.
Figure 11A:
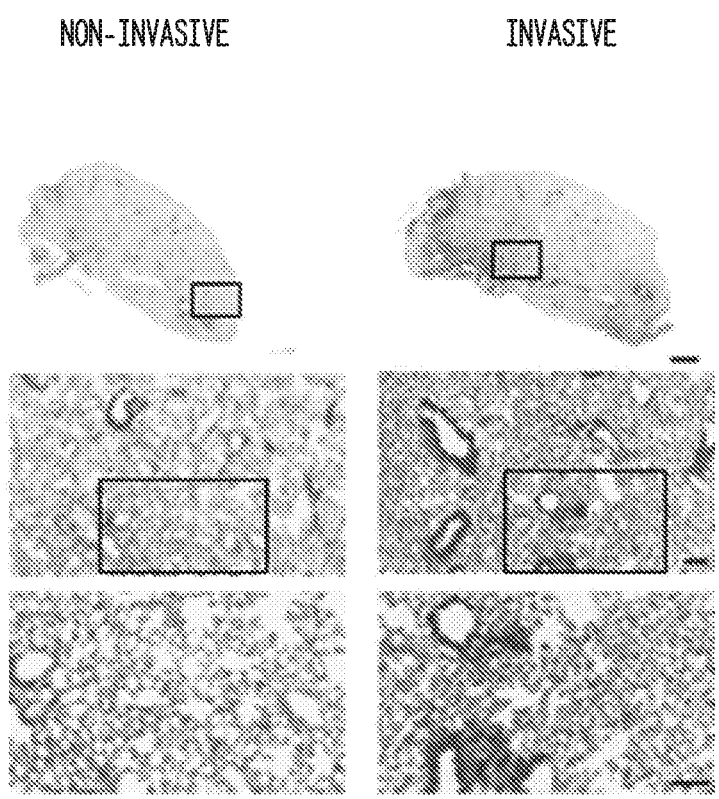
FIG. 11A-FIG. 11I shows up-regulation of PD-1 ligands in invasive fibroblasts.
Figure 11B:
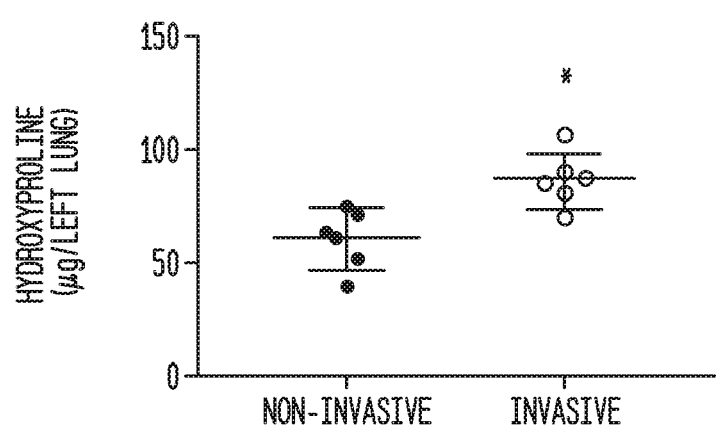

Previous studies have demonstrated that fibroblasts from IPF patients acquire an invasive phenotype that is essential for severe fibrogenesis (2, 25-27). This phenotype is regulated by hyaluronan synthase 2 (HAS2), CD44, beta-arrestins, as well as an α6(β1)-integrin-mediated mechanosensing mechanism (2, 25-27). To demonstrate the fibrogenic potential of invasive fibroblasts in vivo, invasive and non-invasive IPF lung fibroblasts were isolated using the matrigel invasion assay (shown schemically in FIG. 10A), and were injected intravenously into NOD-scid-IL2Rγc (−/−) (NSG) mice (humanized SCID IPF model) (28). After 50 days, mice injected with invasive IPF lung fibroblasts showed more diffuse interstitial fibrosis and increased hydroxyproline in the lung than mice injected with non-invasive IPF lung fibroblasts (FIG. 11A, FIG. 11B).

Figure 10B:
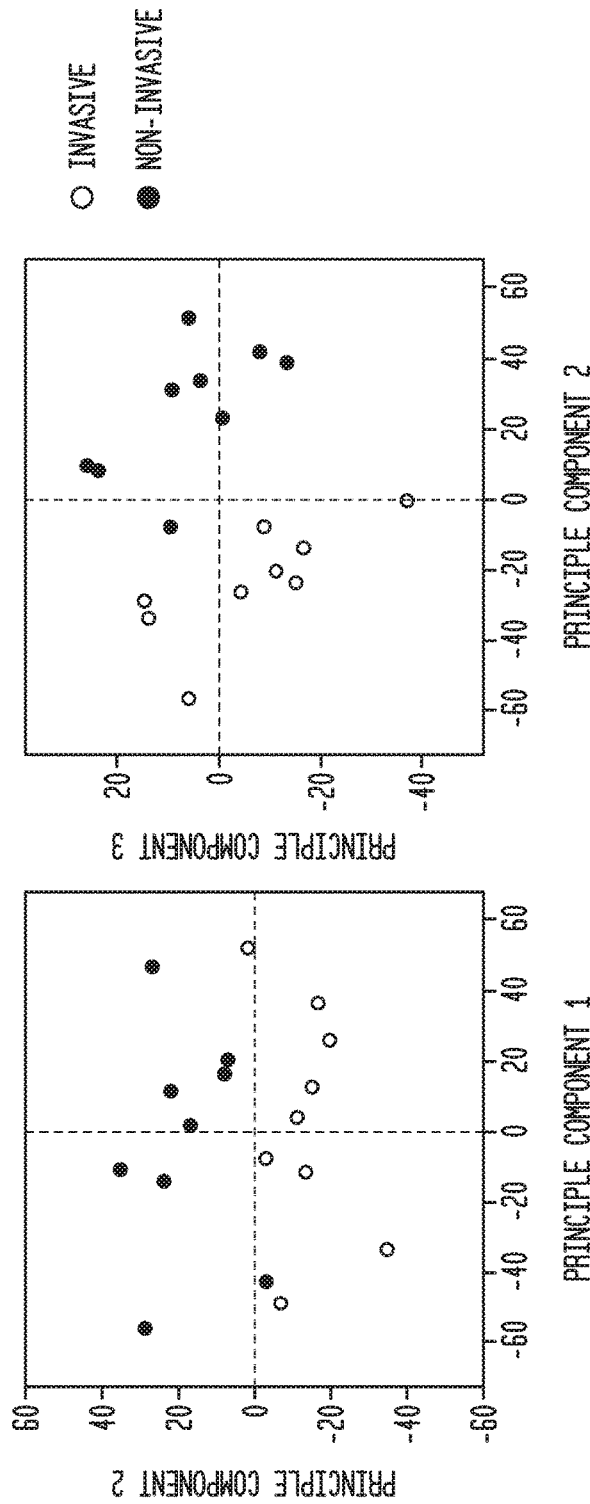
Figure 10C:
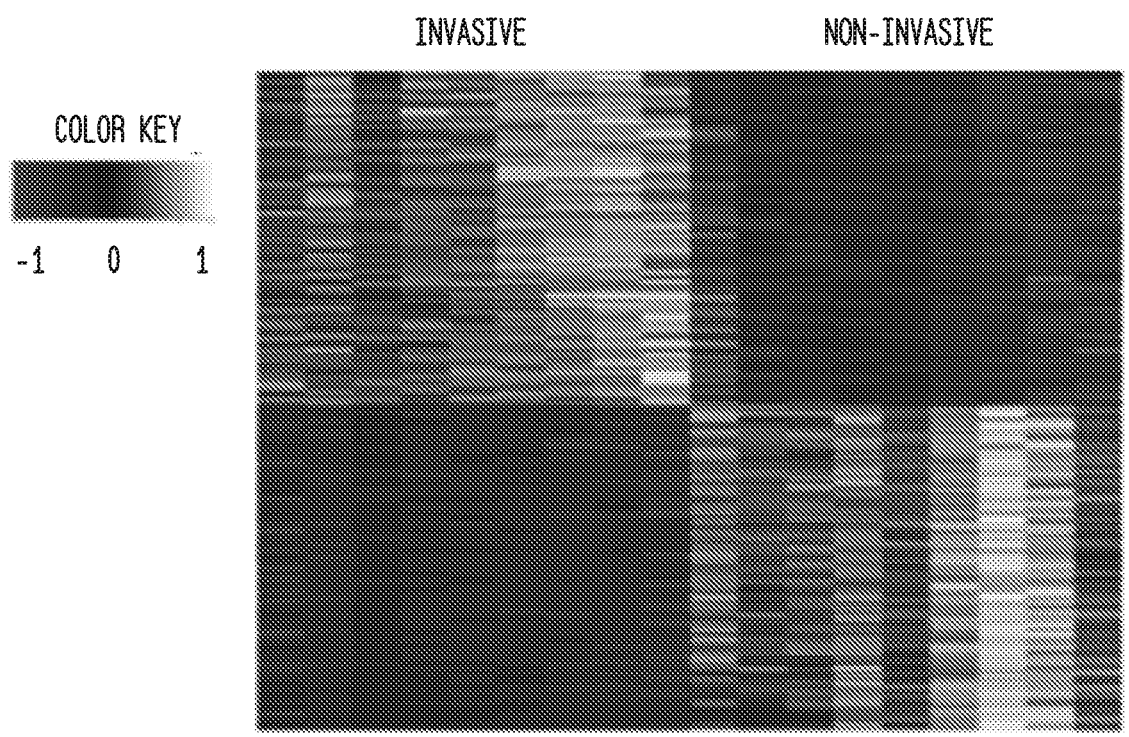
Figure 12A:
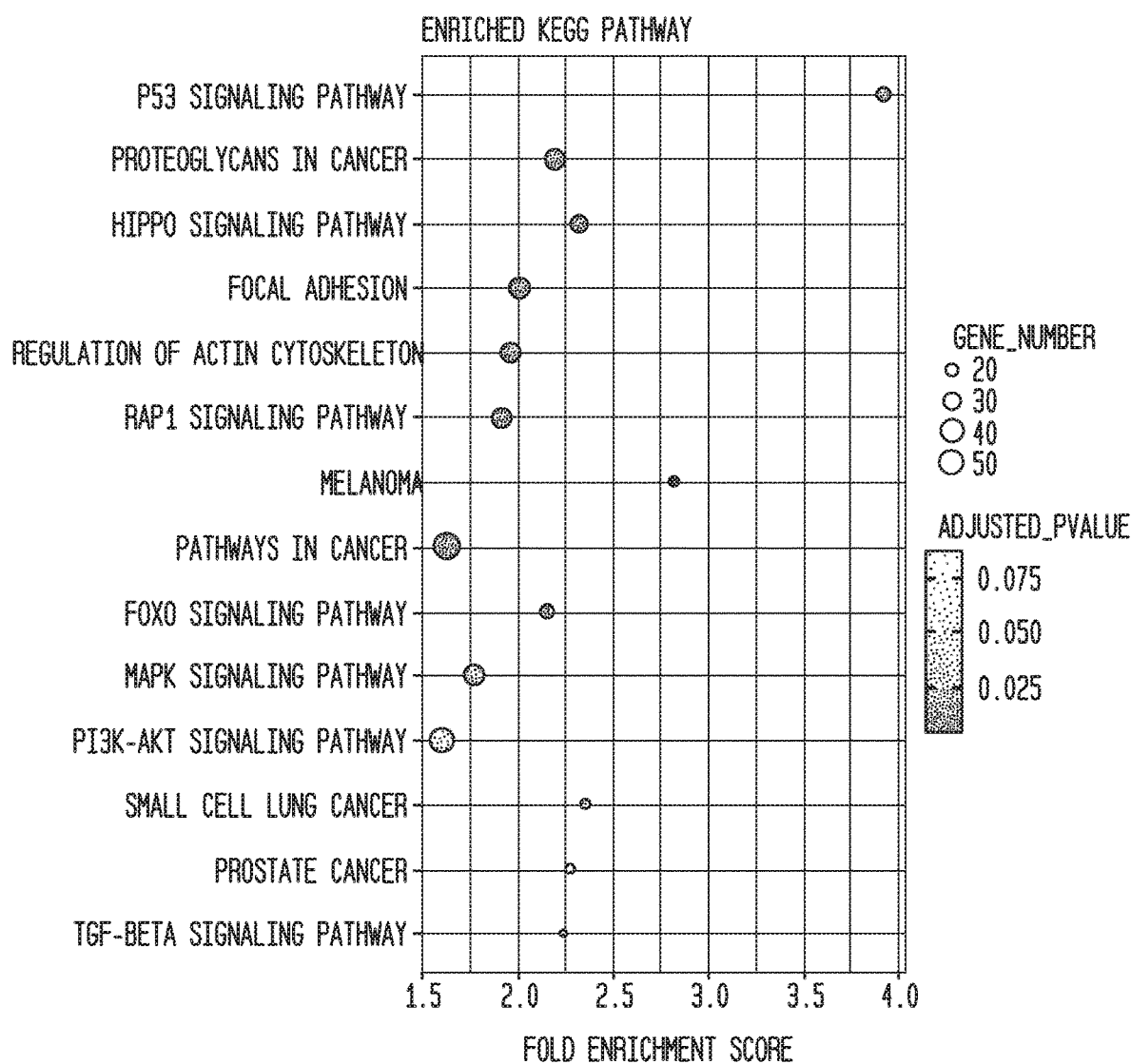
FIGS. 12A and 12B show KEGG pathway enrichment analysis of 1,405 DE genes, of RNA-seq data (FIG. 12A) and relative gene expression of TP53 signaling pathways in RNA-seq (n=9 per group) analysis (FIG. 12B). The P value of each gene between invasive and non-invasive was less than 0.05.
Figure 12B:
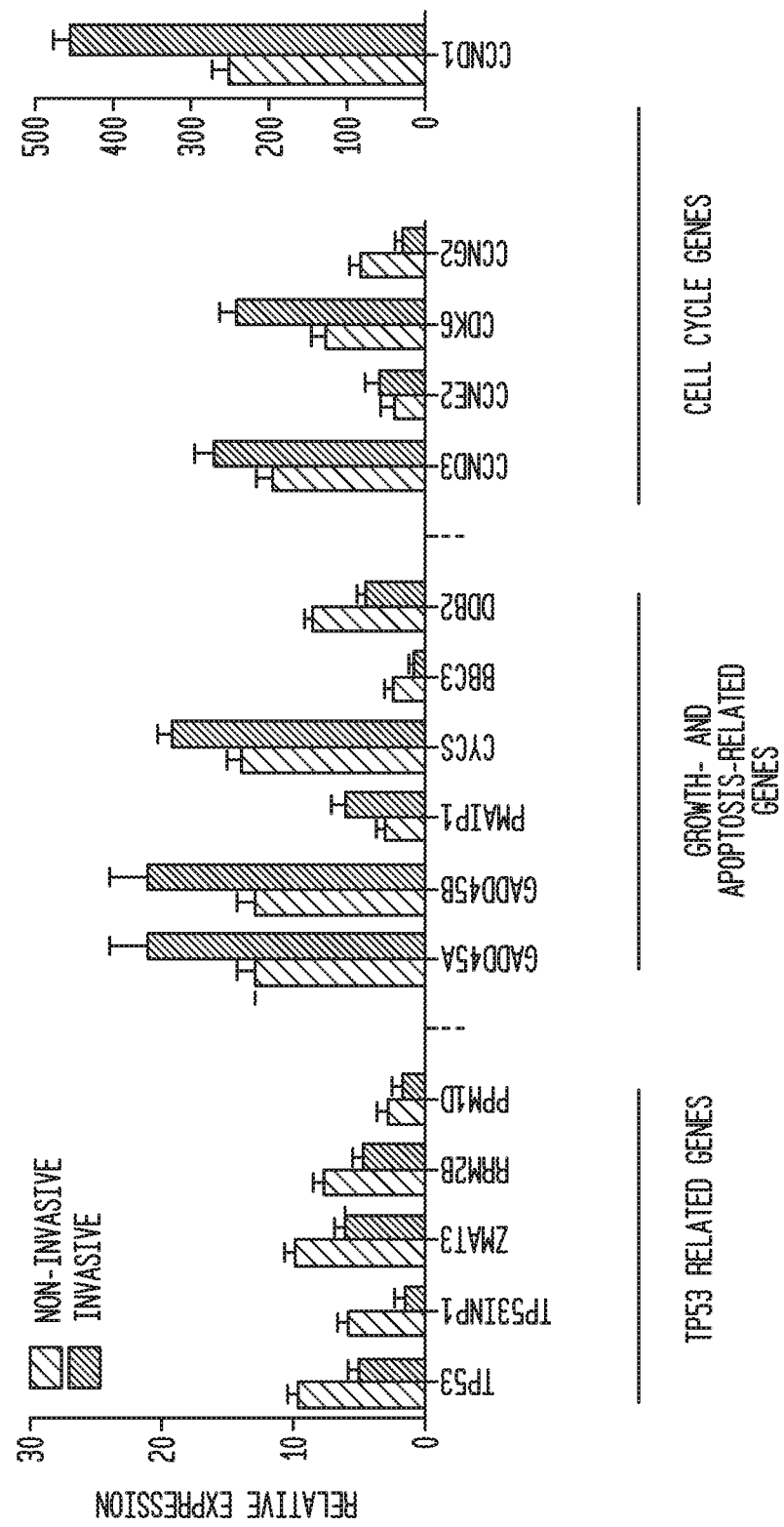

Example 8. Comparison of Invasive and Non-Invasive IPF Lung Fibroblast Gene Expression To gain insights into mechanisms that regulate invasion, invasive and non-invasive IPF lung fibroblast gene expression was compared using RNA-seq. A total of 1,405 differentially expressed (DE) genes were identified, among them, 719 DE genes were up-regulated, and 686 DE genes were down-regulated (FIG. 10B, FIG. 10C). Kyoto Encyclopedia of Genes and Genomes (KEGG) pathway analysis for DE genes revealed that the p53 signaling pathway, focal adhesion, regulation of actin cytoskeleton, MAPK and cancer signaling pathways were significantly correlated with the lung fibroblast invasive phenotype (FIGS. 12A and B).

Figure 10D:
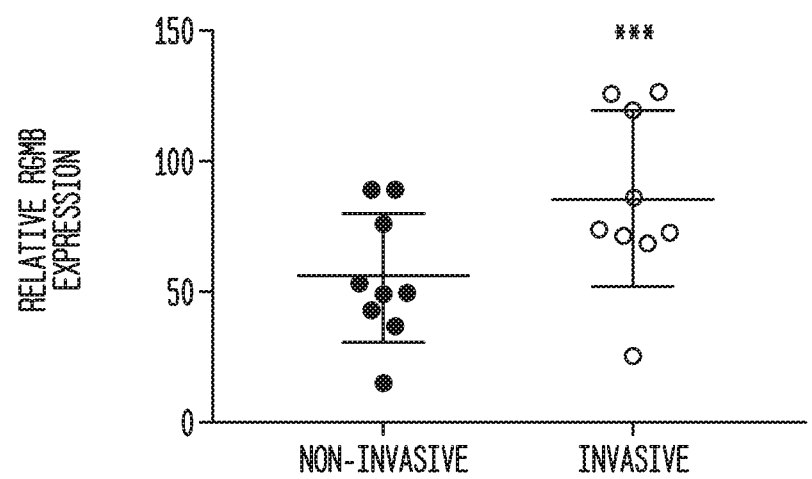
Figure 11C:
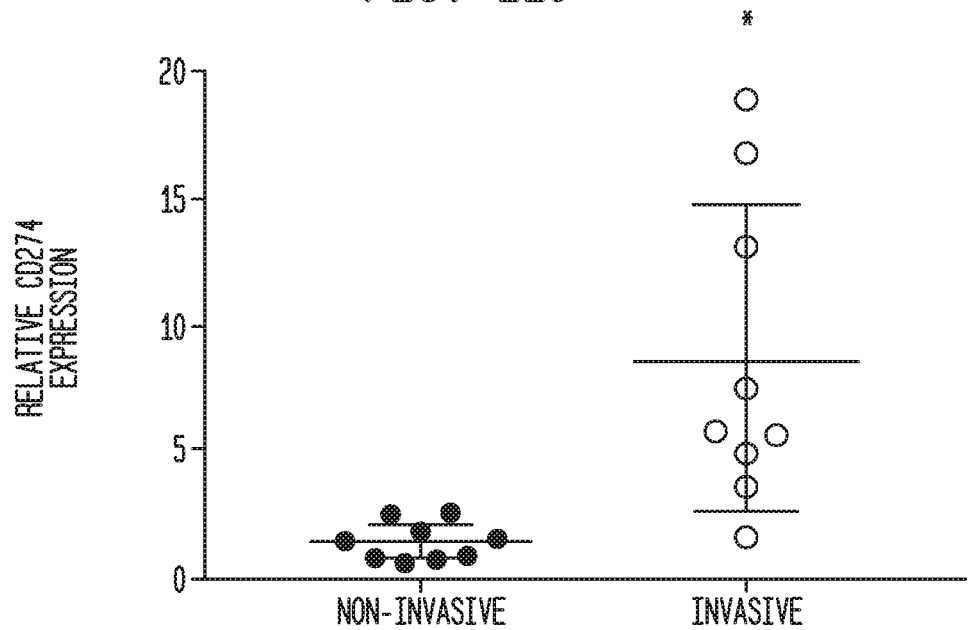
Figure 11D:
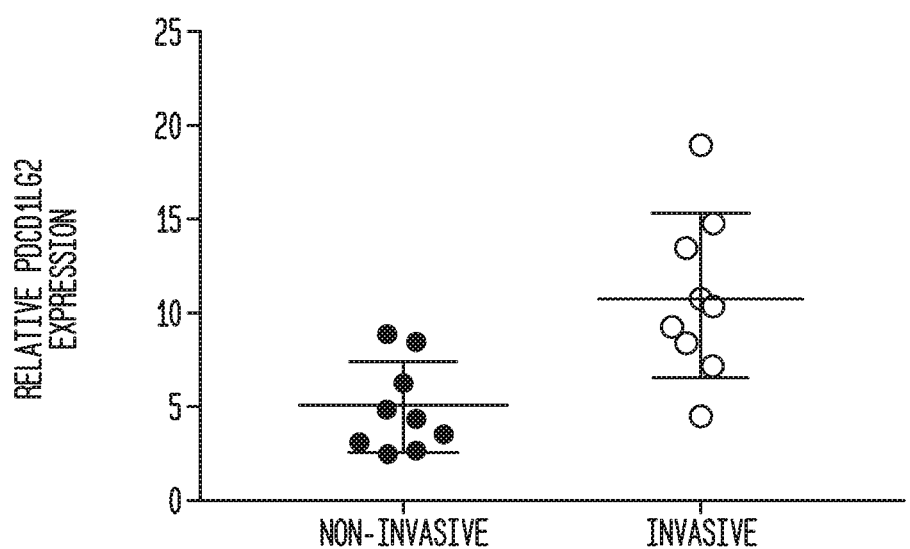

Example 9. Expression of Checkpoint Inhibitor Ligands is Upregulated in IPF Invasive Lung Fibroblasts Immune checkpoints are regulators for maintaining systemic immune homeostasis and self-tolerance (29). Among them, the PD1 pathway is utilized by cancer cells to escape the surveillance of the immune system (2). PD-1/PD-L1 blockade with monoclonal antibodies provides significant clinical benefits for patients with various cancers (29, 30). A few studies suggest PD-1 ligands are expressed on stromal cells (33, 34). There were more CD4+ and CD8+ cells in lung tissues and PD-1+ lymphocytes in peripheral blood from patients with pulmonary fibrosis than that from healthy controls (35). It was found that mRNAs for both checkpoint PD1 ligands, CD274 (PD-L1) and PDCD1LG2 (PD-L2) were significantly upregulated in invasive fibroblasts (FIG. 11C, FIG. 11D). Expression of RGMB, a binding partner for PD-L2 (36), was also upregulated in the IPF invasive lung fibroblasts (FIG. 10D). The expression of other stimulatory or inhibitory checkpoint molecules were either not expressed or not altered in the IPF invasive lung fibroblast (Table 1, shown below). In Table 1, N/A means not available.

TABLE 1

| Gene Expression | Stimulatory Checkpoint Molecules |
|---|---|
| N/A | CD27 |
| N/A | CD28 |
| N/A | CD40 |
| N/A | IL2RB |
| N/A | TNFRSF9 |
| N/A | TNFRSF4 |
| N/A | TNFRSF18 |
| N/A | ICOS |

| Gene Expression | Inhibitory Checkpoint Molecules |
|---|---|
| N/A | ADORA2A |
| No change | CD276 |
| N/A | VTCN1 |
| N/A | BTLA |
| N/A | CTEA-4 |
| N/A | IDO1 |
| N/A | KIR3DL1 |
| N/A | LAG3 |
| N/A | PDCD1 |
| N/A | HAVCR2 |
| N/A | C10orf54 |

Figure 11E:
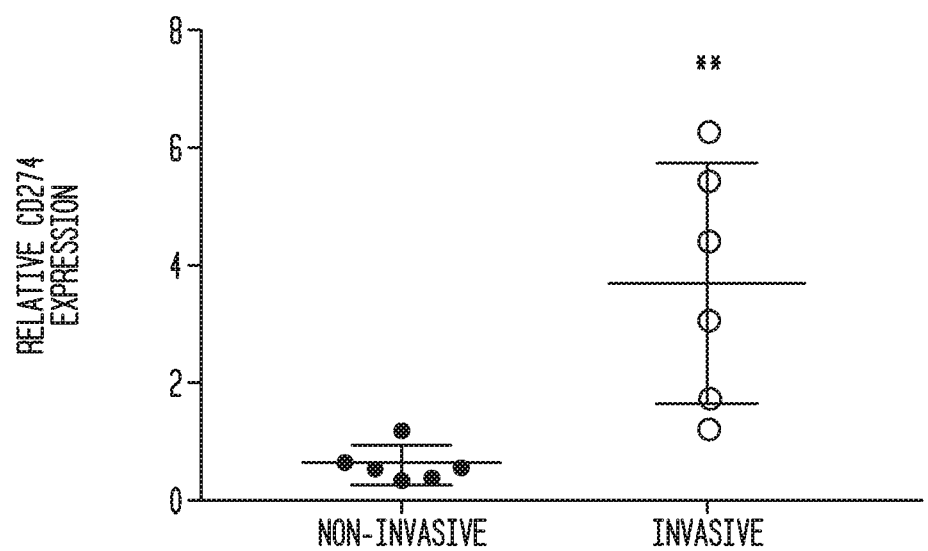
Figure 11F:
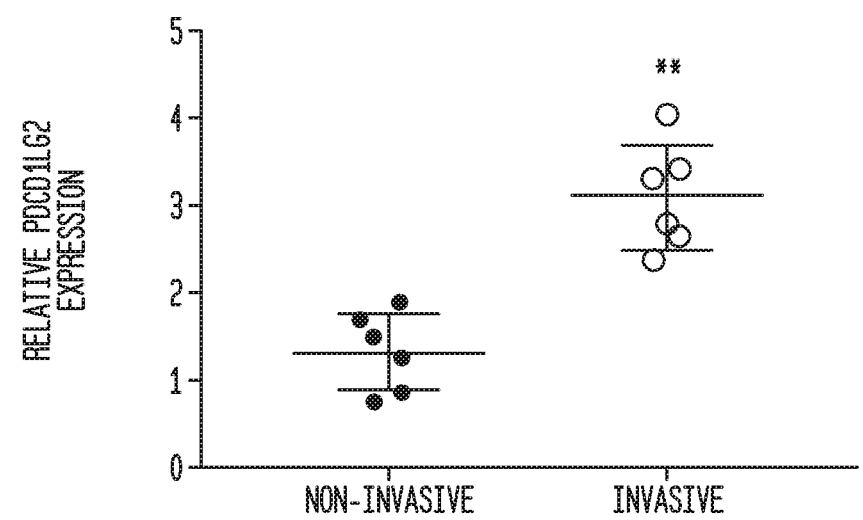
Figure 11G:
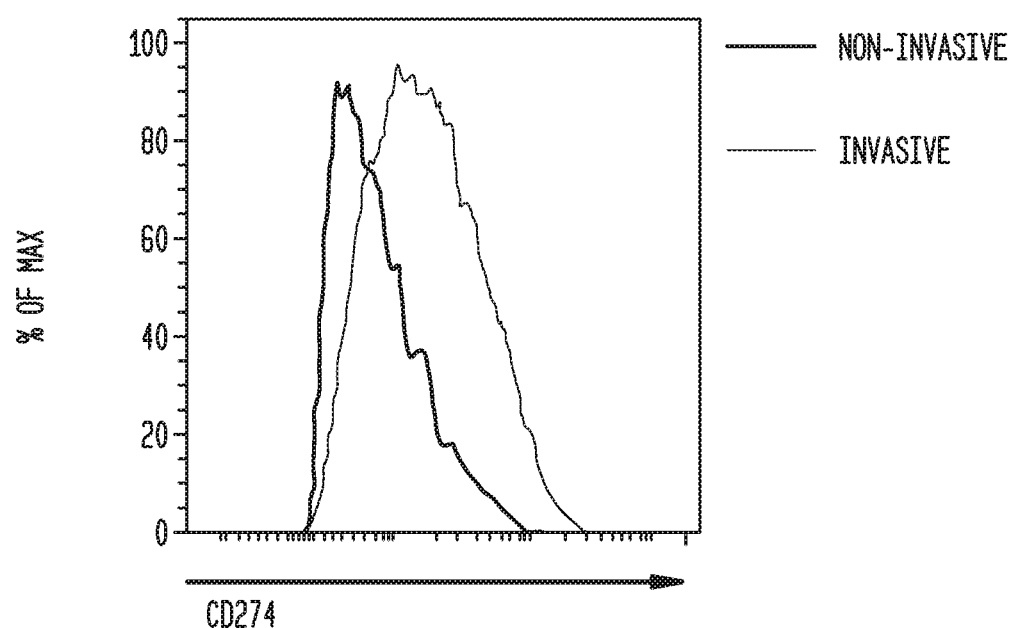
Figure 11H:
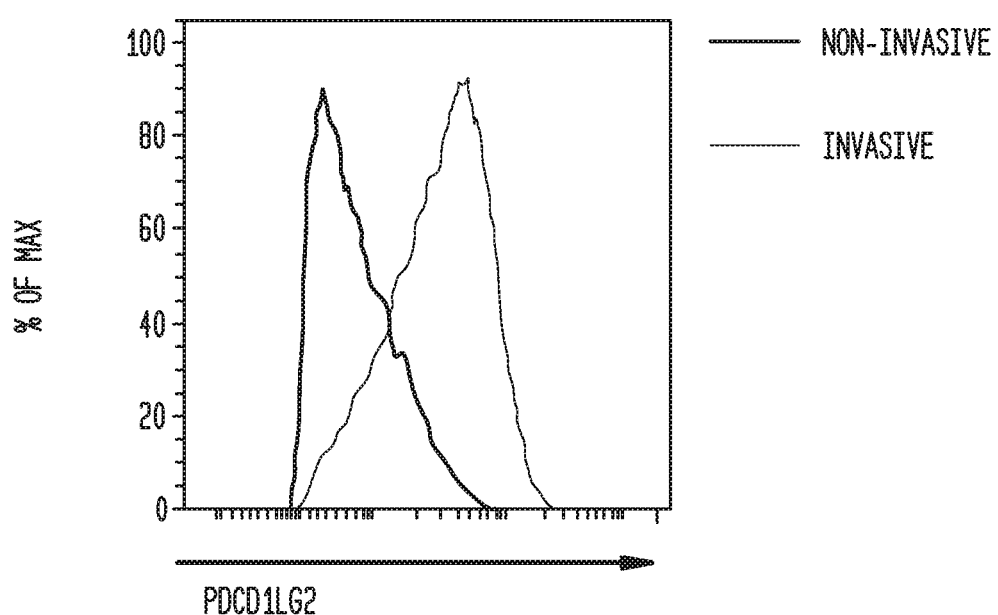
Figure 11I:
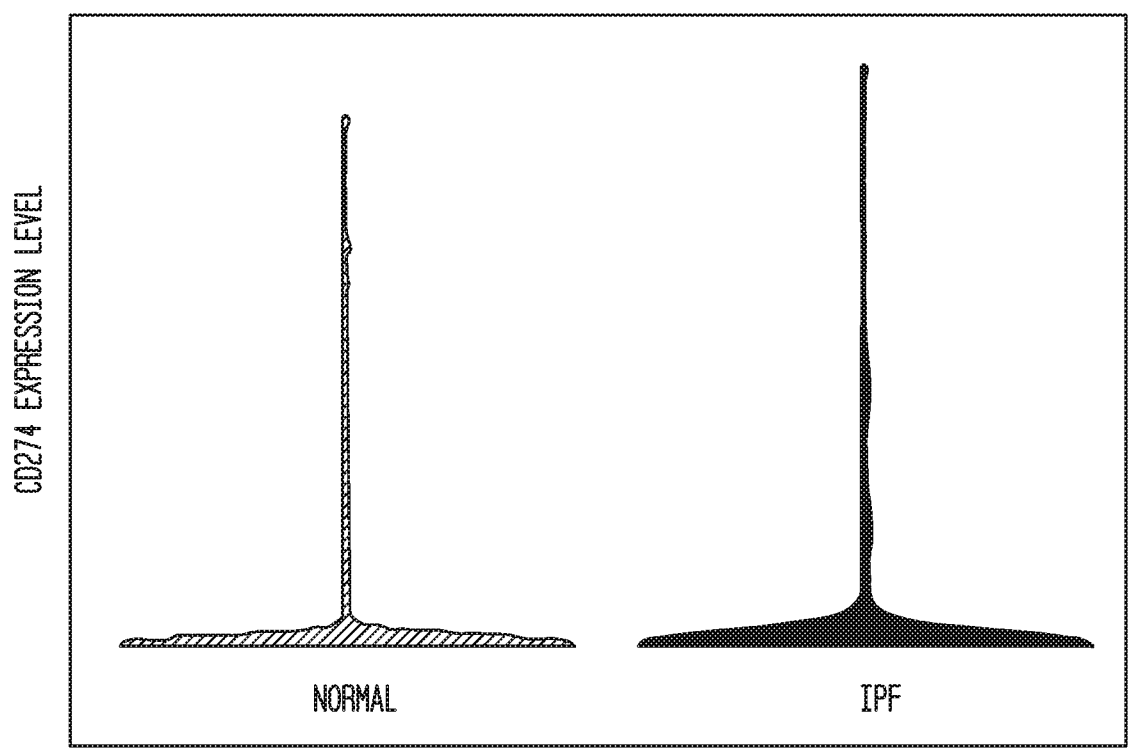
Figure 13A:
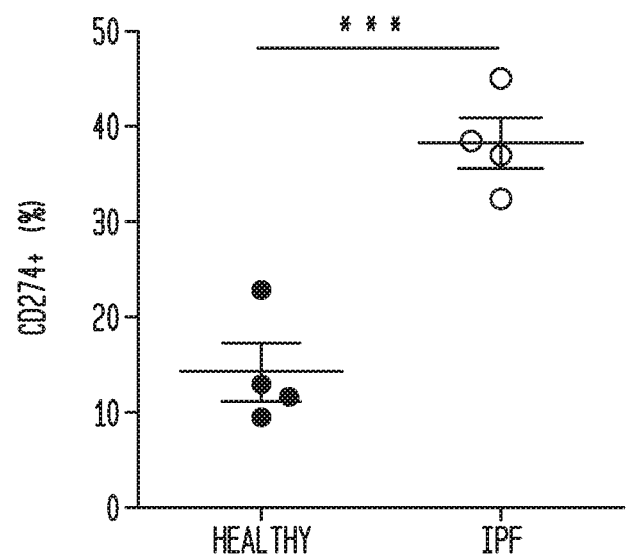
FIG. 13A shows cell surface expression of CD274 in healthy and IPF lung fibroblasts (n=4 per group).
Figure 13B:
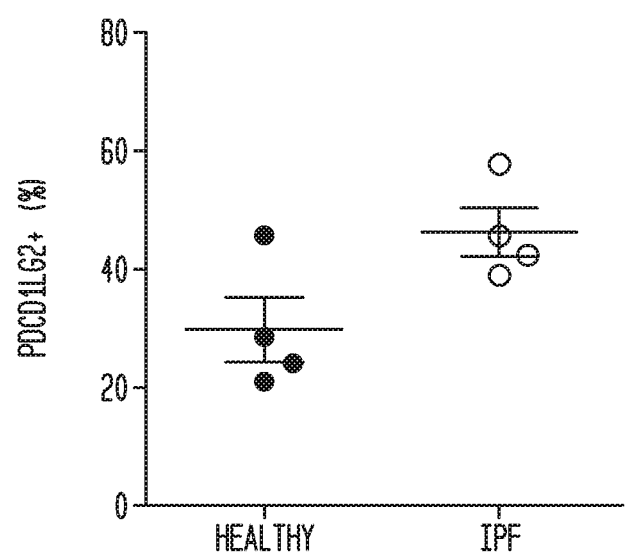
FIG. 13B shows PDCD1LG2 expression in healthy and IPF lung fibroblasts (n=4 per group). Data are mean±sem. ***P<0.001 by student's t test.
Figure 13C:
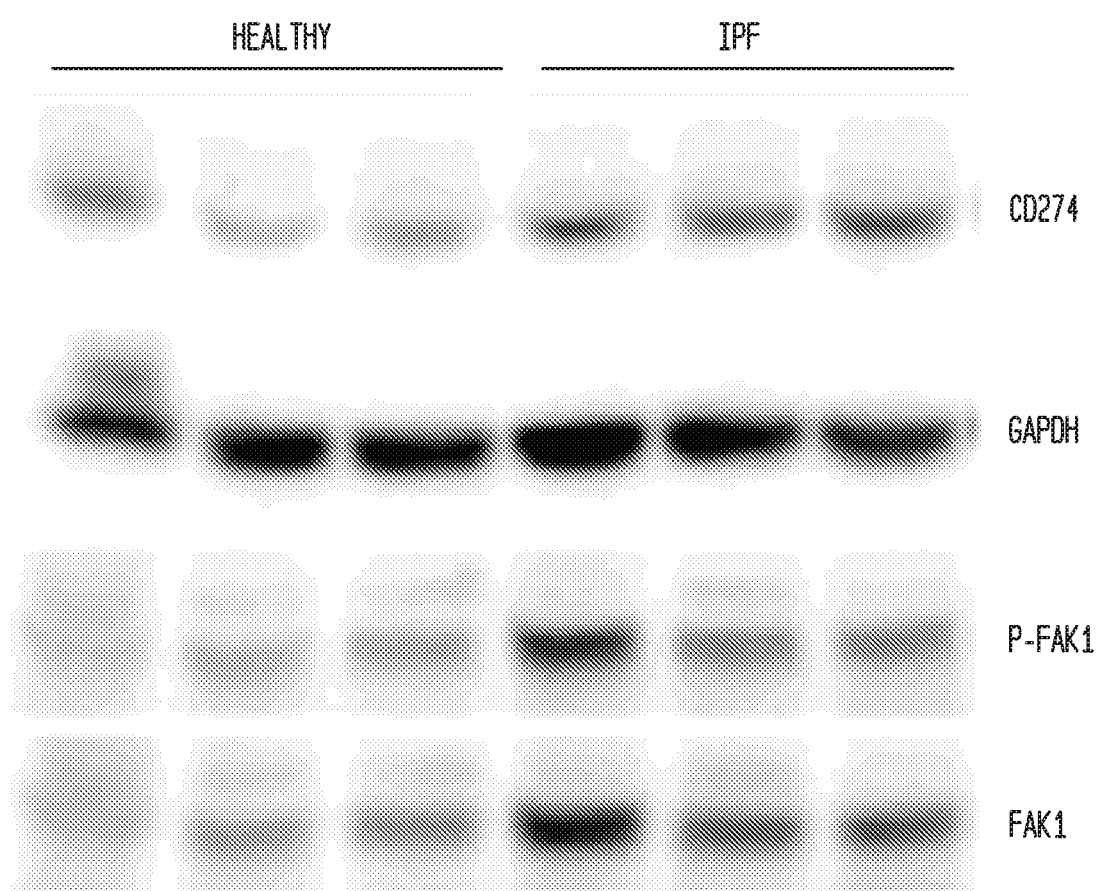
FIG. 13C shows Western blot analyses of CD274, p-FAK1, FAK1 and GAPDH in healthy and IPF lung fibroblasts. GAPDH served as equal loading control.
Figure 13D:
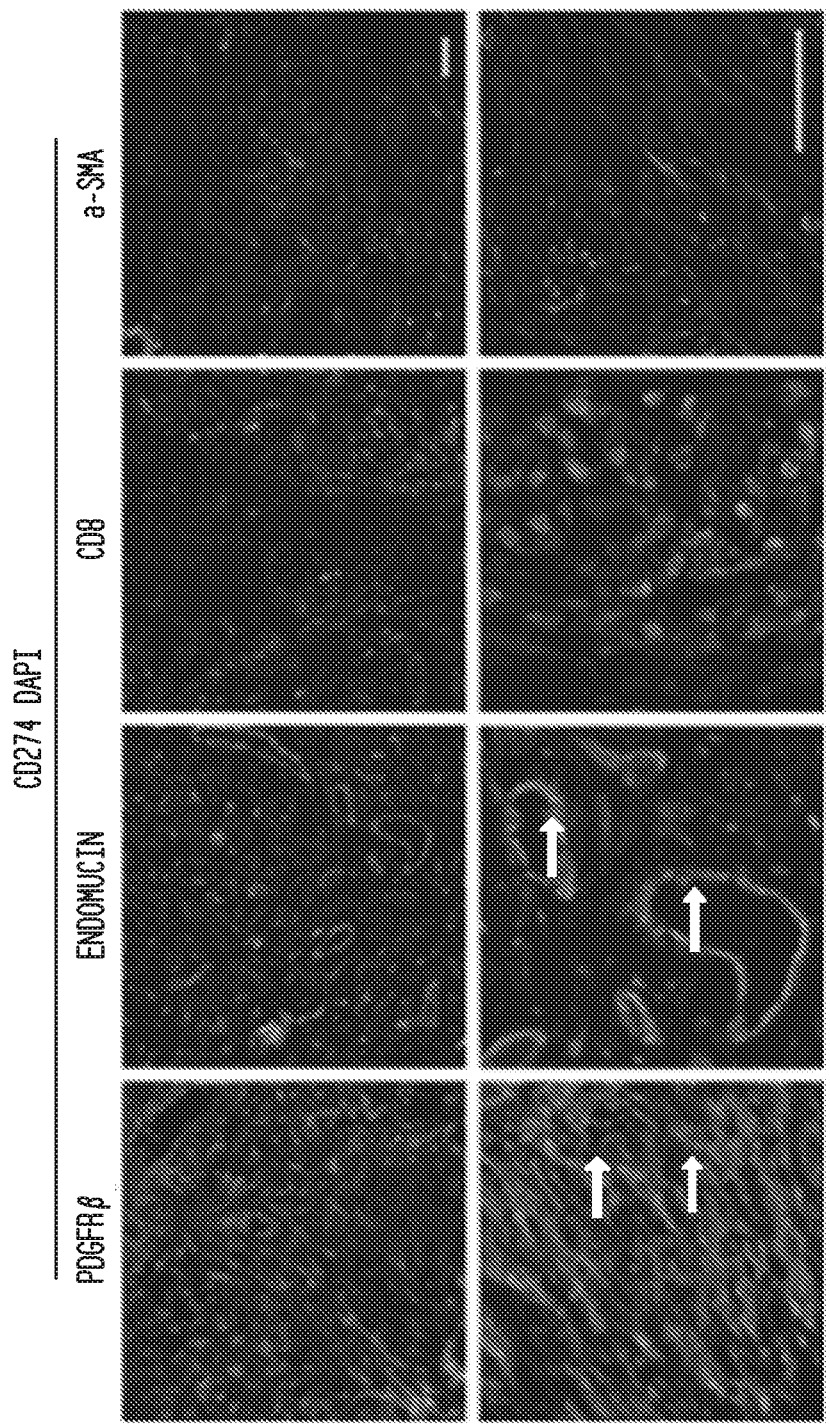
FIG. 13D shows immuno-co-staining of CD274 and PDGFRβ, Endomucin, CD8α or α-SMA. Scale bar: 50 pm.

The RNA-seq data was validated using qRT-PCR (FIG. 11E, FIG. 11F) and flow cytometric analysis (FIG. 11G, FIG. 11H). Cell surface expression (FIG. 11G, FIG. 11H and FIG. 13A, FIG. 13B) and total protein expression of CD274 was higher on the IPF lung fibroblasts than on fibroblasts from healthy controls (FIG. 13C). CD274 expression was co-localized with a small portion of PDGFRβ+ (lung fibroblast marker) and Endomucin+ (endothelial cell marker) cells, but not with α-SMA+ cells (myofibroblast marker). CD274 expression was also found adjacent to CD8 T cells (FIG. 13D). The enhanced expression of CD274 was further confirmed with total single cell lung homogenate from IPF or healthy control subjects by using single-cell RNA-seq analysis (FIG. 11I).

Figure 14A:
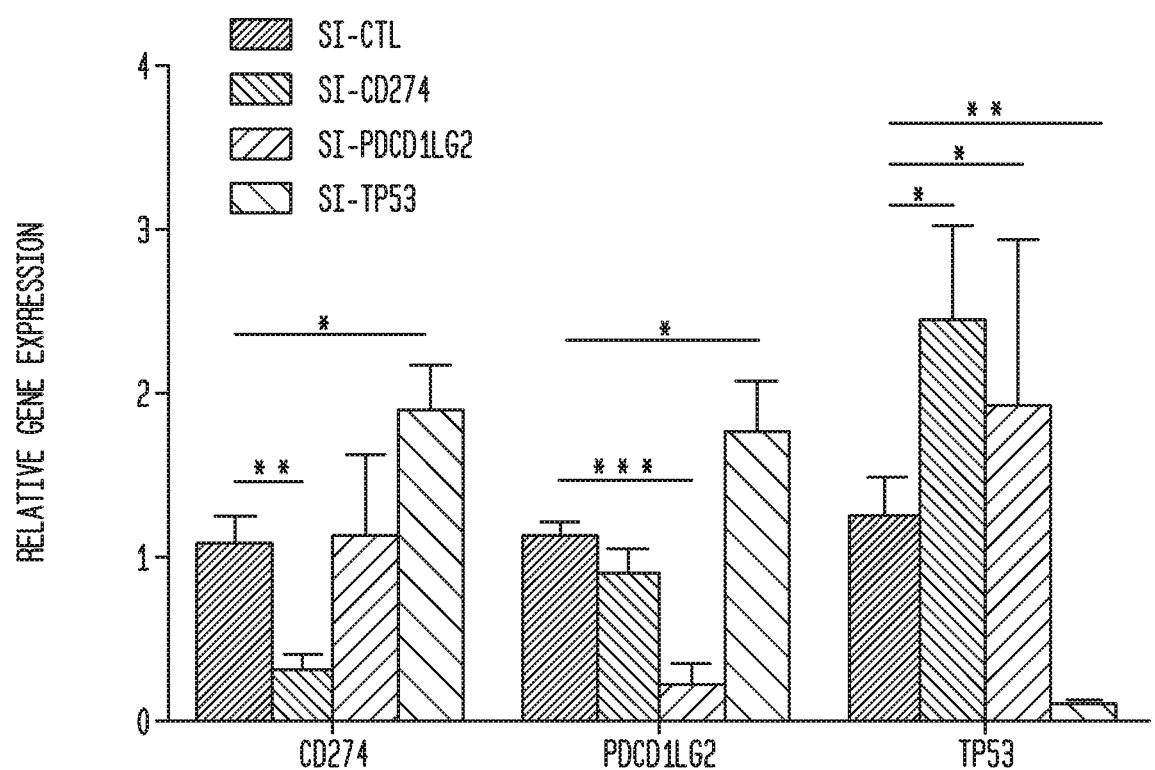
FIG. 14A is a graph that shows gene expression (n=3 per group) of CD274, PDCD1LG2, TP53 and GAPDH in IPF lung fibroblasts treated Si-CTL, Si-CD274, Si-PDCD1LG2 or Si-TP53.
Figure 14C:
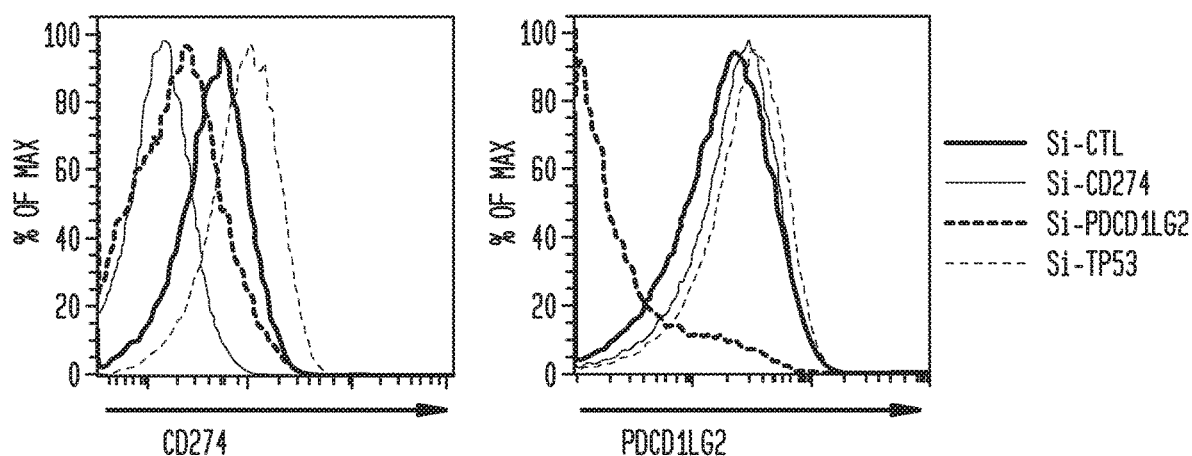
FIG. 14C contains graphs that show cell surface expression of CD274 and PDCD1LG2 in IPF lung fibroblasts treated Si-CTL, Si-CD274, Si-PDCD1LG2 or Si-TP53 after 68 hours.
Figure 14D:
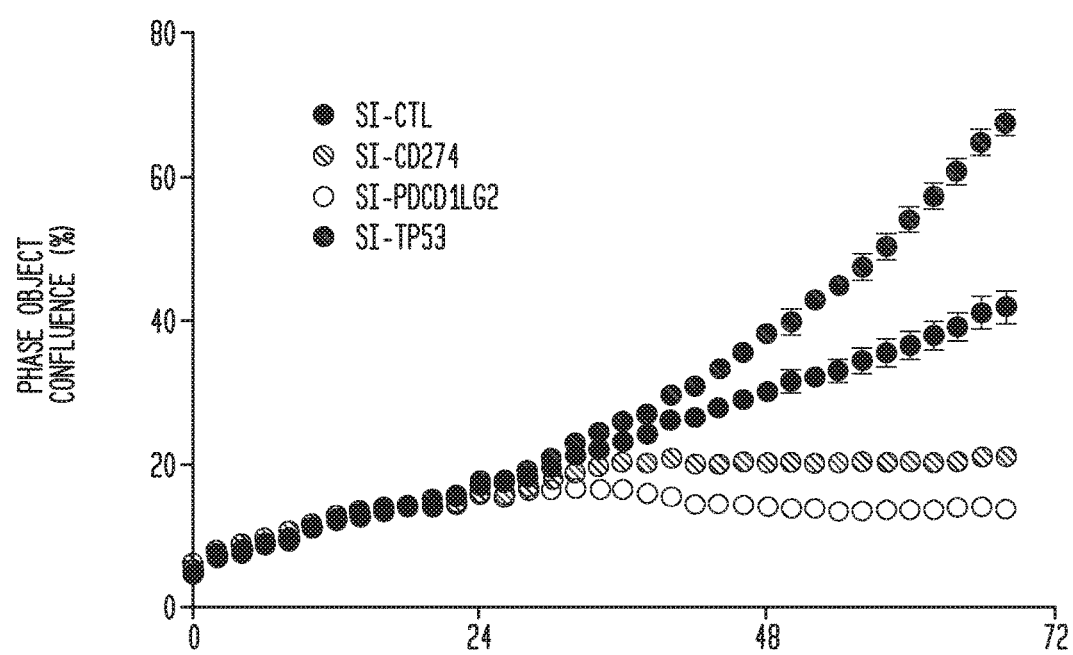
FIG. 14D shows a representative cell growth curve of lung fibroblast treated with Si-CTL, Si-CD274, or Si-PDCD1LG2.
Figure 14E:
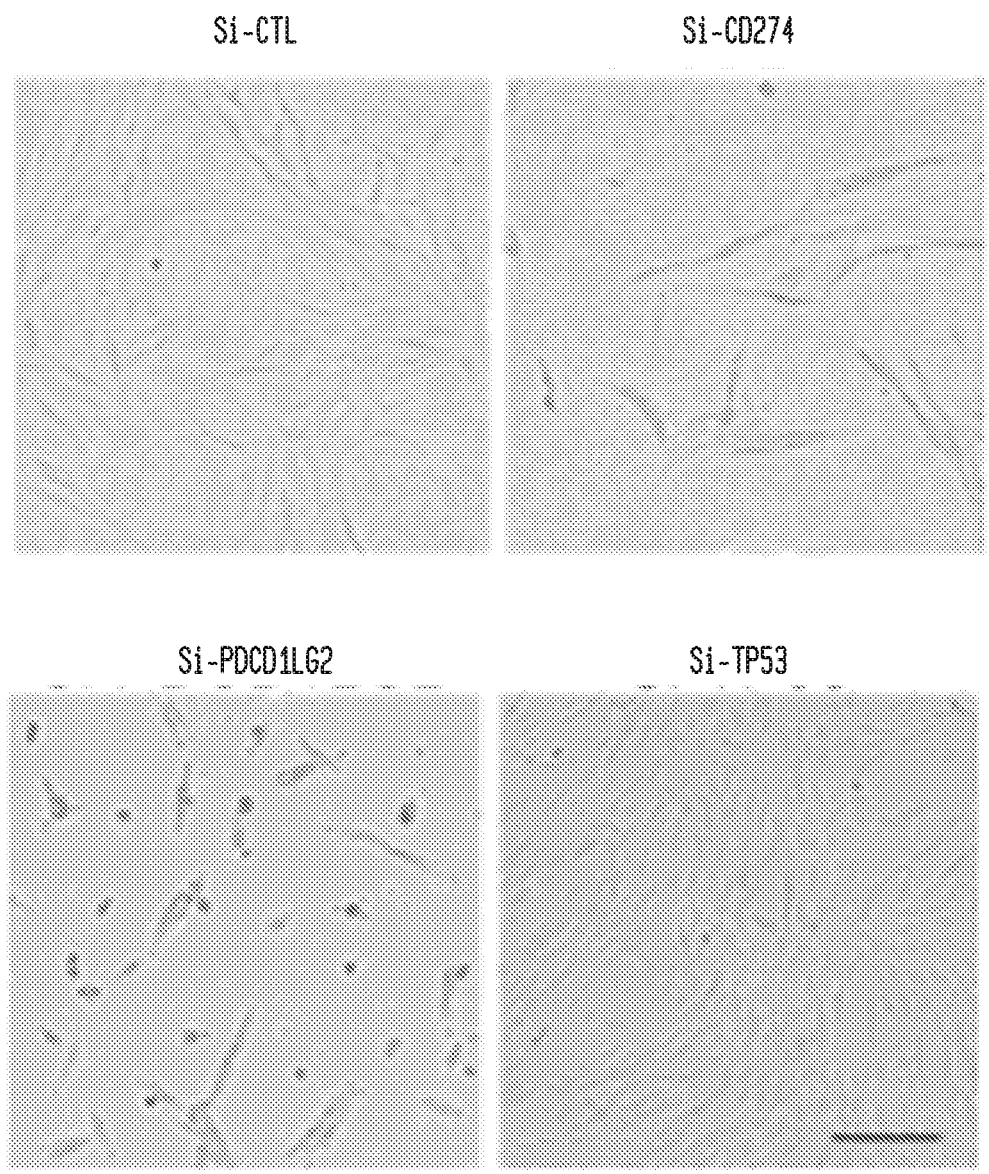
FIG. 14E shows a representative image of lung fibroblast treated with Si-CTL, Si-CD274, or Si-PDCD1LG2 after 68 hours. Scale bar: 150 µm.
Figure 14F:
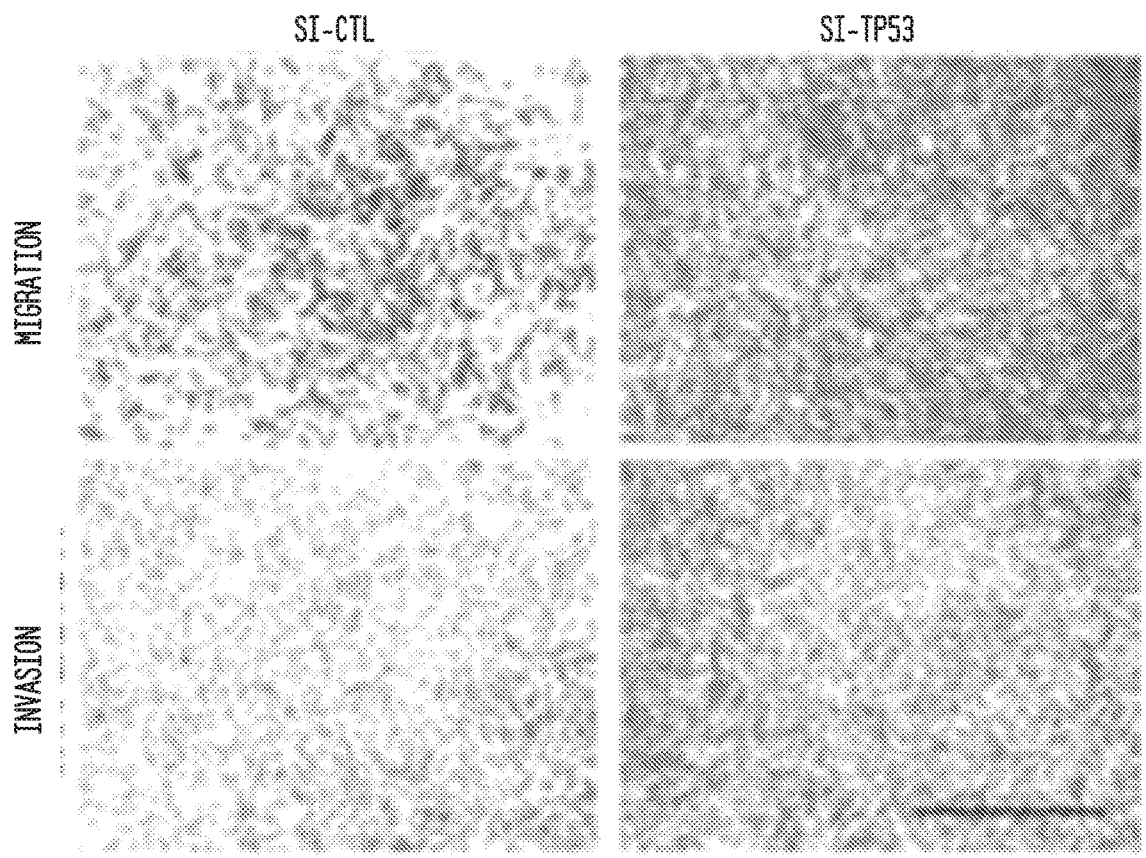
FIG. 14F and FIG. 14G show results of an in vitro migration and invasion assay; equal number of cells were seeded in the upper part of transwells.
Figure 14G:
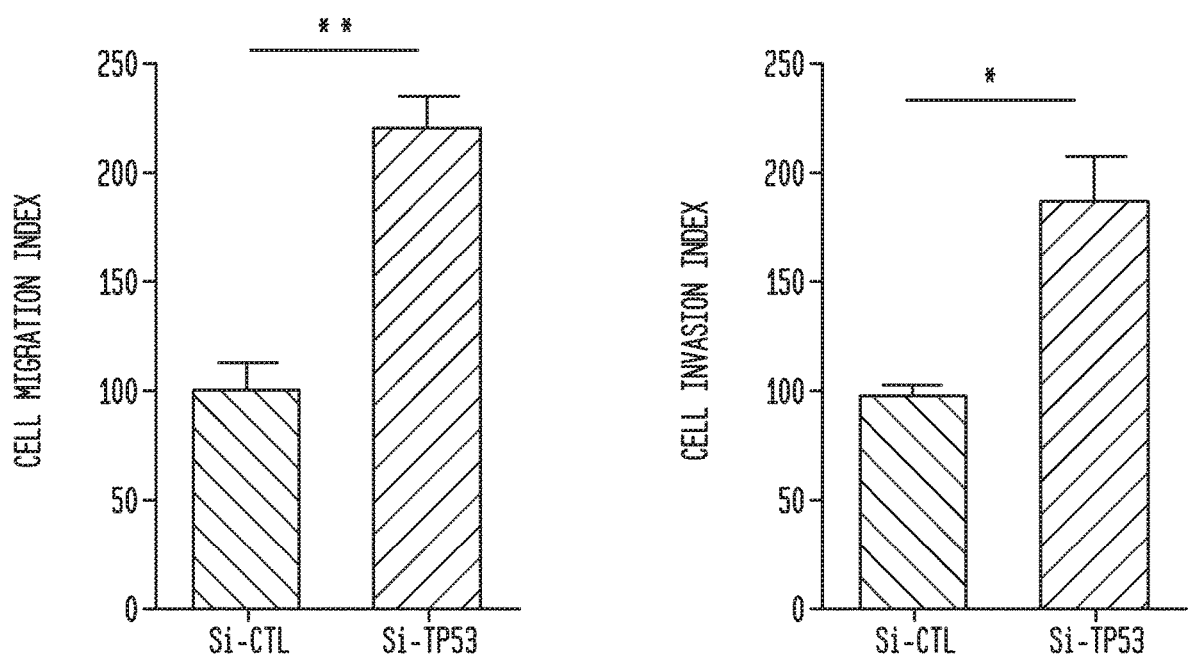

Example 10. Tumor-Supressor p53 Effects on Checkpoint Inhibitor Ligands and Migration and Invasion of Lung Fibroblasts Tumor-suppressor p53 (encoded by TP53) modulates the tumor immune response by regulating PD-L1 expression (37). Knockdown of TP53 in lung fibroblasts from IPF patients upregulated gene, total protein and cell surface expression of CD274 and PDCD1LG2 (FIG. 14A-FIG. 14C). On the other hand, knockdown of CD274 or PDCD1LG2 in lung fibroblasts upregulated TP53 gene expression, suggesting a reciprocal negative regulatory loop (FIG. 14A-FIG. 14C). Functionally, knockdown of TP53 promoted fibroblast growth, while knockdown of CD274 or PDCD1LG2 inhibited fibroblast growth (FIG. 14D, FIG. 14E). Knockdown of TP53 also enhanced the migration and invasive capacities of lung fibroblast (FIG. 14F, FIG. 14G).

Figure 15A:
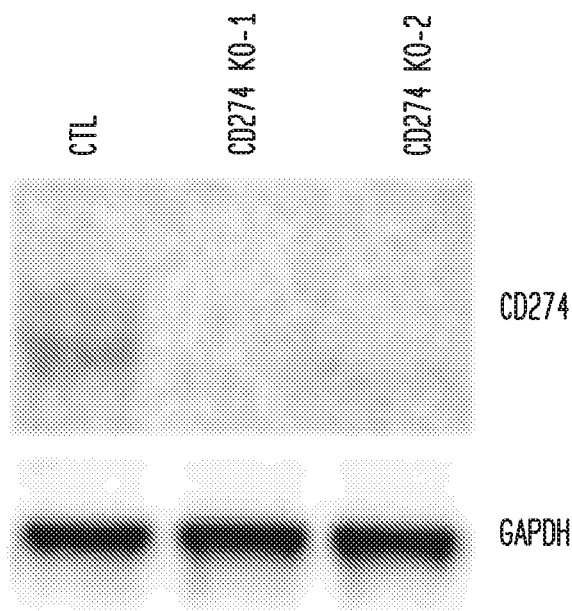
FIG. 15A shows Western blot analyses of CD274, and GAPDH in CTL and CD274 KO IPF lung fibroblasts. GAPDH served as equal loading control.
Figure 15B:
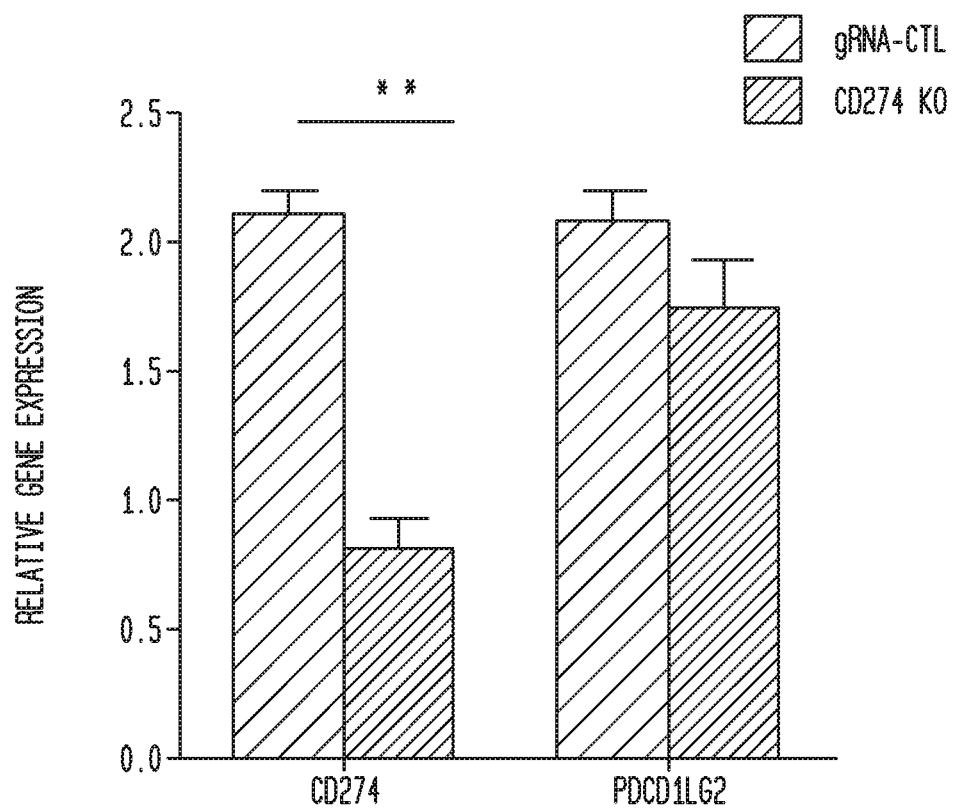
FIG. 15B is a graph that shows gene expression of CD274, PDCD1LG2 in CTL and CD274 KO IPF lung fibroblasts.
Figure 15C:
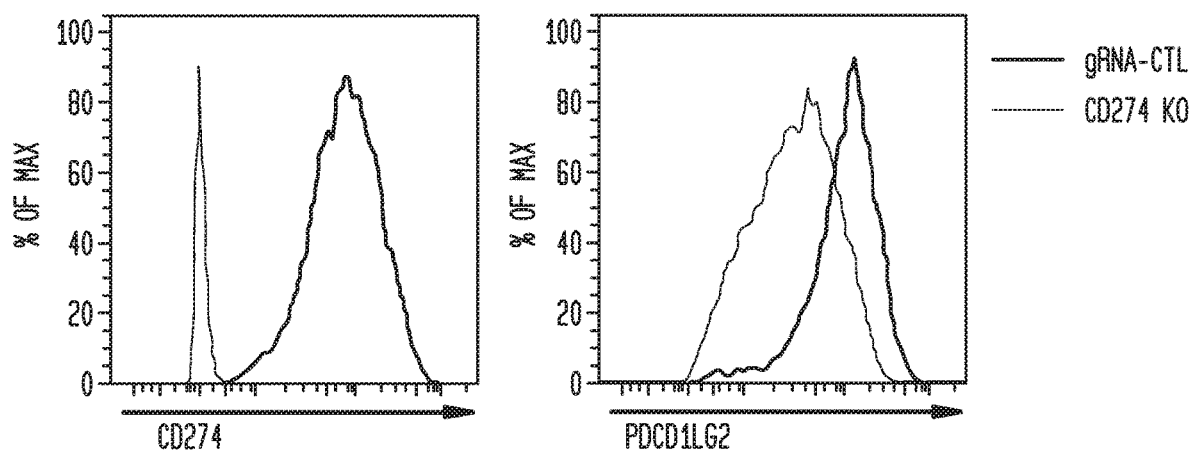
FIG. 15C is a graph that shows cell surface expression of CD274, PDCD1LG2 in CTL and CD274 KO IPF lung fibroblasts.
Figure 15D:
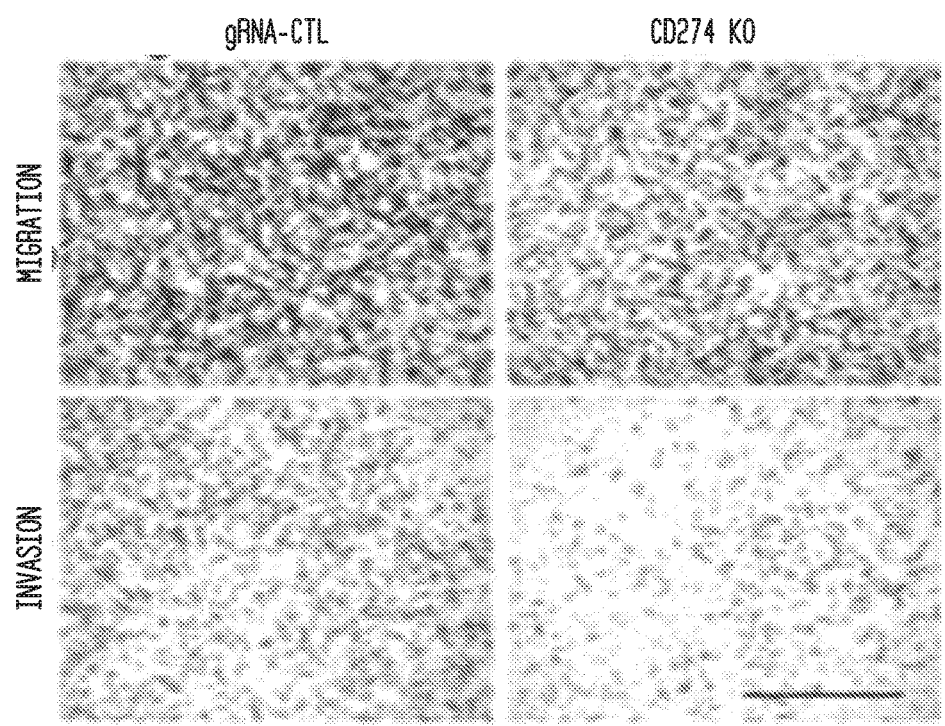
FIG. 15D shows representative images of migrated and invasive CTL and CD274 KO IPF fibroblasts.
Figure 15E:
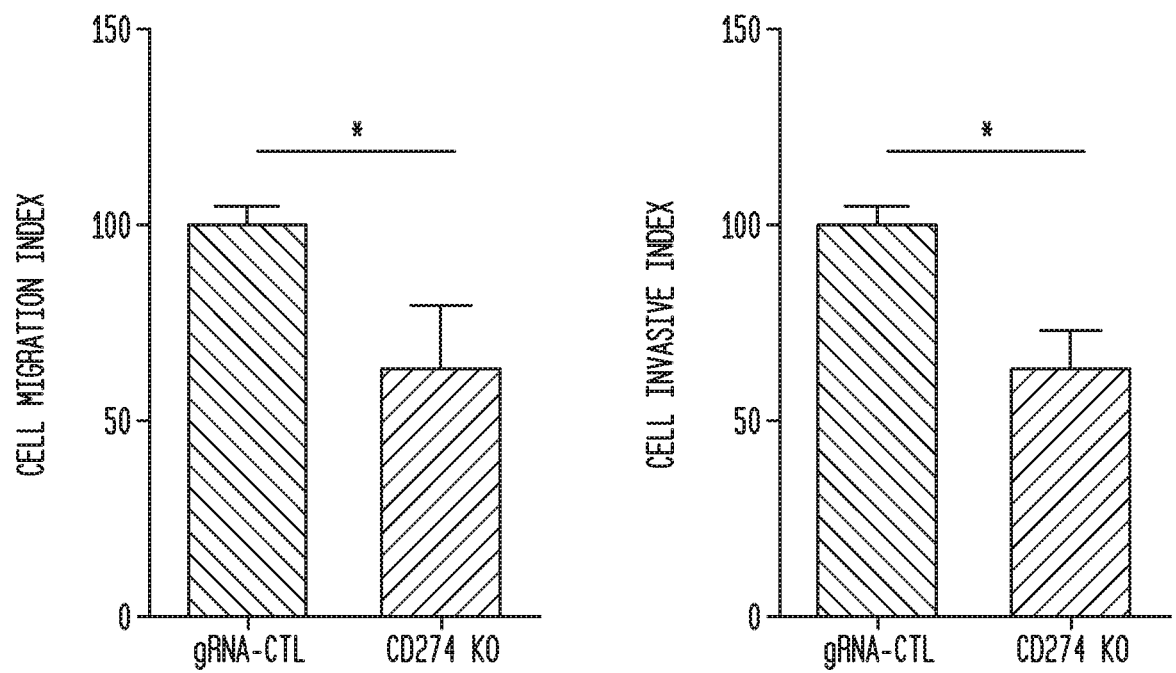
FIG. 15E are graphs that show cell migration or invasion index, which was calculated as the number of cells attached to the bottom of control or Matrigel-coated membrane after 24h, normalized to respective CTL lung fibroblasts. Scale bar: 1 mm. Data are mean±sem (n=3 per group). * P<0.05; **P<0.01 by student's t test (FIG. 15B, FIG. 15E).
Figure 16A:
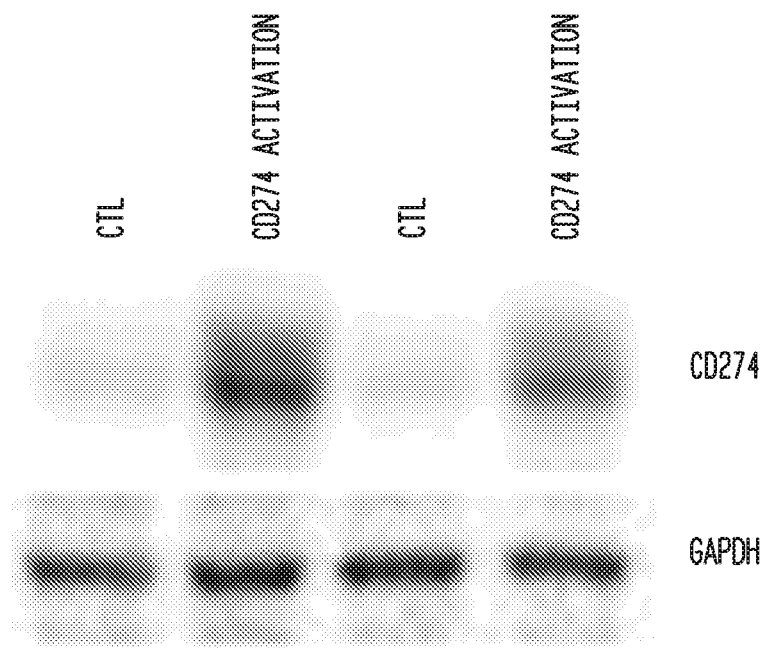
FIG. 16A shows Western blot analysis of CD274 and GAPDH in CTL and CD274 Activation IPF lung fibroblasts. GAPDH served as equal loading control.
Figure 16B:
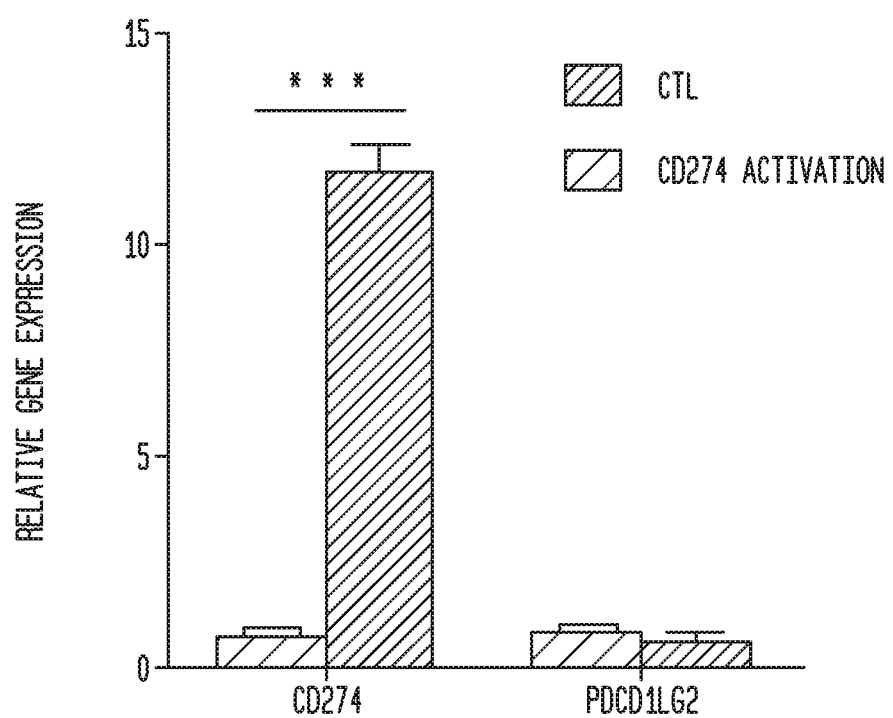
FIG. 16B is a graph that shows gene expression of CD274, PDCD1LG2 in CTL and CD274 Activation IPF lung fibroblasts.
Figure 16C:
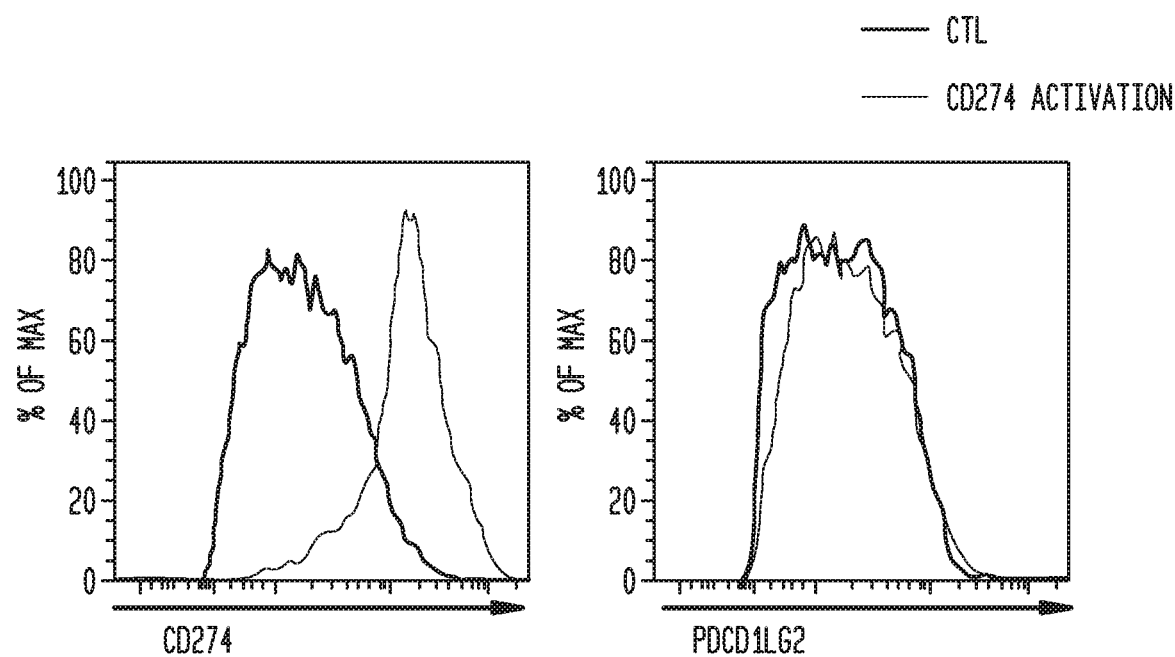
FIG. 16C is a graph that shows cell surface expression of CD274, PDCD1LG2 in CTL and CD274 Activation IPF lung fibroblasts.
Figure 16D:
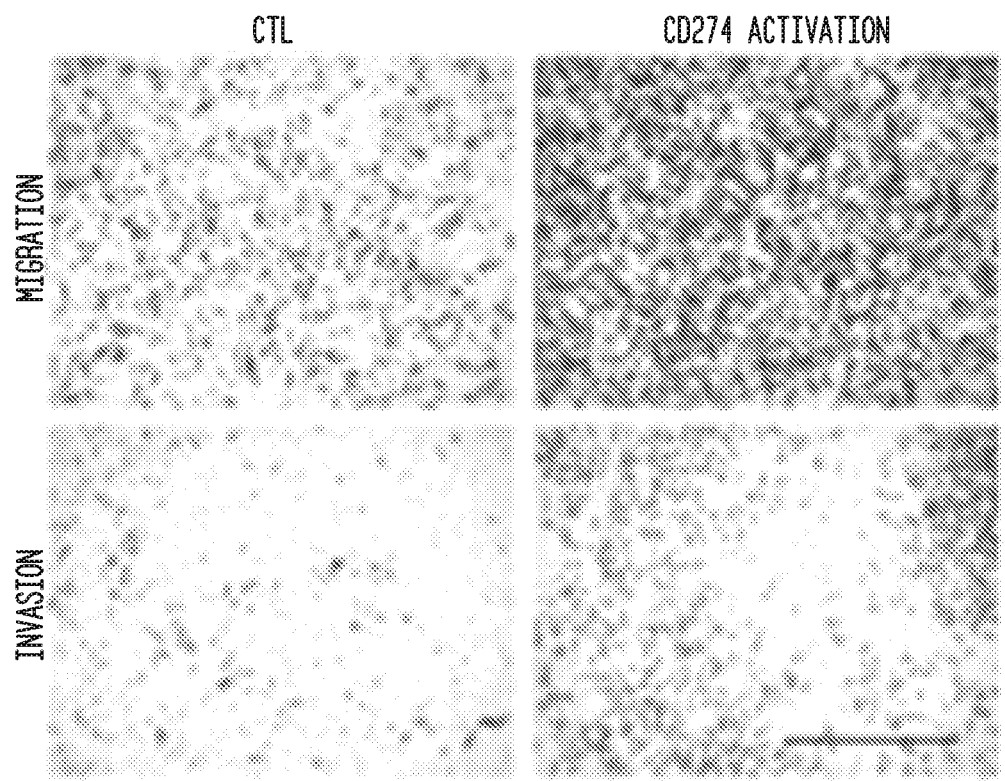
FIG. 16D shows representative images of migrating and invasive CTL and CD274 Activation IPF fibroblasts.
Figure 16E:
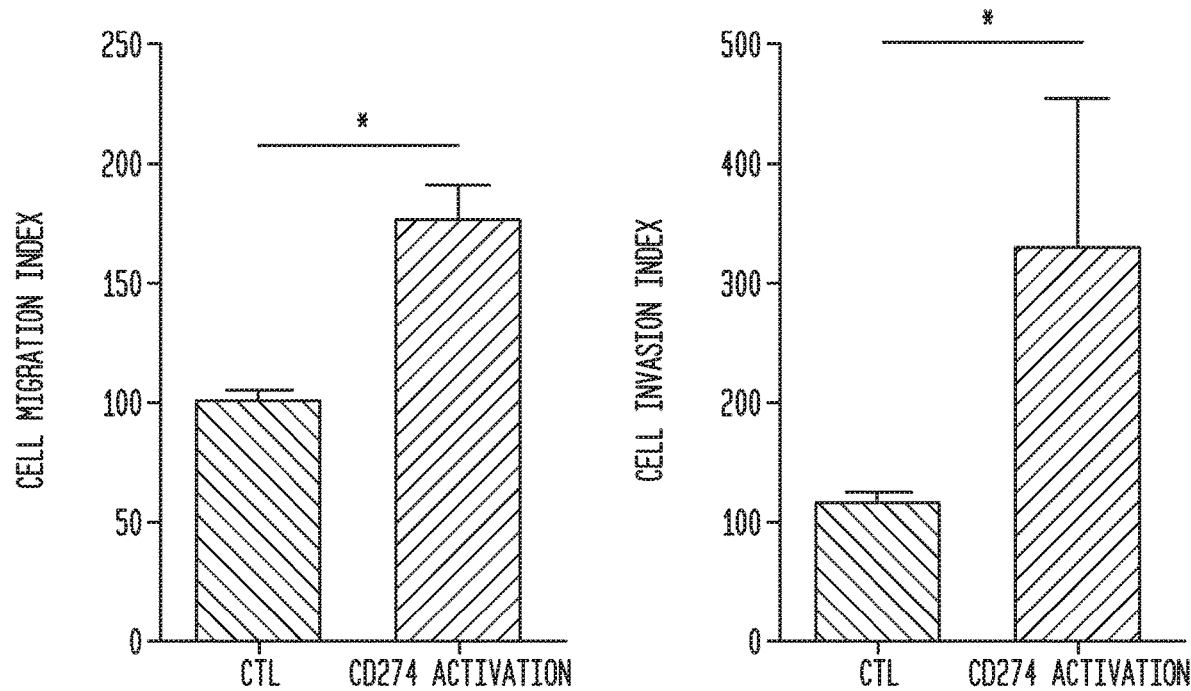
FIG. 16E shows graphs that show cell migration index or invasion index, which was calculated as the number of cells attached to the bottom of control or Matrigel-coated membrane after 24h, normalized to respective CTL lung fibroblasts. Scale bar: 1 mm. Data are mean±sem (n=3 per group). * P<0.05; *** P<0.001 by student's t test (FIG. 16B, FIG. 16E).

Using CRISPR technology, CD274 knockout (KO) (FIG. 15A-FIG. 15C) and overexpression (FIG. 16A-FIG. 16C) in IPF lung fibroblasts was generated. CD274 deletion blunted cell migration and invasion (FIG. 15D, FIG. 15E), whereas CD274 activation promoted these functions in IPF lung fibroblasts (FIG. 16D, FIG. 16E).

Briefly, for the CD274 KO, Cas9 expressing cell line was generated (Invitrogen LentiArray Cas9 Lentivirus, A32069, thermofisher, USA). sgRNA expression clones targeting CD274 (HCP208443-SG01-3-10, genecopoeia, MD, USA), and scrambled sgRNA control plasmid (CCPCTR01-SG01-10, genecopoeia, MD, USA) wereused to generate CD274 KO and CTL cells. For CD274 activation, Pdcd-1L1 Lentiviral Activation Particles (sc-401140-LAC, Santa Cruz, Calif., USA) was used.

Figure 17:
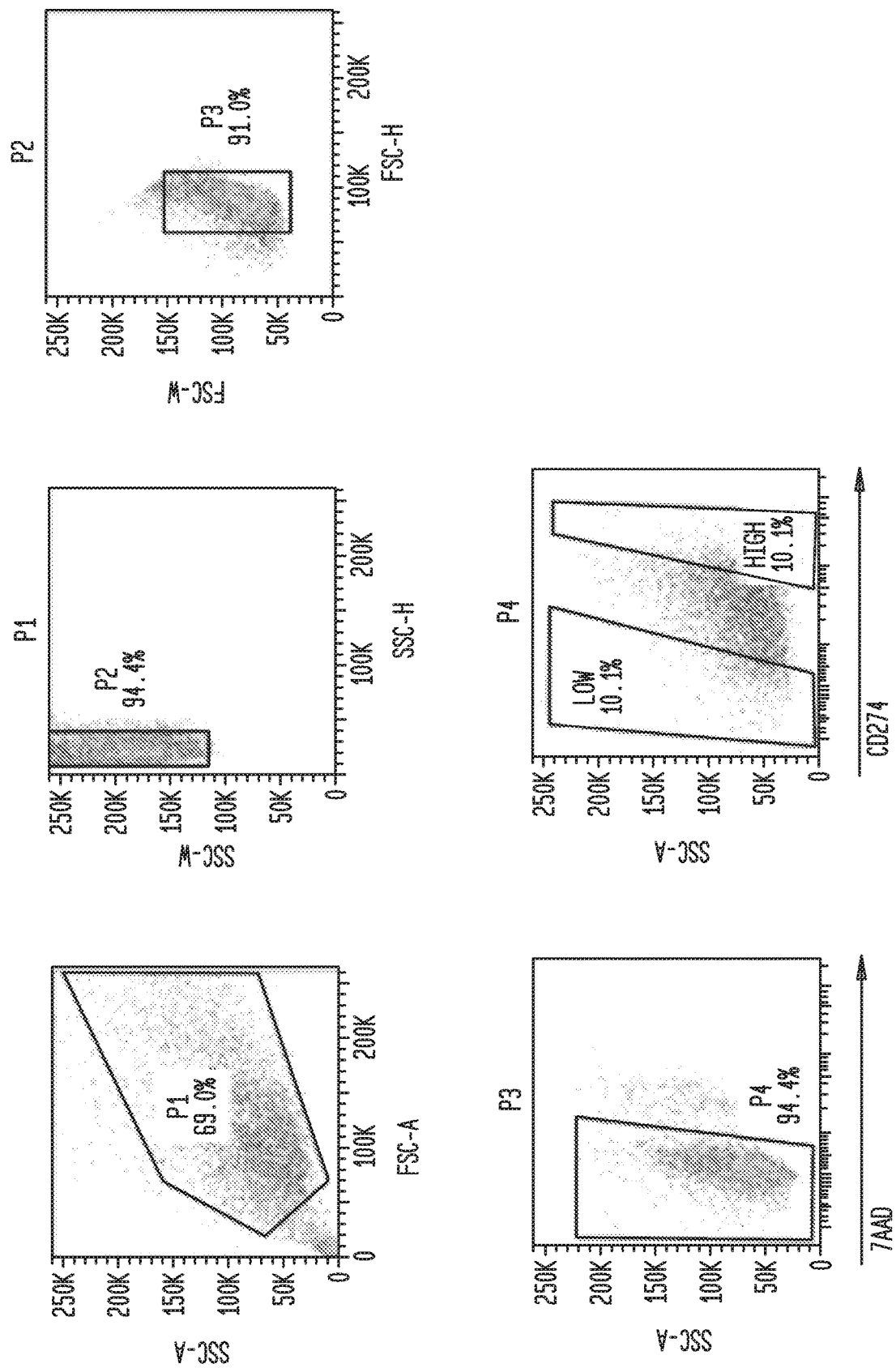
FIG. 17 shows the results of Fluorescence-activated cell sorting of $CD274^{high}$ and $CD274^{low}$ expression cells. 7-aminoactinomycin D (7AAD) was used to exclude of nonviable cells.
Figure 18A:
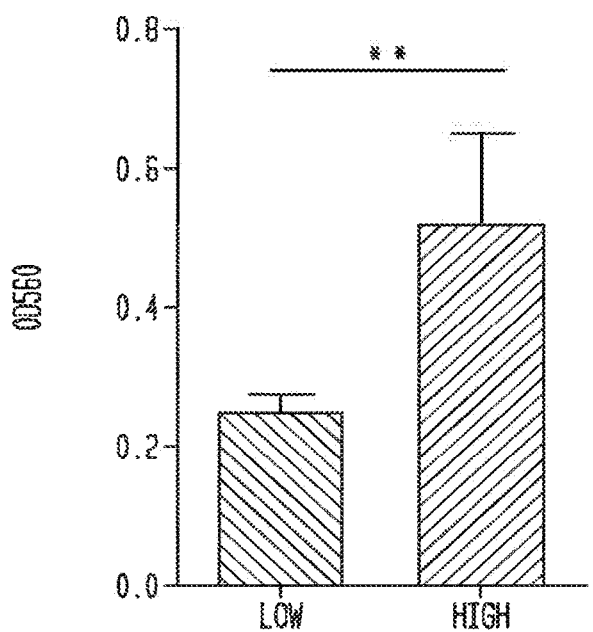
FIG. 18A is a graph that shows Col IV-mediated Cell Adhesion. $CD274^{high}$ and $CD274^{low}$ cells were harvested by flow sorting. Then these cells were allowed to attach to a Col IV coated 48-well plate for 1 hr at 100,000 cells/well in serum free medium. Adherent cells were stained with and quantified at OD 560 nm after extraction.
Figure 18B:
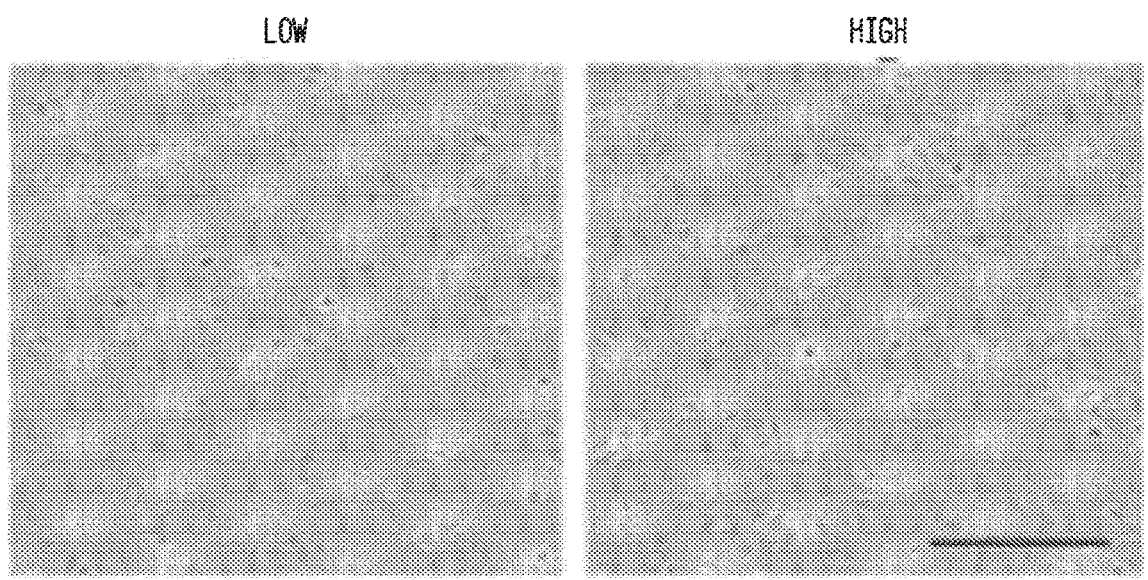
FIG. 18B is a representative image of CD274$^{high}$ and CD274$^{low}$ cells after 1 hr culture on Col IV coated plate. Scale bar: 300 μm.
Figure 18C:
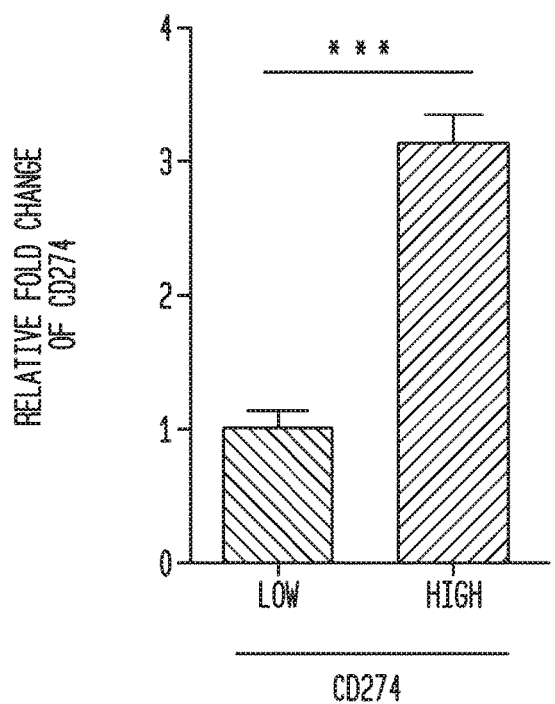
FIG. 18C is a panel of graphs that show quantification of p-FAK1, FAK1, CD274 and PDCD1LG2 protein expression level in CD274 low and high expression lung fibroblasts. Throughout, data are mean±sem (n=5 per group). ** P<0.01 by student's t test.
Figure 18C:
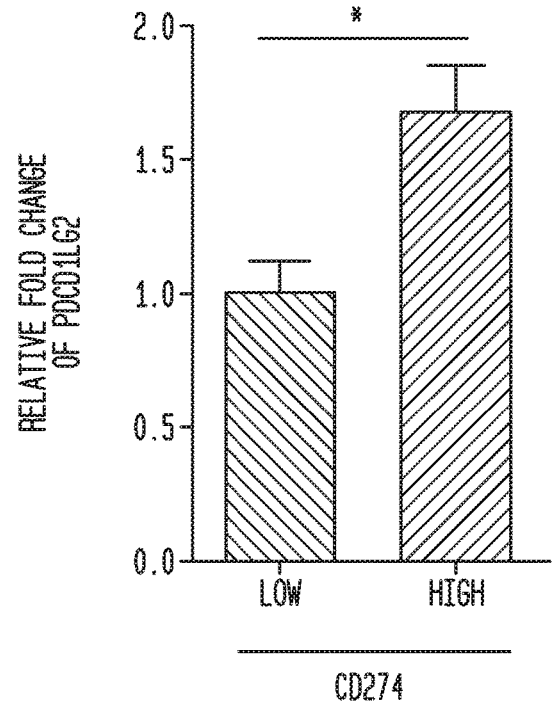
Figure 18C:
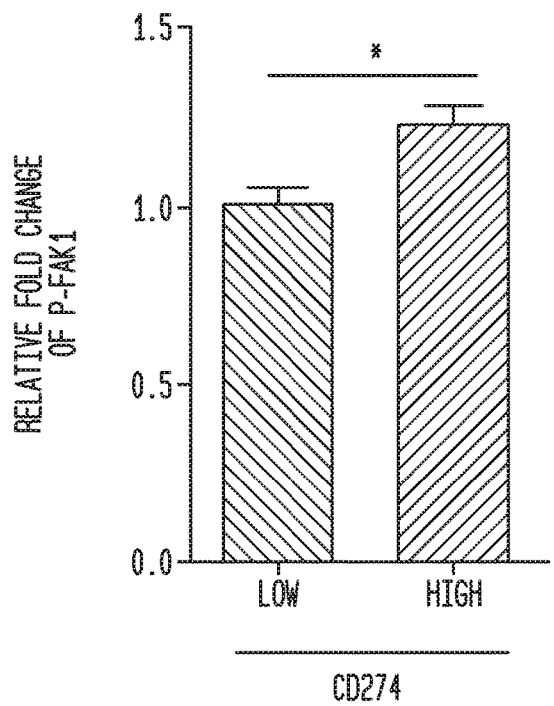
Figure 18C:
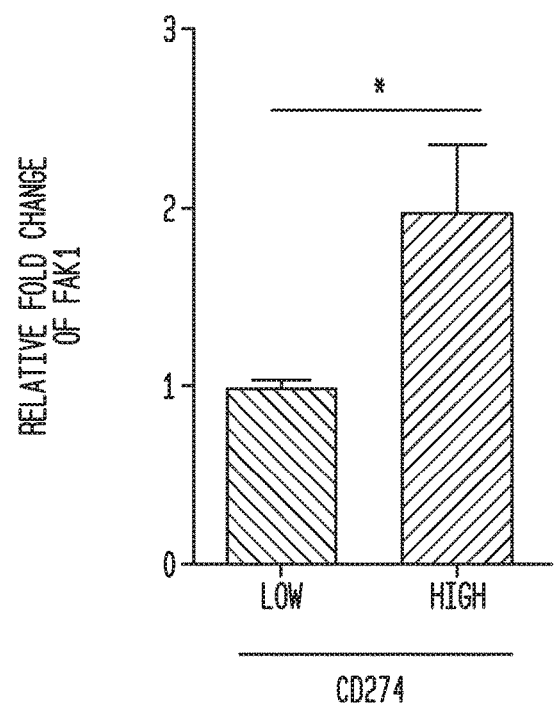
Figure 19A:
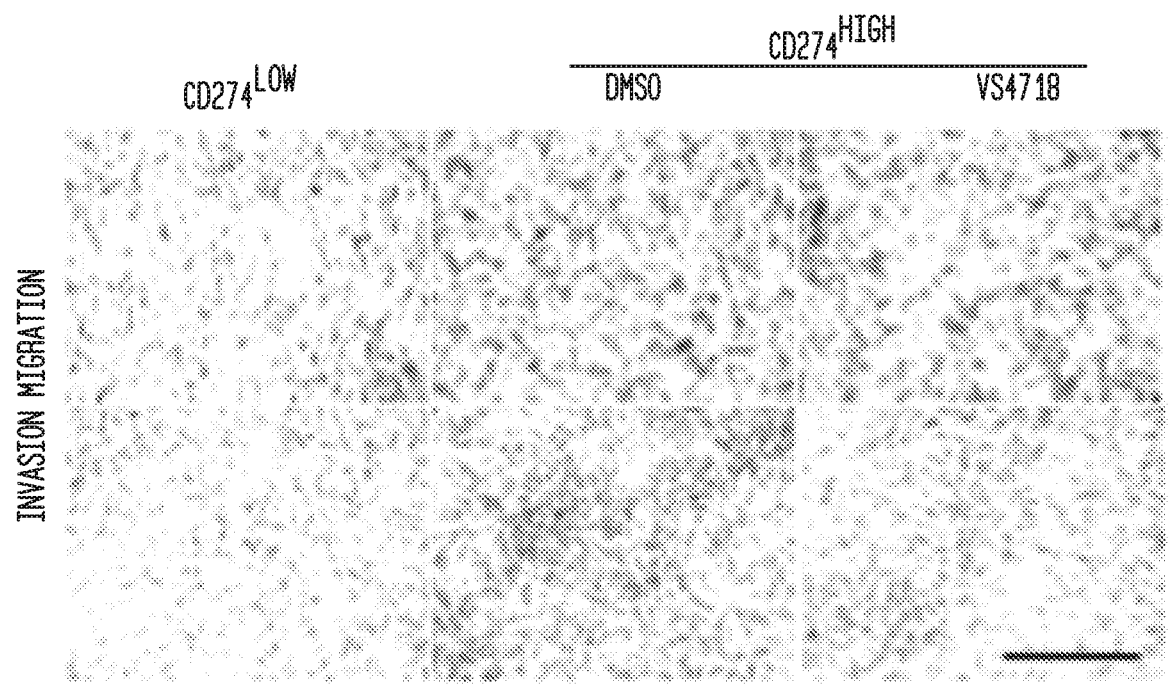
FIG. 19A-J show CD274 and FAK signaling are required for lung fibroblast invasion. In the experimental results shown in FIG. 19A-FIG. 19C, equal number of cells were seeded in the upper part of transwells and cell migration and invasion assays were performed (n=3 per group).
Figure 19B:
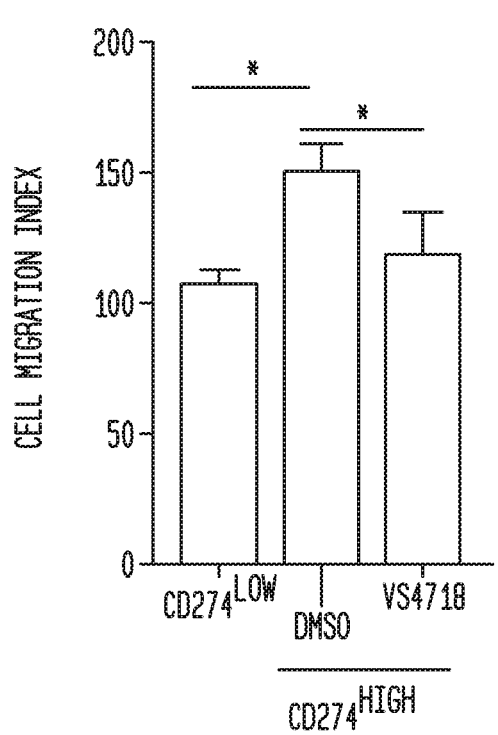
Figure 19C:
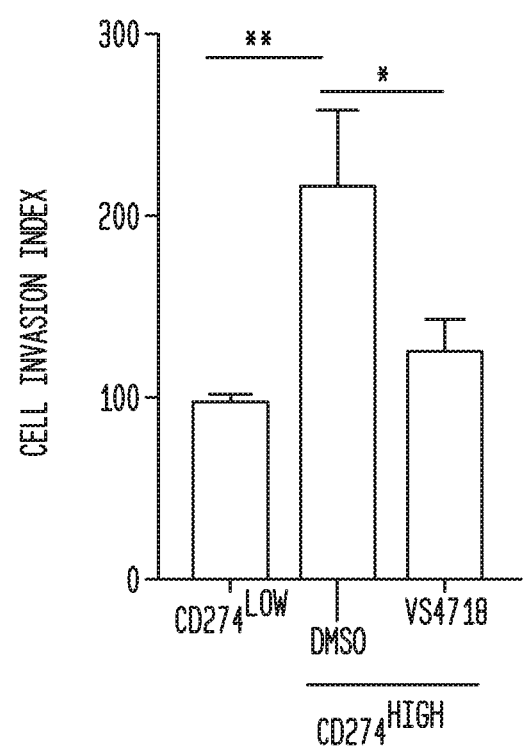

Example 11. CD274 at Cell Surface is Associated with Increased Lung Fibroblast Cell Adhesion, Migration and Invasion $CD274^{high}$ and $CD274^{low}$ expressing cells were harvested by fluorescence-activated cell sorting from IPF explant tissue (FIG. 17), and it was found that increased expression of CD274 at the cell surface is associated with increased lung fibroblast cell adhesion (FIG. 18A-FIG. 18C), migration and invasion (FIG. 19A-FIG. 19C).

Example 12. Phosphorylated FAK1 and Total FAK1 Expression is Increased in IPF and $CD247^{high}$ Lung Fibroblasts Focal adhesion kinase (FAK), a nonreceptor tyrosine kinase, plays an essential role in multiple biological functions, including cell survival, proliferation, migration, adhesion, and invasion (38). FAK signaling also has been implicated in pathologic fibrosis in several tissues (39, 40).

Figure 19D:
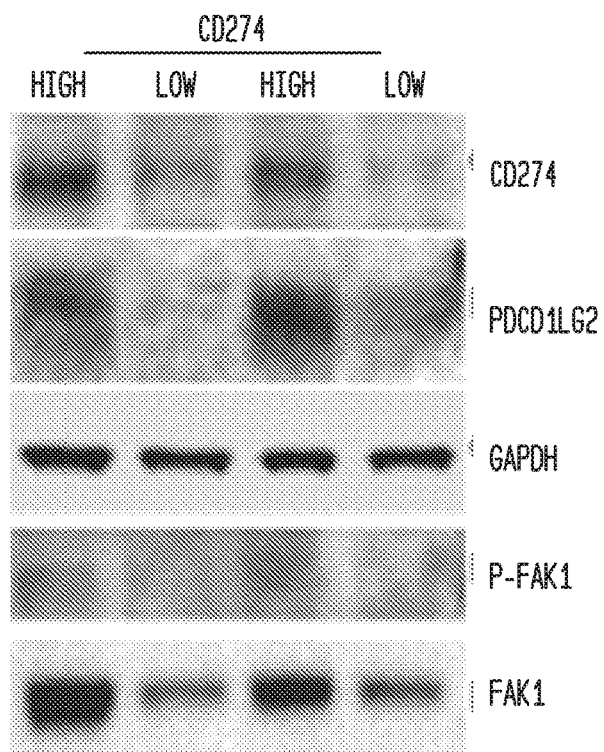

It was found that phosphorylated FAK1 and total FAK1 expression was also increased in IPF lung fibroblasts (FIG. 13C), as well as in the $CD274^{high}$ lung fibroblasts (FIG. 19D). VS4718, a small molecule inhibitor of FAK, significantly blocked cell migration and invasion of lung fibroblasts (FIG. 19A-FIG. 19C).

Figure 19E:
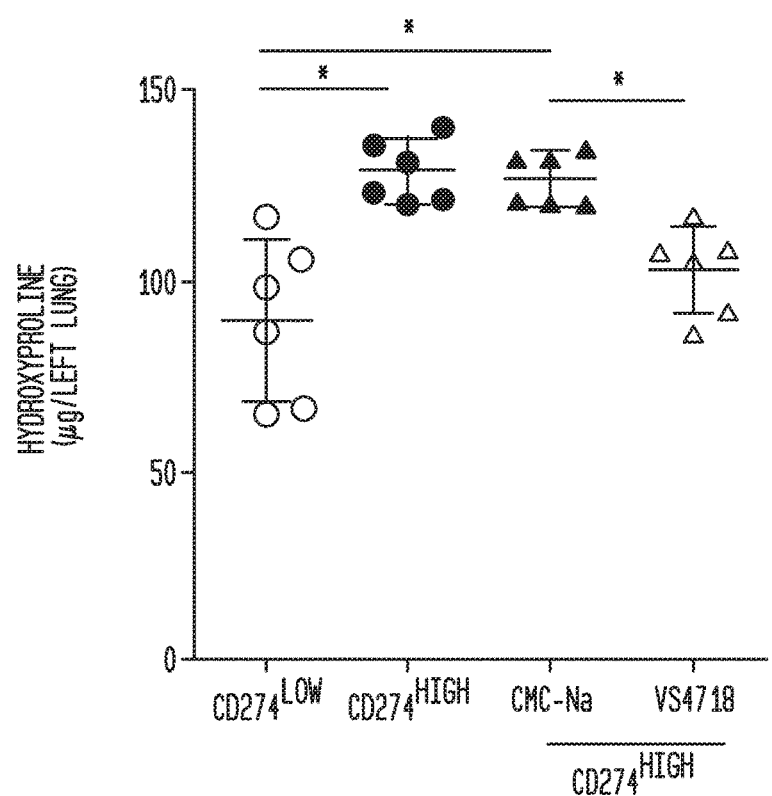
Figure 19F:
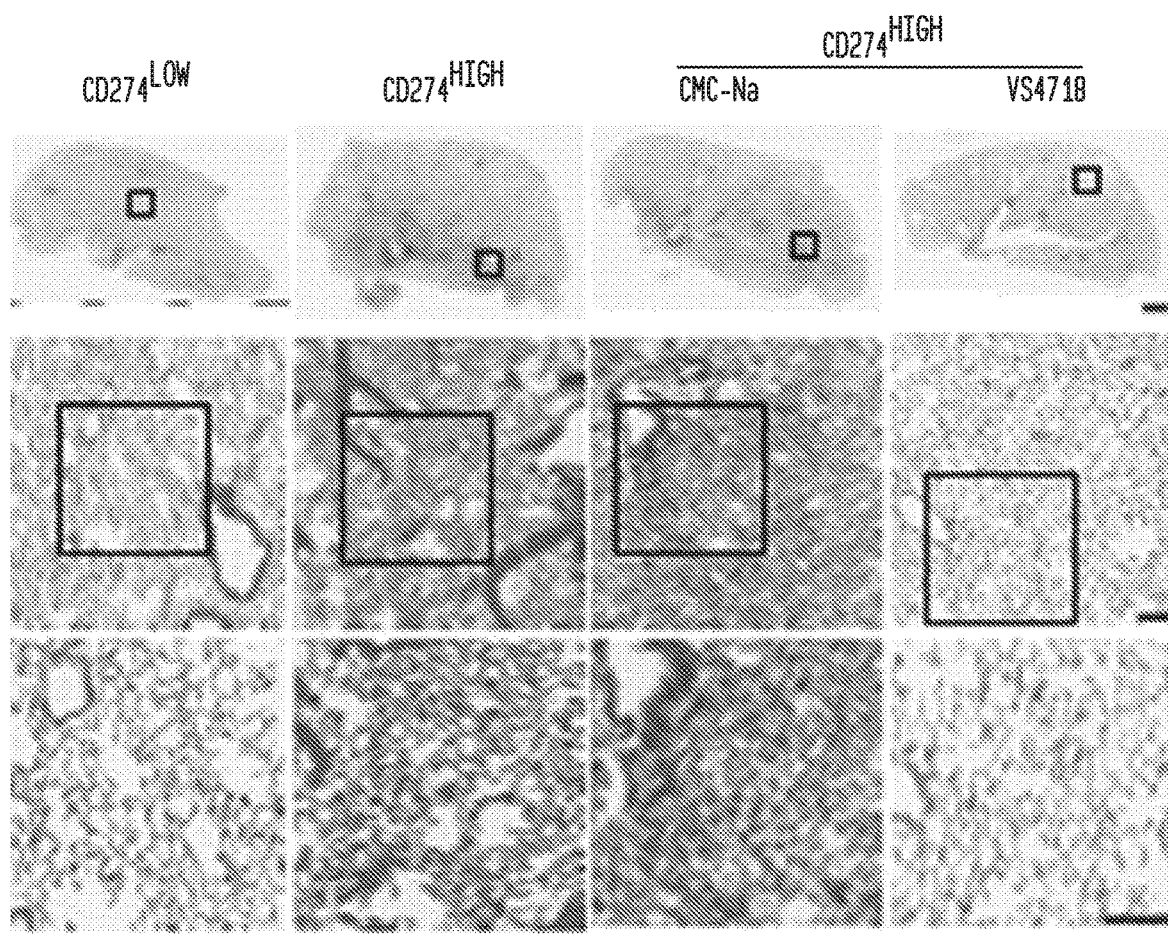
Figure 19G:
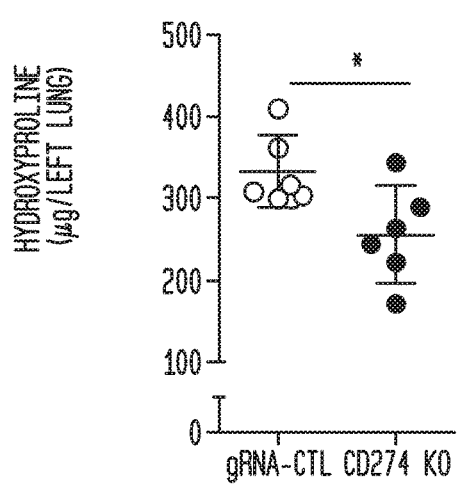
Figure 19H:
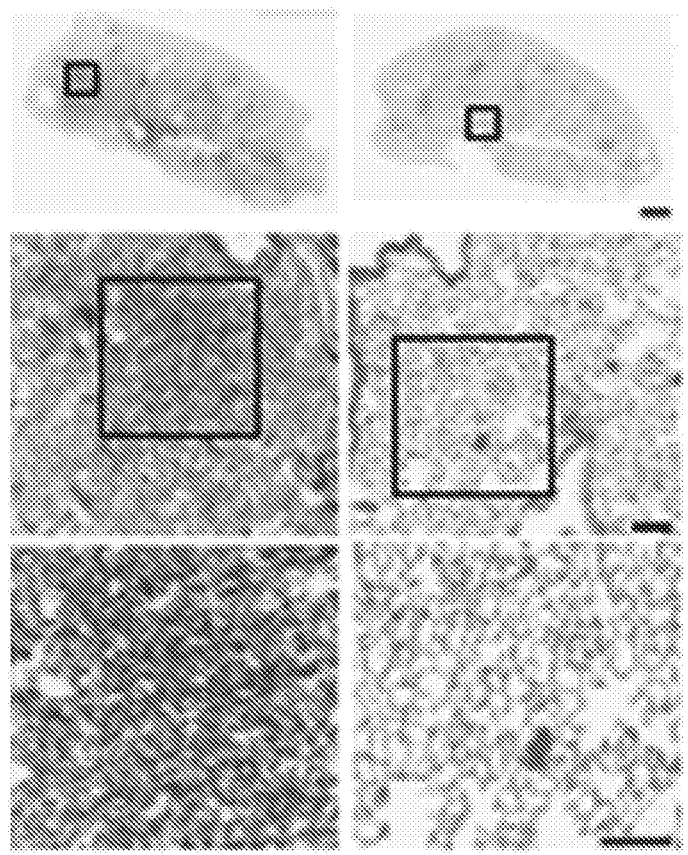
Figure 19I:
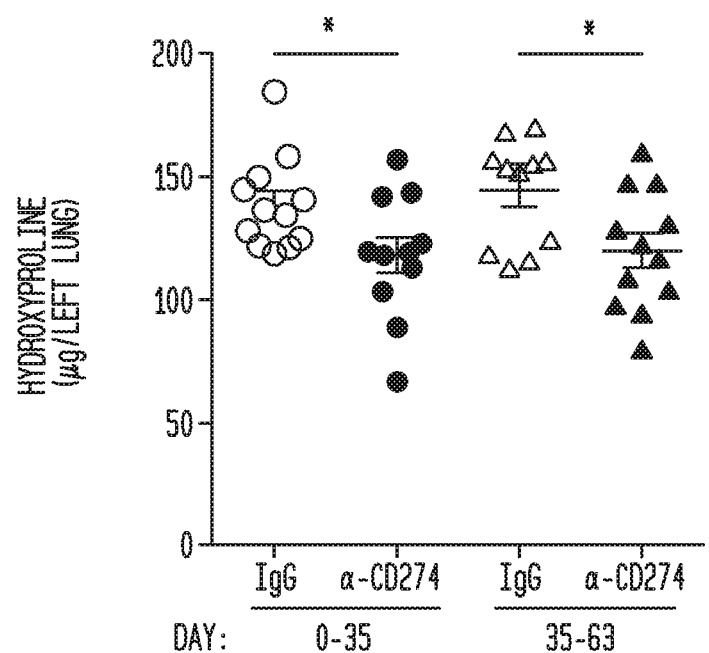
Figure 19J:
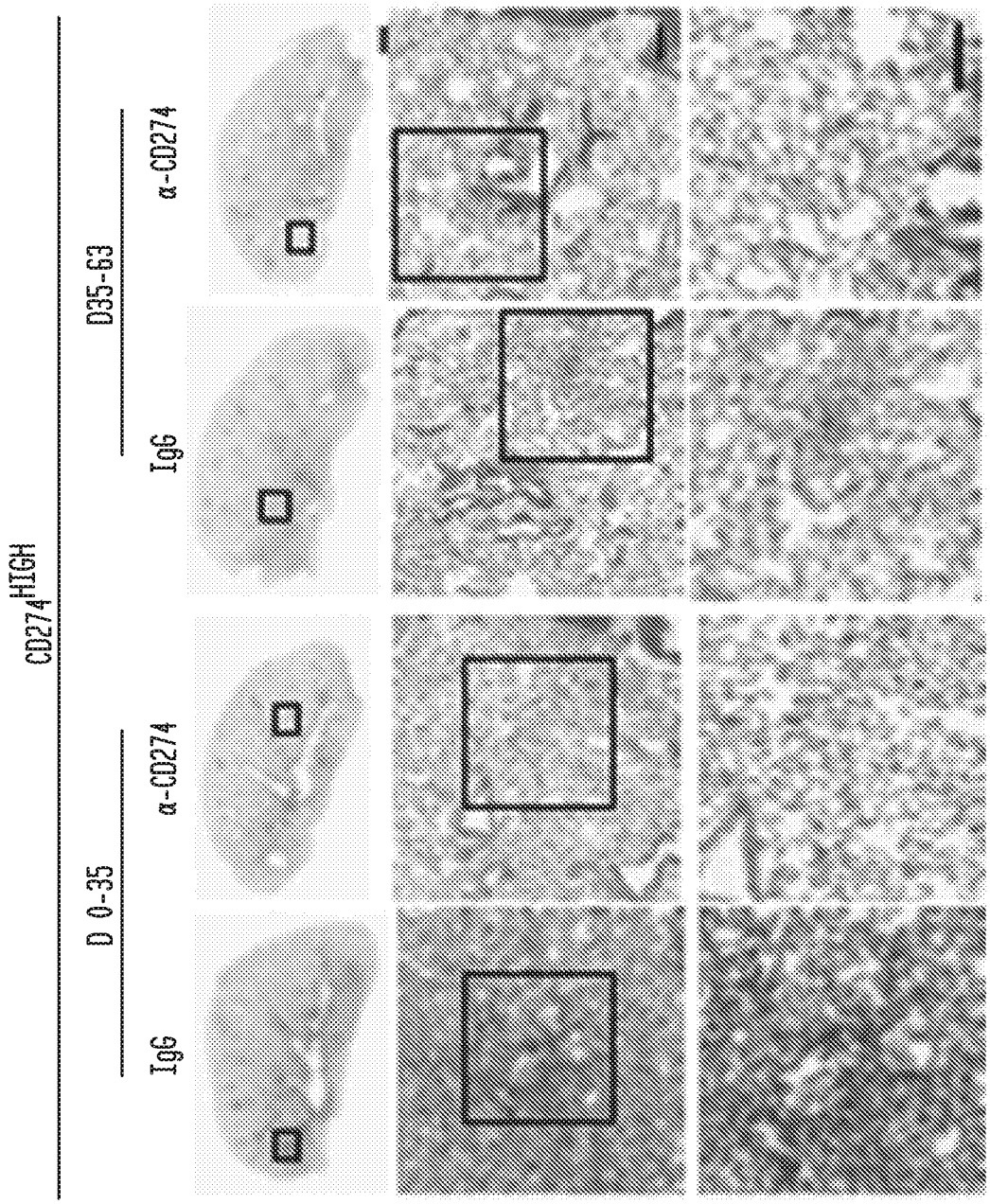

Example 13. Role of CD274 on Fibrosis In Vivo $CD274^{high}$ or $CD274^{low}$ lung fibroblasts were injected into NSG mice to investigate the role of CD274 on fibrosis in vivo. Mice receiving $CD274^{high}$ fibroblasts developed significantly more lung fibrosis than the mice receiving $CD274^{low}$ fibroblasts (FIG. 19E, FIG. 19F). It was further found that there was less diffuse interstitial fibrosis and a decrease in hydroxyproline in the lungs of the NSG mice injected with CD274 KO lung fibroblasts as compared with mice receiving control guide RNA (gRNA) lung fibroblasts (FIG. 19G, FIG. 19H). Moreover, VS4718 treatment prevented the development of fibrosis in the mice receiving $CD274^{high}$ lung fibroblasts, compared with vehicle (CMC-Na) treated mice (FIG. 19E, FIG. 19F). Furthermore, blocking CD274 by anti-CD274 neutralizing antibody (α-CD27; InVivoMab anti-human PD-L1, clone: 29E.2A3) attenuated the development of fibrosis at both early (day 0-day 35) and late stages (day 35-day 63) of fibrogenesis (FIG. 19I, FIG. 19J).

The Examples provided herein support the concept that invasive fibroblasts drive progressive lung fibrogenesis. The Examples also suggest that IPF and lung cancer share a number of similarities genetically or epigenetically. Targeting the immune checkpoint components has been a treatment breakthrough in a number of cancers, albeit not without complications including pneumonitis (41). The role of immune checkpoints in stromal regulation of tumor growth and metastasis is an area of active investigation and, without being bound by theory, the hypothesis has been developed that part of the efficacy of immune checkpoint inhibition may be due to effects on the tumor microenvironment (12). Recently, human mesenchymal stem cells were reported to attenuate lung fibrosis through the PD-1/PD-L1 pathway in bleomycin-induced pulmonary fibrosis in humanized mice (35), although the mechanisms differ. These Examples presented herein suggest that targeting $CD274^{high}$ expressing cells in IPF could be a promising approach to inactivating invasive fibroblasts and attenuating and potentially reversing established pulmonary fibrosis.

REFERENCES

1. White E S, Lazar M H, and Thannickal V J. Pathogenetic mechanisms in usual interstitial pneumonia/idiopathic pulmonary fibrosis. *J Pathol.* 2003; 201(3):343-54.
2. Li Y, Jiang D, Liang J, Meltzer E B, Gray A, Miura R, Wogensen L, Yamaguchi Y, and Noble P W. Severe lung fibrosis requires an invasive fibroblast phenotype regulated by hyaluronan and CD44. *The Journal of experimental medicine.* 2011 208(7): 1459-71.
3. Bell C H, Healey E, van Erp S, Bishop B, Tang C, Gilbert R J, Aricescu A R, Pasterkamp R J, and Siebold C. Structure of the repulsive guidance molecule (RGM)-neogenin signaling hub. *Science.* 2013; 341(6141):77-80.
4. Xiao Y, Yu S, Zhu B, Bedoret D, Bu X, Francisco L M, Hua P, Duke-Cohan J S, Umetsu D T, Sharpe A H, et al. RGMb is a novel binding partner for PD-L2 and its engagement with PD-L2 promotes respiratory tolerance. *The Journal of experimental medicine.* 2014; 211(5):943-59.
5. Ostrand-Rosenberg S, Horn L A, and Haile S T. The programmed death-1 immune-suppressive pathway: barrier to antitumor immunity. *J Immunol.* 2014; 193(8): 3835-41.
6. Blank C, Brown I, Peterson A C, Spiotto M, Iwai Y, Honjo T, and Gajewski T F. PD-L1/B7H-1 inhibits the effector phase of tumor rejection by T cell receptor (TCR) transgenic CD8+ T cells. *Cancer Res.* 2004; 64(3):1140-5.
7. Keir M E, Butte M J, Freeman G J, and Sharpe A H. PD-1 and its ligands in tolerance and immunity. *Annu Rev Immunol.* 2008; 26(677-704.
8. Nguyen L T, and Ohashi P S. Clinical blockade of PD1 and LAGS—potential mechanisms of action. *Nat Rev Immunol.* 2015; 15(1):45-56.
9. Brown J A, Dorfman D M, Ma F R, Sullivan E L, Munoz O, Wood C R, Greenfield E A, and Freeman G J. Blockade of programmed death-1 ligands on dendritic cells enhances T cell activation and cytokine production. *J Immunol.* 2003; 170(3):1257-66.
10. Curiel T J, Wei S, Dong H, Alvarez X, Cheng P, Mottram P, Krzysiek R, Knutson K L, Daniel B, Zimmermann M C, et al. Blockade of B7-H1 improves myeloid dendritic cell-mediated antitumor immunity. *Nat Med.* 2003; 9(5): 562-7.
11. Dong H, Strome S E, Salomao D R, Tamura H, Hirano F, Flies D B, Roche P C, Lu J, Zhu G, Tamada K, et al. Tumor-associated B7-H1 promotes T-cell apoptosis: a potential mechanism of immune evasion. *Nat Med.* 2002; 8(8):793-800.
12. Iwai Y, Ishida M, Tanaka Y, Okazaki T, Honjo T, and Minato N. Involvement of PD-L1 on tumor cells in the escape from host immune system and tumor immunotherapy by PD-L1 blockade. *Proc Natl Acad Sci USA.* 2002; 99(19):12293-7.
13. Dong Y, Geng Y, Li L, Li X, Yan X, Fang Y, Li X, Dong S, Liu X, Li X, et al. Blocking follistatin-like 1 attenuates bleomycin-induced pulmonary fibrosis in mice. *The Journal of experimental medicine.* 2015; 212(2):235-52.

14. Noble P W, Barkauskas C E, and Jiang D. Pulmonary fibrosis: patterns and perpetrators. *The Journal of clinical investigation.* 2012; 122(8):2756-62.
15. du Bois R M. Strategies for treating idiopathic pulmonary fibrosis. *Nature reviews Drug discovery.* 2010; 9(2): 129-40.
16. Richeldi L, Davies H R, Ferrara G, and Franco F. Corticosteroids for idiopathic pulmonary fibrosis. *The Cochrane database of systematic reviews.* 20033): CD002880.
17. Davies H R, Richeldi L, and Walters E H. Immunomodulatory agents for idiopathic pulmonary fibrosis. *The Cochrane database of systematic reviews.* 20033): CD003134.
18. Strieter R M, Gomperts B N, and Keane M P. The role of CXC chemokines in pulmonary fibrosis. *The Journal of clinical investigation.* 2007; 117(3):549-56.
19. King T E, Jr., Albera C, Bradford W Z, Costabel U, Hormel P, Lancaster L, Noble P W, Sahn S A, Szwarcberg J, Thomeer M, et al. Effect of interferon gamma-1b on survival in patients with idiopathic pulmonary fibrosis (INSPIRE): a multicentre, randomised, placebo-controlled trial. *Lancet.* 2009; 374(9685):222-8.
20. King T E, Jr., Brown K K, Raghu G, du Bois R M, Lynch D A, Martinez F, Valeyre D, Leconte I, Morganti A, Roux S, et al. BUILD-3: a randomized, controlled trial of bosentan in idiopathic pulmonary fibrosis. *American journal of respiratory and critical care medicine.* 2011; 184(1):92-9.
21. Demedts M, Behr J, Buhl R, Costabel U, Dekhuijzen R, Jansen H M, MacNee W, Thomeer M, Wallaert B, Laurent F, et al. High-dose acetylcysteine in idiopathic pulmonary fibrosis. *N Engl J Med.* 2005; 353(21):2229-42.
22. Noble P W, Albera C, Bradford W Z, Costabel U, Glassberg M K, Kardatzke D, King T E, Jr., Lancaster L, Sahn S A, Szwarcberg J, et al. Pirfenidone in patients with idiopathic pulmonary fibrosis (CAPACITY): two randomised trials. *Lancet.* 2011; 377(9779):1760-9.
23. King T E, Jr., Bradford W Z, Castro-Bernardini S, Fagan E A, Glaspole I, Glassberg M K, Gorina E, Hopkins P M, Kardatzke D, Lancaster L, et al. A phase 3 trial of pirfenidone in patients with idiopathic pulmonary fibrosis. *N Engl J Med.* 2014; 370(22):2083-92.
24. Hornet Moreno B, and Ribas A. Anti-programmed cell death protein-1/ligand-1 therapy in different cancers. *Br J Cancer.* 2015; 112(9):1421-7.
25. Lovgren, A. K., et al. Sci Transl Med 3, 74ra23 (2011).
26. Ahluwalia, N., et al. Am J Respir Cell Mol Biol 54, 831-842 (2016).
27. Chen, H., et al. Nat Commun 7, 12564 (2016).
28. Trujillo, G., et al. Sci Transl Med 2, 57ra82 (2010).
29. Pardoll, D. M. Nat Rev Cancer 12, 252-264 (2012).
30. Hugo, W., et al. Cell 165, 35-44 (2016).
31. Dezutter-Dambuyant, C., et al. Oncoimmunology 5(2016).
32. Beswick, E. J., et al. J Immunol 193, 2218-2229 (2014).
33. Ni, K., et al. Am J Respir Cell Mol Biol (2017).
34. Xiao, Y. P., et al. J Exp Med 211, 943-959 (2014).
35. Cortez, M. A., et al. J Natl Cancer Inst 108(2016).
36. Sulzmaier, F. J., Jean, C. & Schlaepfer, D. D. Nat Rev Cancer 14, 598-610 (2014).
37. Kinoshita, K., et al. Am J Respir Cell Mol Biol 49, 536-543 (2013).
38. Jiang, H., et al. Nat Med 22, 851-860 (2016).
39. Friedman, C. F., Proverbs-Singh, T. A. & Postow, M. A. JAMA Oncol 2, 1346-1353 (2016).

We claim:

1. A method for reducing progression of progressive pulmonary fibrosis in a subject, the method comprising:

selecting a subject having idiopathic pulmonary fibrosis (IPF) and a higher level of total protein expression of PD-L1/CD274 in lung tissue or an upregulation of PD-L1/CD274 and PD-L2/CD273 in invasive pulmonary fibroblasts, as compared to a control subject not suffering from pulmonary fibrosis, for treatment for pulmonary fibrosis, wherein the treatment reduces progression of progressive pulmonary fibrosis; and administering to the subject a pharmaceutical composition comprising a therapeutic amount of a therapeutic agent, wherein the therapeutic agent comprises an inhibitor of programmed death receptor-ligand 1 (PD-L1) selected from the group consisting of atezolizumab (MPDL3280A, TECENTRIQ), avelumab (BAVENCIO, MSB0010718C), durvalumab (MEDI4736, IMFINZI), MDX-1105, YW243.55.S70, and CA-170.

2. The method of claim 1, wherein the method improves lung function in the subject.

3. The method of claim 1, wherein the therapeutic agent is atezolizumab.

4. The method of claim 1, wherein compared to an untreated control subject having IPF, the therapeutic agent:
 (a) decreases the invasiveness of pulmonary fibroblasts in the subject; or
 (b) decreases the migration of pulmonary fibroblasts in the subject; or
 (c) decreases cell adhesion of pulmonary fibroblasts in the subject; or
 (d) decreases pulmonary fibroblast proliferation and differentiation in the subject; or
 (e) decreases extracellular matrix production in the subject; or
 (f) decreases myofibroblast activation in the subject; or
 (g) a combination thereof.

5. The method of claim 1, wherein compared to an untreated control subject having IPF,
 (a) the composition comprises a first therapeutic agent that modulates the programmed cell death pathway in combination with a second therapeutic agent that modulates the programmed cell death pathway in the subject; or
 (b) the composition comprises a therapeutic agent that modulates the programmed cell death pathway and a focal adhesion kinase (FAK) inhibitor in the subject.

6. The method of claim 1, wherein the subject also has upregulation of PD1, PD-L1, PD-L2, or RGMb expression levels in lung tissue of the subject to which the pharmaceutical composition is to be administered, as compared to the control subject not suffering from pulmonary fibrosis.

7. The method of claim 1, wherein the pharmaceutical composition further comprises a focal adhesion kinase (FAK) inhibitor in addition to the therapeutic agent.

8. A method for reducing progression of progressive pulmonary fibrosis in a subject, the method comprising:
 identifying a subject having idiopathic pulmonary fibrosis (IPF) for treatment for pulmonary fibrosis,
 wherein upregulation of PD-L1/CD274 and PD-L2/CD273 is detected in invasive fibroblasts from lung tissue of the subject, as compared to a control subject not suffering from pulmonary fibrosis; and
 administering to the subject a pharmaceutical composition comprising a therapeutic amount of a therapeutic agent comprising an inhibitor of programmed death receptor-ligand 1 (PD-L1) selected from the group consisting of atezolizumab (MPDL3280A, TECENTRIQ), avelumab (BAVENCIO, MSB0010718C), durvalumab (MEDI4736, IMFINZI), MDX-1105, YW243.55.S70, and CA-170,
 wherein the treatment reduces progression of progressive pulmonary fibrosis in the subject.

9. The method of claim 8, wherein the pharmaceutical composition further comprises a focal adhesion kinase (FAK) inhibitor in addition to the therapeutic agent.

10. The method of claim 8, wherein elevated expression of RGMb is detected in the lung tissue of the subject, as compared to the control subject not suffering from pulmonary fibrosis.

11. The method of claim 10, wherein the pharmaceutical composition further comprises a focal adhesion kinase (FAK) inhibitor in addition to the therapeutic agent.

12. The method of claim 8, wherein compared to an untreated control subject having IPF, the therapeutic amount modulates a programmed cell death pathway, and reduces progression of the progressive pulmonary fibrosis in the subject.

13. The method of claim 8, wherein compared to an untreated control subject having IPF, the therapeutic agent decreases expression or biological activity of one or more of PD1, PD-L1, PD-L2, or RGMb in the subject.

14. The method of claim 8, wherein compared to an untreated control subject having IPF, the composition is effective to:
 reduce a symptom of pulmonary fibrosis in the subject;
 reduce lung hydroxyproline levels in the subject;
 reduce lung density of the subject; and/or
 reduce total cell count (TCC) in bronchoalveolar lavage fluid (BALF) from the subject.

15. The method of claim 8, wherein a higher level of total protein expression of PD-L1/CD274 is detected in the lung tissue of the subject, as compared to the control subject not suffering from pulmonary fibrosis.

16. The method of claim 1, wherein compared to an untreated control subject having IPF, the therapeutic amount modulates a programmed cell death pathway, and reduces progression of the progressive pulmonary fibrosis in the subject.

17. The method of claim 1, wherein compared to an untreated control subject having IPF, the therapeutic agent decreases the expression or biological activity of one or more of PD1, PD-L1, PD-L2, or RGMb in the subject.

18. The method of claim 1, wherein compared to an untreated control subject having IPF, the composition is effective to:
 reduce a symptom of pulmonary fibrosis in the subject;
 reduce lung hydroxyproline levels in the subject;
 reduce lung density of the subject; and/or
 reduce total cell count (TCC) in bronchoalveolar lavage fluid (BALF) from the subject.

* * * * *

SEQUENCE LISTING

```
<160> NUMBER OF SEQ ID NOS: 8

<210> SEQ ID NO 1
<211> LENGTH: 175
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140
```

| | | | | | | | | | | | | | | |
|---|---|---|---|---|---|---|---|---|---|---|---|---|---|---|
| Phe | Arg | Leu | Arg | Lys | Gly | Arg | Met | Met | Asp | Val | Lys | Lys | Cys | Gly | Ile |
| 145 | | | | 150 | | | | | 155 | | | | | 160 |

| | | | | | | | | | | | |
|---|---|---|---|---|---|---|---|---|---|---|---|
| Gln | Asp | Thr | Asn | Ser | Lys | Lys | Gln | Ser | Asp | Thr | His | Leu | Glu | Glu |
| | | | 165 | | | | | 170 | | | | | 175 |

<210> SEQ ID NO 2
<211> LENGTH: 3349
<212> TYPE: DNA
<213> ORGANISM: Homo sapiens

<400> SEQUENCE: 2

```
ggcgcaacgc tgagcagctg gcgcgtcccg cgcggcccca gttctgcgca gcttcccgag      60
gctccgcacc agccgcgctt ctgtccgcct gcagggcatt ccagaaagat gaggatattt     120
gctgtcttta tattcatgac ctactggcat ttgctgaacg ccccatacaa caaaatcaac     180
caaagaattt tggttgtgga tccagtcacc tctgaacatg aactgacatg tcaggctgag     240
ggctacccca aggccgaagt catctggaca agcagtgacc atcaagtcct gagtggtaag     300
accaccacca ccaattccaa gagagaggag aagcttttca atgtgaccag cacactgaga     360
atcaacacaa caactaatga gatttttctac tgcactttta ggagattaga tcctgaggaa     420
aaccatacag ctgaattggt catcccagaa ctacctctgg cacatcctcc aaatgaaagg     480
actcacttgg taattctggg agccatctta ttatgccttg gtgtagcact gacattcatc     540
ttccgtttaa gaaaagggag aatgatggat gtgaaaaaat gtggcatcca agatacaaac     600
tcaaagaagc aaagtgatac acatttggag gagacgtaat ccagcattgg aacttctgat     660
cttcaagcag ggattctcaa cctgtggttt aggggttcat cggggctgag cgtgacaaga     720
ggaaggaatg ggcccgtggg atgcaggcaa tgtgggactt aaaaggccca agcactgaaa     780
atggaacctg gcgaaagcag aggaggagaa tgaagaaaga tggagtcaaa cagggagcct     840
ggagggagac cttgatactt tcaaatgcct gagggggctca tcgacgcctg tgacagggag     900
aaaggatact tctgaacaag gagcctccaa gcaaatcatc cattgctcat cctaggaaga     960
cgggttgaga atccctaatt tgagggtcag ttcctgcaga agtgcccttt gcctccactc    1020
aatgcctcaa tttgttttct gcatgactga gagtctcagt gttggaacgg acagtatt     1080
atgtatgagt ttttcctatt tattttgagt ctgtgaggtc ttcttgtcat gtgagtgtgg    1140
ttgtgaatga tttcttttga agatatattg tagtagatgt tacaattttg tcgccaaact    1200
aaacttgctg cttaatgatt tgctcacatc tagtaaaaca tggagtattt gtaaggtgct    1260
tggtctcctc tataactaca agtatacatt ggaagcataa agatcaaacc gttggttgca    1320
taggatgtca cctttattta acccattaat actctggttg acctaatctt attctcagac    1380
ctcaagtgtc tgtgcagtat ctgttccatt taaatatcag ctttacaatt atgtggtagc    1440
ctacacacat aatctcattt catcgctgta accaccctgt tgtgataacc actattattt    1500
tacccatcgt acagctgagg aagcaaacag attaagtaac ttgcccaaac cagtaaatag    1560
cagacctcag actgccaccc actgtccttt tataatacaa tttacagcta tattttactt    1620
taagcaattc ttttattcaa aaaccattta ttaagtgccc ttgcaatatc aatcgctgtg    1680
ccaggcattg aatctacaga tgtgagcaag acaaagtacc tgtcctcaag gagctctatg    1740
tataatgagg agattaacaa gaaaatgtat tattacaatt tagtccagtg tcatagcata    1800
aggatgatgc gagggaaaa cccgagcagt gttgccaaga ggaggaaata ggccaatgtg    1860
gtctgggacg gttggatata cttaaacatc ttaataatca gagtaatttt catttacaaa    1920
gagaggtcgg tacttaaaat aaccctgaaa aataacactg gaattccttt tctagcatta    1980
```

| | |
|---|---|
| tatttattcc tgatttgcct ttgccatata atctaatgct tgtttatata gtgtctggta | 2040 |
| ttgtttaaca gttctgtctt ttctatttaa atgccactaa attttaaatt catacctttc | 2100 |
| catgattcaa aattcaaaag atcccatggg agatggttgg aaaatctcca cttcatcctc | 2160 |
| caagccattc aagtttcctt tccagaagca actgctactg cctttcattc atatgttctt | 2220 |
| ctaaagatag tctacatttg gaaatgtatg ttaaaagcac gtattttttaa aatttttttc | 2280 |
| ctaaatagta acacattgta tgtctgctgt gtactttgct attttttattt attttagtgt | 2340 |
| ttcttatata gcagatggaa tgaatttgaa gttcccaggg ctgaggatcc atgccttctt | 2400 |
| tgtttctaag ttatctttcc catagctttt cattatcttt catatgatcc agtatatgtt | 2460 |
| aaatatgtcc tacatataca tttagacaac caccatttgt taagtatttg ctctaggaca | 2520 |
| gagtttggat tgtttatgt ttgctcaaaa ggagacccat gggctctcca gggtgcactg | 2580 |
| agtcaatcta gtcctaaaaa gcaatcttat tattaactct gtatgacaga atcatgtctg | 2640 |
| gaacttttgt tttctgcttt ctgtcaagta taaacttcac tttgatgctg tacttgcaaa | 2700 |
| atcacatttt ctttctggaa attccggcag tgtaccttga ctgctagcta ccctgtgcca | 2760 |
| gaaaagcctc attcgttgtg cttgaaccct tgaatgccac cagctgtcat cactacacag | 2820 |
| ccctcctaag aggcttcctg gaggtttcga gattcagatg ccctgggaga tcccagagtt | 2880 |
| tcctttccct cttggccata ttctggtgtc aatgacaagg agtaccttgg ctttgccaca | 2940 |
| tgtcaaggct gaagaaacag tgtctccaac agagctcctt gtgttatctg tttgtacatg | 3000 |
| tgcatttgta cagtaattgg tgtgacagtg ttctttgtgt gaattacagg caagaattgt | 3060 |
| ggctgagcaa ggcacatagt ctactcagtc tattcctaag tcctaactcc tccttgtggt | 3120 |
| gttggatttg taaggcactt tatccctttt gtctcatgtt tcatcgtaaa tggcataggc | 3180 |
| agagatgata cctaattctg catttgattg tcacttttttg tacctgcatt aatttaataa | 3240 |
| aatattctta tttatttttgt tacttggtac accagcatgt ccattttctt gtttattttg | 3300 |
| tgtttaataa aatgttcagt ttaacatccc agtggagaaa gttaaaaaa | 3349 |

<210> SEQ ID NO 3
<211> LENGTH: 3691
<212> TYPE: DNA
<213> ORGANISM: Homo sapiens

<400> SEQUENCE: 3

| | |
|---|---|
| ggcgcaacgc tgagcagctg gcgcgtcccg cgcggcccca gttctgcgca gcttcccgag | 60 |
| gctccgcacc agccgcgctt ctgtccgcct gcagggcatt ccagaaagat gaggatattt | 120 |
| gctgtcttta tattcatgac ctactggcat ttgctgaacg catttactgt cacggttccc | 180 |
| aaggacctat atgtggtaga gtatggtagc aatatgacaa ttgaatgcaa attcccagta | 240 |
| gaaaaacaat tagacctggc tgcactaatt gtctattggg aaatggagga taagaacatt | 300 |
| attcaatttg tgcatggaga ggaagacctg aaggttcagc atagtagcta cagacagagg | 360 |
| gcccggctgt tgaaggacca gctctcccctg ggaaatgctg cacttcagat cacagatgtg | 420 |
| aaattgcagg atgcaggggt gtaccgctgc atgatcagct atggtggtgc cgactacaag | 480 |
| cgaattactg tgaaagtcaa tgcccccatac aacaaaatca ccaaagaat tttggttgtg | 540 |
| gatccagtca cctctgaaca tgaactgaca tgtcaggctg agggctaccc caaggccgaa | 600 |
| gtcatctgga caagcagtga ccatcaagtc ctgagtggta agaccaccac caccaattcc | 660 |
| aagagagagg agaagctttt caatgtgacc agcacactga gaatcaacac aacaactaat | 720 |

-continued

```
gagattttct actgcactttt taggagatta gatcctgagg aaaaccatac agctgaattg    780
gtcatcccag aactacctct ggcacatcct ccaaatgaaa ggactcactt ggtaattctg    840
ggagccatct tattatgcct tggtgtagca ctgacattca tcttccgttt aagaaaaggg    900
agaatgatga atgtgaaaaa atgtggcatc aagatacaa actcaaagaa gcaaagtgat    960
acacatttgg aggagacgta atccagcatt ggaacttctg atcttcaagc agggattctc   1020
aacctgtggt ttaggggttc atcggggctg agcgtgacaa gaggaaggaa tgggcccgtg   1080
ggatgcaggc aatgtgggac ttaaaaggcc caagcactga aaatggaacc tggcgaaagc   1140
agaggaggag aatgaagaaa gatggagtca acagggagc ctggagggag accttgatac   1200
tttcaaatgc ctgaggggct catcgacgcc tgtgacaggg agaaaggata cttctgaaca   1260
aggagcctcc aagcaaatca tccattgctc atcctaggaa gacgggttga gaatccctaa   1320
tttgagggtc agttcctgca gaagtgccct ttgcctccac tcaatgcctc aatttgtttt   1380
ctgcatgact gagagtctca gtgttggaac gggacagtat ttatgtatga gttttcccta   1440
tttattttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt caccttttatt  1680
taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
ctttgccata taatctaatg cttgtttata tagtgtctgg tattgtttaa cagttctgtc   2400
ttttctatt aaatgccact aaattttaaa ttcatacctt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaatttttt tcctaaatag taacacattg   2640
tatgtctgct gtgtactttg ctattttat ttattttagt gtttcttata tagcagatgg   2700
aatgaatttg aagttcccag ggctgaggat ccatgccttc tttgtttcta agttatcttt   2760
cccatagctt ttcattatct ttcatatgat ccagtatatg ttaaatatgt cctacatata   2820
catttagaca accaccattt gttaagtatt tgctctagga cagagtttgg atttgtttat   2880
gtttgctcaa aaggagaccc atgggctctc cagggtgcac tgagtcaatc tagtcctaaa   2940
aagcaatctt attattaact ctgtatgaca gaatcatgtc tggaactttt gttttctgct   3000
ttctgtcaag tataaacttc actttgatgc tgtacttgca aaatcacatt ttcttctgg    3060
aaattccggc agtgtacctt gactgctagc taccctgtgc cagaaaagcc tcattcgttg   3120
```

| | |
|---|---|
| tgcttgaacc cttgaatgcc accagctgtc atcactacac agccctccta agaggcttcc | 3180 |
| tggaggtttc gagattcaga tgccctggga gatcccagag tttcctttcc ctcttggcca | 3240 |
| tattctggtg tcaatgacaa ggagtacctt ggctttgcca catgtcaagg ctgaagaaac | 3300 |
| agtgtctcca acagagctcc ttgtgttatc tgtttgtaca tgtgcatttg tacagtaatt | 3360 |
| ggtgtgacag tgttctttgt gtgaattaca ggcaagaatt gtggctgagc aaggcacata | 3420 |
| gtctactcag tctattccta agtcctaact cctccttgtg gtgttggatt tgtaaggcac | 3480 |
| tttatcccctt ttgtctcatg tttcatcgta aatggcatag gcagagatga tacctaattc | 3540 |
| tgcatttgat tgtcactttt tgtacctgca ttaatttaat aaaatattct tatttatttt | 3600 |
| gttacttggt acaccagcat gtccattttc ttgtttatttt tgtgtttaat aaaatgttca | 3660 |
| gtttaacatc ccagtggaga aagttaaaaa a | 3691 |

<210> SEQ ID NO 4
<211> LENGTH: 3566
<212> TYPE: DNA
<213> ORGANISM: Mus musculus

<400> SEQUENCE: 4

| | |
|---|---|
| tggtccccaa gcctcatgcc aggctgcact tgcacgtcgc gggccagtct cctcgcctgc | 60 |
| agcgtttact atcacggctc caaaggactt gtacgtggtg gagtatgca gcaacgtcac | 120 |
| gatggagtgc agattccctg tagaacggga gctggacctg cttgcgttag tggtgtactg | 180 |
| ggaaaaggaa gatgagcaag tgattcagtt tgtggcagga gaggaggacc ttaagcctca | 240 |
| gcacagcaac ttcaggggga gagcctcgct gccaaaggac cagcttttga agggaaatgc | 300 |
| tgcccttcag atcacagacg tcaagctgca ggacgcaggc gtttactgct gcataatcag | 360 |
| ctacggtggt gcggactaca agcgaatcac gctgaaagtc aatgccccat accgcaaaat | 420 |
| caaccagaga atttccgtgg atccagccac ttctgagcat gaactaatat gtcaggccga | 480 |
| gggttatcca gaagctgagg taatctggac aaacagtgac caccaacccg tgagtgggaa | 540 |
| gagaagtgtc accacttccc ggacagaggg gatgcttctc aatgtgacca gcagtctgag | 600 |
| ggtcaacgcc acagcgaatg atgttttcta ctgtacgttt tggagatcac agccaggca | 660 |
| aaaccacaca gcggagctga tcatcccaga actgcctgca acacatcctc cacagaacag | 720 |
| gactcactgg gtgcttctgg gatccatcct gttgttcctc attgtagtgt ccacggtcct | 780 |
| cctcttcttg agaaaacaag tgagaatgct agatgtggag aaatgtggcg ttgaagatac | 840 |
| aagctcaaaa aaccgaaatg atacacaatt cgaggagacg taagcagtgt tgaaccctct | 900 |
| gatcgtcgat tggcagcttg tggtctgtga agaaagggc ccatgggaca tgagtccaaa | 960 |
| gactcaagat ggaacctgag ggagagaacc aagaaagtgt tgggagagga gcctggaaca | 1020 |
| acggacattt tttccaggga gacactgcta agcaagttgc ccatcagtcg tcttgggaaa | 1080 |
| tggattgagg gttcctggct tagcagctgg tccttgcaca gtgacctttt cctctgctca | 1140 |
| gtgccgggat gagagatgga gtcatgagtg ttgaagaata agtgccttct atttatttg | 1200 |
| agtctgtgtg ttctcacttt gggcatgtaa ttatgactgg tgaattctga cgacatgata | 1260 |
| gatcttaaga tgtagtcacc aaactcaact gctgcttagc atcctccgta actactgata | 1320 |
| caagcaggga acacagaggt cacctgcttg gtttgacagg ctcttgctgt ctgactcaaa | 1380 |
| taatctttat ttttcagtcc tcaaggctct tcgatagcag ttgttctgta tcagccttat | 1440 |
| aggtgtcagg tatagcactc aacatctcat ctcattacaa tagcaaccct catcaccata | 1500 |

-continued

| | |
|---|---|
| gcaacagcta acctctgtta tcctcacttc atagccagga agctgagcga ctaagtcact | 1560 |
| tgcccacaga gtatcagctc tcagatttct gttcttcagc cactgtcctt tcaggataga | 1620 |
| atttgtcgtt aagaaattaa tttaaaaact gattattgag tagcattgta tatcaatcac | 1680 |
| aacatgcctt gtgcactgtg ctggcctctg agcataaaga tgtacgccgg agtaccggtc | 1740 |
| ggacatgttt atgtgtgtta atactcaga gaaatgttca ttaacaagga gcttgcattt | 1800 |
| tagagacact ggaaagtaac tccagttcat tgtctagcat tacatttacc tcatttgcta | 1860 |
| tccttgccat acagtctctt gttctccatg aagtgtcatg aatcttgttg aatagttctt | 1920 |
| ttattttta atgtttcta tttaaatgat attgacatct gaggcgatag ctcagttggt | 1980 |
| aaaaccctt cctcacaagt gtgaaaccct gagtcttatc cctagaaccc acataaaaaa | 2040 |
| cagttgcgta tgtttgtgca tgcttttgat cccagcacta gggaggcaga ggcaggcaga | 2100 |
| tcctgagctc tcattgacca cccagcctag cctacatggt tagctccagg cctacaggag | 2160 |
| ctggcagagc ctgaaaaacg atgcctagac acacacacac acacacacac acacacacac | 2220 |
| acacacacac accatgtact catagaccta agtgcaccct cctacacatg cacacacata | 2280 |
| caattcaaac acaaatcaac agggaattgt ctcagaatgg tccccaagac aaagaagaag | 2340 |
| aaaaacacca aaccagctct attccctcag cctatcctct ctactccttc ctagaagcaa | 2400 |
| ctactattgt ttttgtatat aaatttaccc aacgacagtt aatatgtaga atatatatta | 2460 |
| aagtgtctgt caatatatat tatctctttc tttctttctt cctttctttc tttctttctt | 2520 |
| tctttctttc tttctttctt tctttctttc ttccttcctt ccttccttcc ttccttcctt | 2580 |
| ccttcctttc tttctttctt tcttttttc tgtctatctg tacctaaatg gttgctcact | 2640 |
| atgcattttc tgtgctcttc gccctttta tttaatgtat ggatatttat gctgcttcca | 2700 |
| gaatggatct aaagctcttt gtttctaggt tttctccccc atccttctag gcatctctca | 2760 |
| cactgtctag gccagacacc atgtctgctg cctgaatctg tagacaccat ttataaagca | 2820 |
| cgtactcacc gagtttgtat ttggcttgtt ctgtgtctga ttaaagggag accatgagtc | 2880 |
| cccagggtac actgagttac cccagtacca agggggagcc ttgtttgtgt ctccatggca | 2940 |
| gaagcaggcc tggagccatt ttggtttctt ccttgacttc tctcaaacac agacgcctca | 3000 |
| cttgctcatt acaggttctc cttttgggaat gtcagcattg ctccttgact gctggctgcc | 3060 |
| ctggaaggag cccattagct ctgtgtgagc ccttgacagc tactgcctct ccttaccaca | 3120 |
| ggggcctcta agatactgtt acctagaggt cttgaggatc tgtgttctct gggggagga | 3180 |
| aaggaggagg aacccagaac tttcttacag ttttccttgt tctgtcacat gtcaagactg | 3240 |
| aaggaacagg ctgggctacg tagtgagatc ctgtctcaaa ggaaagacga gcatagccga | 3300 |
| accccggtg gaaccccctc tgttacctgt tcacacaagc ttattgatga gtctcatgtt | 3360 |
| aatgtcttgt ttgtatgaag tttaagaaaa tatcgggttg ggcaacacat tctatttatt | 3420 |
| cattttattt gaaatcttaa tgccatctca tggtgttgga ttggtgtggc acttttattct | 3480 |
| tttgtgttgt gtataaccat aaattttatt ttgcatcaga ttgtcaatgt attgcattaa | 3540 |
| tttaataaat atttttattt attaaa | 3566 |

<210> SEQ ID NO 5
<211> LENGTH: 3706
<212> TYPE: DNA
<213> ORGANISM: Rattus norvegicus

<400> SEQUENCE: 5

| | |
|---|---|
| tctttgctac ggataagacc aggaaatcgc cctccccagc ctccagccag gctgcagcta | 60 |

```
cgcgacttgc cagtctcctc gcctacaggt aagtctcaaa ccatgaggat atttgctgtc    120
cttatagtca cagcctgcag tcacgtgcta gcggcattta ccatcacagc tccaaaggac    180
ctgtacgtgg tggagtatgg cagcaatgtc acgatggaat gcagattccc agtagaacag    240
aaattggacc tgcttgcctt agtggtgtac tgggaaaagg aagacaagga agttattcag    300
tttgtggagg gagaggagga cctgaagcct caacacagca gcttcagggg gagagccttc    360
ttgccaaagg accagctttt gaaggggaac gcggtgcttc agatcacaga tgtcaagctg    420
caggacgcag gtgtctactg ctgcatgatc agctatggtg gagcggacta caagcgaatc    480
acattgaaag tcaacgctcc ataccgcaaa atcaaccaaa gaatttccat ggatccagcc    540
acttctgagc atgaactaat gtgccaggct gagggttacc agaagccgat agtgatctgg    600
acaaacagtg accaccagtc cctgagtggg gaaacaactg tcaccacttc ccagactgag    660
gagaagcttc tcaacgtgac cagcgttctg agggtcaacg caacagctaa tgatgttttc    720
cactgtacgt tctggagagt acactcaggg gagaaccaca cggctgaact gatcatccca    780
gaactgcctg taccacgtct cccacataac aggacacact gggtactcct gggatccgtc    840
cttttgttcc tcatcgtggg gttcaccgtc ttcttctgct tgagaaaaca agtgagaatg    900
ctagatgtgg aaaaatgcgg cttcgaagat agaaattcaa agaaccgaaa tgatacacag    960
ttcgaggaga cgtaagcagt gttgaaccct ctgagcctcg aggcgggatt ggcagcttgt   1020
ggtctgtgaa agaaagggcc cgtgggacat gggtccaggg actcaaaaat ggaaccggag   1080
aggagaagag aacaaagaaa gtgttggaag aggagcctgg gacgaaagac atttctacag   1140
gagacactgc taagcaagtt acccatcagt catctcgggc aataagttga gggttcctca   1200
ttttaacagc tggtcctcgc acaagtgacc tttctctcta cccagtgcct ggatgagagg   1260
cagagtcaca agtgttgaag tgtgagtgcc ttctatttac ttccagtccg tgtgttcttg   1320
ctgtgggcat gtggttatga ctagtgacat aataggcgtt aaaatgcagt caccaaaactc   1380 aactgctgct tagcatcctc tgtaactact ggcacaagca ggaaacgtgg aggtcacatg   1440
gttcgtttga cgggctcttg ctgtccgact tgagtaatct tcattctcag gcctcaaggt   1500
tctgcagtag tagttgttct cttttaaatat ctgctttaca agtgttgggt actatactca   1560
aacatcttat ttcatcacca tggcaaccct catactaacc tctgtcatac tcccttcata   1620
gccaagacgc tgagtgtctg agtaacttga ccacaaaatg acagctatca gatttctatt   1680
tttcagacac tgtcctttca ggatagaatt tgtagctaag aatttaataa taaaaaaaaa   1740
accccgctta ttaggcactt ccacaccaca ccatgccttg tgcactgctc tggcctctga   1800
cagagaagga agccagagtg ccggtcggat ttgcttatgt gtgttcaata ctcaaatcaa   1860
tgctcattaa catggagtct gcattttaaa gacactctcc agttctttgt ctagcattat   1920
atttacctct aatctgttat ccctgccaaa caatctcatg ttctccatga agtgtctagt   1980
cttgttgagt agttctttt tttttttttc tatttaaatg atattgacat ctgaggagac   2040
agctcagttg gtagaattct ttccttacaa gtgggaaacc ctgtttatc cccagaaccc   2100 acataaaaaa cagttgcgta tatctgtgca tgcttaatcc aagcactagg gaggcagaga   2160
caggcagatc tctagctctc accgatcagc cagctccagg tctacaagag ctgacagtgc   2220
ctgagaaaca tgtctacaca cacacacata cacactctca catacatgga ccatgtactc   2280
atacacctaa gtggactctc ttagtgaaca cacatacaat ggtccccaag acaaaacaaa   2340
acaaaaaaaa aataaaccaa actagctcta ttccatcagc ctagccatgc tactcccttc   2400
```

```
ccagaagcaa ctgctattgt ttttgcacat atattttctt aaagacagtt aatatgtata    2460
aatctttgtt aaagtatgtc tgtctgtctg cctgcctgcc tacctatcta cctatctatc    2520
tatccatcca tccatccatc catccaccca tctgtccatc cgtctgtctg tccatctgtc    2580
tgtctatcta cctatctacc tacctacata cctatcatct gtctgtctgt ctttcctaaa    2640
tggtatagga aaactgtacg ttttctatgc actttgccct tttcatttag tgtattgata    2700
cttatgctgc ttccagactg atctaaagat ccataaagag aactgcctca tttctaggtt    2760
ttctttccca tccctctagg cacctctcac actgtctagg ccagacactt gctgcctgta    2820
tctgtagaca tcatttataa agtgtgtact caccgagttt gtgtctactc aaagggaggc    2880
catgggtccc cagggtcact gagtcaaccc agtaccaagg tggagccttg tatctccatg    2940
gcagaagcaa atctggggcc atttctgttt cttccttgac ttcttttcta aaacacagat    3000
gctctaatta cttattacag gttgtccctg gtaatgtcag cattgctcct agacttctgg    3060
gtgccctgga aaagcccgtt agctctgtgt gaacccttaa ggcagctgtc tctccttacc    3120
tcatagacac tgtttcctgg agggtttgag atactgtttc caaaaggtgt tcacttgggc    3180
gaggagggga gggggagccc agaactttgt tactattttc tttgttttgt cacatgtcaa    3240
ggctgaagaa agagcctggg tatgttggcg catgtctcca gttgcaggca gaggcaggtg    3300
gatctctgtg agtttgtggc cagcctggtc tccatagtga attctaagcc agccagggct    3360
cggttacata gtgagatccc gtctcaaagg aaagactggc ctatcagaac cccagtgaa    3420 accccttctg ttacttgttc acacatgttt gttgatgatt ctcgtgttaa tgtcttgttt    3480
gtatgacgtt caagaaaaga tctggttggg caacacattg tatttattca tcttattcaa    3540
aatcttaatg ccatctcatg gcattggatt ggtatggcac tttattcttt tgtgttctgt    3600
ataaccacaa atgaaatttt tattttgtgt ctgattgtca ttgtattgca ttaatttaat    3660
aagatattat ttattaaaaa catttgattt ttttctttt taaaaa    3706
```

<210> SEQ ID NO 6
<211> LENGTH: 3909
<212> TYPE: DNA
<213> ORGANISM: Macaca fascicularis

<400> SEQUENCE: 6

```
aaatcaaggt gcgttcagat gttggcttgt tgtaaatttc tgtttatatt aataacatac      60
caaatgtgga tttgttttaa tcttcggaac tctttccggt gaaaacctca tttacaagaa     120
aactggactg acaggtttca cttttctgttt catttctata catagcttta ttcctaggac     180
accaacacca ctcgctaccc aaactgaaag cttccccgat tccgccgaag gtcaggaaag     240
tccaatgccg ggcaaactgg atttgctgcc ttgcgcagag gtgggcggga ccccgcctcc     300
gggccgggcg ccaagttgag cagctggcac gcctcgcgaa gccccagtcc tgaagcccca     360
gtcctgcgct gcttcccgag gctccgcacc agccgcgctt ctctctgcct gcagcacatt     420
ccagaaagat gaggatattt gctgtcttta tattcacgat ctactggcat ttgctgaatg     480
catttactgt cacggttccc aaggacctat atgtggtaga gtatggcagc aatatgacaa     540
ttgaatgcaa attcccagta gaaaaacaat tagacctgac ttcactaatt gtctattggg     600
aaatggagga taagaacatt attcaatttg tgcatggaga ggaagacctg aaggttcagc     660
atagtaacta cagacagagg gcccagctgt tgaaggacca gctctccctg ggaaatgctg     720
cacttcggat cacagatgtg aaattgcagg atgcaggggt ttaccgctgc atgatcagct     780
atggtggtgc cgactacaag cggattaccg tgaaagtcaa tgctccatac aacaaaatca    840
```

```
accaaagaat tttggttgtc gatccagtca cctctgaaca tgaactaaca tgtcaggctg    900
agggctaccc caaggccgaa gtcatttgga caagcagtga ccatcaagtc ctgagtggta    960
agaccaccac caccaattcc aagagagagg agaagctttt aaatgtgacc agcacactga   1020
gaatcaacac aacagctaat gagattttct actgcatttt taggagatta gatcctgagg   1080
aaaaccatac agctgaattg gtcatcccag aactacctct ggcgcttcct ccaaatgaaa   1140
ggactcactt ggtaattctg ggagccatct ttttactcct tggtgtagca ctgacattca   1200
tcttctattt aagaaaaggg agaatgatgg atatgaaaaa atgtggcatt cgagttacaa   1260
actcaaagaa gcaacgtgat acacaattgg aggagacgta atccagcatt ggaacttctg   1320
atcttcaagc agggattctc agcctgtggt ttgggggttc gtcagggctg agcatgacca   1380
gaggaatgaa tgggcccgtg ggatgcatgc agtatgggac ttaaaaggcc caagcactga   1440
aaatggaacc tggcgaaagc agaggaggag aatgaagaaa atggagttga acagggagc    1500 gtggagggag accttgatac tttcaaatgc ctgaggggct catcggtgca tgtgacaggg   1560
agaaaggata cttctgaaca aggagcctcc aagcaaatca tccactgctc atcttaggaa   1620
aacgggttga gaatccctaa tttgagggtc agttcctgca gaagtgccct ttgcctccac   1680
tcaatgcctc aatttgtttt ctgcgtgact gagggtccca gtgttggaac agtatttatg   1740
tatgagattt tcctatttat tttgagtctg tgaggtcttc ttgtcatggg agtgtggttg   1800
tgaatgattt cttttgaaga tatattgtag tagatgttac aattttgtcg ccaaactaaa   1860
cttgatgctt aatgacttgc tcacatctag taaaacatgg agtatttgta aggtgcttgg   1920
tctcctctat aactacaagt acacattgga agcataaaga tcaaaccgtt gatttgtata   1980
ggatgtcacc tttatttaac ccattaatac tctgattgac ttaatcttat tctcagacct   2040
caagtgtctg tgcagtatct gttccattta aatatcagct ttataattat gtggtaccat   2100
acacacataa tctcctttca tcgctgtaac caccctgttg tgatgaccac tattatttta   2160
cccattgtac agctgaggaa gcaaacagat taagtaactt gccaaaacca gtaaatagca   2220
gagctcagac tgccacccac tgtccttta taatacaatt tacagctata ttttacttta    2280
agcaattcat ttattcaaaa cccatttatt aagtgccctt gcaatatcaa tcactgtacc   2340
aggcattgaa tctacagatg tgagcaagag aaagtacctg tcctcaagga gcttggagta   2400
taataaggag attaataaga aaatatatta ttacaatcta gtccagtgtc atagcataag   2460
gatgatgtga ggagaaaagc tgagcagtgt tgccaagagg aggaaatagg ccaatgtggt   2520
ctgggacagt tgaatgtatt taaacatctt aataatcaaa gtaattttca tttacaaaga   2580
gaagtcagta cttaaaataa ccctgaaaaa taacactgga attccttttc tagcattata   2640
tttatccctg atttgccttt gccatacaat ctaatgcttg tttatatagt gtctgatatt   2700
gtttaacagt tctgtctttt ctattcaaat gctattaaat tttaaattca tacctttcca   2760
tgattcaaaa ttcaaaagat cccatgggag atggtttgaa atctccact tcatcctcca   2820 agccattcaa gtttcctttc cagaagcaac tgctactgcc ttttattcat atgttcttct   2880
aaagatagtc tacatttgga aatgtatgtt aaaagcatat attttttaaat tttttttccct  2940 aaatagtaac acattatatg tctgctgtgc actttgctat ttttatttat tgtagtgttt   3000
cttatgtagc agatggaatg aatttgaagc tcccaagggt caggacacat gccttctttg   3060
tttctaagtt atcttttccca tagctttttca taatcttttca tatgatttag tacatgttaa   3120
atatgtgcta catatacatt tagacaacca gcatttgtta agtatttgct ctaggactga   3180
```

-continued

```
gtttggattt atgtttgctc aaaaggagac ccatgggctc tccagggtgc actgagtcaa    3240
tctagtccta aaaagcaatc ttattattaa ctctgtatga cagaatcata tctggaactt    3300
ttgttttctg ctttctgtca agtataaact tcactttgat gctgtacttg caaaatcaca    3360
ttttctttct ggaaattcca gtagtgtacc ttgactgcta gttaccctgt gccagaaaag    3420
cctcattcgt tgtgcttgaa ccctttaatg ccaccagctg tcatcactac acaggcctcc    3480
taagaggctt cctggaggtt ttgagattca gatgccctga gagatcccag agttccttt     3540 ccctcttggc cacattctgg tgtcagtgac aaggaatacc ttcgctttgc cacccgtcaa    3600
ggttgaagaa acagcgtctc caacagagct ccttgtgtta tctgtttgta catgtgcatt    3660
tgtacagtaa tttgtgtgac agtgttcttt gtgtgaatta caggcaagaa ctgtggctga    3720
gcaaggcaca tagtctactc agtctattcc taactcctcc ttttggtgtt ggatttgtaa    3780
ggcactttat cccttttgtc tcatgtttca tcgtaaatgg cataggcaga gatgatatct    3840
aattctgcat ttgattgtca cttttttgtac ctgcattaat ttaataaaat atccttattt   3900
attttgtta                                                            3909
```

<210> SEQ ID NO 7
<211> LENGTH: 273
<212> TYPE: PRT
<213> ORGANISM: Homo sapiens

<400> SEQUENCE: 7

```
Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240
```

```
Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Ile

<210> SEQ ID NO 8
<211> LENGTH: 288
<212> TYPE: PRT
<213> ORGANISM: Homo sapiens

<400> SEQUENCE: 8

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```